US006982431B2

(12) United States Patent
Modlin et al.

(10) Patent No.: US 6,982,431 B2
(45) Date of Patent: *Jan. 3, 2006

(54) SAMPLE ANALYSIS SYSTEMS

(75) Inventors: Douglas N. Modlin, Palo Alto, CA (US); Glenn R. Edwards, Palo Alto, CA (US); John C. Owicki, Palo Alto, CA (US); Michael T. Taylor, Newark, CA (US); Samuel A. Marquiss, Santa Clara, CA (US)

(73) Assignee: Molecular Devices Corporation, Sunnyvale, CA (US)

( * ) Notice: Subject to any disclaimer, the term of this patent is extended or adjusted under 35 U.S.C. 154(b) by 25 days.

This patent is subject to a terminal disclaimer.

(21) Appl. No.: 10/218,897

(22) Filed: Aug. 13, 2002

(65) Prior Publication Data

US 2003/0127609 A1 Jul. 10, 2003

Related U.S. Application Data

(63) Continuation-in-part of application No. 10/041,532, filed on Jan. 7, 2002, now abandoned, and a continuation-in-part of application No. 10/004,647, filed on Dec. 3, 2001, and a continuation-in-part of application No. 10/012,255, filed on Nov. 12, 2001, and a continuation-in-part of application No. 09/836,575, filed on Apr. 16, 2001, now abandoned, and a continuation-in-part of application No. 09/778,224, filed on Feb. 6, 2001, and a continuation-in-part of application No. 09/767,434, filed on Jan. 22, 2001, now Pat. No. 6,486,947, and a continuation-in-part of application No. 09/765,869, filed on Jan. 19, 2001, now Pat. No. 6,466,316, and a continuation-in-part of application No. 09/759,711, filed on Jan. 12, 2001, and a continuation-in-part of application No. 09/733,370, filed on Dec. 8, 2000, now abandoned, and a continuation-in-part of application No. 09/710,061, filed on Nov. 10, 2000, and a continuation-in-part of application No. 09/629,599, filed on Jul. 31, 2000, now Pat. No. 6,469,311, and a continuation-in-part of application No. 09/478,819, filed on Jan. 5, 2000, now Pat. No. 6,488,892, and a continuation-in-part of application No. 09/349,733, filed on Jul. 8, 1999, now abandoned, and a continuation-in-part of application No. 09/302,158, filed on Apr. 2, 1999, and a continuation-in-part of application No. 09/144,578, filed on Aug. 31, 1998.

(51) Int. Cl.
*G01N 15/06* (2006.01)

(52) U.S. Cl. ....................................... 250/573; 250/225
(58) Field of Classification Search ................ 250/576, 250/573, 574, 225, 461.2, 338.5; 356/343, 356/317, 318, 417; 422/63, 82.08
See application file for complete search history.

(56) References Cited

U.S. PATENT DOCUMENTS

| 2,056,791 A | 10/1936 | Logan |
| 2,719,214 A | 9/1955 | Potter |

(Continued)

FOREIGN PATENT DOCUMENTS

| CA | 2099542 | 1/1994 |
| DE | 29805613 U1 | 7/1998 |

(Continued)

OTHER PUBLICATIONS

Donald G. Fink and H. Wayne Beaty, Standard Handbook for Electrical Engineers, pp. 22-2 through 22-5 (11$^{th}$ ed. 1978).

(Continued)

*Primary Examiner*—Que T. Le
(74) *Attorney, Agent, or Firm*—Kolisch Hartwell, P.C.

(57) ABSTRACT

Systems, and components thereof, for analyzing samples. These systems include apparatus and methods for generating, transmitting, detecting, and/or analyzing light, including without limitation high-throughput optical screening devices for analyzing samples at one or more assay sites. These systems also include apparatus and methods for supporting samples for analysis, including without limitation multiwell sample holders such as microplates.

27 Claims, 59 Drawing Sheets

U.S. PATENT DOCUMENTS

| | | | |
|---|---|---|---|
| 3,013,467 A | 12/1961 | Minsky | |
| 3,423,581 A | 1/1969 | Baer | |
| 3,516,736 A | 6/1970 | Weaver | |
| 3,540,858 A | 11/1970 | Rochte et al. | |
| 3,849,654 A | 11/1974 | Malvin | |
| 3,885,162 A | 5/1975 | Geertz | |
| 3,925,162 A | 12/1975 | Kanno | |
| 3,932,023 A | 1/1976 | Humer | |
| 4,011,451 A | 3/1977 | Nelson | |
| 4,027,198 A | 5/1977 | Linkroum | |
| 4,053,381 A | 10/1977 | Hamblen et al. | |
| 4,067,653 A | 1/1978 | Fletcher et al. | |
| 4,074,939 A | 2/1978 | Rabl | |
| 4,076,420 A | 2/1978 | De Maeyer et al. | |
| 4,100,416 A | 7/1978 | Hirschfeld | |
| 4,144,452 A | 3/1979 | Harte | |
| 4,150,870 A | 4/1979 | d'Auria | |
| 4,203,670 A | 5/1980 | Bromberg | |
| 4,240,751 A | 12/1980 | Linnecke et al. | |
| 4,245,052 A | 1/1981 | Lund | |
| 4,292,273 A | 9/1981 | Butz et al. | |
| 4,296,326 A | 10/1981 | Haslop et al. | |
| 4,341,957 A | 7/1982 | Wieder | |
| 4,349,510 A * | 9/1982 | Kolehmainen et al. | ....... 422/66 |
| 4,374,120 A | 2/1983 | Soini et al. | |
| 4,397,560 A | 8/1983 | Andresen | |
| 4,425,427 A | 1/1984 | Luderer | |
| 4,451,149 A | 5/1984 | Noeller | |
| 4,451,433 A | 5/1984 | Yamashita et al. | |
| 4,459,360 A | 7/1984 | Marinkovich | |
| 4,472,661 A | 9/1984 | Culver | |
| 4,485,430 A | 11/1984 | Achiaga Fustel | |
| 4,490,216 A | 12/1984 | McConnell | |
| 4,501,970 A | 2/1985 | Nelson | |
| 4,545,958 A | 10/1985 | Dopatka | |
| 4,547,527 A | 10/1985 | Ingram | |
| 4,567,847 A | 2/1986 | Linner | |
| 4,591,550 A | 5/1986 | Hafeman et al. | |
| 4,599,315 A | 7/1986 | Terasaki et al. | |
| 4,622,208 A | 11/1986 | Namba et al. | |
| 4,626,684 A | 12/1986 | Landa | |
| 4,646,214 A | 2/1987 | Mendleski | |
| 4,656,127 A | 4/1987 | Mundy | |
| 4,685,801 A | 8/1987 | Minekane | |
| 4,699,512 A | 10/1987 | Koshi | |
| 4,699,978 A | 10/1987 | Barton | |
| 4,704,255 A | 11/1987 | Jolley | |
| 4,704,353 A | 11/1987 | Humphries et al. | |
| 4,707,067 A | 11/1987 | Haberland et al. | |
| 4,707,440 A | 11/1987 | Stavrianopoulos | |
| 4,721,669 A | 1/1988 | Barton | |
| 4,724,217 A | 2/1988 | Miller | |
| 4,730,921 A | 3/1988 | Klein et al. | |
| 4,735,778 A | 4/1988 | Maruyama et al. | |
| 4,737,464 A | 4/1988 | McConnell et al. | |
| 4,738,825 A | 4/1988 | Kelln et al. | |
| 4,741,619 A | 5/1988 | Humphries et al. | |
| 4,753,501 A | 6/1988 | Battle | |
| 4,758,786 A | 7/1988 | Hafeman | |
| 4,762,420 A | 8/1988 | Bowley | |
| 4,772,453 A | 9/1988 | Lisenbee | |
| 4,784,275 A | 11/1988 | Fridge | |
| 4,801,804 A | 1/1989 | Rosenthal | |
| 4,802,768 A | 2/1989 | Gifford et al. | |
| 4,808,828 A | 2/1989 | Kitamori et al. | |
| 4,810,096 A | 3/1989 | Russell et al. | |
| 4,822,733 A | 4/1989 | Morrison | |
| 4,826,660 A | 5/1989 | Smith et al. | |
| 4,849,330 A | 7/1989 | Humphries et al. | |
| 4,851,331 A | 7/1989 | Vary et al. | |
| D303,149 S | 8/1989 | Andersen | |
| 4,855,930 A | 8/1989 | Chao et al. | |
| 4,861,554 A | 8/1989 | Sakuma | |
| 4,863,849 A | 9/1989 | Melamede | |
| 4,868,103 A | 9/1989 | Stavrianopoulos et al. | |
| 4,873,633 A | 10/1989 | Mezei et al. | |
| 4,877,745 A | 10/1989 | Hayes et al. | |
| 4,877,965 A | 10/1989 | Dandliker et al. | |
| 4,883,579 A | 11/1989 | Humphries et al. | |
| 4,885,087 A | 12/1989 | Kopf | |
| 4,892,409 A | 1/1990 | Smith | |
| 4,897,548 A | 1/1990 | Döme et al. | |
| 4,911,794 A | 3/1990 | Parce et al. | |
| 4,915,812 A | 4/1990 | Parce et al. | |
| 4,923,819 A | 5/1990 | Fernandez et al. | |
| 4,931,402 A | 6/1990 | Abplanalp | |
| 4,936,682 A | 6/1990 | Hoyt | |
| 4,942,127 A | 7/1990 | Wada et al. | |
| 4,948,442 A | 8/1990 | Manns | |
| 4,956,275 A | 9/1990 | Zuk et al. | |
| 4,962,020 A | 10/1990 | Tabor et al. | |
| 4,963,658 A | 10/1990 | Kung et al. | |
| 4,963,815 A | 10/1990 | Hafeman | |
| 4,968,148 A | 11/1990 | Chow et al. | |
| 4,978,608 A | 12/1990 | Kung et al. | |
| 4,979,093 A | 12/1990 | Laine et al. | |
| 4,979,821 A | 12/1990 | Schutt et al. | |
| 5,004,806 A | 4/1991 | Kung | |
| 5,009,488 A | 4/1991 | Fay et al. | |
| 5,011,770 A | 4/1991 | Kung et al. | |
| 5,018,866 A | 5/1991 | Osten | |
| 5,020,995 A | 6/1991 | Levy | |
| 5,034,613 A | 7/1991 | Denk et al. | |
| 5,039,219 A | 8/1991 | James et al. | |
| 5,047,215 A | 9/1991 | Manns | |
| 5,058,045 A | 10/1991 | Ma | |
| 5,082,628 A | 1/1992 | Andreotti et al. | |
| 5,084,246 A | 1/1992 | Lyman et al. | |
| 5,091,652 A | 2/1992 | Mathies et al. | |
| 5,095,517 A | 3/1992 | Monguzzi et al. | |
| 5,096,807 A | 3/1992 | Leaback | |
| 5,104,804 A | 4/1992 | Humphries | |
| 5,110,556 A | 5/1992 | Lyman et al. | |
| 5,112,134 A | 5/1992 | Chow et al. | |
| 5,160,702 A | 11/1992 | Kopf-Sill et al. | |
| 5,164,319 A | 11/1992 | Hafeman et al. | |
| 5,169,601 A | 12/1992 | Ohta et al. | |
| 5,192,510 A | 3/1993 | Zoha et al. | |
| 5,196,709 A | 3/1993 | Berndt et al. | |
| 5,198,670 A | 3/1993 | VanCauter et al. | |
| 5,206,568 A | 4/1993 | Björnson et al. | |
| 5,208,161 A | 5/1993 | Saunders et al. | |
| 5,208,651 A | 5/1993 | Buican | |
| 5,216,488 A | 6/1993 | Tuunanen et al. | |
| 5,225,164 A | 7/1993 | Astle | |
| 5,225,543 A | 7/1993 | Eppler et al. | |
| 5,232,858 A | 8/1993 | Wolfbeis et al. | |
| 5,246,867 A | 9/1993 | Lakowicz et al. | |
| 5,252,293 A | 10/1993 | Drbal et al. | |
| 5,256,535 A | 10/1993 | Ylikoski et al. | |
| 5,257,202 A | 10/1993 | Feddersen et al. | |
| 5,262,128 A | 11/1993 | Leighton et al. | |
| 5,270,788 A | 12/1993 | Cercek et al. | |
| 5,273,718 A | 12/1993 | Skold et al. | |
| 5,275,951 A | 1/1994 | Chow et al. | |
| 5,278,048 A | 1/1994 | Parce et al. | |
| 5,279,943 A | 1/1994 | Mathis et al. | |
| 5,281,825 A | 1/1994 | Berndt et al. | |
| 5,283,173 A | 2/1994 | Fields et al. | |
| 5,289,407 A | 2/1994 | Strickler et al. | |
| 5,302,509 A | 4/1994 | Cheeseman | |

| | | | | | |
|---|---|---|---|---|---|
| 5,307,144 A | 4/1994 | Hiroshi et al. | 5,620,894 A | 4/1997 | Barger et al. |
| 5,315,015 A | 5/1994 | Hui et al. | 5,621,280 A | 4/1997 | Antonis et al. |
| 5,317,485 A | 5/1994 | Merjanian | 5,622,821 A | 4/1997 | Selvin et al. |
| 5,319,436 A | 6/1994 | Manns et al. | 5,624,847 A | 4/1997 | Lakowicz et al. |
| 5,323,008 A | 6/1994 | Studholme et al. | 5,626,134 A | 5/1997 | Zuckerman |
| 5,323,010 A | 6/1994 | Gratton et al. | 5,631,127 A | 5/1997 | Sundrehagen |
| 5,334,353 A | 8/1994 | Blattner | 5,631,169 A | 5/1997 | Lakowicz et al. |
| 5,340,716 A | 8/1994 | Ullman et al. | 5,631,734 A | 5/1997 | Stern et al. |
| 5,340,747 A | 8/1994 | Eden | 5,632,982 A | 5/1997 | Sussman et al. |
| 5,341,215 A | 8/1994 | Seher | 5,633,724 A | 5/1997 | King et al. |
| 5,349,436 A | 9/1994 | Fisch | 5,635,402 A | 6/1997 | Alfano et al. |
| 5,353,112 A | 10/1994 | Smith | 5,637,463 A | 6/1997 | Dalton et al. |
| 5,355,215 A | 10/1994 | Schroeder et al. | 5,639,615 A | 6/1997 | Selvin et al. |
| 5,357,095 A | 10/1994 | Weyrauch et al. | 5,641,633 A | 6/1997 | Linn et al. |
| 5,361,626 A | 11/1994 | Colligan et al. | 5,645,800 A | 7/1997 | Masterson et al. |
| 5,384,093 A | 1/1995 | Ootani et al. | 5,648,269 A | 7/1997 | Lakowicz et al. |
| 5,395,503 A | 3/1995 | Parce et al. | 5,650,125 A | 7/1997 | Bosanquet |
| 5,401,465 A | 3/1995 | Smethers et al. | 5,660,792 A | 8/1997 | Koike |
| 5,409,666 A | 4/1995 | Nagel et al. | 5,660,991 A | 8/1997 | Lakowicz et al. |
| 5,409,835 A | 4/1995 | Lakowicz et al. | 5,663,545 A | 9/1997 | Marquiss |
| 5,418,371 A | 5/1995 | Aslund et al. | 5,670,113 A | 9/1997 | Akong et al. |
| 5,420,408 A | 5/1995 | Weyrauch et al. | 5,672,880 A | 9/1997 | Kain |
| 5,436,718 A | 7/1995 | Fernandes et al. | 5,676,943 A | 10/1997 | Baetge et al. |
| 5,443,791 A | 8/1995 | Cathcart et al. | 5,677,196 A | 10/1997 | Herron et al. |
| 5,445,935 A | 8/1995 | Royer | 5,677,280 A | 10/1997 | Barrett et al. |
| 5,449,921 A | 9/1995 | Baba | 5,679,310 A | 10/1997 | Manns |
| 5,457,527 A | 10/1995 | Manns et al. | 5,683,983 A | 11/1997 | Barrett et al. |
| 5,459,300 A | 10/1995 | Kasman | 5,705,045 A | 1/1998 | Park et al. |
| 5,480,804 A | 1/1996 | Niwa et al. | 5,707,813 A | 1/1998 | Dandliker et al. |
| 5,485,530 A | 1/1996 | Lakowicz et al. | 5,723,304 A | 3/1998 | Abuknesha |
| 5,487,872 A | 1/1996 | Hafeman et al. | 5,736,410 A | 4/1998 | Zarling et al. |
| 5,491,343 A | 2/1996 | Brooker | 5,738,825 A | 4/1998 | Rudigier et al. |
| 5,496,697 A | 3/1996 | Parce et al. | 5,741,714 A | 4/1998 | Liberti |
| 5,497,670 A | 3/1996 | Carl | 5,744,320 A | 4/1998 | Sherf et al. |
| 5,500,188 A | 3/1996 | Hafeman et al. | 5,746,974 A | 5/1998 | Massey et al. |
| 5,501,956 A | 3/1996 | Wada et al. | 5,750,410 A | 5/1998 | Dou et al. |
| 5,504,337 A | 4/1996 | Lakowicz et al. | 5,756,050 A | 5/1998 | Ershow et al. |
| 5,512,492 A | 4/1996 | Herron et al. | 5,756,292 A | 5/1998 | Royer |
| 5,516,490 A | 5/1996 | Sanadi | 5,756,304 A | 5/1998 | Jovanovich |
| 5,518,900 A | 5/1996 | Nikiforov et al. | 5,759,494 A | 6/1998 | Szlosek |
| 5,523,573 A | 6/1996 | Hänninen et al. | 5,760,188 A | 6/1998 | Beaudet et al. |
| 5,525,479 A | 6/1996 | Anthony et al. | 5,760,900 A | 6/1998 | Ito et al. |
| 5,527,684 A | 6/1996 | Mabile et al. | 5,763,158 A | 6/1998 | Bohannon |
| 5,527,688 A | 6/1996 | Mallia | 5,766,875 A | 6/1998 | Hafeman et al. |
| 5,528,046 A | 6/1996 | Ishikawa | 5,770,151 A | 6/1998 | Roach et al. |
| 5,529,752 A | 6/1996 | Pontis et al. | 5,770,455 A | 6/1998 | Cargill et al. |
| 5,531,697 A | 7/1996 | Olsen et al. | 5,772,966 A | 6/1998 | Maracas et al. |
| 5,531,698 A | 7/1996 | Olsen | 5,772,967 A | 6/1998 | Wannlund et al. |
| 5,536,662 A | 7/1996 | Humphries et al. | 5,773,257 A | 6/1998 | Nielson et al. |
| 5,537,343 A | 7/1996 | Kikinis et al. | 5,780,857 A | 7/1998 | Harju et al. |
| 5,540,889 A | 7/1996 | Gordon et al. | 5,786,139 A | 7/1998 | Burke et al. |
| 5,541,113 A | 7/1996 | Siddigi et al. | 5,798,035 A | 8/1998 | Kirk et al. |
| 5,542,012 A | 7/1996 | Fernandes et al. | 5,798,083 A | 8/1998 | Massey et al. |
| 5,557,398 A | 9/1996 | Wechsler et al. | 5,798,085 A | 8/1998 | Seaton et al. |
| 5,560,811 A | 10/1996 | Briggs et al. | 5,800,778 A | 9/1998 | Chen et al. |
| 5,561,051 A | 10/1996 | Silverman | 5,800,989 A | 9/1998 | Linn et al. |
| 5,561,068 A | 10/1996 | Rounbehler et al. | 5,801,055 A | 9/1998 | Henderson |
| 5,567,302 A | 10/1996 | Song et al. | 5,811,256 A | 9/1998 | Bryant |
| 5,571,684 A | 11/1996 | Lawrence et al. | 5,820,849 A | 10/1998 | Schmitt-Willich et al. |
| 5,589,136 A | 12/1996 | Northrup et al. | 5,824,557 A | 10/1998 | Burke et al. |
| 5,589,350 A | 12/1996 | Bochner | 5,824,772 A | 10/1998 | Vincent et al. |
| 5,589,351 A | 12/1996 | Harootunian | 5,825,617 A | 10/1998 | Kochis et al. |
| 5,592,289 A | 1/1997 | Norris | 5,827,653 A | 10/1998 | Sammes et al. |
| 5,593,867 A | 1/1997 | Walker et al. | 5,840,256 A | 11/1998 | Demers et al. |
| 5,595,710 A | 1/1997 | Van Dusen et al. | 5,842,582 A | 12/1998 | DeStefano, Jr. |
| 5,599,500 A | 2/1997 | Jones | 5,846,710 A | 12/1998 | Bajaj |
| 5,599,681 A | 2/1997 | Epstein et al. | 5,846,722 A | 12/1998 | Kauvar et al. |
| 5,604,130 A | 2/1997 | Warner et al. | 5,849,547 A | 12/1998 | Cleuziat et al. |
| 5,610,075 A | 3/1997 | Stahl-Rees | 5,853,894 A | 12/1998 | Brown |
| 5,610,287 A | 3/1997 | Nikiforov et al. | 5,858,309 A | 1/1999 | Mathus et al. |
| 5,610,683 A | 3/1997 | Takahashi | 5,858,671 A | 1/1999 | Jones |

| | | |
|---|---|---|
| 5,861,239 A | 1/1999 | Kleyn et al. |
| 5,872,010 A | 2/1999 | Karger et al. |
| 5,873,394 A | 2/1999 | Meltzer |
| 5,874,214 A | 2/1999 | Nova et al. |
| 5,879,632 A | 3/1999 | Demers |
| 5,880,096 A | 3/1999 | Barrett et al. |
| 5,880,296 A | 3/1999 | Imbert et al. |
| 5,882,597 A | 3/1999 | Astle |
| 5,882,930 A | 3/1999 | Baier |
| 5,885,779 A | 3/1999 | Sadowski et al. |
| 5,888,454 A | 3/1999 | Leistner et al. |
| 5,888,728 A | 3/1999 | Olson et al. |
| 5,888,819 A | 3/1999 | Goelet et al. |
| 5,891,621 A | 4/1999 | Chabin et al. |
| 5,891,674 A | 4/1999 | Hillman et al. |
| 5,891,696 A | 4/1999 | Shaw et al. |
| 5,905,571 A | 5/1999 | Butler et al. |
| 5,910,287 A | 6/1999 | Cassin et al. |
| 5,910,574 A | 6/1999 | Presta et al. |
| 5,912,137 A | 6/1999 | Tsien et al. |
| 5,914,230 A | 6/1999 | Liu et al. |
| 5,933,232 A | 8/1999 | Atzler et al. |
| 5,945,283 A | 8/1999 | Kwok et al. |
| 5,948,620 A | 9/1999 | Hurd et al. |
| 5,958,694 A | 9/1999 | Nikiforov |
| 5,959,738 A | 9/1999 | Hafeman et al. |
| 5,961,926 A | 10/1999 | Kolb et al. |
| 5,962,243 A | 10/1999 | Brown et al. |
| 5,981,180 A | 11/1999 | Chandler et al. |
| 5,981,185 A | 11/1999 | Matson et al. |
| 5,989,835 A | 11/1999 | Dunlay et al. |
| 5,993,746 A | 11/1999 | Priha et al. |
| 6,004,744 A | 12/1999 | Goelet et al. |
| 6,013,431 A | 1/2000 | Söderlund et al. |
| 6,013,457 A | 1/2000 | Neuenhofer et al. |
| 6,018,388 A | 1/2000 | Nawracala et al. |
| 6,020,591 A | 2/2000 | Harter et al. |
| 6,025,129 A | 2/2000 | Nova et al. |
| 6,025,985 A | 2/2000 | Leytes et al. |
| 6,027,695 A | 2/2000 | Oldenburg et al. |
| 6,033,100 A | 3/2000 | Marquiss et al. |
| 6,033,605 A | 3/2000 | Szlosek |
| 6,037,136 A | 3/2000 | Beach et al. |
| 6,045,755 A | 4/2000 | Lebl et al. |
| 6,045,996 A | 4/2000 | Cronin et al. |
| 6,054,557 A | 4/2000 | Faure et al. |
| 6,071,748 A * | 6/2000 | Modlin et al. ............... 436/174 |
| 6,100,652 A | 8/2000 | Konopka |
| 6,102,885 A | 8/2000 | Bass |
| 6,113,559 A | 9/2000 | Klopotek |
| 6,121,048 A | 9/2000 | Zaffaroni et al. |
| 6,207,031 B1 | 3/2001 | Adourian et al. |
| 6,232,608 B1 | 5/2001 | Giebeler et al. |
| 6,236,456 B1 | 5/2001 | Giebeler et al. |
| 6,313,471 B1 | 11/2001 | Giebeler et al. |
| 6,316,774 B1 | 11/2001 | Giebeler et al. |

FOREIGN PATENT DOCUMENTS

| | | |
|---|---|---|
| EP | 0 204 109 A2 | 12/1986 |
| EP | 0 222 341 A1 | 5/1987 |
| EP | 0 266 881 A2 | 5/1988 |
| EP | 0 317 074 | 1/1991 |
| EP | 0 259 386 B1 | 4/1991 |
| EP | 0 542 422 A1 | 5/1993 |
| EP | 0 578 067 A1 | 1/1994 |
| EP | 0 317 074 B1 | 12/1996 |
| EP | 0 382 433 B1 | 11/1997 |
| EP | 0 810 438 | 12/1997 |
| EP | 0 648 280 B1 | 5/1999 |
| EP | 0 977 037 A1 | 2/2000 |
| EP | 0 993 916 A2 | 4/2000 |
| EP | 0 995 555 A1 | 4/2000 |
| EP | 1 003 020 A1 | 5/2000 |
| EP | 1 003 039 A1 | 5/2000 |
| GB | 2 215 838 A | 9/1989 |
| GB | 2 228 081 A | 8/1990 |
| JP | 58-102161 | 6/1983 |
| JP | 8-128961 | 5/1996 |
| JP | 9-236607 | 9/1997 |
| JP | 10-2161 | 1/1998 |
| JP | 11-89559 | 4/1999 |
| JP | 11-121577 | 4/1999 |
| WO | WO 91/13075 | 9/1991 |
| WO | WO 92/11039 | 7/1992 |
| WO | WO 92/15712 | 9/1992 |
| WO | WO 93/19206 | 9/1993 |
| WO | WO 94/29024 | 12/1994 |
| WO | WO 95/12607 | 5/1995 |
| WO | WO 95/21271 | 8/1995 |
| WO | WO 97/22719 | 6/1997 |
| WO | WO 97/35033 | 9/1997 |
| WO | WO 97/44134 | 11/1997 |
| WO | WO 97/45739 | 12/1997 |
| WO | WO 98/05962 | 2/1998 |
| WO | WO 98/18956 | 5/1998 |
| WO | WO 98/46981 | 10/1998 |
| WO | WO 98/59066 | 12/1998 |
| WO | WO 99/04228 | 1/1999 |
| WO | WO 99/08233 | 2/1999 |
| WO | WO 99/11774 | 3/1999 |
| WO | WO 99/23466 | 5/1999 |
| WO | WO 99/29894 | 6/1999 |
| WO | WO 99/31431 | 6/1999 |
| WO | WO 99/60383 | 11/1999 |
| WO | WO 00/00819 | 1/2000 |
| WO | WO 00/11220 | 3/2000 |
| WO | WO 00/47693 | 8/2000 |
| WO | WO 00/48990 | 8/2000 |
| WO | WO 00/48991 | 8/2000 |
| WO | WO 00/50877 | 8/2000 |
| WO | WO 00/55372 | 9/2000 |
| WO | WO 00/66269 | 11/2000 |

OTHER PUBLICATIONS

*Fundamentals of Light Microscopy*, Spencer, Cambridge University Press, 1982.

Joseph R. Lakowicz, Principles of Fluorescence Spectroscopy, First Edition, Sep. 1983.

*A System for Rapid DNA Sequencing with Fluorescent Chain–Terminating Dideoxynucleotides*, Prober et al., *Science*, pp. 336–341, Oct. 16, 1987.

*Time–Resolved Fluorescence of Lanthanide Probes and Applications in Biotechnology*, Soini et al., *CRC Critical Reviews in Analytical Chemistry*, vol. 18, No. 2, 1987.

*Solid Phase DNA Sequencing Using the Biotin–Avidin System*, Stahl et al., *Nucleic Acids Res.*, vol. 16, No. 7, pp. 3025–3038, Apr. 11, 1988 (abstract only).

*Synthetic Peptide Analogues Differentially After the Binding Affinities of Cyclic Nucleotide Dependent Protein Kinases for Nucleotide Substrates*, Bhatnagar et al., *Biochemistry* vol. 27, No. 6, pp. 1988–1994, 1988.

Stratagene 1988 Catalog excerpt, 1988.

*Direct Solid Phase Sequencing of Genomic and Plasmid DNA Using Magnetic Beads as Solid Support*, Hultman et al., *Nucleic Acids Res.*, vol. 17, No. 13, pp. 4937–4946, Jul. 11, 1989 (abstract only).

*Basic Fluorescence Microscopy*, Taylor et al., *Methods in Cell Biology*, vol. 29, pp. 207–237, 1989.

*Quantitative Fluorescence Microscopy Using Photomultiplier Tubes and Imaging Detectors*, Wampler et al., *Methods in Cell Biology*, vol. 29, pp. 239–267, 1989.
*Three–Dimensional Confocal Fluorescence Microscopy*, Brakenhoff et al., *Methods in Cell Biology*, vol. 30, pp. 379–389, 1989.
*RNA Sequencing Using Fluorescent–Labeled Dideoxynucleotides and Automated Fluorescence Detection*, Bauer, *Nucleic Acids Res.*, vol. 18, No. 4, pp. 879–884, Feb. 25, 1990 (abstract only).
Kary B. Mullis, "The Unusual Origin of the Polymerase Chain Reaction," *Scientific American*, pp. 56–65, Apr. 1990.
*A Primer–Guided Nucleotide Incorporation Assay in the Genotyping of Apolipoprotein E*, Syvanen et al., *Genomics*, vol. 8, No. 4, pp. 684–692, Dec. 1990 (abstract only).
*Trapped–Oligonucleotide Nucleotide Incorporation (TONI) Assay, A Simple Method for Screening Point Mutations*, Prezant et al., *Hum. Mutat.*, vol. 1, No. 2, pp. 159–164, 1992 (abstract only).
*A Brief Survey of Methods for Preparing Protein Conjugates with Dyes, Haptens, and Cross–Linking Reagents*, Brinkley, *Bioconjugate Chemistry*, vol. 3, No. 1, pp. 59–70, Jan./Feb. 1992.
*Laser Scanning Confocal Microscopy of Living Cells*, Lemasters et al., *Optical Microscopy: Emerging Methods and Applications*, pp. 339–345, 1993.
*Luminescent Lanthanide Complexes as Photochemical Supramolecular Devices*, Sabbatini et al., *Coordination Chemistry Reviews*, vol. 123, pp. 201–228, 1993.
*Time–Resolved Fluorescence Lifetime Imaging*, vandeVen et al., *Optical Microscopy: Emerging Methods and Applications*, pp. 373–389, 1993.
*Time–Resolved Fluorescence of a new Europium Chelate Complex: Demonstration of Highly Sensitive Detection of Protein and DNA Samples*, Saha et al., *J. Am. Chem. Soc.*, vol. 115, No. 23, pp. 11032–11033, 1993.
*Electrochemiluminescence: A New Diagnostic and Research Tool*, Yang et al., *Bio/Technology*, vol. 12, pp. 193–194, Feb. 1994.
*Processing of cDNA and Genomic Kilobase–Size Clones for Massive Screening, Mapping and Sequencing by Hybridization*, Drmanac et al., *BioTechniques*, vol. 17, No. 2, pp. 328–336, 1994.
*High Throughput Screening Using Dynamic Fluorescence*, Swift et al., *SPIE*, vol. 2388, pp. 182–189, Feb. 6–8, 1995.
*Fluorescence–Based DNA Minisequence Analysis for Detection of Known Single–Base Changes in Genomic DNA*, Kobayashi et al., *Mol. Cell Probes*, vol. 9, No. 3, pp. 175–182, Jun. 1995 (abstract only).
*Hybridization of Fluorescein–Labeled DNA Oligomers Detected by Fluorescence Anisotropy with Protein Binding Enhancement*, Kumke et al., *Anal. Chem.*, vol. 67, No. 21, Nov. 1, 1995.
*Fluorescence Energy Transfer Immunoassay Based on a Long–Lifetime Luminescent Metal–Ligand Complex*, Young et al., *Analytical Biochemistry*, vol. 232, pp. 24–30, 1995.
Jeffrey Sipior et al., "A Lifetime–Based Optical $CO_2$ Gas Sensor with Blue or Red Excitation and Stokes or Anti–Stokes Detection," *Analytical Biochemistry*, 227, 309–318 (1995).
*Time Resolved Detection of Lanthanide Luminescence for Ultrasensitive Bioanalytical Assays*, Dickson et al., *J. Photochem. Photobiol. B. Biol.*, vol. 27, pp. 3–19, 1995.

PCR Reaction Vessels brochure, Corning Costar Corporation, Sep. 1996.
Jonathan Burke, "Gene Genie," *The Red Herring*, internet pages 1–7, Dec. 1996.
Chemical Abstracts No. 124:160,011; abstract for Lindstroem et al., Electron transport properties in dye–sensitized nanocrystalline/nanostructured titanium dioxide films: J. Phys. Chem. vol. 100 (8), pp. 3084–3088, 1996.
*Comparative Study of Fluorescent Ternary Terbium Complexes. Application in Enzyme Amplified Fluorimetric Immunoassay for α–fetoprotein*, Veiopoulou et al., *Analytics Chimica Acta*, vol. 335, pp. 177–184, 1996.
Handbook of Fluorescent Probes and Research Chemicals, Haugland, Sixth Edition, 1996.
*Multiplex, Fluorescent, Solid–Phase Minisequencing for Efficient Screening of DNA Sequence Variation*, Pastinen et al., *Clinical Chemistry*, vol. 42, No. 9, pp. 1391–1397, 1996.
David Stipp, "Gene Chip Breakthrough," *Fortune*, internet pp. 1–12, Mar. 31, 1997.
Miniprep 50 Mini Sample Processor brochure, Tecan AG, Jun. 1997.
Advanced Microplate Washers brochure, Tecan AG, Jul. 1997.
The Society for Biomolecular Screening, $3^{rd}$ Annual Conference and Exhibition, p. 59, Sep. 9, 22–25.
Genesis Series Robotic Sample Processors brochure, Tecan AG, Oct. 1997.
Genesis Robotic Microplate Processor brochure, Tecan AG, Nov. 1997.
Miniprep 75 Robotic Sample Processor brochure, Tecan AG, Nov. 1997.
Electrochemiluminescence: A Technology Review internet pages, IGEN, printed Dec. 16, 1997.
*A Homogeneous Method for Genotyping with Fluorescence Polarization*, Gibson et al., *Clinical Chemistry*, vol. 43, No. 8, pp. 1336–1341, 1997.
A Measure of Brilliance, TR717 Microplate Luminometer brochure, Tropix, Inc., 1997.
Chemical Abstracts No. 126:72,240; abstract for Hermann et al., "Structure of Nanocrystalline TiO2 Powders and Precursor to Their Highly Efficient Photosensitizer", Chem. Mater. vol. 9 (2), pp. 430–439, 1997.
*Development of Luminescent Lanthanide Chelate Labels for Diagnostic Assays*, Hemmila et al., *Journal of Alloys and Compounds*, Vo. 249, pp. 158–162, 1997.
*Towards Materials with Planned Properties: Dinuclear f–f Helicates and d–f Non–Covalent Podates Based on Benzimidazole–Pyridine Binding Units*, Bunzli et al., *Journal of Alloys and Compounds*, vol. 249, pp. 14–24, 1997.
*Water–Soluble Neutral calyx[4]arene–Lanthanide Complexes: Synthesis and Luminescence Properties*, Steemers et al., *J. Org. Chem.*, vol. 62, pp. 4229–4235, 1997.
*Template–Directed Dye–Terminator Incorporation (TDI) Assay: A Homogeneous DNA Diagnostic Method Based on Fluorescence Resonance Energy Transfer*, Chen et al., *Nucleic Acids Research*, vol. 25, No. 2, pp. 347–353, 1997.
*Minisequencing: A Specific Tool for DNA Analysis and Diagnostics on Oligonucleotide Arrays*, Pastinen et al., *Genome Research*, vol. 7, pp. 606–614, 1997.
*Fluorescence Polarization Applications Guide*, PanVera Corporation, pp. 6–1 through 6–4, Jan. 1998 Edition.
Advanced Microplate Detection Systems brochure, Tecan AG, Feb. 1998.
The SPECTRA Family brochure, Tecan AG, Feb. 1998.

GeneChip Probe Array Synthesis, Affymetrix, internet pp. 1–2, Mar. 17, 1998.
Assist Plate Handling Device brochure, Labysystems, May 1998.
Tecan Spectrafluor—A Step Forward in Microplate Fluorometry, internet description pages, printed from internet on Jun. 17, 1998.
Wallac Time–Resolved Fluorometry—The Key to Improved Assay Sensitivity, internet description pages, Jul. 7, 1998.
Wallac 1234 DELFIA Fluorometer, internet description page, Jul. 7, 1998.
Wallac 1420 VICTOR Multilabel Counter, internet description pages, Jul. 7, 1998.
Wallac 1420 VICTOR$^2$ Multilabel Counter, internet description pages, Jul. 7, 1998.
Wallac 1442 ARTHUR Multi–Wavelength Fluoroimager, internet description page, Jul. 7, 1998.
Wallac Labelling Reagents for Time–Resolved Fluorometry, internet description page, Jul. 7, 1998.
Genesis Assay Workstation brochure, Tecan AG, Jul. 1998.
Genesis Logistics Workstation brochure, Tecan AG, Jul. 1998.
*Homogeneous Time–Resolved IL–2–IL–2Rα Assay Using Fluorescence Resonance Energy Transfer*, Stenroos et al., *Cytokine*, vol. 10, No. 7, pp. 495–499, Jul. 1998.
*Mutation Detection and Single–Molecule Counting Using Isothermal Rolling–Circle Amplification*, Lizardi et al., *Nature Genetics*, vol. 19, No. 3, pp. 225–232, Jul. 1998.
Polarion brochure, Tecan AG, Aug. 1998.
*Illuminating the SNP Genomic Code*, Czarnik, *Modern Drug Discovery*, pp. 49–55, Nov./Dec. 1998.
A Catalog of Reagents, Microplates and Accessories of Life Science Research, Book 2, Packard BioScience Company, Dec. 1998.
*Fixed Polarizer Ellipsometry for Simple and Sensitive Detection of Thin Films Generated by Specific Molecular Interactions: Applications in Immunoassays and DNA Sequence Detection*, Ostroff et al., *Clinical Chemistry*, vol. 44, No. 9, pp. 2031–2035, 1998.
CytoFluor Fluorescence Multi–Well Plate Reader brochure, PerSeptive Biosystems, 1998.
Setting the Standard, the HTS Compatibility Program brochure, Corning Incorporated, 1998.
Microplate Instrumentation Catalogue 1998, Labsystems, 1998.
Luc–Screen brochure, Tropix, Inc., 1998.
Xpress–Screen brochure, Tropix, Inc., 1998.
Nunc Products 1998–1999 Catalog, Nalge Nunc International, 1998.
*The Human Genome Project: Challenges and Opportunities*, Washington University in St. Louis, Mar. 5, 1999.
Advanced Microplate Washers, Tecan AG, Apr. 1999.
*Everything's Great When it Sits on a Chip*, Sinclair, *The Scientist*, vol. 13, No. 11, May 24, 1999.
*Assay Miniturization for High–Throughput Screening*, Panfili, Sep. 1999.
Snapshot ddNTP Primer Extension Kit product bulletin, PE Biosystems, Oct. 1999.
PanVera Postings, Issue 5, PanVera Corporation, Oct. 1999.
CyBi™–Disk brochure, CyBio AG, Oct. 1999.
TWISTER™, Tecan's Automated Microplate Handler brochure, Tecan AG, Nov. 1999.
Magellan, Instrument Control and Data Analysis Software brochure, Tecan AG, Nov. 1999.
Handout Information, Tips and Tricks . . . Automated Liquid–Handling in the Microplate Format, CyBio AG, Nov. 1999.
*Kinase Assay Based on Thiophosphorylation and Biotinylation*, Jeong et al., *BioTechniques*, vol. 27, pp. 1232–1238, Dec. 1999.
Absorbance Readers brochure, Tecan AG, Dec. 1999.
ULTRA—The Solution for HTS and Assay Development brochure, Tecan Austria GmbH, Dec. 1999.
*Fluorescence Polarization in Homogenous Nucleic Acid Analysis*, Chen, et al., *Genome Research*, vol. 9, pp. 492–498, 1999.
Joseph R. Lakowicz, Principles of Fluorescence Spectroscopy, Second Edition, 1999.
*Terbium and Rhodamine as Labels in a Homogeneous Time–Resolved Fluorometric Energy Transfer Assay of the β Subunit of Human Chorionic Gonadotropin in Serum*, Blomberg et al., *Clinical Chemistry*, vol. 45, No. 6, pp. 855–861 1999.
*Mono(di)nuclear Europium(III) Complexes of Macrobi(tri) cyclic Cryptands Derived from Diazatetralactams as Luminophores in Aqueous Solution*, Galaup et al., *Helvetica Chimica Acta*, vol. 82, pp. 543–560, 1999.
*Synthesis, Time–Resolved Luminescence, NMR Spectroscopy, Circular Dichroism and Circularly Polarised Luminescence Studies of Enantiopure Macrocyclic Lanthanide Tetraamide Complexes*, Dickins et al., *Chem. Eur. J.*, vol. 5, No. 3, 1999.
*New Fluorescent Labels for Polarization Assays and Lifetime Imaging*, Analytix, Feb. 2000.
CyBi™–PlateSafe brochure, CyBio Ag, May 2000.
CyBi™–Lumax 1,536 brochure, CyBio AG, May 2000.
CyBi™–Replicator brochure, CyBio AG, May 2000.
CyBi™–Well 2000 brochure, CyBio Ag, May 2000.
Packard BioScience Company Introduces the Fusion™ Universal Microplate Analyzer press release, Packard BioScience Company, Jun. 29, 2000.
SPECTRAmax® GEMINI XS brochure, Molecular Devices Corp., Jun. 2000.
SPECTRAmax® PLUS$^{384}$ brochure, Molecular Devices Corp., Jun. 2000.
*Tris(2,2'bipyridyl)ruthenium(II)* internet pages, OMLC, printed Jul. 3, 2000.
CoreHTS, Estrogen Receptor –α & –β Competitor Assays brochure, PanVera Corporation, Jul. 2000.
Protein Tyrosine Kinase Assay Kits flyer, PanVera Corporation, Jul. 2000.
Protein Kinase C Assay Kits flyer, PanVera Corporation, Jul. 2000.
Labcyte: Research and Clinical Instruments for Life Sciences brochure, Arlena Research LLC, Aug. 1, 2000.
Fusion™, Universal Microplate Analyzer, Packard BioScience Company, Aug. 2000.
ProxiPlate internet description page, Packard BioScience Company, printed Sep. 17, 2000.
Approaching the 2 µL to 10 µL Range: 384 Well Small Volume vs. 1536 Well Plates poster, Greiner Labortechnik, Sep. 2000.
*Lifetime– and Color–Tailored Fluorophores in the Micro– to Millisecond Time Regime*, Chen et al., *J. Am. Chem. Soc.*, vol. 122, pp. 657–660, 2000.
*Spectroscopic Properties and Design of Highly Luminescent Lanthanide Coordination Complexes*, de Sa et al., *Coordinate Chemistry Reviews*, vol. 196, pp. 165–195, 2000.

*Luminescence and Structure of Europium Compounds*, Vicentini et al., *Coordination Chemistry Reviews*, vol. 196, pp. 353–382, 2000.

CyBi™–Screen–Machine: One System–Many Solutions brochure, CyBio AG, 2000.

*Development of High Throughput Screening Assays Using Fluorescence Polarization: Nuclear Receptor–Ligand–Binding and Kinase/Phosphatase Assays*, Parker et al., *Journal of Biomolecular Screening*, vol. 5, No. 2, 2000.

Reacti–Bind™ Metal Chelate High Binding Capacity Plates flyer, Pierce Chemical Company, 2000.

Reacti–Bind™ Metal Chelate Plates flyer, Pierce Chemical Company, 2000.

Reacti–Bind™ NeutrAvidin™ High Binding Capacity (HBC) Coated Plates flyer, Pierce Chemical Company, 2000.

Reacti–Bind™ NeutrAvidin™ and Streptavidin Coated Plates flyer, Pierce Chemical Company, 2000.

Nunc Life Science Discovery Products catalog, Nalge Nunc International Corporation, 2000.

FLUOstar Galaxy brochure, BMG Labtechnologies GmbH, undated.

Reacti–Bind™ Streptavidin High Binding Capacity (HBC) Coated Plates flyer, Pierce Chemical Company, 2000.

Falcon HTS FluoroBlok Inserts description page, Becton Dickinson, undated.

FLIPR 384: Essential Technology for Drug Discovery brochure, Molecular Devices Corp., undated.

Acumen Explorer brochure, Acumen, undated LUMIstar Galaxy brochure, BMG Labtechnologies GmbH, undated.

NEPHELOstar brochure, BMG Labtechnologies GmbH, undated.

POLARstar Galaxy brochure, BMG Labtechnologies GmbH, undated.

POLARstar Galaxy flyer, BMG Labtechnologies GmbH, undated.

REMP 384 Tube Technology flyer, REMP (USA) Inc., undated.

REMP 96–Technology flyer, REMP (USA) Inc., undated.

High Throughput Screening brochure, Greiner America, Inc., undated.

Protein Kinase C (PKC) tech specs, PanVera Corporation, undated.

PW 384 brochure, PanVera Corporation, undated.

\* cited by examiner

SECOND ELLIPSE IS OPTIONAL, CAN
ALSO WORK WITH 1 NON-DICHROIC

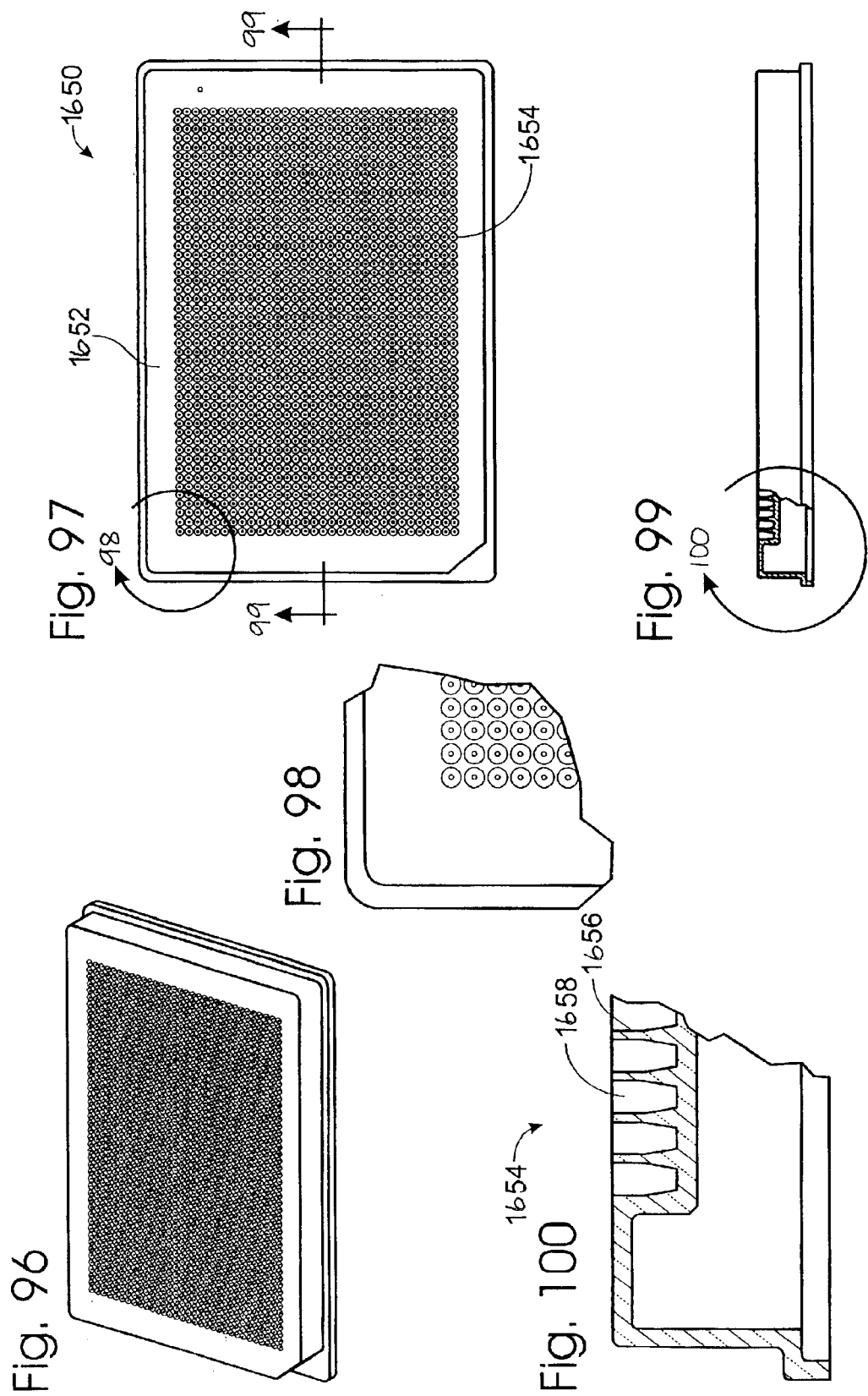

SAMPLE ANALYSIS SYSTEMS

CROSS-REFERENCES

This application is a continuation-in-part of the following U.S. patent applications, which are incorporated herein by reference in their entirety for all purposes: Ser. No. 09/144,578, filed Aug. 31, 1998 now U.S. Pat. No. 6,499,366; Ser. No. 09/302,158, filed Apr. 29, 1999 now U.S. Pat. No. 6,576,476; Ser. No. 09/349,733, filed Jul. 8, 1999, now abandoned; Ser. No. 09/478,819, filed Jan. 5, 2000, now U.S. Pat. No. 6,488,892; Ser. No. 09/629,599, filed Jul. 31, 2000, now U.S. Pat. No. 6,469,311; Ser. No. 09/710,061, filed Nov. 10, 2000; Ser. No. 09/733,370, filed Dec. 8, 2000, now abandoned; Ser. No. 09/759,711, filed Jan. 12, 2001; Ser. No. 09/765,869, filed Jan. 19, 2001, now U.S. Pat. No. 6,466,316; Ser. No. 09/767,434, filed Jan. 22, 2001, now U.S. Pat. No. 6,486,947; Ser. No. 09/778,224, filed Feb. 6, 2001; Ser. No. 09/836,575, filed Apr. 16, 2001, now abandoned; Ser. No. 10/004,647, filed Dec. 3, 2001 U.S. Pat. No. 6,498,335; Ser. No. 10/012,255, filed Nov. 12, 2001; and Ser. No. 10/041,532, filed Jan. 7, 2002, now abandoned.

U.S. patent application Ser. No. 09/144,578, in turn, claims priority from various U.S., PCT, and provisional patent applications. The '578 application is a continuation of the following patent applications: U.S. patent application Ser. No. 09/062,472, filed Apr. 17, 1998, now U.S. Pat. No. 6,071,748; PCT patent application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; and U.S. patent application Ser. No. 09/118,341, filed Jul. 16, 1998, now U.S. Pat. No. 6,025,985. These parent applications, in turn, claim priority from additional applications, as identified therein. The '578 application also (directly and/or through its parent applications) is based upon and claims benefit under 35 U.S.C. §119(e) of the following U.S. provisional patent applications, each of which is now expired: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

U.S. patent application Ser. No. 09/302,158, in turn, is a divisional continuation application of U.S. patent application Ser. No. 09/146,081, filed Sep. 2, 1998, now U.S. Pat. No. 6,187,267. The '081 application, in turn, is a continuation of the following patent applications: U.S. patent application Ser. No. 09/062,472, filed Apr. 17, 1998, now U.S. Pat. No. 6,071,748; PCT Patent Application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; U.S. patent application Ser. No. 09/118,341, filed Jul. 16, 1998, now U.S. Pat. No. 6,025,985; U.S. patent application Ser. No. 09/144,575, filed Aug. 31, 1998, now U.S. Pat. No. 6,159,425; and U.S. patent application Ser. No. 09/144,578, filed Aug. 31, 1998. These parent applications, in turn, claim priority from additional applications, as identified therein. The '081 application, in turn, also (directly and/or through its parent applications) is based upon and claims benefit under 35 U.S.C. §119(e) of the following U.S. provisional patent applications, each of which is now expired: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

U.S. patent application Ser. No. 09/349,733, in turn, claims priority from various U.S., PCT, and provisional patent applications. The '733 application is a continuation of the following patent applications: U.S. patent application Ser. No. 09/062,472, filed Apr. 17, 1998, now U.S. Pat. No. 6,071,748; U.S. patent application Ser. No. 09/156,318, filed Sep. 18, 1998, now U.S. Pat. No. 6,258,326; U.S. patent application Ser. No. 09/160,533, filed Sep. 24, 1998, now U.S. Pat. No. 6,097,025; PCT Patent Application Ser. No. PCT/US98/23095, filed Oct. 30, 1998, now abandoned; PCT Patent Application Ser. No. PCT/US99/01656, filed Jan. 25, 1999, now abandoned; PCT Patent Application Ser. No. PCT/US99/03678, filed Feb. 19, 1999, now abandoned; and PCT Patent Application Ser. No. PCT/US99/08410, filed Apr. 16, 1999, now abandoned. These parent applications, in turn, claim priority from additional applications, as identified therein. The '733 application, in turn, also (directly and/or through its parent applications) is based upon and claims benefit under 35 U.S.C. §119(e) of the following U.S. provisional patent applications, each of which is now expired: Ser. No. 60/092,203, filed Jul. 9, 1998; Ser. No. 60/094,275, filed Jul. 27, 1998; Ser. No. 60/094,276, filed Jul. 27, 1998; Ser. No. 60/094,306, filed Jul. 27, 1998; Ser. No. 60/100,817, filed Sep. 18, 1998; Ser. No. 60/100,951, filed Sep. 18, 1998; Ser. No. 60/104,964, filed Oct. 20, 1998; Ser. No. 60/114,209, filed Dec. 29, 1998; Ser. No. 60/116,113, filed Jan. 15, 1999; Ser. No. 60/117,278, filed Jan. 26, 1999; Ser. No. 60/119,884, filed Feb. 12, 1999; Ser. No. 60/121,229, filed Feb. 23, 1999; Ser. No. 60/124,686, filed Mar. 16, 1999; Ser. No. 60/125,346, filed Mar. 19, 1999; Ser. No. 60/126,661, filed Mar. 29, 1999; Ser. No. 60/130,149, filed Apr. 20, 1999; Ser. No. 60/132,262, filed May 3, 1999; Ser. No. 60/132,263, filed May 3, 1999; Ser. No. 60/135,284, filed May 21, 1999; Ser. No. 60/136,566, filed May 28, 1999; Ser. No. 60/138,311, filed Jun. 9, 1999; Ser. No. 60/138,438, filed Jun. 10, 1999; Ser. No. 60/138,737, filed Jun. 11, 1999; Ser. No. 60/138,893, filed Jun. 11, 1999; and Ser. No. 60/142,721, filed Jul. 7, 1999.

U.S. patent application Ser. No. 09/478,819, in turn, is a continuation of PCT Patent Application Ser. No. PCT/US99/08410, filed Apr. 16, 1999, now abandoned. The '08410 application, in turn, is a continuation of the following U.S. patent applications: Ser. No. 09/062,472, filed Apr. 17, 1998, now U.S. Pat. No. 6,071,748; Ser. No. 09/156,318, filed Sep. 18, 1998, now U.S. Pat. No. 6,258,326; and Ser. No. 09/160,533, filed Sep. 24, 1998, now U.S. Pat. No. 6,097,025. These parent applications, in turn, claim priority from additional applications, as identified therein. The '08410 application, in turn, also (directly and/or through its parent applications) is based upon and claims benefit under 35 U.S.C. §119(e) of the following U.S. provisional patent applications, each of which is now expired: Ser. No. 60/085, 500, filed May 14, 1998; Ser. No. 60/089,848, filed Jun. 19, 1998; Ser. No. 60/114,209, filed Dec. 29, 1998; and Ser. No. 60/119,829, filed Feb. 12, 1999.

U.S. patent application Ser. No. 09/629,599, in turn, is a continuation of U.S. patent application Ser. No. 09/160,533, filed Sep. 24, 1998, now U.S. Pat. No. 6,097,025. The '533 application, in turn, is a continuation of the following patent applications: U.S. patent application Ser. No. 09/062,472, filed Apr. 17, 1998, now U.S. Pat. No. 6,071,748; PCT Patent Application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; U.S. patent application Ser. No. 09/118,341, filed Jul. 16, 1998, now U.S. Pat. No. 6,025,985; U.S. patent application Ser. No. 09/144,575, filed Aug. 31, 1998, now U.S. Pat. No. 6,159,425; U.S. patent application Ser. No. 09/144,578, filed Aug. 31, 1998; U.S. patent application Ser. No. 09/146,081, filed Sep. 2, 1998, now U.S. Pat. No. 6,187,267; U.S. patent application Ser. No. 09/156,318, filed Sep. 18, 1998, now U.S. Pat. No. 6,258,326; and U.S. patent application Ser. No. 09/478,819, filed Jan. 5, 2000, now U.S. Pat. No. 6,488,892. These parent applications, in turn, claim priority from additional applications, as identified therein. The '533 application, in turn, also (directly and/or through its parent applications) is based upon and claims benefit under 35 U.S.C. §119(e) of the following U.S. provisional patent applications, each of which is now expired: Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; Ser. No. 60/094,306, filed Jul. 27, 1998; Ser. No. 60/100,817, filed Sep. 18, 1998; and Ser. No.60/100,951, filed Sep. 18, 1998.

U.S. patent application Ser. No. 09/710,061, in turn, is based upon and claims benefit under 35 U.S.C. §119(e) of U.S. Provisional Patent Application Ser. No. 60/164,633, filed Nov. 10, 1999, now expired.

U.S. patent application Ser. No. 09/733,370, in turn, is a continuation of U.S. patent application Ser. No. 09/144,575, filed Aug. 31, 1998, now U.S. Pat. No. 6,159,425. The '575 application, in turn, is a continuation of the following patent applications: U.S. patent application Ser. No. 09/062,472, filed Apr. 17, 1998, now U.S. Pat. No. 6,071,748; PCT Patent Application Ser. No. PCT/US98/14575, filed Jul. 15, 1998, now abandoned; U.S. patent application Ser. No. 09/118,141, filed Jul. 16, 1998, now U.S. Pat. No. 6,313,960; U.S. patent application Ser. No. 09/118,310, filed Jul. 16, 1998, now U.S. Pat. No. 6,033,100; and U.S. patent application Ser. No. 09/118,341, filed Jul. 16, 1998, now U.S. Pat. No. 6,025,985. These parent applications, in turn, claim priority from additional applications, as identified therein. The '575 application, in turn, also (directly and/or through its parent applications) is based upon and claims benefit under 35 U.S.C. §119(e) of the following U.S. Provisional Patent Applications, each of which is now expired: Ser. No. 60/052,876, filed Jul. 16, 1997; Ser. No. 60/059,639, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,414, filed Feb. 20, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/094,275, filed Jul. 27, 1998; Ser. No. 60/094,276, filed Jul. 27, 1998; and Ser. No. 60/094,306, filed Jul. 27, 1998.

U.S. patent application Ser. No. 09/759,711, in turn, is a continuation of PCT Patent Application Ser. No. PCT/US99/16057, filed Jul. 15, 1999, now abandoned. The '16057 application, in turn, is a continuation of the following applications: U.S. patent application Ser. No. 09/160,533, filed Sep. 24, 1998, now U.S. Pat. No. 6,097,025; and PCT Patent Application Ser. No. PCT/US98/14575, filed Jul. 15, 1998, now abandoned. These parent applications, in turn, claim priority from additional applications, as identified therein. The '16057 application, in turn, also is based upon and claims benefit under 35 U.S.C. §119(e) directly from U.S. Provisional Patent Application Ser. No. 60/093,838, filed Jul. 22, 1998, now expired.

U.S. patent application Ser. No. 09/765,869, in turn, is a continuation of PCT Patent Application Ser. No. PCT/US99/16621, filed Jul. 23, 1999, now abandoned, which, in turn, is based upon and claims benefit under 35 U.S.C. §119(e) of the following U.S. provisional patent applications, each of which is now expired: Ser. No. 60/094,275, filed Jul. 27, 1998; Ser. No. 60/117,278, filed Jan. 27, 1998; and Ser. No. 60/136,566, filed May 28, 1999.

U.S. patent application Ser. No. 09/767,434, in turn, is a continuation of PCT Patent Application Ser. No. PCT/US99/16453, filed Jul. 21, 1999, which, in turn, is based upon and claims benefit under 35 U.S.C. §119(e) of the following U.S. provisional patent applications, each of which is now expired: Ser. No. 60/093,768, filed Jul. 22, 1998; and Ser. No. 60/143,185, filed Jul. 9, 1999.

U.S. patent application Ser. No. 09/778,224, in turn, is a continuation of U.S. patent application Ser. No. 09/777,343, filed Feb. 5, 2001, which, in turn, is a continuation of PCT Patent Application Ser. No. PCT/US00/12277, filed May 3, 2000, now abandoned, which, in turn, is based upon and claims benefit under 35 U.S.C. §119(e) of the following U.S. provisional patent applications, each of which is now expired: Ser. No. 60/132,262, filed May 3, 1999; Ser. No. 60/132,263, filed May 3, 1999; Ser. No. 60/138,737, filed Jun. 11, 1999; Ser. No. 60/138,893, filed Jun. 11, 1999; Ser. No. 60/153,251, filed Sep. 10, 1999; and Ser. No. 60/167,301, filed Nov. 24, 1999.

U.S. patent application Ser. No. 09/836,575, in turn, is based upon and claims benefit under 35 U.S.C. §119(e) of U.S. Provisional Patent Application Ser. No. 60/190,265, filed Mar. 17, 2000, now expired.

U.S. patent application Ser. No. 10/004,647, in turn, is a continuation of U.S. patent application Ser. No. 09/643,221, filed Aug. 19, 2000, now U.S. Pat. No. 6,326,605, which, in turn, is a continuation of PCT Patent Application Ser. No. PCT/US99/03678, filed Feb. 19, 1999. The '03678 application, in turn, is a continuation of the following patent applications: U.S. patent application Ser. No. 09/062,472, filed Apr. 17, 1998, now U.S. Pat. No. 6,071,748; U.S. patent application Ser. No. 09/160,533, filed Sep. 24, 1998, now U.S. Pat. No. 6,097,025; PCT Patent Application Ser. No. PCT/US98/23095, filed Oct. 30, 1998, now abandoned; and PCT Application Ser. No. PCT/US99/01656, filed Jan. 25, 1999, now abandoned. These parent applications, in turn, claim priority from additional applications, as identified therein. The '03678 application, in turn, also (directly and/or through its parent applications) is based upon and claims benefit under 35 U.S.C. §119(e) of the following U.S.

provisional patent applications, each of which is now expired: Ser. No. 60/075,414, filed Feb. 20, 1998; Ser. No. 60/082,253, filed Apr. 17, 1998; and Ser. No. 60/100,951, filed Sep. 18, 1998.

U.S. patent application Ser. No. 10/012,255, in turn, is a continuation-in-part of the following U.S. patent applications: Ser. No. 09/626,208, filed Jul. 26, 2000, now abandoned; Ser. No. 09/766,131, filed Jan. 19, 2001, now abandoned; Ser. No. 09/765,874, filed Jan. 19, 2001, now U.S. Pat. No. 6,483,582; Ser. No. 09/767,316, filed Jan. 22, 2001; Ser. No. 09/767,579, filed Jan. 22, 2001, now U.S. Pat. No. 6,317,207; Ser. No. 09/770,720, filed Jan. 25, 2001, now abandoned; and Ser. No. 09/722,247, filed Nov. 24, 2000, now abandoned. U.S. patent application Ser. No. 09/626,208, in turn, is a continuation of PCT Patent Application Ser. No. PCT/US99/01656, filed Jan. 25, 1999, now abandoned. The '01656 application is a continuation-in-part of the following patent applications: U.S. patent application Ser. No. 09/062,472, filed Apr. 17, 1998, now U.S. Pat. No. 6,071,748; U.S. patent application Ser. No. 09/160,533, filed Sep. 24, 1998, now U.S. Pat. No. 6,097,025; and PCT Application Ser. No. PCT/US98/23095, filed Oct. 30, 1998, now abandoned. These parent applications, in turn, claim priority from additional applications, as identified therein. The '01656 application also is based upon and claims benefit under 35 U.S.C. §119(e) directly from the following U.S. provisional patent applications, each of which is now expired: Ser. No. 60/072,499, filed Jan. 26, 1998; Ser. No. 60/072,780, filed Jan. 27, 1998; Ser. No. 60/075,806, filed Feb. 24, 1998; and Ser. No. 60/084,167, filed May 4, 1998. U.S. patent application Ser. No. 09/766,131, in turn, is a continuation of PCT Patent Application Ser. No. PCT/US99/16286, filed Jul. 26, 1999, now abandoned, which is based upon and claims benefit under 35 U.S.C. §119(e) of U.S. Provisional Patent Application Ser. No. 60/094,306, filed Jul. 27, 1998, now expired. U.S. patent application Ser. No. 09/765,874, in turn, is a continuation of PCT Patent Application Ser. No. PCT/US99/16287, filed Jul. 26, 1999, now abandoned, which is based upon and claims benefit under 35 U.S.C. §119(e) of U.S. Provisional Patent Application Ser. No. 60/094,276, filed Jul. 27, 1998, now expired. U.S. patent application Ser. No. 09/767,316, in turn, is a continuation of PCT Patent Application Ser. No. PCT/US00/00895, filed Jan. 14, 2000, now abandoned, which is based upon and claims benefit under 35 U.S.C. §119(e) of the following U.S. provisional patent applications, each of which is now expired: Ser. No. 60/116,113, filed Jan. 15, 1999; Ser. No. 60/135,284, filed May 21, 1999; and Ser. No. 60/167,463, filed Nov. 24, 1999. U.S. patent application Ser. No. 09/767,579, in turn, is a continuation of PCT Patent Application Ser. No. PCT/US00/04543, filed Feb. 22, 2000, now abandoned, which is based upon and claims benefit under 35 U.S.C. §119(e) of U.S. Provisional Patent Application Ser. No. 60/121,229, filed Feb. 23, 1999, now expired. U.S. patent application Ser. No. 09/770,720, in turn, is a continuation of PCT Patent Application Ser. No. PCT/US00/06841, filed Mar. 15, 2000. The '06841 application is a continuation-in-part of the following patent applications: PCT Patent Application Ser. No. PCT/US99/08410, filed Apr. 16, 1999, now abandoned; U.S. patent application Ser. No. 09/349,733, filed Jul. 8, 1999, now abandoned; PCT Patent Application Ser. No. PCT/US00/00895, filed Jan. 14, 2000, now abandoned; and U.S. patent application Ser. No. 09/494,407, filed Jan. 28, 2000, now U.S. Pat. No. 6,297,108. These parent applications, in turn, claim priority from additional applications, as identified therein. The '06841 application also is based upon and claims benefit under 35 U.S.C. §119(e) directly from the following U.S. provisional patent applications, each of which is now expired: Ser. No. 60/124,686, filed Mar. 16, 1999; Ser. No. 60/125,346, filed Mar. 19, 1999; Ser. No. 60/135,284, filed May 21, 1999; Ser. No. 60/184,719, filed Feb. 24, 2000; and Ser. No. 60/184,924, filed Feb. 25, 2000. U.S. patent application Ser. No. 09/722,247, in turn, is a continuation-in-part of U.S. patent application Ser. No. 09/626,208, filed Jul. 26, 2000, now abandoned, which claims priority from additional applications, as indicated above. U.S. patent application Ser. No. 09/722,247 also is based upon and claims benefit under 35 U.S.C. §119(e) directly from the following U.S. provisional patent applications, each of which is now expired: Ser. No. 60/167,463, filed Nov. 24, 1999; and Ser. No. 60/182,419, filed Feb. 14, 2000.

U.S. patent application Ser. No. 10/041,532, in turn, is a continuation of PCT Patent Application Ser. No. PCT/US00/18547, filed Jul. 7, 2000, now abandoned, which, in turn, is based upon and claims benefit under 35 U.S.C. §119(e) of U.S. Provisional Patent Application Ser. No. 60/142,721, filed Jul. 7, 1999, now expired.

This application incorporates by reference in their entirety for all purposes the following U.S. patent applications: Ser. No. 08/840,553, filed Apr. 14, 1997; Ser. No. 09/062,472, filed Apr. 17, 1998, now U.S. Pat. No. 6,071,748; Ser. No. 09/118,141, filed Jul. 16, 1998, now U.S. Pat. No. 6,313,960; Ser. No. 09/118,310, filed Jul. 16, 1998, now U.S. Pat. No. 6,033,100; Ser. No. 09/118,341, filed Jul. 16, 1998, now U.S. Pat. No. 6,025,985; Ser. No. 09/144,575, filed Aug. 31, 1998, now U.S. Pat. No. 6,159,425; Ser. No. 09/144,578, filed Aug. 31, 1998; Ser. No. 09/146,081, filed Sep. 2, 1998, now U.S. Pat. No. 6,187,267; Ser. No. 09/156,318, filed Sep. 18, 1998, now U.S. Pat. No. 6,258,326; Ser. No. 09/160,533, filed Sep. 24, 1998, now U.S. Pat. No. 6,097,025; Ser. No. 09/494,407, filed Jan. 28, 2000, now U.S. Pat. No. 6,297,018; Ser. No. 09/556,030, filed Apr. 20, 2000; Ser. No. 09/596,444, filed Jun. 19, 2000; Ser. No. 09/626,208, filed Jul. 26, 2000; Ser. No. 09/643,221, filed Aug. 18, 2000, now U.S. Pat. No. 6,326,605; Ser. No. 09/722,247, filed Nov. 24, 2000; Ser. No. 09/765,874, filed Jan. 19, 2001; Ser. No. 09/766,131, filed Jan. 19, 2001; Ser. No. 09/767,316, filed Jan. 22, 2001; Ser. No. 09/767,579, filed Jan. 22, 2001, now U.S. Pat. No. 6,317,207; Ser. No. 09/768,742, filed Jan. 23, 2001; Ser. No. 09/768,661, filed Jan. 23, 2001; Ser. No. 09/768,765, filed Jan. 23, 2001, now U.S. Pat. No. 6,310,687; Ser. No. 09/770,720, filed Jan. 25, 2001; Ser. No. 09/770,724, filed Jan. 25, 2001; Ser. No. 09/777,343, filed Feb. 5, 2001; Ser. No. 09/844,655, filed Apr. 27, 2001; Ser. No. 10/003,030, filed Oct. 29, 2001; and Ser. No. 10/061,416, filed Feb. 1, 2002.

This application also incorporates by reference in their entirety for all purposes the following U.S. provisional patent applications: Ser. No. 60/052,876, filed Jul. 16, 1997; Ser. No. 60/059,639, filed Sep. 20, 1997; Ser. No. 60/059,640, filed Sep. 20, 1997; Ser. No. 60/063,811, filed Oct. 31, 1997; Ser. No. 60/072,499, filed Jan. 26, 1998; Ser. No. 60/072,780, filed Jan. 27, 1998; Ser. No. 60/075,806, filed Feb. 24, 1998; Ser. No. 60/082,253, filed Apr. 17, 1998; Ser. No. 60/084,167, filed May 4, 1998; Ser. No. 60/085,335, filed May 13, 1998; Ser. No. 60/085,500, filed May 14, 1998; Ser. No. 60/089,848, filed Jun. 19, 1998; Ser. No. 60/093,768, filed Jul. 22, 1998; Ser. No. 60/093,838, filed Jul. 22, 1998; Ser. No. 60/094,275, filed Jul. 27, 1998; Ser. No. 60/094,276, filed Jul. 27, 1998; Ser. No. 60/094,306, filed Jul. 27, 1998; Ser. No. 60/100,951, filed Sep. 18, 1998; Ser. No. 60/104,964, filed Oct. 20, 1998; Ser. No. 60/116,113, filed Jan. 15, 1999; Ser. No. 60/117,278, filed Jan. 26, 1999; Ser. No. 60/119,829, filed Feb. 12, 1999; Ser. No. 60/121,229, filed Feb. 23, 1999; Ser. No. 60/124,686, filed Mar. 16, 1999; Ser. No. 60/125,346, filed Mar. 19, 1999; Ser. No. 60/126,661, filed Mar. 29, 1999; Ser. No. 60/130,149, filed Apr. 20, 1999; Ser. No. 60/132,262, filed May 3, 1999; Ser. No. 60/132,263, filed May 3, 1999; Ser. No. 60/135,284, filed May 21, 1999; Ser. No. 60/136,566, filed May 28, 1999; Ser. No. 60/138,311, filed Jun. 9, 1999; Ser. No. 60/138,438, filed Jun. 10, 1999; Ser. No. 60/138,737, filed Jun. 11, 1999; Ser. No. 60/138,893, filed Jun. 11, 1999; Ser. No. 60/142,721, filed Jul. 7, 1999; Ser. No. 60/143,185, filed Jul. 9, 1999; Ser. No. 60/153,251, filed Sep. 10, 1999; Ser. No. 60/164,633, filed Nov. 10, 1999; Ser. No. 60/167,301, filed Nov. 24, 1999; Ser. No. 60/167,463, filed Nov. 24, 1999; Ser. No. 60/182,419, filed Feb. 14, 2000; Ser. No. 60/184,719, filed Feb. 24, 2000; Ser. No. 60/184,924, filed Feb. 25, 2000; Ser. No. 60/197,324, filed Apr. 14, 2000; Ser. No. 60/244,012, filed Oct. 27, 2000; Ser. No. 60/267,639, filed Feb. 10, 2001; Ser. No. 60/376,969, filed Apr. 30, 2002; Ser. No. 60/83,197, filed May 22, 2002; Ser. No. 60/383,198, filed May 22, 2002; and Ser. No. 60/383,311, filed May 22, 2002.

This application also incorporates by reference in their entirety for all purposes the following PCT patent applications: Ser. No. PCT/US98/14575, filed Jul. 15, 1998; Ser. No. PCT/US98/23095, filed Oct. 30, 1998; Ser. No. PCT/US99/01656, filed Jan. 25, 1999; Ser. No. PCT/US99/03678, filed Feb. 19, 1999; Ser. No. PCT/US99/08410, filed Apr. 16, 1999; Ser. No. PCT/US99/16057, filed Jul. 15, 1999; Ser. No. PCT/US99/16453, filed Jul. 21, 1999; Ser. No. PCT/US99/16286, filed Jul. 26, 1999; Ser. No. PCT/US99/16287, filed Jul. 26, 1999; Ser. No. PCT/US99/16621, filed Jul. 23, 1999; Ser. No. PCT/US99/24707, filed Oct. 19, 1999; Ser. No. PCT/US00/00895, filed Jan. 14, 2000; Ser. No. PCT/US00/04543, filed Feb. 22, 2000; Ser. No. PCT/US00/06841, filed Mar. 15, 2000; Ser. No. PCT/US00/12277, filed May 3, 2000; Ser. No. PCT/US00/15774, filed Jun. 9, 2000; and Ser. No. PCT/US00/18547, filed Jul. 7, 2000.

This application also incorporates by reference in their entirety for all purposes the following additional materials: K. E. van Holde, PHYSICAL BIOCHEMISTRY ($2^{nd}$ ed. 1985); William Bains, BIOTECHNOLOGY FROM A TO Z (1993); Richard P. Haugland, HANDBOOK OF FLUORESCENT PROBES AND RESEARCH CHEMICALS ($6^{th}$ ed. 1996); Paul Horowitz & Winfield Hill, THE ART OF ELECTRONICS (1980); Joseph R. Lakowicz, PRINCIPLES OF FLUORESCENCE SPECTROSCOPY ($2^{nd}$ ed. 1999); Bob Sinclair, EVERYTHING'S GREAT WHEN IT SITS ON A CHIP: A BRIGHT FUTURE FOR DNA ARRAYS , 13 THE SCIENTIST, May 24, 1999, at 18; and Charles R. Cantor and Paul R. Schimmel, BIOPHYSICAL CHEMISTRY (1980).

FIELD OF THE INVENTION

The invention relates to systems, and components thereof, for analyzing samples. These systems include apparatus and methods for generating, transmitting, detecting, and/or analyzing light, including without limitation high-throughput optical screening devices for analyzing samples at one or more assay sites. These systems also include apparatus and methods for supporting samples for analysis, including without limitation multiwell sample holders such as microplates.

BACKGROUND OF THE INVENTION

High-throughput screening devices such as optical analyzers and microplates are important tools in the pharmaceutical research industry, particularly for the discovery and development of new drugs.

The "drug discovery process" involves the synthesis and testing, or screening, of candidate drug compounds against a target. The candidate drug compounds are molecules or other species that might mediate a disease by affecting a target. The target is a biological (or biologically active) molecule, such as an enzyme, receptor, or other protein or nucleic acid, that is believed to play a role in the onset, progression, and/or symptoms of a disease.

FIG. 1 shows stages of the drug discovery process, which include (A) target identification, (B) compound selection, (C) assay development, (D) screening (including primary screening for hits, secondary screening for lead compounds, and optimization (or tertiary screening) of lead compounds), and (E) clinical evaluation.

A. Target Identification

A target is identified based on its anticipated role in the prevention or progression of a disease. Until recently, scientists using conventional methods had identified only a few hundred targets, many of which have not been comprehensively screened. However, recent developments in molecular biology and genomics have led to a dramatic increase in the number of targets available for drug discovery research.

B. Compound Selection

A library of compounds is selected, following target identification, to screen against the target. Compounds historically have been synthesized one at a time or obtained from natural sources. Pharmaceutical companies, using conventional synthetic techniques over decades, have compiled compound libraries of hundreds to thousands of compounds. However, recent advances in combinatorial chemistry and other chemical synthetic techniques, as well as licensing arrangements, have enabled industrial and academic groups to increase greatly the supply and diversity of compounds available for screening against targets. As a result, many researchers are gaining access to libraries of hundreds of thousands of compounds, in months rather than years.

C. Assay Development

A biological test or assay is developed, after selection of a target, but before screening compounds against the target, to measure the effect(s) of compounds on the activity of the target. Assay development involves selection and optimization of an assay that will measure performance of a compound against the selected target.

Assays may be classified broadly as either biochemical or cellular. Biochemical assays usually are performed with purified molecular targets, which generally have certain advantages, such as speed, convenience, simplicity, and specificity. Cellular assays are performed with living cells, which may sacrifice speed and simplicity, but which may provide information that is more relevant biologically. Researchers use both biochemical and cellular assays in drug discovery research.

Biochemical and cellular assays may use a variety of detection modalities, including photoluminescence, chemiluminescence, absorbance, and/or scattering. Photoluminescence and chemiluminescence assays typically involve determining the amount of light that is emitted from excited electronic states arising from the absorption of light or a chemical reaction, respectively. Absorbance and scattering assays typically involve determining the amount of light that is transmitted through or scattered from a composition relative to the amount of light incident on the composition, respectively.

These different detection modalities each may use a variety of equipment. For example, photoluminescence assays typically employ at least a light source, detector, and filter; absorbance and scattering assays typically employ at least a light source and detector; and chemiluminescence assays typically employ at least a detector. Moreover, the type of light source, detector, and/or filter employed typically varies even within a single detection modality. For example, among photoluminescence assays, photoluminescence intensity and steady-state photoluminescence polarization assays may use a continuous light source, and time-resolved photoluminescence polarization assays may use a time-varying light source.

Adding to this variability, the types of assays that are desired for high-throughput screening are evolving constantly. In particular, as new assays are developed in research laboratories, tested, and then published in literature and/or presented at scientific conferences, these new assays become popular, and many become available commercially. New or adaptable analytical equipment may be required to support the most popular commercially available assays.

D. Screening/Clinical Evaluation

Following selection of a target, compound library, and assay, the library is "screened" by running assays to determine the effects of compounds in the library on the target, if any. Compounds that have an effect on the target are termed "hits." The statistical probability of obtaining hits may be increased by increasing the number of compounds screened against the target. Once a compound is identified as a hit, a number of secondary screens are performed to evaluate its potency and specificity for the intended target. This cycle of repeated screening continues until a small number of lead compounds are selected. The lead compounds are optimized by further screening. Optimized lead compounds with the greatest therapeutic potential may be selected for clinical evaluation.

E. Shortcomings

Due to the recent dramatic increase in the number of available compounds and targets, a bottleneck has resulted at the screening stage of the drug discovery process. Historically, screening has been a manual, time-consuming process. Recently, screening has become more automated, and standard high-density containers known as microplates have been developed to facilitate automated screening. Microplates are multiwell sample plates that include a plurality of sample wells for containing a plurality of samples. Microplates with 96, 384, and 768 wells have been developed for use in the high-throughput screening industry. In addition, some high-throughput screening laboratories are experimenting with higher-density microplates, with 1536, 3456, and even 9600 wells.

FIG. 2 shows a stack of overlapping microplates with various well densities. Plate 30 has 96 wells. Plate 32 has 384 wells. Plate 34 has 1536 wells. Plate 36 has 3456 wells. Plate 38 has 9600 wells. FIG. 2 illustrates the substantial differences in well dimensions and densities that may be used in high-throughput screening assays. Many analyzers are not flexible enough to read microplates having different numbers of wells, such that it currently may be necessary to provide different analyzers for different modes of analysis. Moreover, many analyzers are not sensitive or accurate enough to read results from the smaller wells associated with the higher-density microplates. Inadequate sensitivity may result in missed hits, limited research capabilities, increased costs of compounds, assays, and reagents, and lower throughput.

Screening an increasing number of compounds against an increasing number of targets requires a system that can operate with a high degree of automation, analytical flexibility, and speed. In particular, because high-throughput applications may involve repeating the same operations hundreds of thousands of times, even the smallest shortcomings are greatly magnified. Current screening systems operate with various degrees of automation. Automation, from sample dispensing to data collection, enables round-the-clock operation, thereby increasing the screening rate. Automated high-throughput screening systems usually include combinations of assay analyzers, liquid handling systems, robotics, computers for data management, reagents and assay kits, and microplates.

Most analyzers in use today are not designed specifically for high-throughput screening purposes. They are difficult and expensive to integrate into a high-throughput screening environment. Moreover, even after the analyzer is integrated into the high-throughput screening environment, there often are many problems, including increased probability of system failures, loss of data, time delays, and loss of costly compounds and reagents.

Most analyzers in use today also offer only a single assay modality, such as absorbance or chemiluminescence, or a limited set of modalities with non-optimum performance. To perform assays using different detection modes, researchers generally must switch single-mode analyzers and reconfigure the high-throughput screening line. Alternatively, researchers may set up the high-throughput screening line with multiple single-mode analyzers, which often results in critical space constraints.

Thus, prior sample analysis systems generally have not recognized the need to provide analytic flexibility and high performance for assay development as well as ease of use and smooth automation interface for the high-throughput screening laboratory. A real need exists for a versatile, sensitive, high-throughput screening apparatus and multiwell sample holders that can handle multiple detection modalities and wide ranges of sample volumes and variations in container material, geometry, size, and density format while reliably maintaining a high level of sensitivity.

SUMMARY OF THE INVENTION

The invention provides systems, and components thereof, for analyzing samples. These systems include apparatus and methods for generating, transmitting, detecting, and/or analyzing light, including without limitation high-throughput optical screening devices for analyzing samples at one or more assay sites. These systems also include apparatus and methods for supporting samples for analysis, including without limitation multiwell sample holders such as microplates.

BRIEF DESCRIPTION OF THE FIGURES

FIG. 88 is a top view of a 96-well microplate, in accordance with aspects of the invention.

FIG. 89 is a cross-sectional view of the microplate in FIG. 88, taken generally along line 89—89 in FIG. 88.

FIG. 90 is a first enlarged portion of the cross-sectional view in FIG. 89, showing details of a sample well.

FIG. 91 is a second enlarged portion of the cross-sectional view in FIG. 89, showing details of a reference fiducial.

FIG. 96 is a perspective view of a 1536-well microplate, in accordance with aspects of the invention.

FIG. 97 is a top view of the microplate in FIG. 96.

FIG. 98 is an enlarged portion of the top view in FIG. 97, showing details of the sample wells.

FIG. 99 is a cross-sectional view of the microplate in FIG. 97, taken generally along line 99—99 in FIG. 97.

FIG. 100 is an enlarged portion of the cross-sectional view in FIG. 99, showing details of the sample wells.

DETAILED DESCRIPTION OF THE INVENTION

Figure 1:
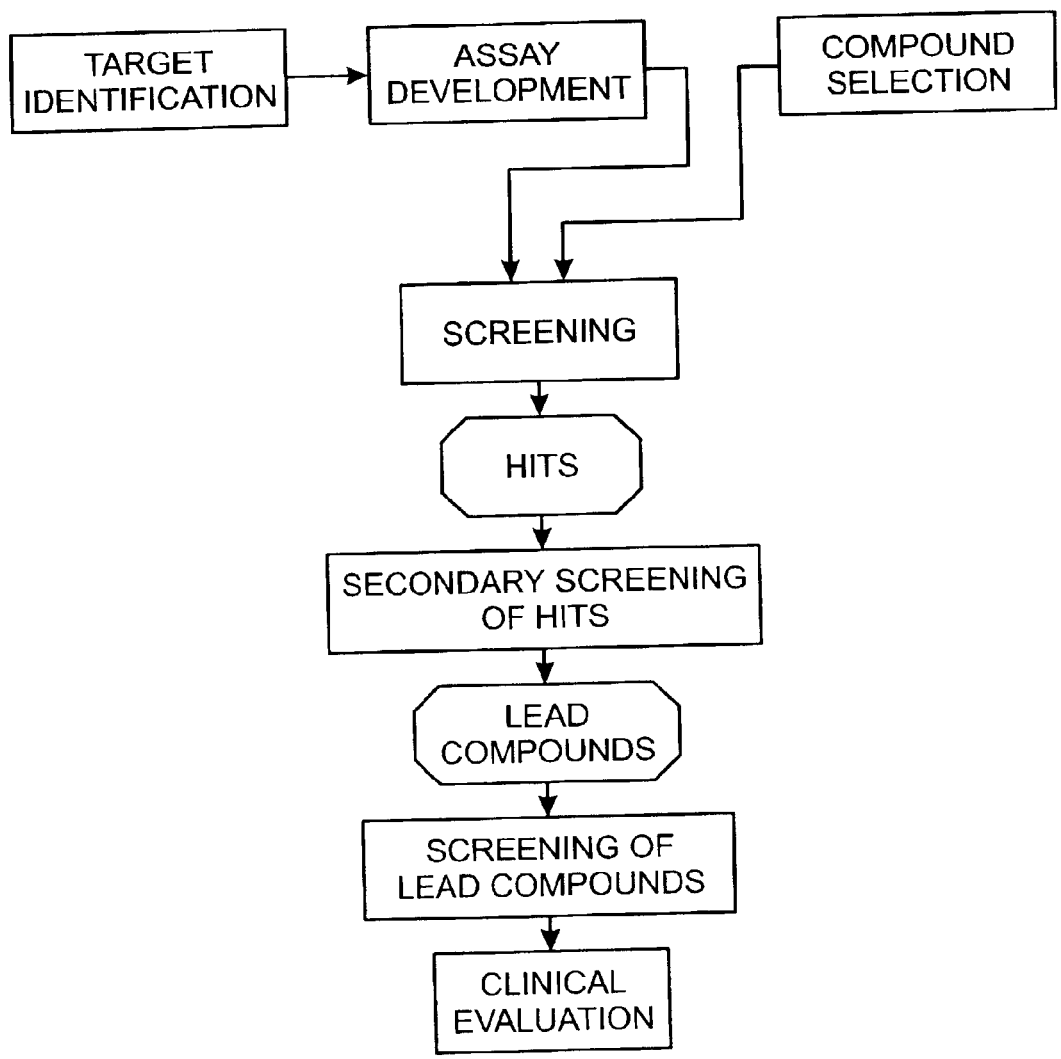
FIG. 1 is a flow chart showing elements of the drug discovery process.
Figure 2:
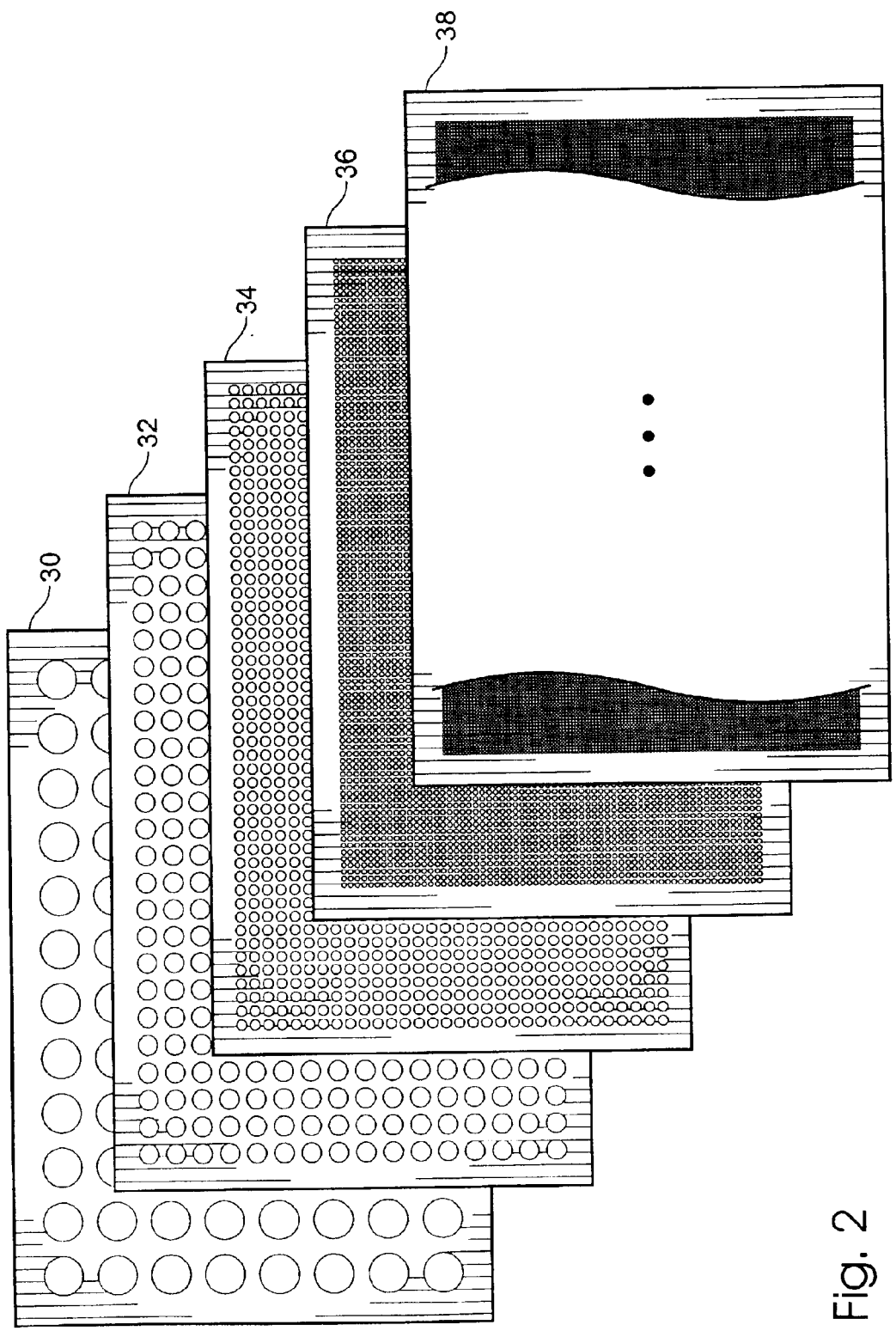
FIG. 2 is a top view of overlapping microplates showing variations in well density.

The invention provides systems, and components thereof, for analyzing samples. These systems include apparatus and methods for generating, transmitting, detecting, and/or analyzing light, including without limitation high-throughput optical screening devices for analyzing samples at one or more assay sites. These systems also include apparatus and methods for supporting samples for analysis, including without limitation multiwell sample holders such as microplates.

The systems provided by the invention, in many instances, may be selected and/or fine-tuned for screening targets with flexibility, durability, and/or convenience. Flexibility means that the systems can be used with a variety of samples and sample assays. Durability means that the systems can be used repeatedly, at high throughput, in laboratory and industrial settings. Convenience means that the systems can be used with only minimal user intervention, while also allowing assays to be run in smaller containers with reduced volumes.

The systems may achieve these and/or other objectives, in a variety of ways. For example, the systems may include an optical system that reduces or minimizes sample interfacial boundary interference, thereby permitting reduction in assay volume in existing formats such as 96 or 384 well plates, and/or utilization of denser formats such as 768, 1536, 3456, or 9600 well plates. Alternatively, or in addition, the systems may include an ability to switch automatically between different modes, including absorbance, scattering, photoluminescence, photoluminescence polarization, time-resolved photoluminescence, photoluminescence lifetime, and/or chemiluminescence modalities, among others. Alternatively, or in addition, the systems may include sample holders adapted for use with particular optical systems, including those that generate and/or detect light from a sensed volume and/or evanescent field.

The systems, and/or components thereof, may be used alone and/or in conjunction with all or part(s) of the systems described in the patents, patent applications, and other materials identified above under Cross-References, including but not limited to the following U.S. patent applications: Ser. No. 09/778,224, filed Feb. 6, 2001 (including sample-handling such as fluidics); and Ser. No. 10/061,416, filed Feb. 1, 2002 (also including sample-handling such as fluidics). These supplementary materials are incorporated herein by reference in their entirety for all purposes.

These and other aspects of the systems are described below, including among others the (I) optical system, (II) optics heads and the generation of sensed volumes, (III) application of sensed volumes, (IV) light source and detector modules, (V) filter wheel assemblies, (VI) sample transporter, (VII) input/output mechanisms, (VIII) sample feeder, (IX) scanning optics head, (X) arc lamp power supply, (XI) assay modes, (XII) analyzer setup, calibration, and reading, (XIII) measurement modes, (XIV) broad-range light detection system, (XV) signal enhancement, (XVI) preferred light sources, (XVII) epi-absorbance system, (XVIII) sample holders, and (XIX) luminescence polarization system.

I. Optical System

This section describes optical systems, including apparatus and methods, in accordance with aspects of the invention. These systems may be used for generating, transmitting, detecting, and/or analyzing light, and for transmitting light to and/or from a sample. The systems may include (1) a stage for supporting the sample, (2) one or more light sources for delivering light to the sample, (3) one or more detectors for receiving light transmitted from the sample and converting it to a signal, (4) first and second optical relay structures for relaying light between the light source, sample, and detector, and/or (5) a processor for analyzing the signal from the detector. The systems may limit detection to a sensed volume, which may comprise only a portion of the composition.

System components may be chosen to improve or optimize speed, sensitivity, and/or dynamic range, for one or more assays. For example, optical components with low intrinsic luminescence may be used to enhance sensitivity in luminescence assays by reducing background. System components also may be shared by different assays, or dedicated to particular assays. For example, steady-state photoluminescence assays may use a continuous light source, time-resolved photoluminescence assays may use a time-varying light source, and chemiluminescence assays may not use a light source. Similarly, steady-state and time-resolved photoluminescence assays may both use a first detector, and chemiluminescence assays may use a second detector.

FIGS. 3–6 show an exemplary embodiment of an optical system from an analyzer 90 constructed in accordance with aspects of the invention. This optical system includes separate (though integrated) photoluminescence (or, more generally, incident-light-based) and chemiluminescence optical systems. The optical system, in other embodiments, may include one or the other of these systems, alone or in combination with yet other systems. These and other aspects of the invention are described below, including (A) an exemplary photoluminescence (or incident-light-based) optical system, and (B) an exemplary chemiluminescence optical system. This disclosure is supplemented by the patents, patent applications, and other materials identified above under Cross-References, including but not limited to U.S. Provisional Patent Application Ser. No. 60/082,253, filed Apr. 17, 1998; U.S. Provisional Patent Application Ser. No. 60/164,633, filed Nov. 10, 1999; U.S. patent application Ser. No. 09/062,472, filed Apr. 17, 1998, now U.S. Pat. No. 6,071,748; U.S. patent application Ser. No. 09/146,081, filed Sep. 2, 1998, now U.S. Pat. No. 6,187,267; U.S. patent application Ser. No. 09/160,533, filed Sep. 24, 1998, now U.S. Pat. No. 6,097,025; U.S. patent application Ser. No. 09/302,158, filed Apr. 29, 1999; U.S. patent application Ser. No. 09/629,599, filed Jul. 31, 2000; U.S. patent application Ser. No. 10/003,030, filed Oct. 29, 2001; U.S. patent application Ser. No. 10/012,255, filed Nov. 12, 2001; U.S. patent application Ser. No. 10/061,416, filed Feb. 1, 2002; and Joseph R. Lakowicz, PRINCIPLES OF FLUORESCENCE SPECTROSCOPY ($2^{nd}$ ed. 1999). These supplementary materials are incorporated herein by reference in their entirety for all purposes.

A. Photoluminescence (or Incident-Light-Based) Optical System

Figure 3:
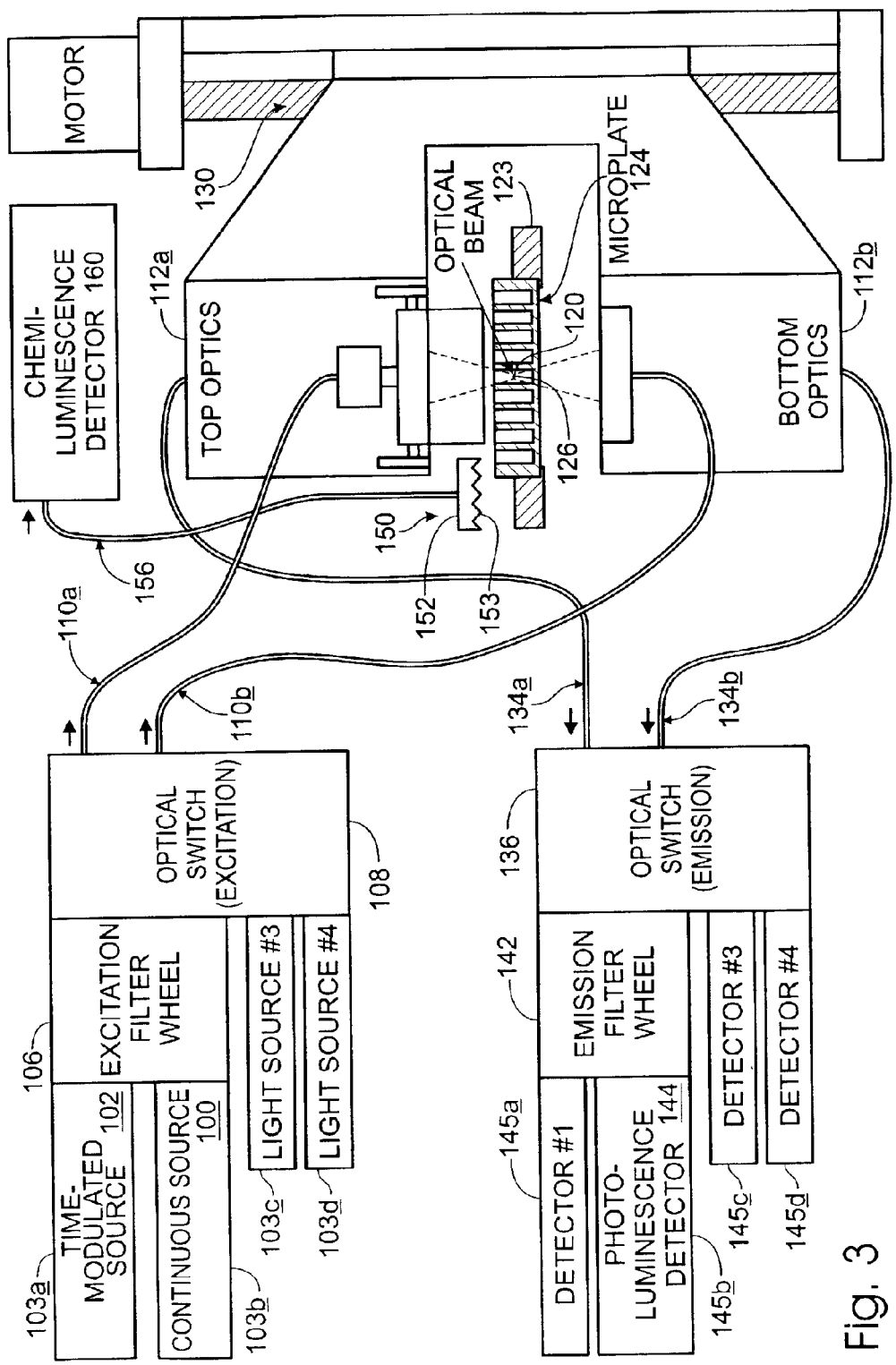
FIG. 3 is a schematic view of an optical analyzer, in accordance with aspects of the invention.
Figure 4:
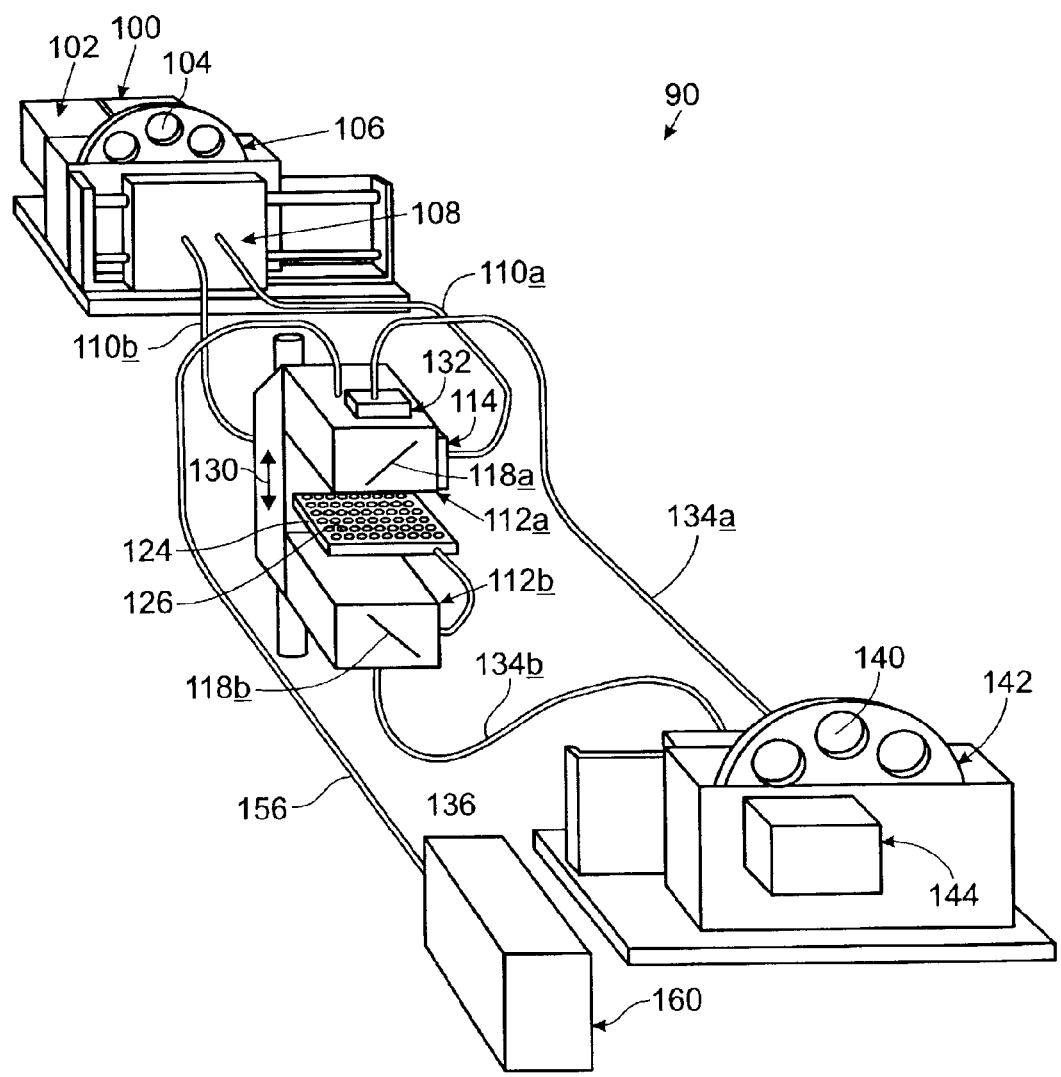
FIG. 4 is a schematic partial perspective view of the analyzer shown in FIG. 3.
Figure 5:
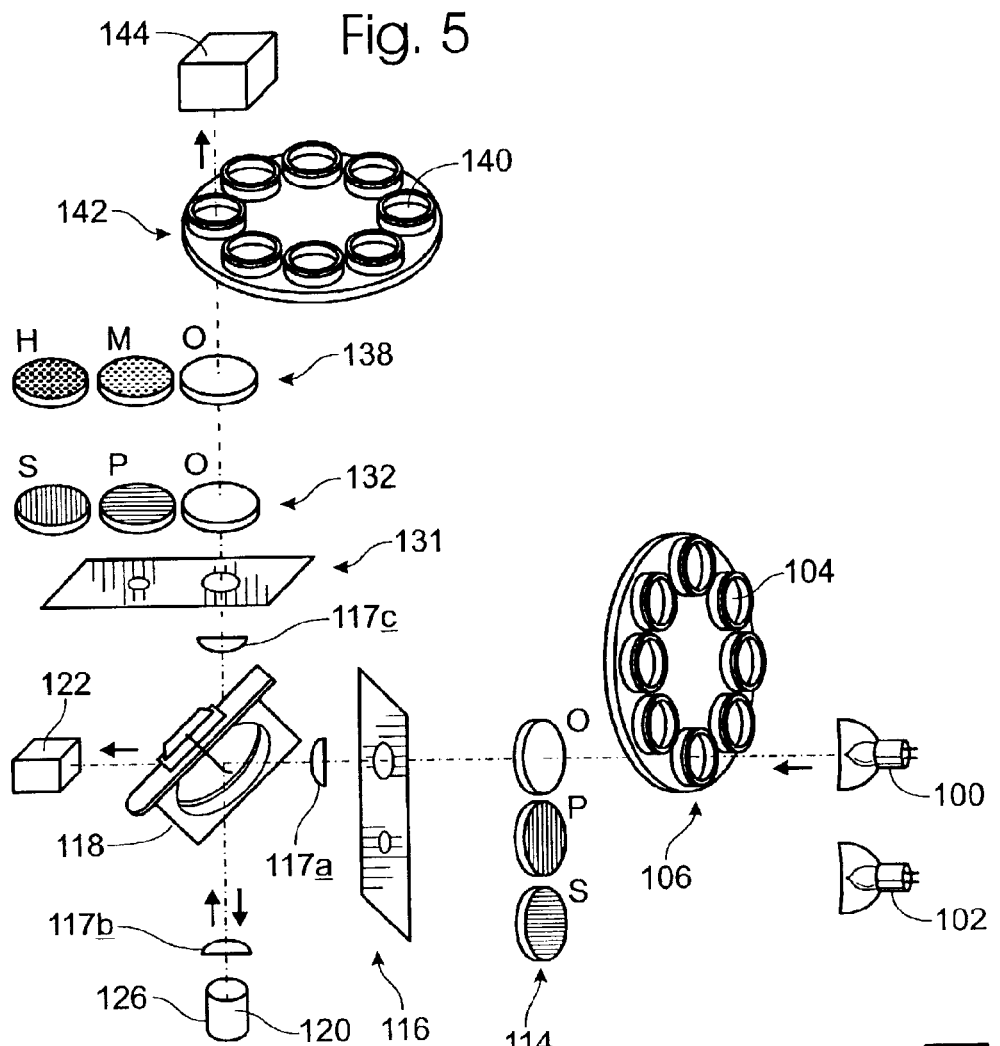
FIG. 5 is a schematic view of portions of a photoluminescence optical system from the analyzer shown in FIG. 3.

FIGS. 3–5 show the photoluminescence (or incident-light-based) optical system of apparatus 90. As configured here, apparatus 90 includes a continuous light source 100 and a time-modulated light source 102. Apparatus 90 includes light source slots 103a–d for four light sources, although other numbers of light source slots and light sources also could be provided. Light source slots 103a–d function as housings that may surround at least a portion of each light source, providing some protection from radiation and explosion. The direction of light transmission through the incident light-based optical system is indicated by arrows.

Continuous source 100 provides light for absorbance, photoluminescence, and scattering assays, among others. Continuous light source 100 may include arc lamps, incandescent lamps, fluorescent lamps, electroluminescent devices, lasers, laser diodes, and light-emitting diodes (LEDs), among others. Preferred continuous sources include (1) a high-intensity, high color temperature xenon arc lamp, such as a CERMAX xenon lamp (Model Number LX175F; ILC Technology, Inc.), and (2) an LED, such as a NICHIA-brand bright-blue LED (Model Number NSPB500; Mountville, Pa.), which is particularly useful with analytes that absorb blue light. Color temperature is the absolute temperature in Kelvin at which a blackbody radiator must be operated to have a chromaticity equal to that of the light source. A high color temperature lamp produces more visible light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the duty cycle of the flash source, increasing sensitivity and reducing read times. Apparatus 90 may include a modulator mechanism configured to vary the intensity of light incident on the composition without varying the intensity of light produced by the light source.

Time-modulated source 102 provides light for time-resolved absorbance and/or photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps and other sources whose intensity can be modulated extrinsically using a suitable optical modulator. Intrinsically modulated continuous light sources are especially well suited for frequency-domain measurements in that they are generally easier to operate and more reliable.

If the light source must be extrinsically modulated, an optical modulator may be used. The optical modulator generally includes any device configured to modulate incident light. The optical modulator may be acousto-optical, electro-optical, or mechanical, among others. Suitable modulators include acousto-optical modulators, Pockels cells, Kerr cells, liquid crystal devices (LCDs), chopper wheels, tuning fork choppers, and rotating mirrors, among others. Mechanical modulators may be termed "choppers," and include chopper wheels, tuning fork choppers, and rotating mirrors, among others. Suitable mechanical modulators are described in the following U.S. patent applications, which are incorporated herein by reference in their entirety for all purposes: Ser. No. 09/765,874, filed Jan. 19, 2001; and Ser. No. 10/012,255, filed Nov. 12, 2001.

In apparatus 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. For example, a spectral filter may be used to block the red edge of the broadspectrum light produced by the blue LED described above. In apparatus 90, spectrum is altered by an excitation interference filter 104, which preferentially transmits light of preselected wavelengths and preferentially absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers and laser diodes, which output light of only a single wavelength. Therefore, excitation filter wheel 106 may be mounted in the optical path of some light source slots 103a,b but not other light source slots 103c,d. Alternatively, the filter wheel may include a blank station that does not affect light passage.

Light next passes through an excitation optical shuttle (or switch) 108, which positions an excitation fiber optic cable 110a,b in front of the appropriate light source to deliver light to top or bottom optics heads 112a,b respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In apparatus 90, polarization is altered by excitation polarizers 114, which are included only with top optics head 112a for top reading; however, such polarizers also can be included with bottom optics head 112b for bottom reading. Excitation polarization filters 114 may include an s-polarizer S that passes only s-polarized light, a p-polarizer P that passes only p-polarized light, and a blank O that passes substantially all light, where polarizations are measured relative to the beamsplitter. Excitation polarizers 114 also may include a standard or ferro-electric liquid crystal display (LCD) polarization switching system. Such a system may be faster than a mechanical switcher. Excitation polarizers 114 also may include a continuous mode LCD polarization rotator with synchronous detection to increase the signal-to-noise ratio in polarization assays. Excitation polarizers 114 may be incorporated as an inherent component in some light sources, such as certain lasers, that intrinsically produce polarized light.

Light at one or both optics heads also may pass through an excitation "confocal optics element," which generally comprises any mechanism for focusing light into a "sensed volume." In apparatus 90, the confocal optics element includes a set of lenses 117a–c and an excitation aperture 116 placed in an image plane conjugate to the sensed volume, as shown in FIG. 5. Aperture 116 may be implemented directly, as an aperture, or indirectly, as the end of a fiber optic cable. Preferred apertures have diameters of 1 mm and 1.5 mm. Lenses 117a,b project an image of aperture 116 onto the sample, so that only a preselected or sensed volume of the sample is illuminated. The area of illumination will have a diameter corresponding to the diameter of the excitation aperture.

Light traveling through the optics heads is reflected and transmitted through a beamsplitter 118, which reflects light toward a composition 120 and transmits light toward a light monitor 122. Both the reflected and transmitted light pass through lens 117b, which is operatively positioned between beamsplitter 118 and composition 120.

Beamsplitter 118 is used to direct excitation or incident light toward the sample and light monitor, and to direct light leaving the sample toward the detector. The beamsplitter is changeable, so that it may be optimized for different assay modes or compositions. In some embodiments, switching between beamsplitters may be performed manually, whereas, in other embodiments, such switching may be performed automatically. Moreover, the device may be designed automatically to sense and optionally to respond to the particular installed beamsplitter, as described in U.S. Provisional Patent Application Ser. No. 60/383,311, filed May 22, 2002. Automatic switching may be performed based on direct operator command, or based on an analysis of the sample by the instrument. If a large number or variety of photoactive molecules are to be studied, the beamsplitter should be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable light leaving the sample to the detector. If one or a few related photoactive molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

The beamsplitter more generally comprises any optical device for dividing a beam of light into two or more separate beams. A simple beamsplitter (such as a 50:50 beamsplitter) may include a very thin sheet of glass inserted in the beam at an angle, so that a portion of the beam is transmitted in a first direction and a portion of the beam is reflected in a different second direction. A more sophisticated beamsplitter (such as a dichroic or multi-dichroic beamsplitter) may include other prismatic materials, such as fused silica or quartz, and may be coated with a metallic or dielectric layer having the desired transmission and reflection properties, including dichroic and multi-dichroic transmission and reflection properties. In some beamsplitters, two right-angle prisms are cemented together at their hypotenuse faces, and a suitable coating is included on one of the cemented faces.

Light monitor 122 is used to correct for fluctuations in the intensity of light provided by the light sources. Such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The sample (or composition) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the composition may involve measuring the presence, concentration, or physical properties (including interactions) of a photoactive analyte in such a composition. Composition may refer to the contents of a single microplate well, or several microplate wells, depending on the assay. In some embodiments, such as a portable apparatus, the stage may be extrinsic to the instrument.

The sample holder can include microplates, biochips, or any array of samples in a known format. In apparatus 90, the preferred sample holder is a microplate 124, which includes a plurality of microplate wells 126 for holding compositions. Microplates are multiwell (typically rectangular) holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in a 8×12 rectangular array on 9 millimeter centers.

The sensed volume typically has an hourglass shape, with a cone angle ranging between about 15° and 35° and a minimum diameter ranging between about 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume, as described in U.S. patent application Ser. No. 09/478,819, filed Jan. 5, 2000, which is incorporated herein by reference in its entirety for all purposes.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In apparatus 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 3 and 4. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and has been used in the past for absorbance assays. In apparatus 90, epi modes are supported, so the excitation and emission light travel the same path in the optics head, albeit in opposite or anti-parallel directions. However, trans modes also can be used with additional sensors, as described below. In apparatus 90, top and bottom optics heads move together and share a common focal plane. However, in other embodiments, top and bottom optics heads may move independently, so that each can focus independently on the same or different sample planes. In some embodiments, the optics head and/or sample holder may be independently scanned, for example, as described in U.S. patent application Ser. No. 09/768,765, filed Jan. 23, 2001, which is incorporated herein by reference in its entirety for all purposes.

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes that accumulate on the bottom of the holder.

Light is transmitted by the composition in multiple directions. A portion of the transmitted light will follow an emission pathway to a detector. Transmitted light passes through lens 117c and may pass through an emission aperture 131 and/or an emission polarizer 132. In apparatus 90, the emission aperture is placed in an image plane conjugate to the sensed volume and transmits light substantially exclusively from this sensed volume. In apparatus 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In apparatus 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In apparatus 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the sample without absorption. Examples include beamsplitters, which transmit some light along one path and reflect other light along another path, and diffractive beamsplitters (e.g., acousto-optic modulators), which deflect light along different paths through diffraction. Examples also include hot mirrors or windows that transmit light of some wavelengths and absorb light of other wavelengths.

Light next may pass through an emission interference filter 140, which may be housed in an emission filter wheel 142. In apparatus 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance, photoluminescence, and scattering assays. In apparatus 90, there is one detector 144, which detects light from all modes. A preferred detector is a photomultiplier tube (PMT). Apparatus 90 includes detector slots 145a–d for four detectors, although other numbers of detector slots and detectors also could be provided.

More generally, detectors comprise any mechanism capable of converting energy, from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, (3) point, and/or (4) imaging modes, among others, for example, as described in U.S. patent application Ser. No. 09/643,221, filed Aug. 18, 2000, which is incorporated herein by reference in its entirety for all purposes.

B. Chemiluminescence Optical System

Figure 6:
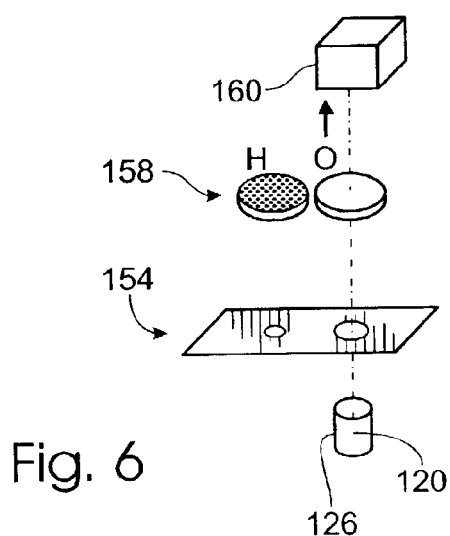
FIG. 6 is a schematic view of portions of a chemiluminescence optical system from the analyzer shown in FIG. 3.

FIGS. 3, 4, and 6 show the chemiluminescence optical system of analyzer 90. Because chemiluminescence follows a chemical event rather than the absorption of light, the chemiluminescence optical system does not require a light source or other excitation optical components. Instead, the chemiluminescence optical system requires only selected emission optical components. In analyzer 90, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the photoluminescence optical system. The chemiluminescence optical system also can be used for other assay modes that do not require illumination, such as electrochemiluminescence.

The chemiluminescence optical path begins with a chemiluminescent composition 120 held in a sample container 126. The composition and sample container are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample container. A portion of the light transmitted through the top of the well is collected using a chemiluminescence head 150, as shown in FIG. 3, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the composition. Detecting from a sensed volume reduces contributions to the chemiluminescence signal resulting from "cross talk," which is pickup from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156. This fiber optic cable, which may be replaced by any suitable mechanism for directing light from the sample toward the detector, is analogous to excitation and emission fiber optic cables 110a,b and 134a,b in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In analyzer 90, intensity is altered by chemiluminescence neutral density filters 158. Light also may pass through other filters, if desired.

Light last passes to a detector, which converts light into signals that may be processed by the analyzer. In analyzer 90, there is one chemiluminescence detector 160. This detector may be selected to optimize detection of blue/green light, which is the type most often produced in chemiluminescence. A preferred detector is a photomultiplier tube, selected for high quantum efficiency and low dark count at chemiluminescence wavelengths (400–500 nanometers).

II. Optics Heads and the Generation of Sensed Volumes

This section describes systems, including top and/or bottom optics heads, for the transmission and/or detection of light, including the generation of sensed volumes. This disclosure is supplemented by the patents, patent applications, and publications identified above under Cross-References, particularly U.S. patent application Ser. No. 09/062,472, filed Apr. 17, 1998, now U.S. Pat. No. 6,071,748; U.S. patent application Ser. No. 09/146,081, filed Sep. 2, 1998, now U.S. Pat. No. 6,187,267; U.S. patent application Ser. No. 09/160,533, filed Sep. 24, 1998, now U.S. Pat. No. 6,097,025; U.S. patent application Ser. No. 09/302,158, filed Apr. 29, 1999; and U.S. patent application Ser. No. 09/629,599, filed Jul. 31, 2000. These supplementary materials are incorporated herein by reference in their entirety for all purposes.

Figure 7:
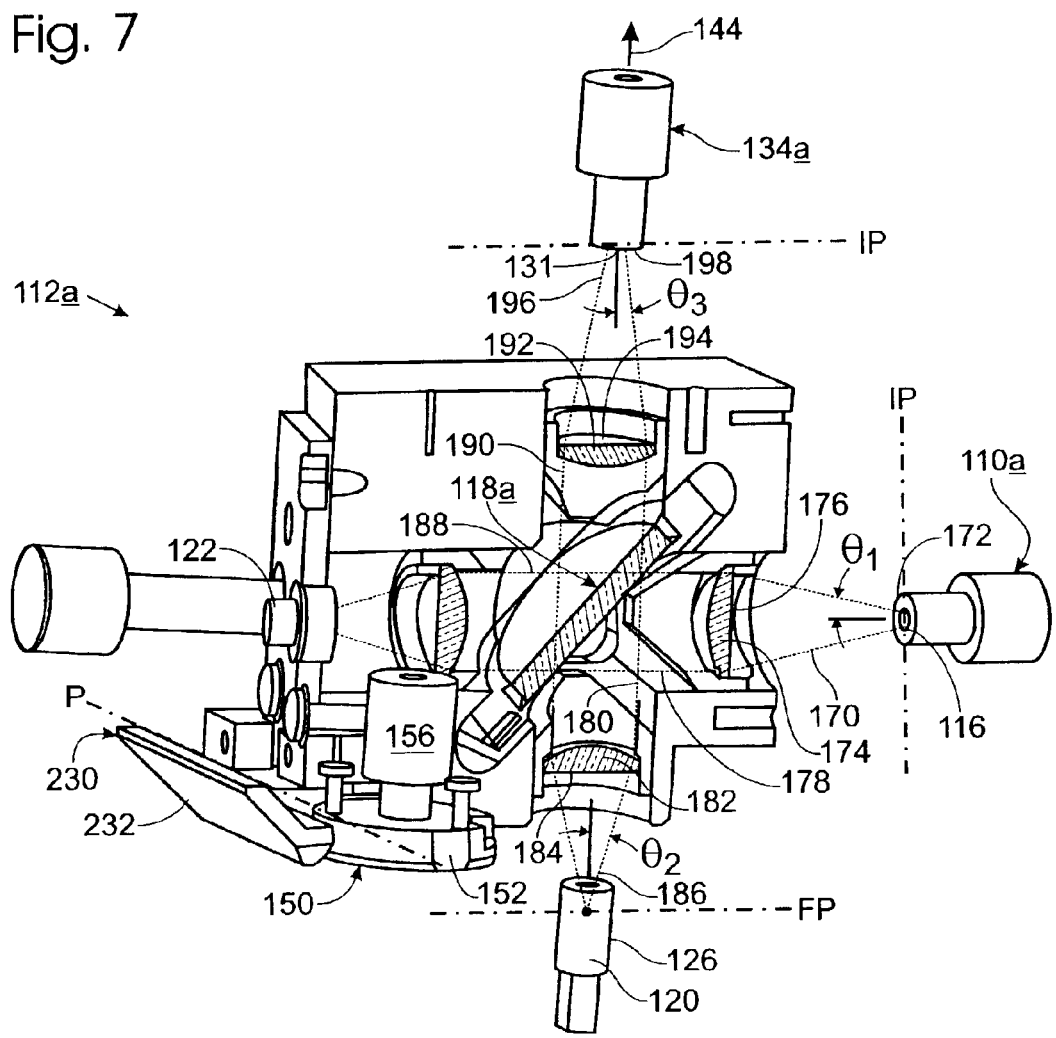
FIG. 7 is a cross-sectional perspective view of a top optics head, in accordance with aspects of the invention.
Figure 7A:
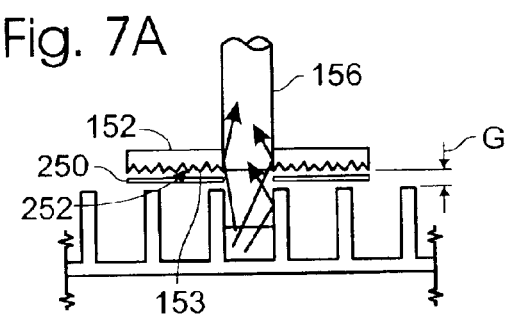
Figure 11:
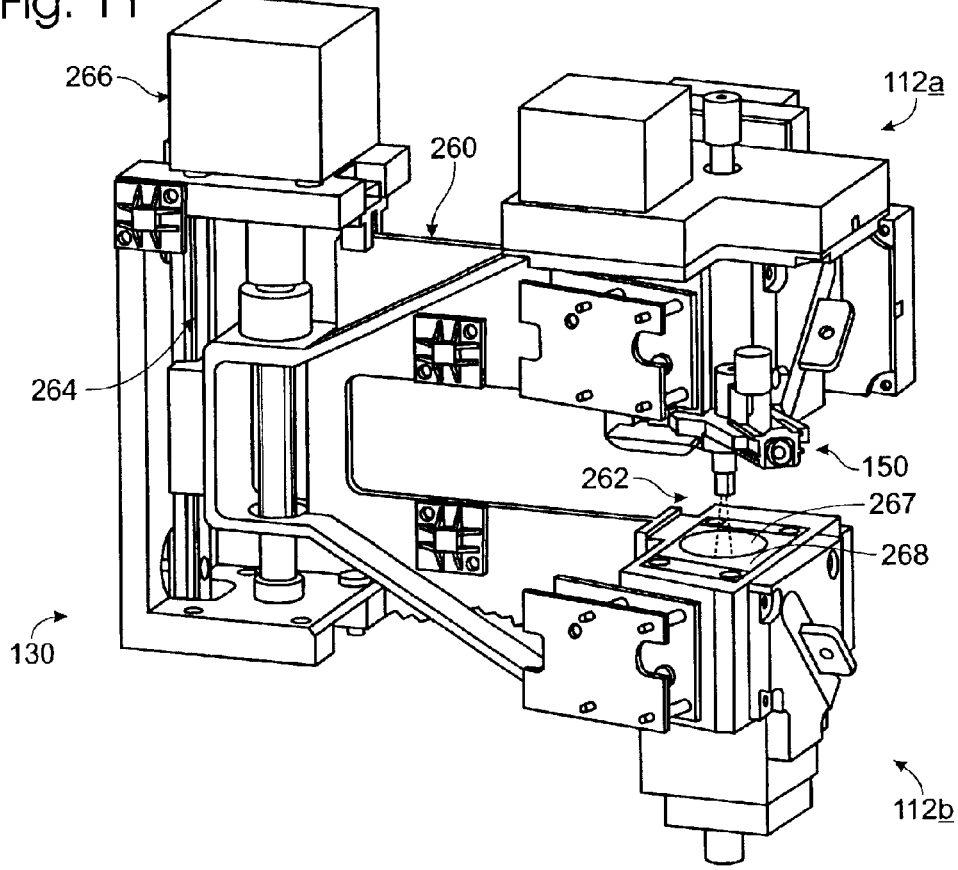
FIG. 11 is a partial perspective view of top and bottom optics heads, in accordance with aspects of the invention.
Figure 12:
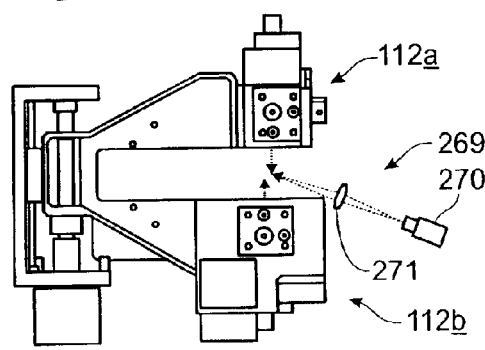
FIG. 12 is a partially schematic side elevation view of the optics assembly shown in FIG. 11, showing side illumination and an offset between the top and bottom optics head.

FIG. 7 shows a cross-sectional view of top optics head 112a, which is used together with fiber optic cables 110a, 134a and apertures 116, 131, as shown in FIG. 5, to create the sensed volume. Top optics head 112a is substantially similar to bottom optics head 112b, as shown in FIGS. 11 and 12, except that top optics head 112a includes chemiluminescence head 150 and excitation and emission polarizers 114, 132 (not shown), and that bottom optics head 112b includes a window and drip lip (described below).

Excitation light arrives at top optics head 112a through excitation fiber optic cable 110a. Fiber optic cables are cylindrical waveguides that transmit light through a process known as total internal reflection. Fiber optic cables are characterized by a numerical aperture, which describes the maximum angle through which the fiber optic cable can collect light for total internal reflection. The higher the numerical aperture, the greater the angle over which the fiber optic cable can collect and transmit light. The numerical aperture is defined as NA=n sin θ, where NA is the numerical aperture, n is the index of refraction of the medium adjacent the fiber optic cable, and θ is the half angle of the cone of transmitted or incident light. In top optics head 112a, the medium adjacent the fiber optic cable is air, so n≅1.

Excitation light exits fiber optic cable 110a through excitation aperture 116 at a cone angle $\theta_1$ determined in part by the numerical aperture of the fiber optic cable. In top optics head 112a, exiting excitation light forms a first cone 170 of excitation light, with its apex positioned just inside the tip 172 of fiber optic cable 110a. First cone 170 of excitation light passes through an excitation polarizer 114 (not shown), and then through a first plano-convex converging lens 174, whose plan side 176 is oriented toward fiber optic cable 110a. First lens 174 is positioned so that it substantially converts first cone 170 of excitation light into a first cylinder 178 of excitation light. This conversion is accomplished by positioning tip 172 substantially at the focal point of first lens 174.

First cylinder 178 of excitation light impinges on beamsplitter 118a. Beamsplitter 118a reflects a reflected cylinder portion 180 of excitation light toward composition 120 in sample well 126. Reflected cylinder portion 180 passes through a second plano-convex converging lens 182, whose plan side 184 is oriented away from beamsplitter 118a. Second lens 182 converts reflected cylinder portion 180 of excitation light into a second cone 186 of excitation light, which is focused onto and thus delivered to composition 120 in sample well 126. The cone angle $\theta_2$ of second cone 186 is determined in part by the numerical aperture of second lens 182, and may be different from the cone angle $\theta_1$ describing excitation light exiting fiber optic cable 110a.

Beamsplitter 118a also transmits a transmitted cylinder portion 188 of the excitation light to light monitor 122, which functions as described above. The optics used to focus the transmitted light into the light monitor may be substantially similar to the optics used to focus the reflected light into the sample well. Alternatively, the optics may include a lensless system, such as a black tapered cone to direct light.

The excitation light may induce photoluminescence within the composition. Photoluminescence (or emission) light has longer wavelengths than the associated excitation light. This is due to conservation of energy; in photoluminescence, the emission light has lower energy (and so longer wavelength) than the excitation light, because some of the energy of the excitation light is lost nonradiatively.

A conical portion of the emission light substantially coextensive with second cone 186 of excitation light passes back through second lens 182, which converts the conical portion into a cylindrical portion of emission light substantially coextensive with reflected cylinder 180 of excitation light.

Emission light next impinges on beamsplitter 118a, which transmits a cylinder portion 190 of emission light toward photoluminescence detector 144. Beamsplitter 118a typically is chosen to accommodate one of two different scenarios. If a large number or variety of luminescent molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable emission light to the detector. If one or a few related luminescent molecules are to be studied, the beamsplitter needs only to be able to accommodate light at a limited number of wavelengths; in this case, a "dichroic" or "multichroic" beamsplitter is optimal. Such a beamsplitter can be designed for the appropriate set of molecules and will reflect most or substantially all of the excitation light, while transmitting most or substantially all of the emission light. This is possible because the reflectivity and transmissivity of the beamsplitter can be varied with wavelength.

Cylinder portion 190 of emission light transmitted through beamsplitter 118a passes through a third plano-convex converging lens 192, whose plan side 194 is oriented away from the beamsplitter. In first optics head 112a, emission light first may pass through an emission polarizer 132, as shown in FIG. 5. Third lens 192 focuses the cylindrical portion 190 of emission light into a third cone of light 196 that impinges on emission fiber optic cable 134a for transmission to photoluminescence detector 144. To be transmitted by the fiber, the light should be focused onto emission aperture 131 at the tip 198 of the fiber as a spot comparable in size to the diameter of the fiber optic cable. Moreover, the incident cone angle $\theta_3$ should not exceed the inverse sine of the numerical aperture of the fiber.

A property of the optical arrangement in top optics head 112a is that the tips 172, 198 of fiber optic cables 110a, 134a and the sensed volume of the composition are "confocal." Confocal means that all three objects are in conjugate focal planes, so that whenever one is in focus, all are in focus. The sensed volume of the composition lies in a focal or sample plane FP of the system, and the tips of the fiber optic cables lie in image planes IP of the system. The detector also may be placed in an image plane, so that it detects the composition in focus. The tips of the fiber optic cables may be said to lie in intermediate image planes, because light passes through these planes, and the detector may be said to lie in a terminal image plane, because light terminates on the detector.

The sensed volume may be created by placing confocal optics elements in or near one or more intermediate image planes. A preferred confocal optics element is an aperture. If such an aperture is placed in the excitation optical path, an image of the aperture will be focused onto the composition. As a result, only a portion of the composition within the focal plane corresponding to the shape and proportional to the size of the aperture will be illuminated, and only luminescent molecules in or near that portion of the focal plane will be induced to emit photoluminescence. If such an aperture is placed in the emission optical path, an image of the aperture will be focused onto the detector. Luminescence that ordinarily would focus onto a part of the detector outside the image of the aperture will be blocked or masked from reaching the detector.

The "shape" (or intensity profile) of the sensed volume depends on the confocal optics elements, such as excitation and emission apertures 116, 131, the light source, and the numerical apertures of the lenses and fiber optic cables. Generally, the intensity of the light incident on (or emitted from) the sensed volume will be greatest at the center of the sensed volume, and will decay monotonically in all directions away from the center. Most of the intensity will lie within a distance equal to about one aperture diameter from the center of the sensed volume in the Z direction, and within about one-half an aperture diameter from the center of the sensed volume in the X and Y directions.

FIG. 7 also shows a sample container sensor switch 230, which is used to prevent damage to optics head 112a by preventing the optics head from physically contacting a sample container. Sample container sensor switch 230 is mounted about a pivot axis P adjacent chemiluminescence head 150. Sample container sensor switch 230 includes a sensor surface 232 positioned so that a sample container must contact the sensor surface before contacting any component of top optics head 112a. Contact between a sample container and sensor surface 232 causes sample container sensor switch 230 to pivot about pivot axis P, activating an electrical circuit that turns off power to the mechanism(s) used to move the sample container.

A sample container sensor switch is especially important in an analyzer designed for use with a variety of sample containers, because it reduces the likelihood of damage both from exotic sample holders with unusual dimensions and from standard sample holders with aberrant or misidentified dimensions. The sample container sensor switch may detect impending contact between the sample container and optics head (1) mechanically, as in the preferred embodiment, (2) optically, as with an electric eye, (3) acoustically, as with an ultrasonic detector, or (4) by other mechanisms. For example, the sample container sensor switch may include a linear voltage displacement transducer (LVDT), which measures displacement by creating a voltage proportional to the displacement.

FIG. 7 also shows a chemiluminescence head 150, which includes a chemiluminescence baffle 152 and a chemiluminescence fiber optic cable 156. Chemiluminescence head 150 is mounted on top optics head 112a, but also could be mounted on bottom optics head 112b or on both top and bottom optics heads 112a,b.

Figure 8:
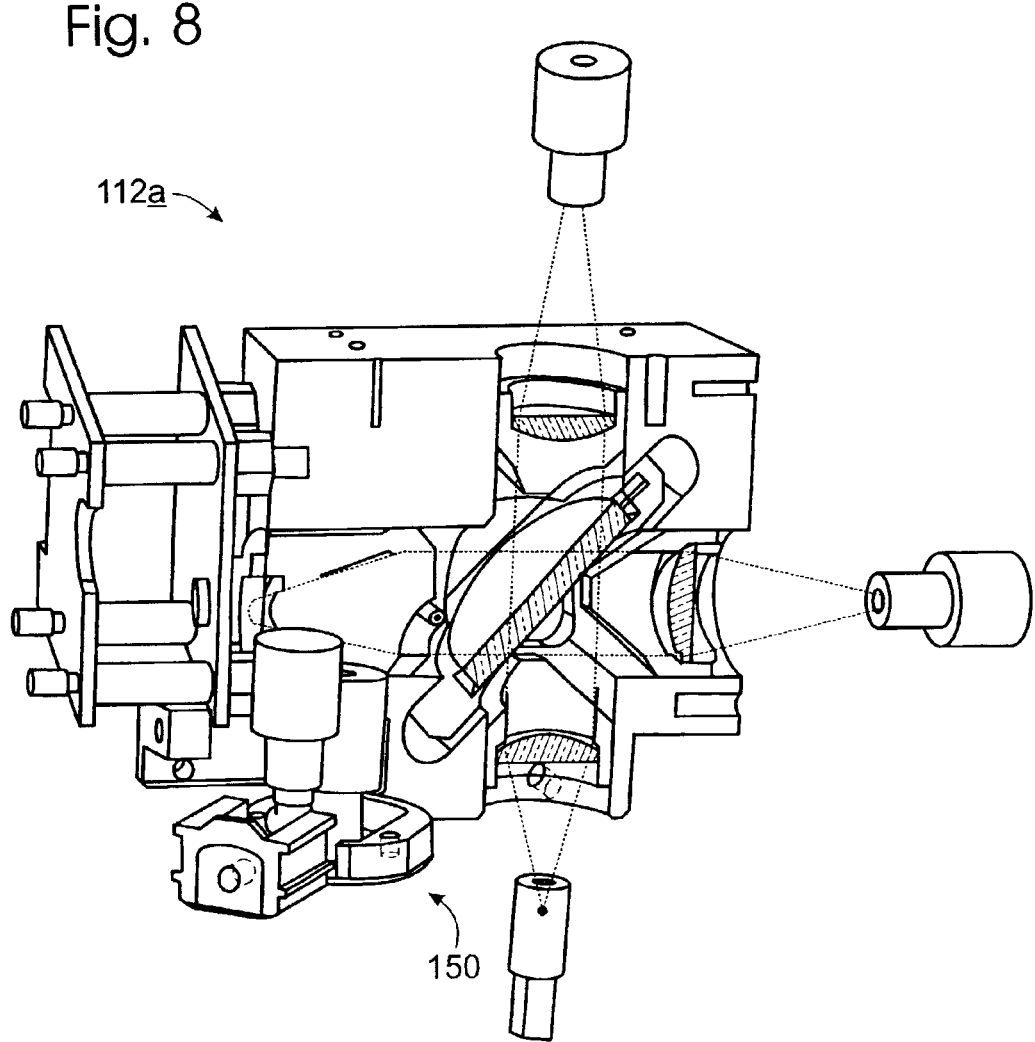
FIG. 8 is a cross-sectional perspective view of an alternative top optics head, in accordance with aspects of the invention.

FIG. 8 shows an alternative embodiment of top optics head 112a, which includes an alternative embodiment of chemiluminescence head 150.

Figure 9:
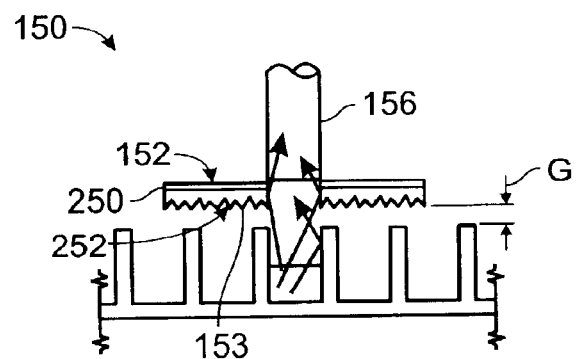
FIG. 9 is a partially schematic cross-sectional view of a chemiluminescence head, in accordance with aspects of the invention.

FIG. 9 shows an alternative view of chemiluminescence head 150. In chemiluminescence, emission light sensitivity is maximized by detecting as much emission light as possible from the top of the sample container. In analyzer 90, this is accomplished by placing fiber optic cable 156 directly above and aligned with the center of the microplate well or other sample container. A high numerical aperture fiber optic cable may be used to collect most or substantially all of the light emitted from the composition. A preferred fiber optic cable has a numerical aperture of 0.22 and is formed of silica for low autoluminescence.

Detection of chemiluminescence light further is enhanced by positioning fiber optic cable 156 so that the gap G or flying height between the fiber optic cable and the top of the sample container is as small as possible. Generally, if the gap between the top of the microplate and the fiber optic cable is small compared to the diameter of the fiber optic cable, most of the emission light will be collected. In analyzer 90, preferred values of G lie in the range 0.25–1.5 mm, depending on the type of microplate. The preferred values allow for normal variations in microplate thickness and minimize the possibility of contacting liquid that may be on the surface of the microplate. This is accomplished by accurate calibration of the travel of the optical head along the Z-axis relative to a reference point on the Z-axis. The height of various microplates can be stored in software so that G can be set by the instrument to a preselected value.

Gap G also can be determined empirically using a precision top-of-plate sensor, which is mounted on the bottom of the upper optics head. The height of the plate is measured by slowly moving the optics head toward the plate until the top-of-plate sensor indicates that a known flying height has been achieved. With this approach, the height of the plate need not be known in advance. Moreover, if a microplate mistakenly is inserted into the machine with a greater than expected height, the top-of-plate sensor can be used to prevent the optics head from colliding with the microplate.

Chemiluminescence head 150 also includes a chemiluminescence baffle 152, which supports fiber optic cable 156 and an aperture support slide 250 and which also minimizes detection of ambient light and chemiluminescence from neighboring wells. Detection from neighboring wells may be referred to as "cross talk." In analyzer 90, chemiluminescence baffle 152 is generally circular and includes a black surface 252 with rugosities 153 designed to absorb light. Chemiluminescence baffle 152 may have a diameter at least about twice the diameter of the fiber optic cable, and may be configured to allow low cross talk to be achieved at comfortable flying heights.

Figure 10:
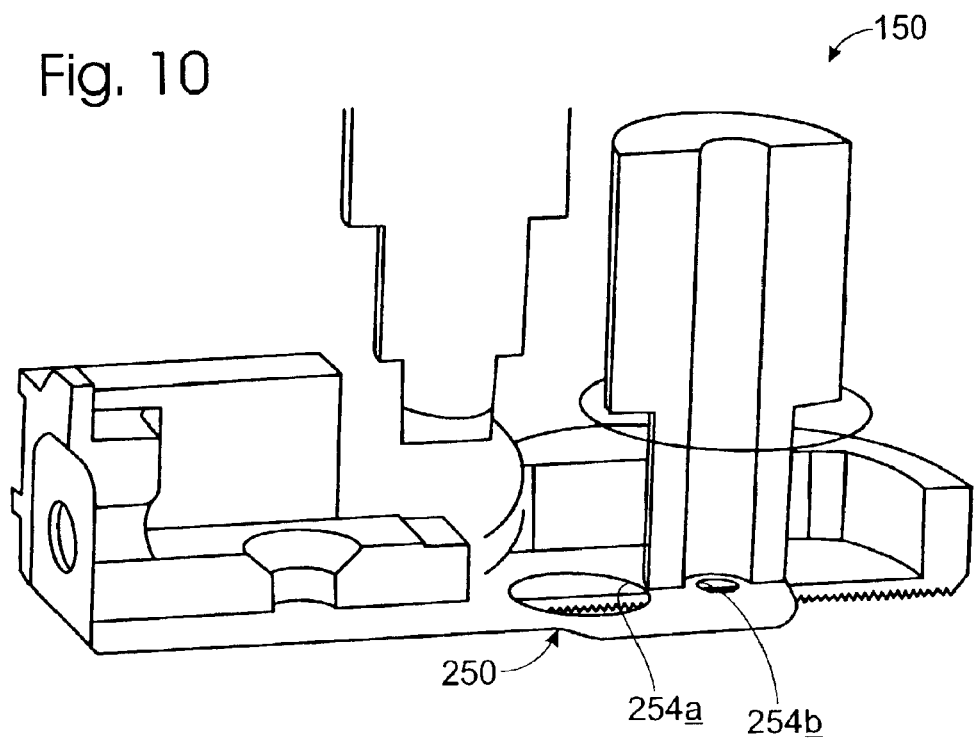
FIG. 10 is a cross-sectional perspective view of a portion of the chemiluminescence head shown in FIG. 8.

FIG. 10 shows a partially cross-sectional perspective view of chemiluminescence head 150. Chemiluminescence head 150 includes a fiber optic cable 156 and an aperture support plate 250 containing apertures 254a,b that determine an "effective" entrance diameter for the fiber optic cable. In turn, the effective entrance diameter for the fiber optic cable determines the size of the sensed volume within the sample. To maximize signal, apertures 254a,b generally are chosen substantially to equal the diameter of the microplate well. Large apertures 254a having diameters larger than fiber optic cable 156, and small apertures 254b having diameters smaller than fiber optic cable 156 may be placed in front of the fiber optic cable. A moveable aperture support slide 250 may include separate apertures for 96, 384, 768, 1536, 3456, and 9600 well plates, among others, where each aperture is optimized for the well size associated with a particular microplate. Alternatively, a fixed aperture support slide 250 may include a continuous iris diaphragm aperture, where the size of the continuous diaphragm may be optimized for a range of well sizes.

Alternative embodiments of the chemiluminescence optical system could include a plurality of chemiluminescence heads optically connected to a plurality of chemiluminescence detectors. The chemiluminescence heads could be mounted as a linear array or as a matrix. For example, a linear array of 8 or 12 chemiluminescence heads optically connected to 8 or 12 detectors could be used to detect simultaneously from entire rows or columns of a 96-well microplate. Moreover, the same arrays also could be used with the appropriate apertures to detect from higher-density plates in which the well-to-well spacing is evenly divisible into the well-to-well spacing in the 96-well plate, as for 384 and 1536-well plates. The chemiluminescence heads also could be mounted as a matrix that could detect from one or more plate formats.

Other alternative embodiments of the chemiluminescence optical system could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

These alternative embodiments may be used with alternative embodiments of chemiluminescence baffle 152. For example, with a fiber optic bundle, cross-talk between wells within the matrix can be minimized by keeping G as small as possible and/or by applying an anti-reflective coating to the face of the fiber bundle. An anti-reflective coating can reduce reflected light from about 4% to less than 1%. In addition, a baffle having a rough black surface as described above could be placed around the outside of the fiber bundle, like a collar, to minimize pick-up from areas of the plate that are not under the bundle.

FIG. 11 shows the relationship between top and bottom optics heads 112a,b and chemiluminescence head 150. Top and bottom optics heads 112a,b are coupled to an optics head support structure 260, which includes a gap 262 through which a stage and sample container can pass. Optics head support structure 260 is configured so that the relative positions of top and bottom optics heads 112a,b are fixed.

FIG. 11 also shows a Z-axis adjustment mechanism 130, which is used to adjust the position of a sensed volume within a composition. Z-axis adjustment mechanism 130 includes a support track 264 that is substantially parallel to a Z-axis on which optics head support structure 260 is mounted. Z-axis adjustment mechanism 130 also includes a motor 266 for moving optics head support structure 260 along support track 264. The position of a sensed volume within a composition positioned in gap 262 is adjusted by moving top and bottom optics heads 112a,b relative to the composition. Movement relative to the composition may be effected by moving the optics heads while keeping the composition stationary, as here, or by moving the composition while keeping the optics heads stationary, among other mechanisms.

FIG. 11 also shows aspects of bottom optics head 112b. Generally, bottom optics head 112b resembles top optics head 112a. However, bottom optics head 112b includes a window 267 and an elevated drip lip 268 that are not included on top optics head 112a. Window 267 and drip lip 268 prevent fluid dripped from a microplate from entering bottom optics head 112b. Fluid dripped from a microplate is a concern with bottom optics head 112b because the bottom optics head is positioned below the microplate during analysis.

FIGS. 11 and 12 show further aspects of bottom optics head 112b. Generally, light is directed through bottom optics head 112b much like light is directed through top optics head 112a. However, light also may be directed by an alternative optical relay structure 269 to the bottom (or top) optics head. Alternative optical relay structure 269 may include a fiber optic cable 270 and focusing lens structure 271. Off-axis illumination eliminates loss of light due to absorption and reflection from the beam splitter and substantially eliminates reflection of incident light into the detection optics, reducing background. Off-axis illumination also may be used for total internal reflection illumination.

FIGS. 11 and 12 also show the relative positions of top and bottom optics heads 112a,b. Top and bottom optics heads 112a,b may be aligned, so that excitation light transmitted by one optics head can be detected by the other optics head, facilitating absorbance assays. A shutter may be positioned between the two optics heads to prevent light from one optics head from entering and exciting fluorescence from the other optics head during luminescence assays. Alternatively, top and bottom optics head 112a,b may be offset, so that light from one optics head cannot enter the other optics head. A small optical relay structure, such as a fiber optic cable, may be positioned adjacent or as part of bottom optics head 112b to detect light in a top illumination and bottom detection mode.

III. Application of Sensed Volumes

The optical systems described above, which may include one or more confocal optics elements, may allow detection of light substantially exclusively from a sensed volume of a composition. This section describes systems, including apparatus and methods, for applying and/or otherwise utilizing sensed volumes for the selective excitation and/or detection of light, particularly luminescence. These and other aspects of the invention are described below, including (A) description of sensed volumes, (B) homogenous vs. cell-based assays, (C) meniscus and geometry, (D) crossplate drift, and (E) sample container sensor switch. This disclosure is supplemented by the patents, patent applications, and publications identified above under Cross-References, particularly U.S. patent application Ser. No. 09/062,472, filed Apr. 17, 1998, now U.S. Pat. No. 6,071,748; U.S. patent application Ser. No. 09/629,599, filed Jul. 31, 2000; U.S. patent application Ser. No. 09/478,819, filed Jan. 5, 2000; and U.S. patent application Ser. No. 09/770,720, filed Jan. 25, 2001. These supplementary materials are incorporated herein by reference in their entirety for all purposes.

A. Description of Sensed Volumes

Figure 13:
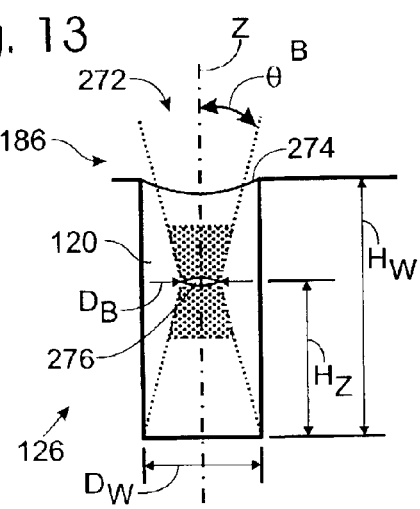
FIGS. 13–16 are schematic views of sensed volumes in microplate wells.

FIG. 13 shows a standard microplate well 126 and an excitation light beam 186 as it illuminates the well. The standard well is cylindrical and may be characterized by a diameter $D_w$ and a height $H_w$. Other wells may have other geometries and be characterized by other quantities; for example, a well could be square and characterized by a width and a height, or a well could be conical and characterized by a cone angle and a height. The interface between composition 120 and the air 272 is termed the meniscus 274 and may be convex, plan, or concave.

Excitation light beam 186 may be focused by the optical system so that it is shaped much like an hourglass along the optical (Z) axis. This hourglass shape arises as the cone of excitation light formed by the optics passes through focus. The diameter $D_B$ of the beam is smallest at the beam's waist 276, corresponding to the focal plane, above and below which the beam diverges monotonically, making an angle $\theta_B$ with respect to the vertical or Z-axis. Values of $D_B$ and $\theta_B$ depend on optical components of the analyzer and may be varied by changing these components. Generally, $D_B$ and $\theta_B$ are inversely related. The distance between the bottom of the well and the beam waist is termed the focal (Z) height, $H_z$.

The shape of the sensed volume, indicated by stippling, may differ in directions parallel and perpendicular to the optical or Z-axis. Parallel to the Z-axis, the shape may be Lorentzian, among others. Perpendicular to the Z-axis, the shape may be Gaussian, or it may be a rounded pulse function, among others. A laser beam might give rise to a Gaussian, whereas a fiber optic bundle might give rise to a rounded pulse function. Generally, lower numerical apertures will create sensed volumes shaped more like cylinders, whereas higher numerical apertures will create sensed volumes shaped more like hourglasses.

The shape and volume of the sensed volume may be adapted like a probe to match the shape and volume of the sample container. Thus, the sensed volume may be expanded for maximum signal in a large sample container, and contracted to avoid nearby walls in a small sample container. The shape and volume of the sample container also may be chosen or designed to conform to the shape and volume of the sensed volume.

Alternatively, the sensed volume may be held constant. In this way, the sensed volume will report on equal volumes of each composition analyzed, so that the analyzer effectively reports "intensive" quantities. Intensive quantities do not depend on the amount of composition in a sample container; in contrast, extensive quantities do depend on the amount of composition in the sample container. This approach can be used to facilitate comparison of results obtained from different-sized sample wells, such as in 96 and 384 well microplates. Alternatively, this approach can be used to facilitate comparison of results obtained from like-sized sample wells containing different volumes of solution, whether by design or by error.

B. Homogeneous vs. Cell-Based Assays

Figure 14:
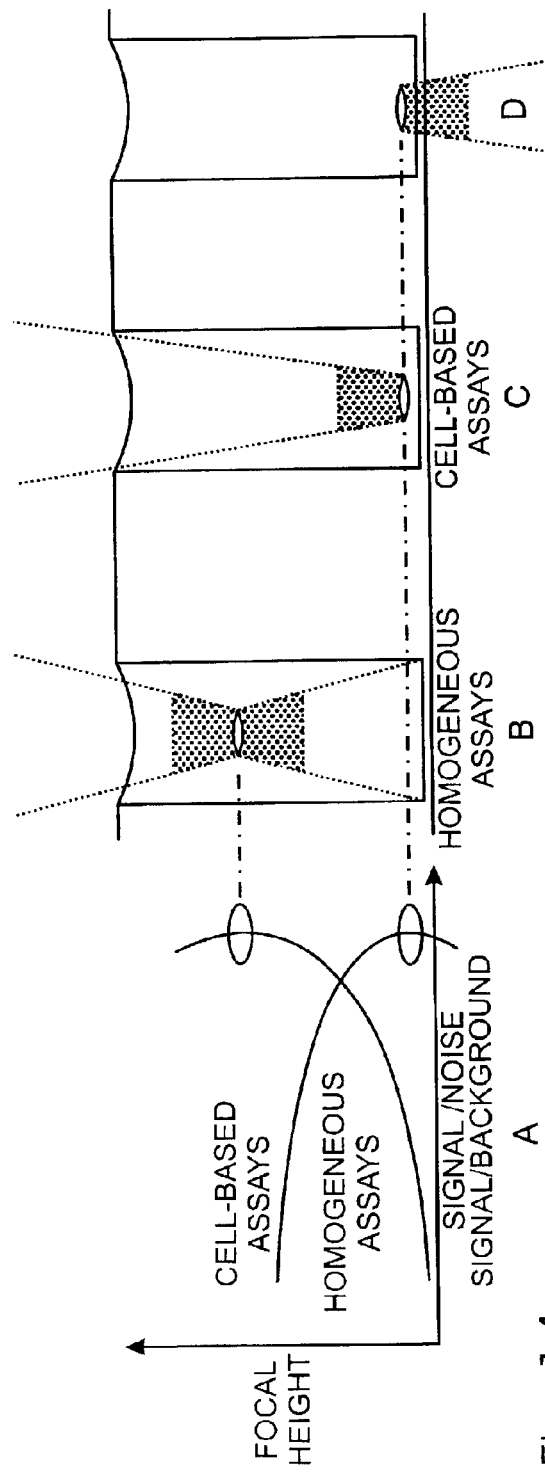

FIG. 14 shows how the signal-to-noise and signal-to-background ratios are affected by focal height for two common assay modes: (1) homogeneous, and (2) cell-based.

B.1 Homogeneous Assay Modes

In homogeneous assays (Panel B), photoluminescent molecules are distributed uniformly throughout the composition, and the optimum signal-to-noise and signal-to-background ratios are obtained regardless of well geometry when the sensed volume is positioned in the middle of the composition (Panel A), so that the sensed volume does not overlap with the meniscus or the bottom or sides of the well. If the meniscus is in the sensed volume, light reflected from the meniscus will be detected. This will decrease sensitivity by increasing background and decreasing signal. If the bottom of the well is in the sensed volume, light reflected from the well bottom will be detected. Moreover, noncomposition photoluminescence arising from fluorescent and other photoluminescent materials that commonly are included in and/or adsorbed to the walls of commercial sample holders such as microplates also will be detected. These two effects will decrease sensitivity by increasing background and decreasing signal. Luminescence measured from the microplate walls will lead to spuriously high luminescence intensities and luminescence polarizations.

B.2 Cell-Based Assay Modes

In cell-based assays (Panels C and D), photoluminescent molecules are concentrated in or near cells growing at the bottom of the well, and the optimum signal-to-noise and signal-to-background ratios are obtained when the sensed-volume is centered about the bottom of the well (Panel A). Such centering may be accomplished either using top optics (Panel C) or bottom optics (Panel D).

Microplate wells having a frusto-conically-shaped portion may be particularly advantageous in some cell-based assays. The conical shape of the well tends to focus cells into a smaller area defined by the substantially flat bottom wall. The conical shape of the well and the selected confocal optics allow substantially all of the cells at the bottom of the well to be detected in the sensed volume, thus maximizing signal sensitivity and reagent utilization regardless of whether the cells are uniformly distributed across the bottom of the well. The conical geometry of the wells also makes it possible to perform cell-based assays from the top without requiring transmission of light through the bottom wall of the well. The geometry is also useful for performing fluorescence polarization assays which may be based on receptor/ligand binding to the bottom of the well.

C. Meniscus and Geometry Effects

The shape and position of the sensed volume within a sample well may be affected by (1) the meniscus (i.e., the fluid/air interface) and (2) the geometry of the sample well, among other factors.

C.1 Meniscus Effects

Figure 15:
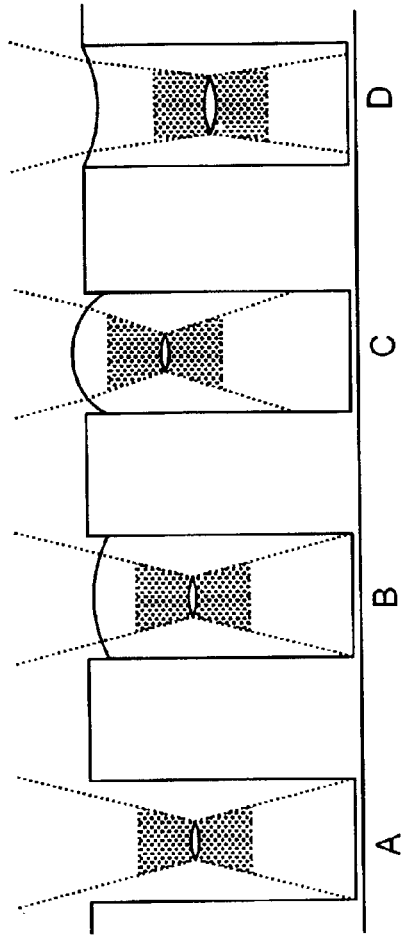

FIG. 15 shows how the meniscus affects the shape and position of the sensed volume within a sample well. The meniscus affects the sensed volume because light is refracted as it crosses the meniscus boundary between the air and the composition. Specifically, light passing from air (with its lower index of refraction) into the composition (with its higher index of refraction) bends toward the normal, as described by Snell's law. Here, the normal is the direction perpendicular to the surface of the meniscus at a given point. If there is no fluid and hence no meniscus, the beam has a nominal undistorted shape (Panel A). If the meniscus is everywhere perpendicular to the light beam, then light passing through the meniscus will not bend, and the beam will retain its nominal undistorted shape (Panel B). For a converging beam, this will occur when the meniscus is appropriately convex. If the meniscus is more than appropriately convex, light will bend toward the middle of the well as it passes through the meniscus, and the sensed volume will be compressed and raised (Panel C). If the meniscus is less than appropriately convex, flat, or concave, light will bend away from the middle of the well as it passes through the meniscus, and the sensed volume will be stretched and lowered (Panel D).

C.2 Geometry Effects

Figure 16:
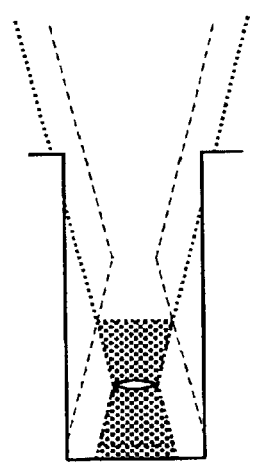
Figure 17:
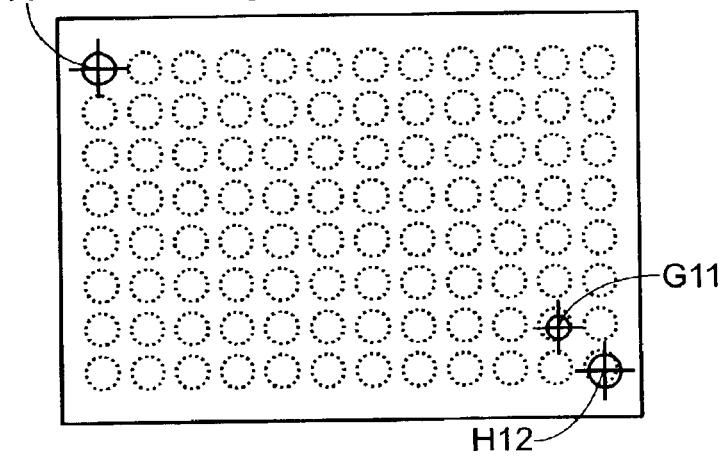
FIG. 17 is a schematic top view of a microplate, showing cross-plate drift.

FIGS. 16 and 17 show how the geometry of the microplate well affects the position of the sensed volume. In particular, if the well is sufficiently narrow relative to the diameter of the beam or if the well is sufficiently deep relative to the angle made by the beam, then the light beam may impinge upon the top walls of the well. In these cases, setting the Z-height too low can reduce sensitivity (1) by decreasing the desired signal because less light enters the well, and (2) by increasing the background because the light beam illuminates the tops of wells. Many microplates are made from materials that are fluorescent or otherwise photoluminescent, and the instrument will detect this photoluminescence from materials at the tops of wells.

D. Cross-Plate Drift

FIG. 17 shows how the geometry of the microplate affects the position of the sensed volume. The analyzer is configured automatically to find the location of each well in a given microplate, beginning with well A1. The analyzer does this using stored parameters describing the dimensions (plate heights, interwell distances, etc.) of the particular microplate style. However, these microplate parameters are nominal values and do not account for unit-to-unit or lot-to-lot variations in microplate geometry. If there is a slight variation in interwell distance, the light beam can be off-center on some wells even though it is perfectly centered on well A1. This effect is termed cross-plate drift.

Cross-plate drift of fluorescence readings may increase as the instrument scans across the microplate as variations are compounded. Typically, drift will be worst at well H12, which is farthest from well A1. Such drift can be reduced by making the stage more accurate, by making the sample containers of a more consistent size, or by increasing $H_Z$, which will reduce the diameter of the beam and put it back into the well. The lattermost approach is shown for well G11.

Figure 18:
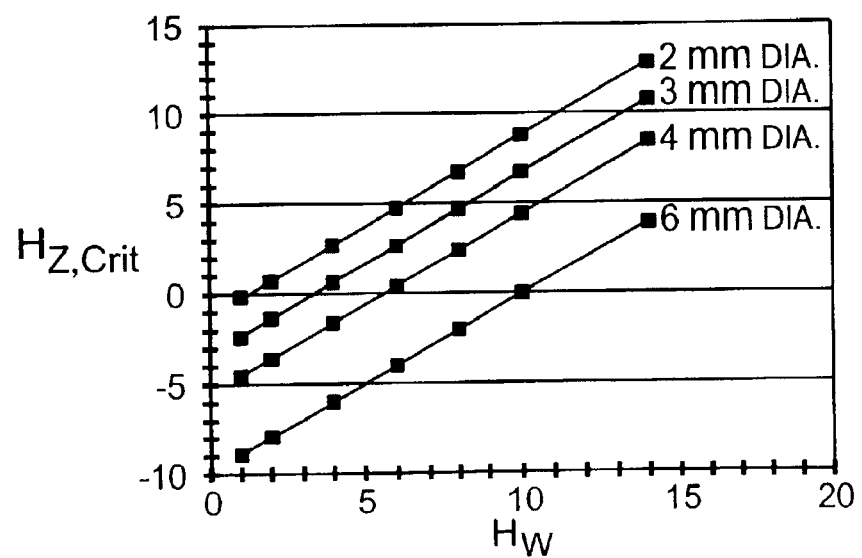
FIG. 18 is a graph showing the relationships between critical Z-height and microplate well height.

Because beam position is a critical determinant of signal-to-noise ratios, Z height must be appropriately maintained; Z height should be kept above a critical focal height, $H_{Z,Crit}$. The height at which the beam first impinges on the walls of the well is the critical focal height, $H_{Z,Crit}$. FIG. 18 shows how $H_{Z,Crit}$ depends on the well height $H_W$ and well diameter $D_W$, for a beam of diameter 1.5 millimeters (mm) and a beam angle $\theta_B$ of 25.4 degrees. Similarly, Table 1 shows how $H_{Z,Crit}$ depends on well height and well diameter for four commercially available microplates.

TABLE 1

| Plate Type | Well Height (mm) | Well Diameter (mm) | $H_{Z,Crit}$ (mm) |
|---|---|---|---|
| Costar Black Flat Bottom 96-Well 3915 | 10.71 | 6.71 | −0.85 |
| Dynatech MicroFluor Round Bottom | 9.99 | 6.78 | −1.72 |
| Costar Black 384-Well 3710 | 11.55 | 3.66 | 6.76 |
| Packard White 384-Well #6005214 | 11.57 | 3.71 | 6.67 |

The increase in $H_{Z,crit}$ shows that for a microplate having a standard height and XY area, as the aspect ratio (length/diameter) and density of wells increases, the ability of a confocal optic system to read small volumes in standard straight-walled wells decreases. This may require reading through the bottom of the well for cell-based assays, which is not always convenient or practical.

Z-height can be optimized for a particular microplate and assay by (1) preparing a test microplate with representative assay (e.g., blanks, positive and negative controls, dilution series), (2) and reading the microplate multiple times at different Z-heights to determine the Z-height that gives the best signal-to-background data. Some combinations of assay and microplate are relatively insensitive to Z-height, while others demonstrate a distinct optimum.

The use of reference fiducials to correct for cross-plate drift and other defects in alignment (as well as to identify plates and/or assays) is described in U.S. patent application Ser. No. 09/156,318, filed Sep. 18, 1998, now U.S. Pat. No. 6,258,326, which is incorporated herein by reference in its entirety for all purposes.

E. Sample Container Sensor Switch

A sample container sensor switch may be mounted on the analyzer (e.g., on the top optics head) to prevent the plate from contacting portions of the analyzer such as the optics head if the plate is misaligned or improperly specified, or if the Z-height is set incorrectly. This sensor may be used to eject a sample holder and/or halt relative movement of the sample holder and analyzer if the sensor detects a fault.

IV. Light Source and Detector Modules

This section describes systems, including apparatus and methods, for transmitting light, particularly through an aperture in a surface substantially without leakage. In one embodiment, the device comprises an optical relay structure having an end configured to transmit light, and an opaque collar positioned around the end and configured to reorient to conform to the surface when the end and the aperture are aligned. In another embodiment, the device comprises an optical relay structure having an end configured to transmit light, and an opaque collar positioned around the end and spring-biased relative to the end, so that the opaque collar is forced against the surface when the end and the aperture are aligned. The devices further may include a stop mechanism for limiting movement of the opaque collar, a registration mechanism for aligning the end and the aperture, and a light source and/or a detector for generating or detecting light, among others These and other aspects of the invention are described below, including (A) background, (B) summary, (C) detailed description, and (D) examples. This disclosure is supplemented by the patents, patent applications, and publications identified above under Cross-References, particularly U.S.

patent application Ser. No. 09/118,310, filed Jul. 16, 1998, now U.S. Pat. No. 6,033,100. These supplementary materials are incorporated herein by reference in their entirety for all purposes.

A. Background

Optical systems typically include many components, which interact to generate, transmit, modify, and detect light. These components often are modular, permitting them to be combined in different ways for different applications. This modularity enhances flexibility but may diminish efficiency. In particular, gaps between modular components may permit stray (e.g., room) light to enter the optical system, lowering the signal-to-background ratio. Such gaps also may permit signal light to exit the system, lowering the signal.

Stray light has been reduced mostly by reducing the amount of ambient light available to enter the system. In some cases, stray light has been reduced by placing the entire optical system in a light-tight room, which is darkened when the optical system is in use. Unfortunately, this approach has a variety of shortcomings. It requires a dedicated room, which wastes space. It also requires the operator of the optical system to work in the dark, which is inherently unsafe, because the operator may have difficulty seeing the equipment, and because the operator may become drowsy. In other cases, stray light has been reduced by placing all or part of the optical system in a light-tight container. Unfortunately, this approach also has a variety of shortcomings. It hinders access to the components. It also reduces flexibility, because components must be chosen and arranged to fit within the container.

Signal light has been retained mostly by precisely aligning the optical system. Unfortunately, this approach also has a variety of shortcomings. In particular, it works best when optical components are fixed in position. It works less well when optical components are subject to vibration or when optical components must be moved during operation, such as in switching among plural light sources, detectors, and optical paths.

B. Summary

The invention provides systems, including devices and methods, for transmitting light through an aperture in a surface substantially without leakage, so that less stray light is introduced into optical systems and less signal light is lost.

These systems may include, in one aspect, (1) an optical relay structure having an end configured to transmit light, and (2) an opaque collar positioned around the end and configured to reorient to conform to the surface when the end and the aperture are aligned, so that a substantially light-tight junction is formed. In this embodiment, the opaque collar further may be spring-biased relative to the end, so that the opaque collar is forced against the surface when the end and the aperture are aligned.

These systems also may include, in another aspect, (1) an optical relay structure having an end configured to transmit light, and (2) an opaque collar positioned around the end and spring-biased relative to the end, so that the opaque collar is forced against the surface when the end and the aperture are aligned, so that a substantially light-tight junction is formed. In this embodiment, the opaque collar may be configured to reorient to conform to the surface when the end and the aperture are aligned.

These systems also may include, in yet other aspects, (1) a stop mechanism for limiting movement of the opaque collar, (2) a registration mechanism for aligning the end and the aperture, (3) a light source and/or a detector for generating or detecting light, and/or (4) methods for forming and maintaining substantially light-tight junctions.

C. Detailed Description

Figure 19:
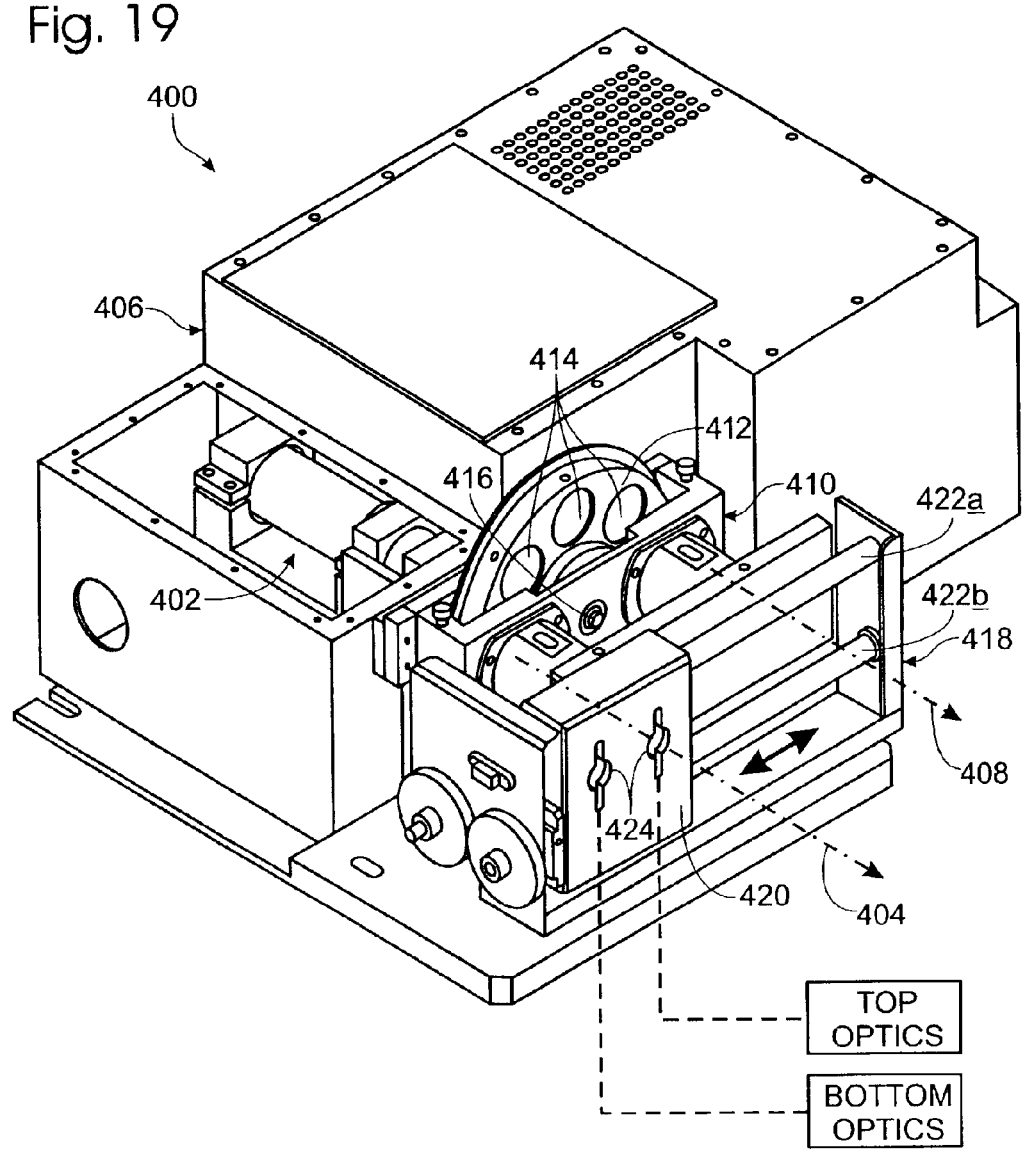
FIG. 19 is a partial perspective view of a light source module, in accordance with aspects of the invention.

FIG. 19 is a perspective view of a light source module 400 employed in an embodiment of the invention. Portions of the module case have been removed to reveal internal componentry. Light source module 400 includes at least two light sources. A flashlamp 402 transmits light along a first light path 404. A second light source, namely, a continuous arc lamp (not shown) housed in compartment 406, transmits light along a second light path 408. A filter wheel assembly 410 is positioned adjacent the light sources. Filter wheel assembly 410 includes a filter wheel 412, which holds a plurality of filters 414. Filter wheel 412 is rotatable around an axis 416, so that a given filter can be positioned interchangeably along light path 404, or along light path 408, by rotating filter wheel 412. A fiber optic shuttle assembly 418 is mounted next to filter wheel assembly 410. Moveable shuttle 420 translates along support tracks 422a and 422b, so that moveable shuttle 420 can be positioned in front of a selected light source for a selected assay application. Two fiber optic ports 424 are provided on an external face of shuttle 420. Fiber optic ports 424 direct light, via fiber optic cables, from a selected source either to a top optics head or to a bottom optics head, above and below a stage holding a sample, respectively.

Figure 20:
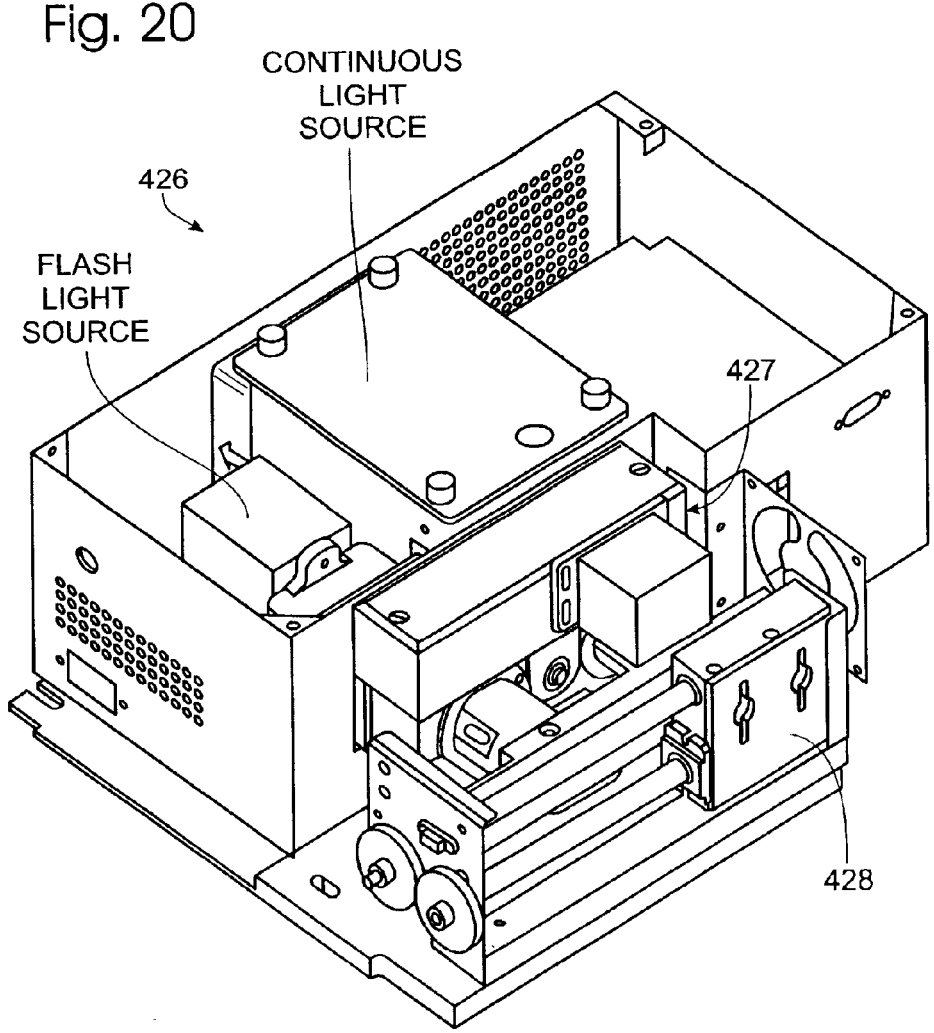
FIG. 20 is a partial perspective view of an alternative light source module, in accordance with aspects of the invention.

FIG. 20 is a perspective view of an alternative light source module 426. In this embodiment, filter wheel assembly 410 of light source module 400 has been replaced by an alternative filter wheel assembly 427. A moveable shuttle 428 is shown in an alternative position relative to moveable shuttle 420 in light source module 400.

Figure 21:
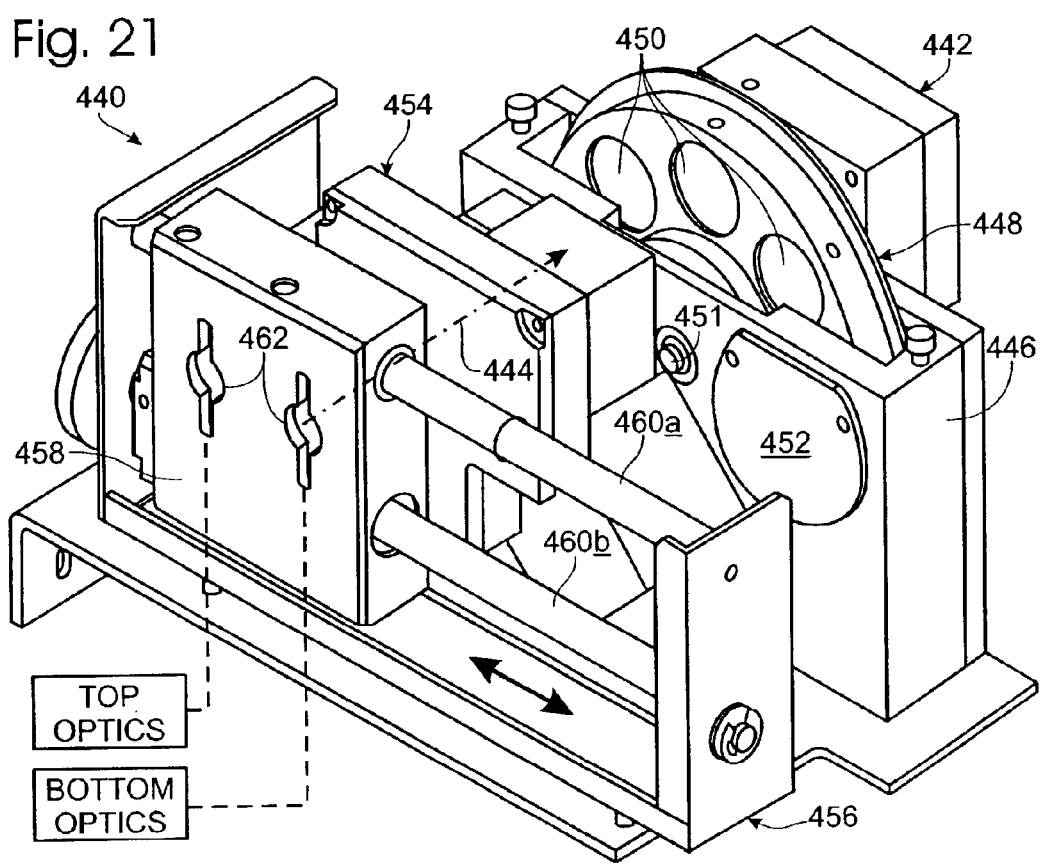
FIG. 21 is a partial perspective view of a detector module, in accordance with aspects of the invention.

FIG. 21 is a perspective view of a detector module 440 employed in an embodiment of the invention. Portions of the module case have been removed to reveal internal componentry. Detector module 440 is similar to light source module 400. A detector 442 receives light directed along a light path 444, originating from a sample. A filter wheel assembly 446 is positioned in front of detector 442. Filter wheel assembly 446 includes a plurality of filters 450 and is rotatable around an axis 451 by a stepper, DC servo, or other motor. The filter wheel can be rotated at a preselected angular speed to allow synchronization with a flash lamp light source and a detector. A port 452 for a second detector is provided in filter wheel assembly 446, so that a second detector can be mounted in detector module 440. A given filter in filter wheel 448 can be positioned along a first light path 444 leading to detector 442, or alternatively can be positioned along a second light path leading to a second detector (not shown). An attenuator mechanism 454 is mounted adjacent filter wheel assembly 446. A fiber optic shuttle assembly 456 is mounted in front of attenuator mechanism 454. Shuttle assembly 456 includes a moveable shuttle 458, which is moveable along upper and lower support tracks 460a and 460b, respectively. An exterior face of shuttle 458 has two fiber optic ports 462, one of which is connected, via a fiber optic cable, to a top optics head above the examination site, the other of which is connected, via a fiber optic cable, to a bottom optics head below the examination site. In operation, moveable shuttle 458 can be moved along support tracks 460a and 460b to connect optically either one of the optics heads to any one of the detectors (if more than one is included in the module), and through any one of filters 450 in filter wheel 448.

Figure 22:
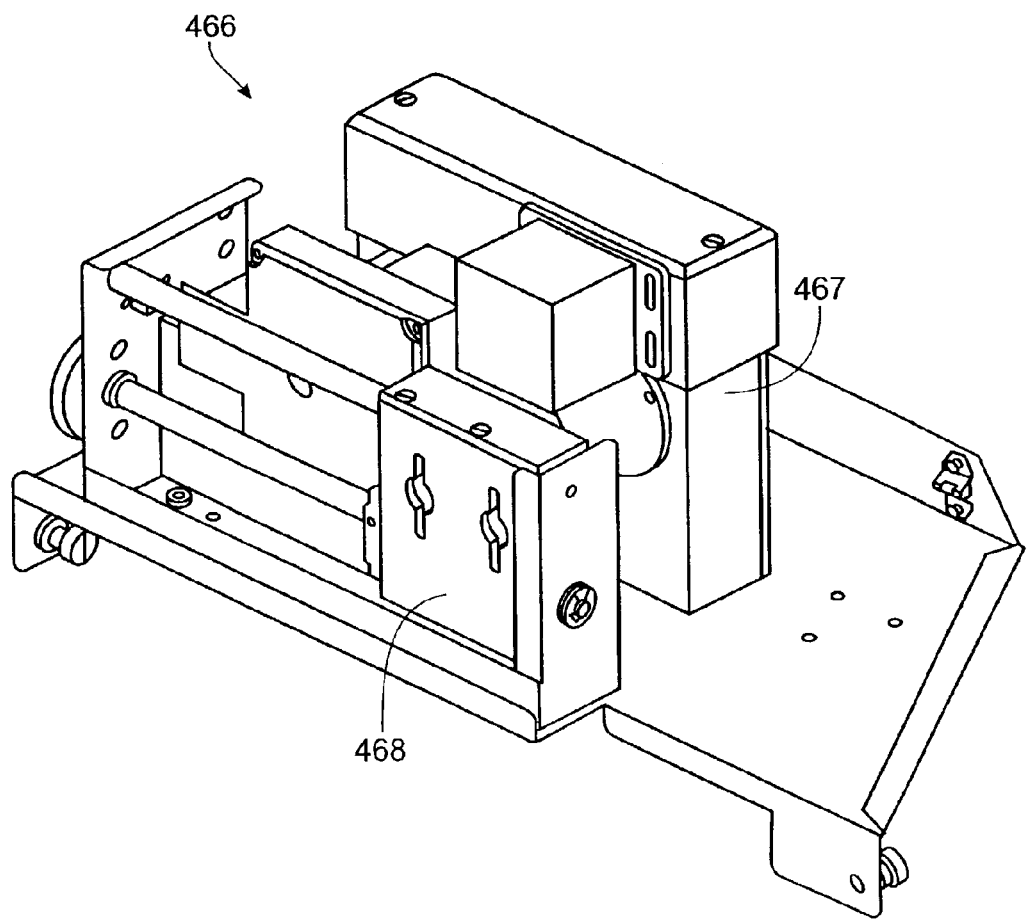
FIG. 22 is a partial perspective view of an alternative detector module, in accordance with aspects of the invention.

FIG. 22 is a perspective view of an alternative detector module 466. In this embodiment, filter wheel assembly 446 of detector module 440 has been replaced by an alternative filter wheel assembly 467. A moveable shuttle 468 is shown in an alternative position relative to moveable shuttle 458 in detector module 440.

Light source and detector modules are designed for flexibility. Additional ports for fiber optics or other optical relay structures may be provided, if desired. The number and configuration of such other ports may be tied to the number and configuration of light-transmission routes through the filter wheel. Optical components also may be connected directly to the moveable shuttle. Such a connection would be especially useful for small, dedicated components, such as a beamsplitter and photodiode-type detector that could sample a portion of the light transmitted through the port to correct for output fluctuations from a light source.

A comparison of FIGS. 19 and 21, and FIGS. 20 and 22, shows that many aspects of light source modules 400 and 426 and detector modules 440 and 466 are the same, particularly the mechanics of filter wheel assemblies 410 and 446, filter wheel assemblies 427 and 467, and fiber optic shuttle assemblies 418 and 456. The light source and detector modules both function as registration mechanisms that align the end of an optical relay structure with an aperture in a surface. This surface may enclose a light source, detector, or other optical component. The light source and detector modules both permit alignment with two such apertures, and with portions of a surface not including an aperture to prevent the optical relay structure from transmitting light. Light source and detector modules also may be configured to transmit light directly from module to module, using air, a tube, or other mechanism to transmit light. If used together in a light detection device, the light source and detector modules provide a great deal of analytical flexibility to select different combinations of light sources, detectors, and filters for different applications, while also being able to select different combinations of top versus bottom illumination and detection orientations.

Figure 23:
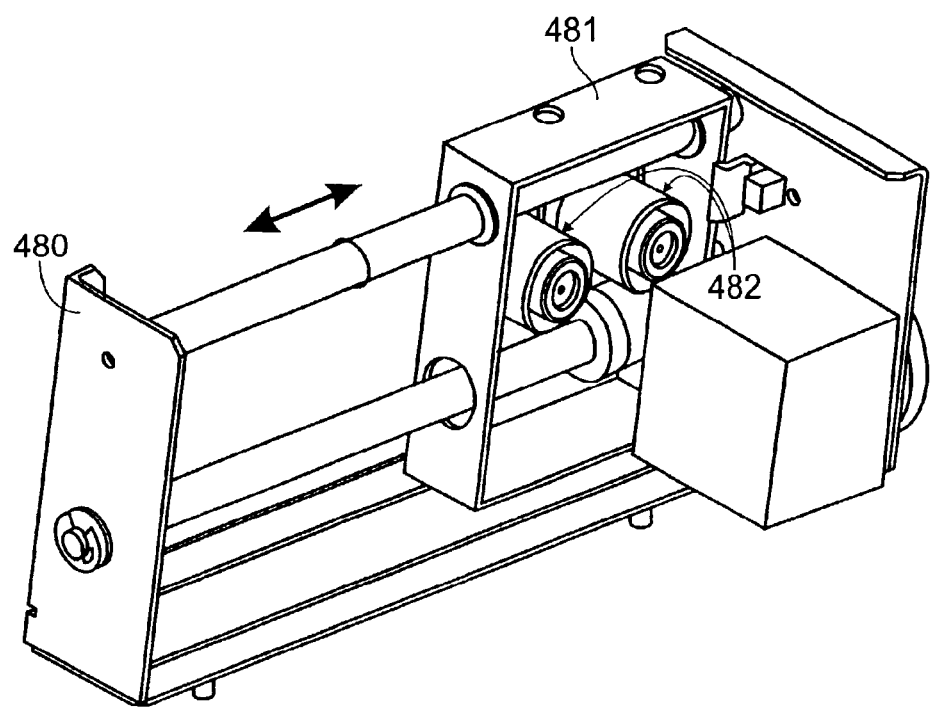
FIG. 23 is a partial perspective view of a fiber optic shuttle assembly, in accordance with aspects of the invention.

FIG. 23 is a partial perspective view of a fiber optic shuttle assembly 480 like those used in light source module 400 and detector module 440. Fiber optic shuttle assembly 480 includes a moveable shuttle 481 and two floating head assemblies 482. Among other applications, each floating head assembly 482 may be used to create and maintain a light-tight connection between selected light sources or detectors and fiber optic cables, such as those that lead to an examination site, or to a top optics head or a bottom optics head, above and below a stage, respectively.

Figure 24:
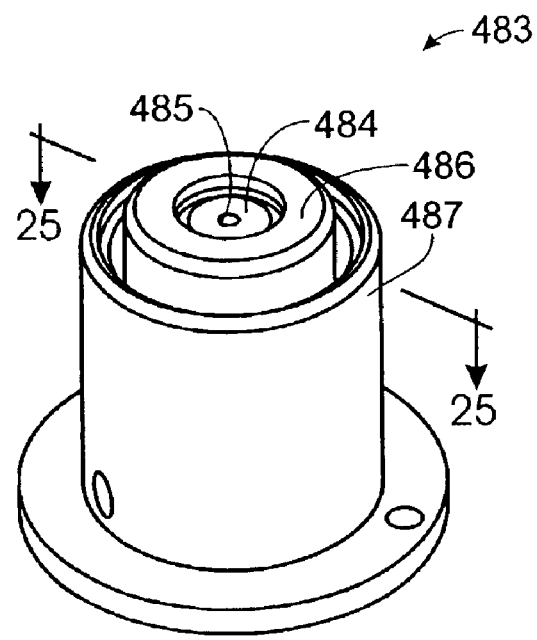
FIG. 24 is a perspective view of a floating head assembly employed in the fiber optic shuttle assembly shown in FIG. 23.

FIG. 24 shows a perspective view of a floating head assembly 483 employed in an embodiment of the invention. Generally, floating head assembly 483 includes a fiber optic ferule 484 having an end 485 configured to transmit light, and an opaque collar 486 positioned around the end. Fiber optic ferule 484 is used to transmit light. Fiber optic ferule 484 may be replaced by a portion of a light source, detector, or other optical component. Opaque collar 486 is used to block light and preferably comprises a hard plastic material. Opaque collar 486 encompasses and extends beyond end 485. An opaque base structure 487 contains additional elements. Together, opaque collar 486 and base structure 487 form a pair of concentric, partially overlapping walls positioned around fiber optic ferule 484.

Figure 25:
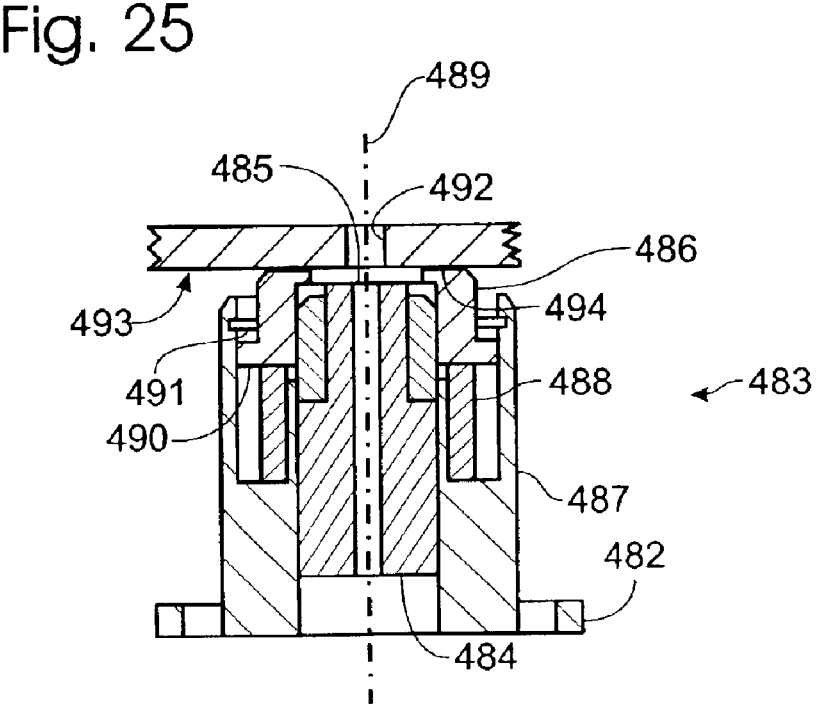
FIG. 25 is a cross-sectional view of the floating head assembly shown in FIG. 24, taken generally along the line 25—25 in FIG. 24.

FIG. 25 is a cross-sectional view of floating head assembly 483. A spring 488 is positioned between portions of opaque collar 486 and base structure 487. Spring 488 generally comprises any elastic body or other device that recovers its original shape when released after being distorted. Spring 488 is configured to spring-bias opaque collar 486 relative to end 485 when spring 488 is compressed between opaque collar 486 and base structure 487. Spring 488 bias pushes opaque collar 486 and base structure 487 in opposite directions parallel to a central axis 489 running through fiber optic ferule 484. A flange 490 on opaque collar 486 contacts a retaining ring 491 on base structure 487 when opaque collar 486 is maximally extended, limiting relative movement of opaque collar 486 and base structure 487. Additional or alternative stop mechanisms also may be employed, such as a set screw.

In use, floating head assembly 483 is positioned such that fiber optic ferule 484 is aligned with an aperture 492 in a surface 493, so that light may be transmitted between fiber optic ferule 484 and aperture 492. When end 485 and aperture 492 are aligned, a leading rim edge 494 of opaque collar 486 is spring-biased or forced against surface 493 by compression of spring 488. Leading rim edge 494 defines an end plane that is moveable relative to central axis 489. Opaque collar 486 and thus leading rim edge 494 automatically float or reorient relative to surface 493, forming a substantially light-tight junction by changing angle relative to central axis 489. This substantially light-tight junction substantially prevents stray light from entering the system, and it substantially prevents signal light from exiting the system. Spring 488 is relatively more compressed where surface 493 is closer to floating head assembly 483 and relatively less compressed where surface 493 is farther from floating head assembly 483, so that contact between opaque collar 486 and surface 493 is maintained for different positions and/or orientations of surface 493. Portions of opaque collar 486 may be formed of a material that deforms under pressure from spring 488 to conform substantially to asperities or other irregularities in surface 493.

Figure 26:
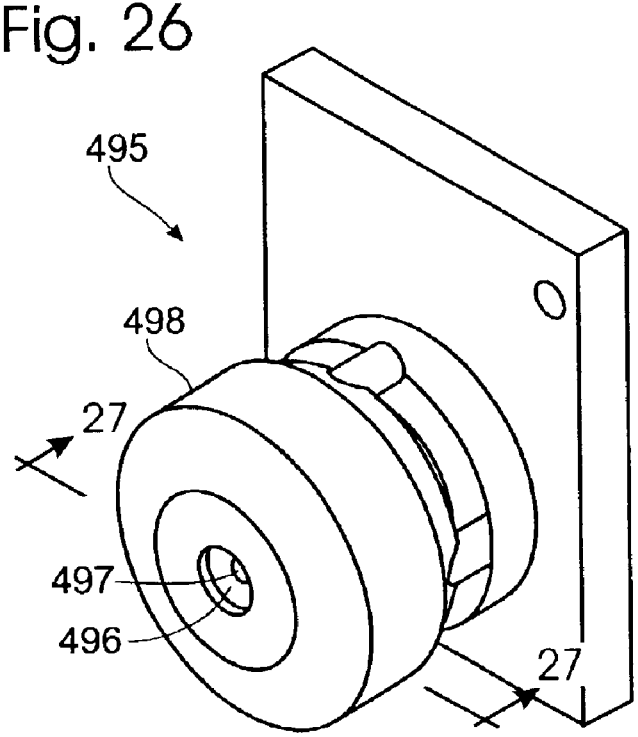
FIG. 26 is a perspective view of an alternative floating head assembly, in accordance with aspects of the invention.

FIG. 26 shows a perspective view of an alternative floating head assembly 495. Generally, alternative floating head assembly 495 includes a fiber optic cable 496 having an end 497 configured to transmit light, and an opaque collar 498 positioned around the end.

Figure 27:
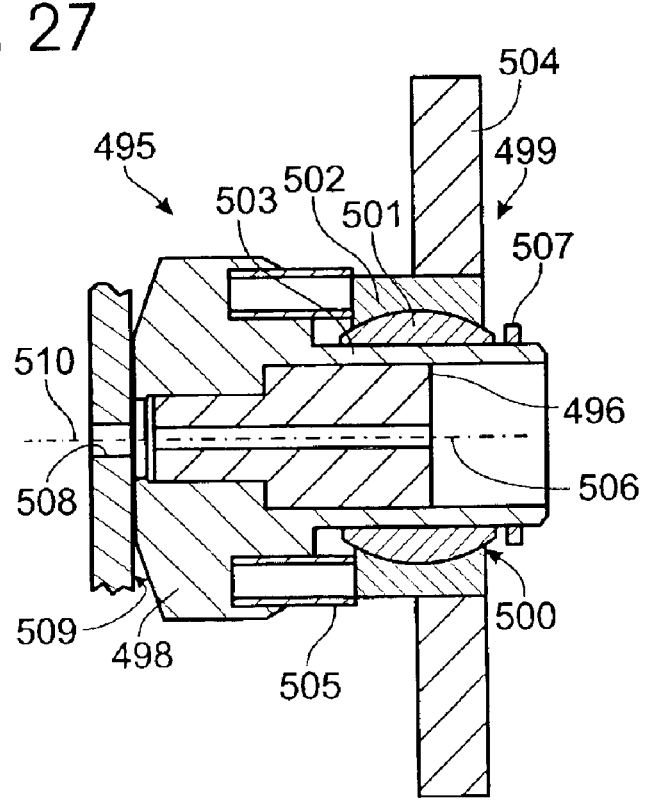
FIG. 27 is a cross-sectional view of the alternative floating head assembly shown in FIG. 26, taken generally along the line 27—27 in FIG. 26.

FIG. 27 shows a cross-sectional view of alternative floating head assembly 495. Fiber optic ferule 496 and opaque collar 498 are supported by a base structure 499 that includes a spherical bearing 500 having an inner race 501 and an outer race 502. Inner race 501 is slidingly connected to a sleeve portion 503 of opaque collar 498 that extends along fiber optic ferule 496. Outer race 502 is connected to a platform structure 504 used for mounting alternative floating head assembly 495. A spring 505 is positioned between portions of opaque collar 498 and outer race 502. Spring 505 bias pushes opaque collar 498 and base structure 499 in opposite directions parallel to a central axis 490 running through fiber optic ferule 496. A retaining ring 507 prevents over-extension of opaque collar 498.

In use, alternative floating head assembly 495 is positioned, like floating head assembly 483, such that fiber optic ferule 496 is aligned with an aperture 508 in a surface 509, so that light may be transmitted between fiber optic ferule 496 and aperture 508. When so aligned, opaque collar 498 and fiber optic ferule 496 are free to compress and extend due to the action of spring 505, and to swivel and reorient due to the action of spherical bearing 500, relative to surface 509. The combined actions of spring 505 and spherical bearing 500 ensure that central axis 506 of fiber optic ferule 496 always is substantially parallel to an aperture axis 510 running through aperture 508, unlike with floating head assembly 483.

D. Examples

The following numbered paragraphs describe additional and/or alternative aspects of the invention:

1. A device for transmitting light through an aperture in a surface, the device comprising (A) an optical relay structure having an end configured to transmit light; and (B) an opaque collar positioned around the end and configured to reorient to conform to the surface when the end and the aperture are aligned, so that a substantially light-tight junction is formed.

2. The device of paragraph 1, wherein the optical relay structure includes a central axis and the opaque collar includes a leading rim edge defining an end plane, the opaque collar reorienting by changing angle relative to the central axis.

3. The device of paragraph 1, wherein the opaque collar is spring-biased relative to the end, so that the opaque collar is forced against the surface when the end and the aperture are aligned.

4. The device of paragraph 1, further comprising (A) a base; (B) a spring operatively associated with the base, wherein the opaque collar is spring-biased relative to the end when the spring is compressed between the opaque collar and the base; and (C) a stop mechanism configured to limit relative movement of the opaque collar and the base.

5. The device of paragraph 1, wherein the optical relay structure includes a fiber optic cable, a light source, or a detector.

6. The device of paragraph 1, wherein the surface is substantially flat.

7. The device of paragraph 1, further comprising a registration mechanism configured to align the end and the aperture.

8. The device of paragraph 7, wherein the surface includes two apertures, and the registration mechanism is capable of aligning the end with either aperture.

9. The device of paragraph 7, wherein the registration mechanism is capable of aligning the end with a portion of the surface not including an aperture to prevent the optical relay structure from transmitting light.

10. The device of paragraph 1, wherein at least a portion of the opaque collar deforms under pressure from the spring substantially to conform to asperities in the surface.

11. The device of paragraph 1, further comprising a light source positioned on a side of the surface opposite the optical relay structure, so that when the end of the optical relay structure is aligned with the aperture, light from the light source can be transmitted through the aperture and optical relay structure substantially without leakage.

12. The device of paragraph 1, further comprising a detector positioned on a side of the surface opposite the optical relay structure, so that when the end of the optical relay structure is aligned with the aperture, light can be transmitted through the optical relay structure and aperture to the detector substantially without leakage.

13. A device for transmitting light through an aperture in a surface, the device comprising (A) an optical relay structure having an end configured to transmit light; and (B) an opaque collar positioned around the end and spring-biased relative to the end, so that the opaque collar is forced against the surface when the end and the aperture are aligned, so that a substantially light-tight junction is formed.

14. The device of paragraph 13, wherein the opaque collar is configured to reorient to conform to the surface when the end and the aperture are aligned.

15. The device of paragraph 13, further comprising (A) a base; (B) a spring operatively associated with the base, wherein the opaque collar is spring-biased relative to the end when the spring is compressed between the opaque collar and the base; and (C) a stop mechanism configured to limit relative movement of the opaque collar and the base.

16. The device of paragraph 13, wherein the optical relay structure includes a fiber optic cable, a light source, or a detector.

17. The device of paragraph 13, wherein the surface is substantially flat.

18. The device of paragraph 13, further comprising a registration mechanism configured to align the end and the aperture.

19. The device of paragraph 18, wherein the surface includes two apertures, and the registration mechanism is capable of aligning the end with either aperture.

20. The device of paragraph 18, wherein the registration mechanism is capable of aligning the end with a portion of the surface not including an aperture to prevent the optical relay structure from transmitting light.

21. The device of paragraph 13, wherein at least a portion of the opaque collar deforms under pressure from the spring substantially to conform to asperities in the surface.

22. The device of paragraph 13, further comprising a light source positioned on a side of the surface opposite the optical relay structure, so that when the end of the optical relay structure is aligned with the aperture, light from the light source can be transmitted through the aperture and optical relay structure substantially without leakage.

23. The device of paragraph 13, further comprising a detector positioned on a side of the surface opposite the optical relay structure, so that when the end of the optical relay structure is aligned with the aperture, light can be transmitted through the optical relay structure and aperture to the detector substantially without leakage.

24. A device for transmitting light through an aperture in a surface, the device comprising (A) an optical relay structure having a central axis and an end configured to transmit light; (B) first and second opaque walls positioned around the end, the opaque walls being concentric and partially overlapping; and (C) a biasing mechanism to force the opaque walls in opposite directions parallel to the central axis, so that the first opaque wall is spring-biased against the surface to form a substantially light-tight junction when the end and the aperture are aligned.

25. The device of paragraph 24, wherein one of the opaque walls has a flange that limits relative movement of the walls.

26. A method of light-tight switching between two light fixtures, the method comprising (A) providing first and second light fixtures housed in first and second light fixture slots, each light fixture slot having an aperture for transmitting light, wherein the apertures are located on a common surface; (B) providing a device for transmitting light through the aperture, the device including (1) an optical relay structure having an end configured to transmit light, and (2) an opaque collar positioned around the end; C) aligning the device with one of the apertures; (D) forming a substantially light-tight junction by reorienting the opaque collar to conform to the surface; and (E) aligning the device with the other of the apertures by translating the device so that the opaque collar maintains substantially light-tight contact with the common surface.

27. The method of paragraph 26, wherein the two light fixtures are light sources.

28. The method of paragraph 26, wherein the two light fixtures are detectors.

29. A method of light-tight switching between two light fixtures, the method comprising (A) providing first and second light fixtures housed in first and second light fixture slots, each light fixture slot having an aperture for transmitting light, wherein the apertures are located on a common surface; (B) providing a device for transmitting light through the aperture, the device including (1) an optical relay structure having an end configured to transmit light and (2) an opaque collar positioned around the end; (C) aligning the device with one of the apertures; (D) forming a substantially light-tight junction by spring-biasing the opaque collar relative to the end, so that the opaque collar is forced against the surface; and (E) aligning the device with the other of the apertures by translating the device so that the opaque collar maintains substantially light-tight contact with the common surface.

V. Filter Wheel Assemblies

This section describes systems, including apparatus and methods, for using optical filters, including a filter holder that allows optical filters to be simply, conveniently, and/or flexibly interchanged. These and other aspects of the invention are described below, including (A) background, (B) summary, (C) detailed description, and (D) examples. This disclosure is supplemented by the patents, patent applications, and publications identified above under Cross-References, particularly U.S. patent application Ser. No. 09/118,141, filed Jul. 16, 1998, now U.S. Pat. No. 6,313,960. These supplementary materials are incorporated herein by reference in their entirety for all purposes.

A. Background

Optical systems typically include many components, which interact to generate, transmit, modify, and detect light. Light may be generated by light sources, transmitted by optical relay structures, and detected by detectors. Light may be modified by optical filters positioned in an optical path in one or both of the light source and detector ends of the instrument.

Optical filters modify the intensity, spectrum, polarization, and other properties of light. "Intensity filters" modify the intensity of light, where intensity is the amount of light per unit area per unit time. Intensity filters may absorb light, dissipating the absorbed energy as heat, or they may reflect or scatter light. "Spectral filters" modify the spectrum of light, where spectrum is the wavelength composition of light. Spectral filters may selectively transmit light of preselected wavelengths and selectively absorb, reflect, or scatter light of other wavelengths. A spectral filter may convert light of many colors into light of one or only a few colors. "Polarization filters" modify the polarization of light, where polarization is the direction of the electric field associated with light.

Different applications or conditions may require different optical filters. For this reason, filter holders have been developed that allow one of a plurality of optical filters to be selected and placed in an optical path. Examples include filter wheels and filter slides. Unfortunately, these filter holders have a number of shortcomings. In particular, the number of optical filters required even for a single application often exceeds the filter-holding capacity of a given filter holder. Therefore, it sometimes is necessary to replace the optical filters within a given filter holder.

Replacing optical filters may be difficult and time-consuming. If individual optical filters are affixed permanently to the filter holder, the entire filter holder may need to be replaced. If individual optical filters are affixed to removable filter cartridges within the filter holder, the filter holder still must be opened, individual filter cartridges removed and replaced, and the filter holder closed again. In known filter holders, filter cartridges must be replaced with the filter holder attached to an associated instrument. Working space may be minimal, and filter cartridges and other components may be dropped into the instrument, where they may cause damage and be difficult to retrieve.

Replacing optical filters within filter cartridges also may be difficult and time-consuming. Many or most optical filters are permanently affixed to any associated filter cartridge, and may not be replaced at all. Other optical filters may be removably affixed to an associated filter cartridge, but replaceable only with a limited selection or number of filters. Filter cartridges with removable optical filters may employ a retaining ring that fits into a groove on the inside of the filter cartridge to hold the optical filter. The groove establishes a predetermined position for the retaining ring, and may limit the thickness or number of replacement filters. Optical filters that are thicker than the provided space will not fit, and optical filters that are thinner than the provided space may require spacers. Filter cartridges with removable optical filters also may employ a threaded retention member that can be screwed into the filter cartridge until a point where it holds the optical filter. This approach may require extra tools and be time-consuming. This approach also may force the retaining ring into a plane that is slightly skewed relative to the filter, misaligning the optical filter.

B. Summary

The invention provides filter cartridges and filter holders that may address one or more of these shortcomings, allowing optical filters to be simply, conveniently, and/or flexibly interchanged.

The invention may provide, in one aspect, a device for holding an optical filter that includes a filter barrel having an inner wall and a stop structure, a removable annular friction member inside the filter barrel, and at least one optical filter sandwiched between the stop structure and the friction member. In this embodiment, the friction member is held in place relative to the inner wall by static friction, without any thread, groove, or adhesive. The filter barrel and friction member may take a variety of forms and may hold optical filters of various sizes and numbers. The friction member may hold the optical filter snugly in place during routine use, while also permitting easy removal when replacing optical filters.

The invention may provide, in another aspect, a tool device for loading an optical filter into a holder. The device includes a funnel structure having a top end and a lower edge configured to rest on top of a filter holder. The funnel structure includes an inner diameter that enlarges gradually in a direction from the lower edge toward the top end. The device also may include a slug for applying pressure to a friction member when loading the optical filter.

The invention may provide, in yet another aspect, an optical filter holder system that includes a holder having a plurality of apertures, and two sets of filter cartridges configured to fit in the apertures. The first set of filter cartridges includes an optical filter permanently fixed in the filter cartridge. The second set of filter cartridges includes a mechanism that permits easy replacement of different optical filters in the same filter cartridge. The filter holder may include a filter wheel, and the mechanism that permits easy replacement my include a filter barrel and friction member.

The invention may provide, in yet another aspect, an optical filter wheel module including an optical filter wheel that is rotatable around a hub structure, and a wheel case having a static portion and a removable portion and at least one set of windows for transmitting light through the wheel case and through a selected optical filter contained in the optical filter wheel. The hub structure is built into the removable portion of the wheel case. The wheel case may be light tight and include more that one set of windows.

The invention may provide, in yet another aspect, a device for holding an optical filter comprising a base having a hub structure, and an elongate filter cartridge having a filter end and a pivot end, the filter end configured to hold at least one optical filter, the pivot end configured turnably to attach to the hub structure, so that an optical filter can be turned between two positions about the hub structure.

C. Detailed Description

Figure 28:
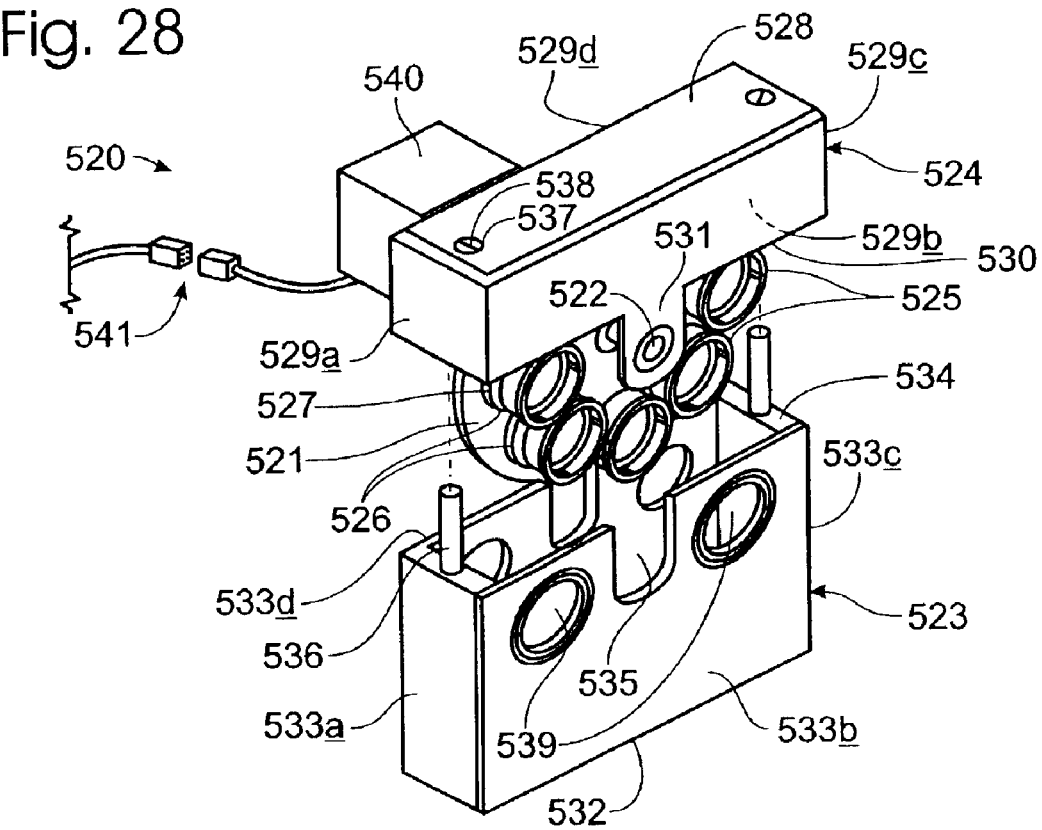
FIG. 28 is a partially exploded perspective view of an optical filter wheel assembly, in accordance with aspects of the invention.

FIG. 28 shows a partially exploded perspective view of an optical filter wheel assembly 520 in accordance with aspects of the invention. Optical filter wheel assembly 520 includes a filter wheel 521 that is rotatable about a hub structure 522, and a wheel case having a static base portion 523 and a removable lid portion 524. Hub structure 522 is built into removable lid portion 524.

Filter wheel 521 holds filter cartridges 525. Filter wheel 521 is substantially circular and includes a plurality of apertures 526 disposed symmetrically about its outer perimeter 527. Apertures 526 are used for mounting filter cartridges 525 and may hold the filter cartridges via friction, threads, or other means. Filter wheel 521 may have a variety of shapes, and apertures 526 may be disposed in a variety of configurations, although a symmetric embodiment is preferred for balance and ease of rotation about hub structure 522.

Removable lid portion 524 holds filter wheel 521. Removable lid portion 524 is substantially rectangular, with an enclosed top 528 and sides 529a–d and an open bottom 530 for receiving filter wheel 521. Opposed flanges 531 extend downward from one pair of opposed sides 529b,d of removable lid portion 524 to support hub structure 522. Filter wheel 521 is rotatably mounted through its center on hub structure 522.

Static base portion 523 holds removable lid portion 524 and filter wheel 521. Static base portion 523 is substantially rectangular, with an enclosed bottom 532 and sides 533a–d and an open top 534 for receiving filter wheel 521. Opposed slots 535 extend downward into one pair of opposed sides 533b,d of static base portion 523 to receive opposed flanges 531. Opposed posts 536 extend upward from the other pair of opposed sides 533a,c of static base portion 523 to be received by opposed holes 537 in opposed sides 529a,c of removable lid portion 524. Flanges 531 and slots 535, and posts 536 and holes 537, individually and collectively form a post-to-hole mating structure that aligns static base portion 523 and removable lid portion 524 when the two portions are mated together to form the wheel case. Captive screws 538 situated in holes 537 and accessible from top 528 may be threaded into posts 536 to hold together removable lid portion 524 and static base portion 523. Static base portion 523 further may be fixed to an instrument platform to form a portion of a light source module, detector module, or other optical assembly, among other applications.

The assembled wheel case is substantially light-tight, except for light that is transmitted through two sets of opposed windows 539 included in static base portion 523. Windows 539 are used for transmitting light through the wheel case and through a selected optical filter contained in a filter cartridge 525 in filter wheel 521. Windows 539 are located on opposite sides of hub structure 522, so that any given optical filter in filter wheel 521 can be rotated into alignment with either set of windows. In turn, light sources, detectors, and other optical components can be aligned with either or both sets of filters. Generally, the wheel case includes at least one set of windows, which may be located on the static portion, removable portion, or other portion of the wheel case.

Filter wheel 521 may be rotated by a drive motor 540, which is attached to removable lid portion 524 in optical filter wheel assembly 520. Drive motor 540 or other driver mechanisms also may be operatively connected to optical filter wheel assembly 520 at other points and in other manners.

FIG. 28 also shows a mechanism by which optical filter wheel assembly 520 may be disassembled and reassembled. Optical filter wheel assembly 520 is disassembled as follows. First, any associated instrument is powered down and unplugged. Second, any secondary housing enclosing optical filter wheel assembly 520 is removed. Third, drive motor 540 is unplugged at its inline connector 541. Fourth, captive screws 538 are loosened. Finally, removable lid portion 524 and filter wheel 521 are pulled out of static base portion 523.

Optical filter wheel assembly 520 may be reassembled as follows. First, filter cartridges 525 are checked to verify that they are properly seated in filter wheel 521, and filter wheel 521 is checked to verify that it rotates smoothly about hub structure 522 when moved by hand. Second, removable lid portion 524 and filter wheel 521 are inserted into static base portion 523, aligning flanges 531 with slots 535, and posts 536 with holes 537. Third, captive screws 538 are tightened. Fourth, drive motor 540 is plugged back in at inline connector 541. Fifth, any secondary housing is replaced. Finally, any associated instrument is plugged back in and powered up, if desired.

Figure 29:
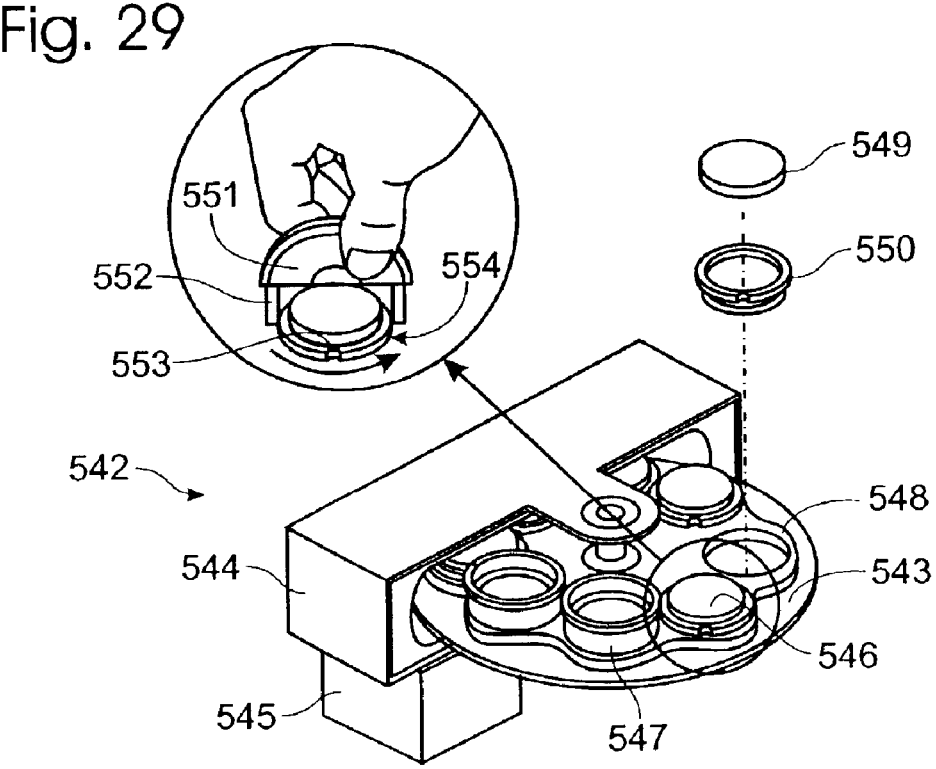
FIG. 29 is a partially exploded perspective view of a portion of an optical filter wheel assembly like that shown in FIG. 28, showing a mechanism by which short filter cartridges may be exchanged.

FIG. 29 shows a partially exploded perspective view of a removable portion 542 of an optical filter wheel assembly, including a filter wheel 543, removable lid portion 544, and drive motor 545. Filter wheel 543 includes a set of "short" filter cartridges 546 and a set of "tall" filter cartridges 547. Filter wheel 543 may hold a variety of filter cartridges, so long as the filter cartridges are configured to fit in apertures 548 in the filter wheel. Generally, opposed apertures in filter wheel 543 should contain matching filter cartridges or a suitable slug to balance the filter wheel and to prevent unfiltered radiation from reaching a detector.

FIG. 29 also shows a mechanism by which short filter cartridges 546 may be removed and replaced. Generally, short filter cartridges 546 include an optical filter 549 permanently affixed by suitable means, such as glue, to a short filter barrel 550 having a low profile. Optical filter 549 may include an intensity filter, a spectral filter, or a polarization filter, among others. Short filter cartridges 546 are removed from filter wheel 543 as follows. First, with the filter wheel removed as described above, the desired short filter cartridge is located by sight or by location. (Filter cartridge locations within the filter wheel may be marked on the filter wheel or elsewhere for reference.) Second, the short filter cartridge is removed by turning it counterclockwise, which unscrews it. The short filter cartridge may be turned by hand or by a special tool, such as a spanner wrench 551 having prongs 552 that engage grooves 553 in the sides of the short filter cartridge 554. Finally, filter changes are noted on the filter wheel or elsewhere and in any associated instrument software. Short filter cartridges 546 may be replaced in filter wheel 543 by reversing the process, turning the short filter cartridge clockwise.

Figure 30:
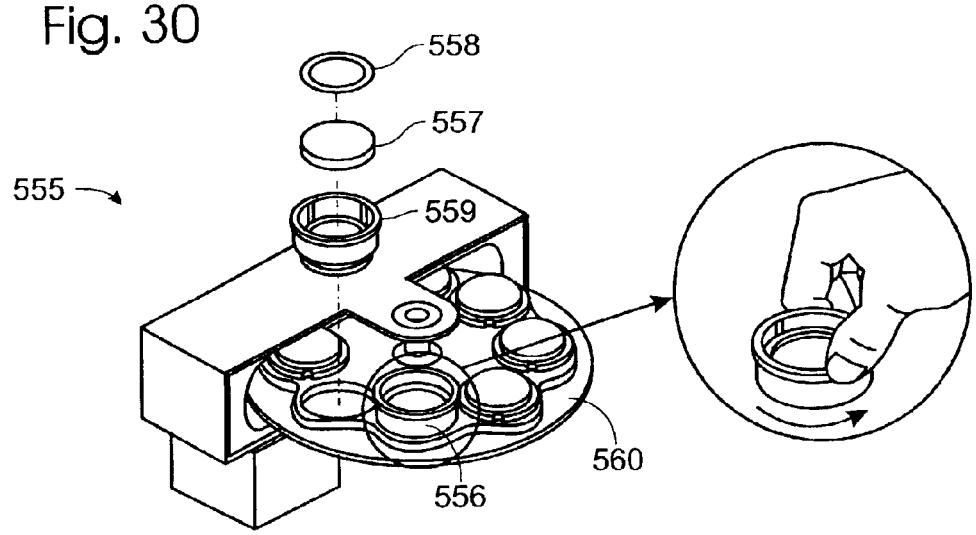
FIG. 30 is a partially exploded perspective view of the portion of the optical filter wheel assembly shown in FIG. 29, showing a mechanism by which tall filter cartridges may be exchanged.

FIG. 30 shows a partially exploded perspective view of a removable portion 555 of an optical filter wheel assembly, as shown in FIG. 29. FIG. 30 also shows a mechanism by which tall filter cartridges 556 may be removed and replaced. Generally, tall filter cartridges 556 include an optical filter 557 affixed by a removable friction member 558 to a tall filter barrel 559. Optical filter 557 may include an intensity filter, a spectral filter, or a polarization filter, among others. Friction member 558 and tall filter barrel 559 may be substantially annular. Tall filter cartridges 556 may be removed from and replaced in filter wheel 560 much like short filter cartridges 546; however, tall filter cartridges 556 generally are turned by hand rather than by a tool.

Figure 31:
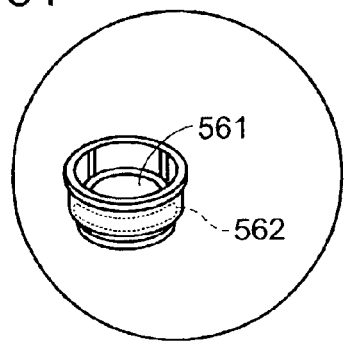
FIG. 31 is a perspective view showing a mechanism by which optical filters may be placed in a tall filter cartridge.
Figure 32:
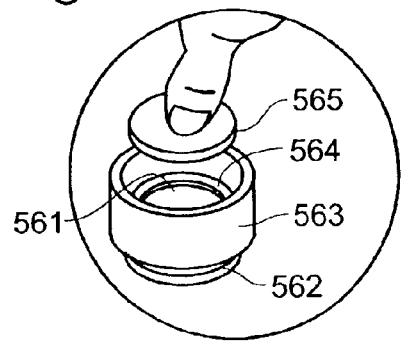
FIG. 32 is a perspective view showing a mechanism by which a friction member may be pressed into place using a funnel and slug.

FIGS. 31 and 32 show a perspective view of a mechanism by which optical filters may be replaced in the tall filter cartridges. First, as shown in FIG. 31, the optical filter 561 is placed in the tall filter barrel 562. Optical filter 561 should be oriented properly if one side is different than the other. Additional optical filters 561 can be placed in tall filter barrel 562, if desired. Second, as shown in FIG. 32, a funnel structure 563 is placed on top of tall filter barrel 562. Third, an annular friction member 564 is placed in funnel structure 563, followed by a slug 565. Slug 565 and optical filter 561 have approximately equivalent peripheral dimensions, including radii. Fourth, slug 565 is pushed down through funnel structure 563 to compress friction member 564, which should fit snugly against optical filter 561. Finally, slug 565 and funnel structure 563 are removed. The completed tall filter cartridge then can be installed in a filter wheel, as described above.

Optical filter 561 also may be replaced by other techniques. Generally, the tall filter cartridges incorporate a mechanism that permits easy replacement of different optical filters in the same cartridge, enhancing the flexibility of the tall cartridges.

Optical filter 561 may be removed from the tall filter cartridge as follows. First, a lint-free cloth is placed on a work surface. Second, the installed optical filter 561 (or slug 565) is pushed gently near its center with a gloved finger or thumb, which will cause the optical filter 561 and friction member 564 to drop out of tall filter barrel 562. Removed optical filter 561 should be stored so that it will not become dirty or scratched.

Figure 33:
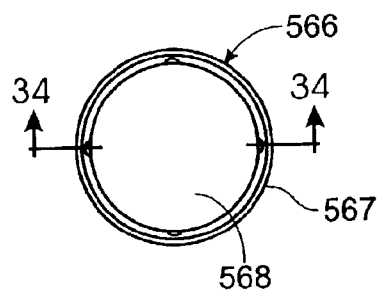
FIG. 33 is a top view of a short filter cartridge, in accordance with aspects of the invention.
Figure 34:
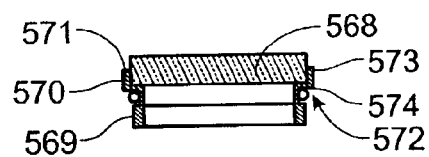
FIG. 34 is a cross-sectional view of the short filter cartridge shown in FIG. 33, taken generally along the line 34—34 in FIG. 33.

FIGS. 33 and 34 show detailed views of a short filter cartridge 566, which includes a short filter barrel 567 and optical filter 568. Short filter barrel 567 is substantially annular, with a threaded lower portion 569 that screws into an aperture in a filter wheel, and a graspable upper portion 570 having a knurled rim 571 that may be turned by hand. Optical filter 568 is supported by upper portion 570, and mounts adjacent a stop structure 572 and inner wall 573 on short filter barrel 567, so that it is substantially centered relative to short filter barrel 567. Stop structure 572 includes an edge 574 oriented substantially perpendicular to a principal plane of optical filter 568 and to inner wall 573.

Figure 35:
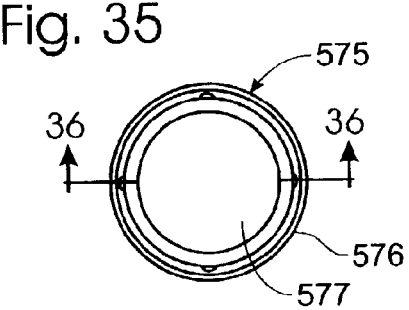
FIG. 35 is a top view of a tall filter cartridge, in accordance with aspects of the invention.
Figure 36:
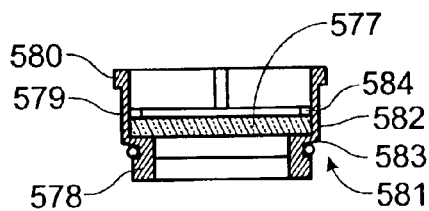
FIG. 36 is a cross-sectional view of the tall filter cartridge shown in FIG. 35, taken generally along the line 36—36 in FIG. 35.

FIGS. 35 and 36 show detailed views of a tall filter cartridge 575, which includes a tall filter barrel 576 and optical filter 577. Tall filter cartridge 575 resembles short filter cartridge 566 in many respects. Tall filter barrel 576 is substantially annular, with a threaded lower portion 578 that screws into an aperture in a filter wheel, and a graspable upper portion 579 having a knurled rim 580 that may be turned by hand. Optical filter 577 is supported by upper portion 579, and mounts adjacent a stop structure 581 and inner wall 582. Stop structure 581 includes an edge 583 oriented substantially perpendicular to a principal plane of optical filter 577 and to inner wall 582. Inner wall 582 may be substantially perpendicular to the optical filter, as here, or it may have a funnel portion that graduates in diameter in a direction toward the stop structure, among other configurations. Lower portion 569 of short filter barrel 567 is substantially identical to lower portion 578 of tall filter barrel 576. However, upper portion 570 of short filter barrel 567 is shorter than upper portion 579 of tall filter barrel 576, giving it a lower profile. In addition, optical filter 568 of short filter barrel 567 is permanently affixed to upper portion 570, whereas optical filter 577 of tall filter barrel 576 is removably sandwiched in upper portion 579 between stop structure 581 and a friction member 584. Friction member 584 holds optical filter 577 in place relative to inner wall 582 in tall filter cartridge 575 by static friction, without any thread, groove, or adhesive. For this reason, among others, optical filters of various numbers and sizes may be secured.

Friction member 584 may take a variety of forms, including a compressible ring having an uncompressed outer diameter greater than the inner diameter of inner wall 582. The compressible ring may exert a force on the inner wall that provides sufficient static friction to hold an optical filter snugly in place during routine use, while also permitting easy removal when replacing optical filters.

Figure 37:
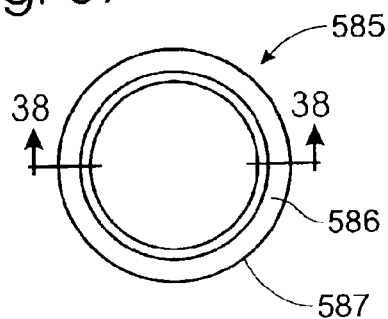
FIG. 37 is a top view of a funnel structure, in accordance with aspects of the invention.
Figure 38:
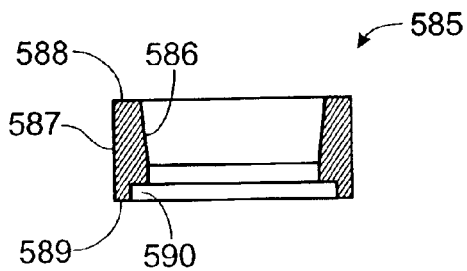
FIG. 38 is a cross-sectional view of the funnel structure shown in FIG. 37, taken generally along the line 38—38 in FIG. 37.

FIGS. 37 and 38 show detailed views of a funnel structure 585, which is used for loading an optical filter into a tall filter cartridge or other holder as described above. Funnel structure 585 is substantially annular and includes inner and outer walls 586, 587 and a top end 588 and lower edge 589. Lower edge 589 includes a groove 590 adjacent inner wall 586 configured to rest on top of a filter cartridge or other holder. The inner diameter of funnel structure 585 measured between inner walls 586 enlarges gradually in a direction from lower edge 589 to top end 588.

Figure 39:
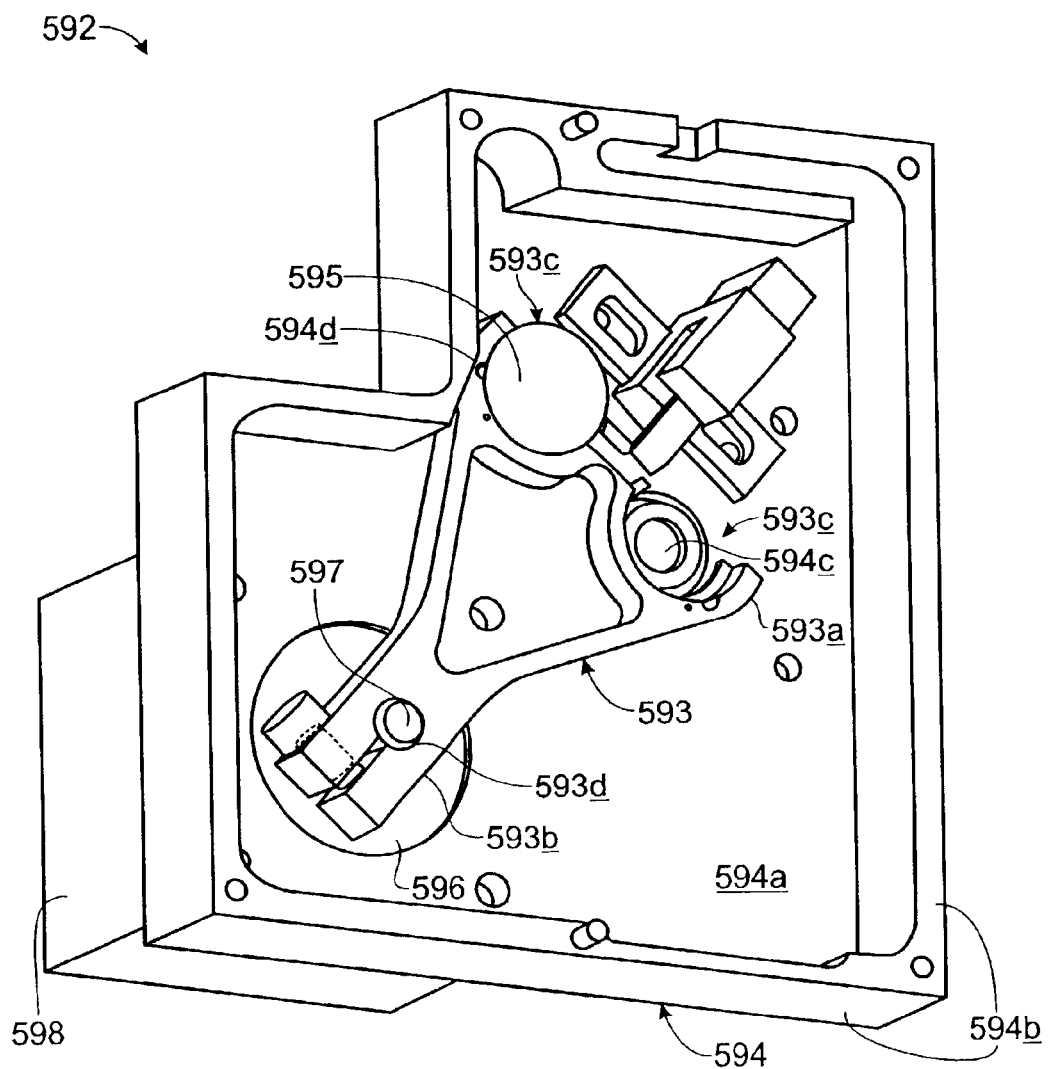
FIG. 39 is a perspective view of a pivotable filter cartridge, in accordance with aspects of the invention.

FIG. 39 shows a partial perspective view of an alternative filter holder assembly 592 in accordance with aspects of the invention. Filter holder assembly 592 includes an elongate filter cartridge 593 and a base 594. Elongate filter cartridge 593 includes a filter end 593a and a pivot end 593b. Filter end 593b is configured to hold optical filters, and includes two filter slots 593c in which optical filters 595 may be glued or otherwise attached. Generally, the filter end may hold one or more optical filters, using slots, apertures, short or tall filter cartridges, or other mechanisms. Filter slots may be left open so that light passes unfiltered, or filter slots may be filled with filters so that light is filtered, or filled with slugs or other opaque structures so that light is blocked. Pivot end 593b is configured turnably to attach to a hub structure, and includes an aperture 593d for receiving a drive axle or other pivot structure. Generally, the pivot end may attach through any means to any suitable drive mechanism. Elongate filter cartridge 593 is fan shaped, filter end 593a being wider than pivot end 593b, although other shapes also are possible.

Base 594 generally supports elongate filter cartridge 593. Base 594 includes a hub structure 596 and major and minor walls 594a,b that substantially surround elongate filter cartridge 593 on all but one side. Elongate filter cartridge 593 is turnably attached at its pivot end 593b to hub structure 596 through a drive axle 597, about which it may turn. Base 594 also includes a window 594c in major wall 594a.

Elongate filter cartridge 593 may be used for moving an optical filter in and out of an optical path, much like a filter wheel or filter slide, by turning elongate filter cartridge 593 about hub structure 596. Because elongate filter cartridge 593 may move one or a few filters in and out of an optical path by turning through a limited angle, it may be configured to require less space than a filter wheel of comparable radius. A drive mechanism 598 may be controlled or base 594 may be configured to limit the angle through which elongate filter cartridge 593 may turn. For example, in filter holder assembly 592, a position 594d on minor wall 594b forms a stop structure that physically limits movement if drive mechanism 594d attempts to turn elongate filter cartridge 593 past the wall.

D. Examples

The following numbered paragraphs describe additional and/or alternative aspects of the invention:

1. A device for holding an optical filter, the device comprising (A) a filter barrel having an inner wall and a stop structure; (B) a removable annular friction member inside the filter barrel; and (C) at least one optical filter sandwiched between the stop structure and the friction member, wherein the friction member is held in place relative to the inner wall by static friction, without any thread, groove, or adhesive.

2. The device of paragraph 1, wherein the inner wall is substantially parallel to the optical filter.

3. The device of paragraph 1, wherein the inner wall has a funnel portion that graduates in diameter in a direction progressing away from the stop structure.

4. The device of paragraph 1, wherein the friction member is a compressible ring having an uncompressed outer diameter greater than the inner diameter of the inner wall.

5. The device of paragraph 4, wherein the compressible ring exerts a force on the inner wall that provides sufficient static friction to hold the optical filter snugly in place during routine use, while also permitting easy removal when replacing optical filters.

6. The device of paragraph 1, wherein the optical filter is an intensity filter, a spectral filter, or a polarization filter.

7. A tool device for loading an optical filter into a holder, the device comprising a funnel structure having a top end and a lower edge configured to rest on top of a filter holder, wherein the funnel structure has an inner diameter that enlarges gradually in a direction from the lower edge toward the top end.

8. The device of paragraph 7, further comprising a slug for applying pressure to a friction member when loading the optical filter, wherein the slug and the optical filter have approximately equivalent peripheral dimensions.

9. An optical filter holder system, the system comprising (A) a holder having a plurality of apertures; and (B) first and second sets of filter cartridges configured to fit in the apertures, each of the first set of filter cartridges having an optical filter permanently fixed in the filter cartridge, each of the second set of filter cartridges having a mechanism that permits easy replacement of different optical filters in the same filter cartridge.

10. The system of paragraph 9, wherein the holder includes a filter wheel.

11. The system of paragraph 9, wherein each of filter cartridges has a lower portion that is threaded to screw into any one of the apertures.

12. The system of paragraph 9, wherein the mechanism comprises (A) a filter barrel having an inner wall and a stop structure; and (B) a removable annular friction member inside the filter barrel, wherein an optical filter can be sandwiched securely inside the filter barrel between the stop structure and the friction member, wherein the friction member is held in place relative to the inner wall by static friction, without any thread, groove, or adhesive.

13. An optical filter wheel module, the module comprising (A) an optical filter wheel that is rotatable around a hub structure; and (B) a wheel case having a static portion and a removable portion, and at least one set of windows for transmitting light through the wheel case and through a selected optical filter contained in the optical filter wheel, wherein the hub structure is built into the removable portion of the wheel case.

14. The module of paragraph 13, wherein the wheel case is substantially light-tight, except for light that is transmitted through the windows.

15. The module of paragraph 13, wherein the windows are in the static portion of the wheel case.

16. The module of paragraph 13, wherein the windows are in the removable portion of the wheel case.

17. The module of paragraph 13, wherein the wheel case has a second set of windows, the sets of windows being located on opposite sides of the hub structure, so that any given optical filter in the optical filter wheel can be rotated into alignment with either set of windows.

18. The module of paragraph 13, further comprising a post-to-hole mating structure that aligns the portions of the wheel case.

19. The module of paragraph 13, wherein the static portion of the wheel case is fixed to an instrument platform.

20. The module of paragraph 13, further comprising a driver mechanism configured to rotate the optical filter wheel.

21. A device for holding an optical filter, the device comprising (A) a base having a hub structure; and (B) an elongate filter cartridge having a filter end and a pivot end, the filter end configured to hold at least one optical filter, the pivot end configured turnably to attach to the hub structure, so that an optical filter can be turned between two positions about the hub structure.

22. The device of paragraph 21, wherein the filter end is configured to hold two optical filters side by side, so that either optical filter can be aligned with a selected position about the hub structure.

23. The device of paragraph 21, wherein the base substantially surrounds the elongate filter cartridge on at least one side, the base including at least one window for transmitting light through the base and through a selected optical filter aligned with the window.

24. The device of paragraph 21, wherein the base is configured to limit the angle through which the elongate filter cartridge may turn.

25. The device of paragraph 21, wherein the elongate filter cartridge generally is fan shaped, the filter end being wider than the pivot end.

26. The device of paragraph 21, further including a driver mechanism configured to turn the elongate filter cartridge.

27. A device for holding an optical filter, the device comprising (A) a base having a hub structure; and (B) an elongate filter cartridge having a filter portion and a pivot portion, the filter portion configured to hold at least one optical filter, the pivot portion configured turnably to attach to the hub structure, so that an optical filter can be turned about the hub structure between two positions.

28. The device of paragraph 27, the elongate filter cartridge having opposed ends, wherein the filter portion is near an end.

29. The device of paragraph 27, the elongate filter cartridge having opposed ends, wherein the pivot portion is near an end.

30. The device of paragraph 27, wherein the filter portion is configured to hold two optical filters side by side, so that either optical filter can be aligned with a selected position about the hub structure.

31. The device of paragraph 27, wherein the base substantially surrounds the elongate filter cartridge on at least one side, the base including at least one window for transmitting light through the base and through a selected optical filter aligned with the window.

32. The device of paragraph 31, wherein the base is substantially light tight, except for light that is transmitted through the window.

33. The device of paragraph 27, wherein the base is configured to limit the angle through which the elongate filter cartridge may turn.

34. The device of paragraph 27, wherein the elongate filter cartridge generally is fan shaped, the filter portion being wider than the pivot portion.

35. The device of paragraph 27, further including a drive mechanism configured to turn the elongate filter cartridge.

36. The device of paragraph 27, wherein the base is fixed to an instrument platform.

37. The device of paragraph 27, the separation between the filter portion and pivot portion forming a radius, wherein the base is configured to use less space than would be required to support a filter wheel of comparable radius.

38. The device of paragraph 27, further comprising an optical filter.

39. The device of paragraph 38, wherein the optical filter is an intensity filter, a spectral filter, or a polarization filter.

40. The device of paragraph 27, the filter portion being configured to hold two optical filters, further comprising first and second optical filters, the first optical filter being at least partially transparent and the second optical filter being opaque, wherein the device may be used to transmit or block light by switching between the two filters.

41. The device of paragraph 40, wherein the second optical filter is a portion of the elongate filter cartridge.

42. The device of paragraph 27, the filter portion including first and second filter slots configured to receive optical filters, further comprising an optical filter, wherein the first filter slot holds the optical filter and the second filter slot is empty, and wherein the device may be used to transmit filtered or unfiltered light by switching between the two filter slots.

43. The device of paragraph 27, further comprising a stop structure configured to limit the angle through which the elongate filter cartridge may turn.

44. A device for holding an optical filter, the device comprising (A) a base having a hub structure; and (B) a filter cartridge member having a filter-holding portion configured to hold at least one optical filter and an acentric pivot portion configured to rotatably mount on the hub structure.

45. The device of paragraph 44, wherein the filter-holding portion is configured to hold at least two optical filters.

46. The device of paragraph 45, wherein each filter holding portion is substantially equidistant from the pivot portion.

47. The device of paragraph 46, wherein the filter cartridge member is elongate.

48. A method of filtering light, the method comprising (A) selecting an elongate filter cartridge having a filter portion and a pivot portion, the filter portion having at least one filter slot configured to hold an optical filter; (B) mounting an optical filter in one of the filter slots; (C) transmitting light through the optical filter; and (D) rotating the elongate filter cartridge about the pivot portion, so that the light is no longer incident on the optical filter.

49. The method of paragraph 48, the filter cartridge including at least two filter slots, the optical filter being mounted in a first filter slot, wherein the step of rotating includes turning the elongate filter cartridge until the light is incident upon the second filter slot.

50. The method of paragraph 49, wherein the second filter slot includes an opaque filter, so that substantially no light is transmitted through the second slot.

51. The method of paragraph 49, wherein the second filter slot is empty, so that substantially all the light is transmitted through the second slot.

VI. Sample Transporter

This section describes systems, including apparatus and methods, for supporting and transporting sample holders, particularly as part of an analyzer for high-throughput screening. These and other aspects of the invention are described below, including (A) background, (B) summary, (C) detailed description, and (D) examples. This disclosure is supplemented by the patents, patent applications, and publications identified above under Cross-References, particularly U.S. patent application Ser. No. 09/144,575, filed Aug. 31, 1998, now U.S. Pat. No. 6,159,425; and U.S. patent application Ser. No. 09/733,370, filed Dec. 8, 2000. These supplementary materials are incorporated herein by reference in their entirety for all purposes.

A. Background

Sample analyzers preferably are capable of handling a variety of sample containers and assay formats with both analytical flexibility and speed, particularly for high-throughput applications, which may involve repeating the same operations hundreds of thousands of times, greatly magnifying even the smallest shortcomings. One way to increase analytical flexibility and speed is to use robots and other devices to automate high-throughput screening procedures. For example, robots permit analyzers to run 24 hours a day. Unfortunately, current robotic systems have a number of shortcomings. For example, robots may have difficulty setting and positioning a sample container in a holder, particularly if different sample containers are of different sizes. Thus, there is a need for improved sample transporters, particularly those capable of reproducibly accepting and positioning sample containers.

B. Summary

The invention provides systems for supporting and transporting sample holders.

These systems may include, in one aspect, a sample container support device that includes (1) a holder including shelf structure and associated frame structure at least partially defining a support area for supporting a microplate, and (2) a first releasable clamp mechanism that applies a force against a first side of the microplate, thereby securing the microplate in the holder. The support area is slightly larger than an expected peripheral dimension of the sample container. The sample container support device may include a second releasable clamp mechanism that applies a force against a second side of the sample container, thereby securing the sample container in the holder from two sides. The first and second releasable clamp mechanisms may operate in series, and/or may position the sample container in a preselected portion of the holder.

These systems also may include, in another aspect, a sample container support device that includes a holder including (1) shelf structure and associated frame structure at least partially defining a support area for supporting a sample container, (2) a central opening that permits analysis of a sample to be carried out from below the holder, and (3) an open end that permits a sample container transfer device to enter the support area of the holder.

These systems also may include, in yet another aspect, a sample container support device that includes (1) a holder, and (2) drive mechanisms that move the holder between a docking station outside an analyzer and an examination site inside the analyzer, so that the holder can function both as a sample delivery device in and out of the analyzer, and as a moveable stage for supporting the sample container at the examination site. The first and second drive mechanisms may be capable of optimizing the acceleration/deceleration profiles of the sample container to minimize shaking of samples contained within the sample container.

These systems also may include, in yet another aspect, a method of automatically feeding sample containers in and out of an analyzer that includes (1) automatically delivering a sample container just outside an opening to the analyzer, (2) moving a gripping device from inside the analyzer, through the opening, to a location immediately below the sample container, and (3) gently placing the sample container onto the gripping device. The method further may include clamping the sample container in the holder by applying a first force against a first side of the sample container, a second force against a second side of the sample container, and/or serially performing the clamping steps.

C. Detailed Description

FIGS. 40–43 show a transport mechanism or stage, which generally comprises any mechanism for supporting a composition in a sample container for analysis by an analyzer. For example, in analyzer 90, the stage includes a transporter 600 and base platform 700.

Figure 40:
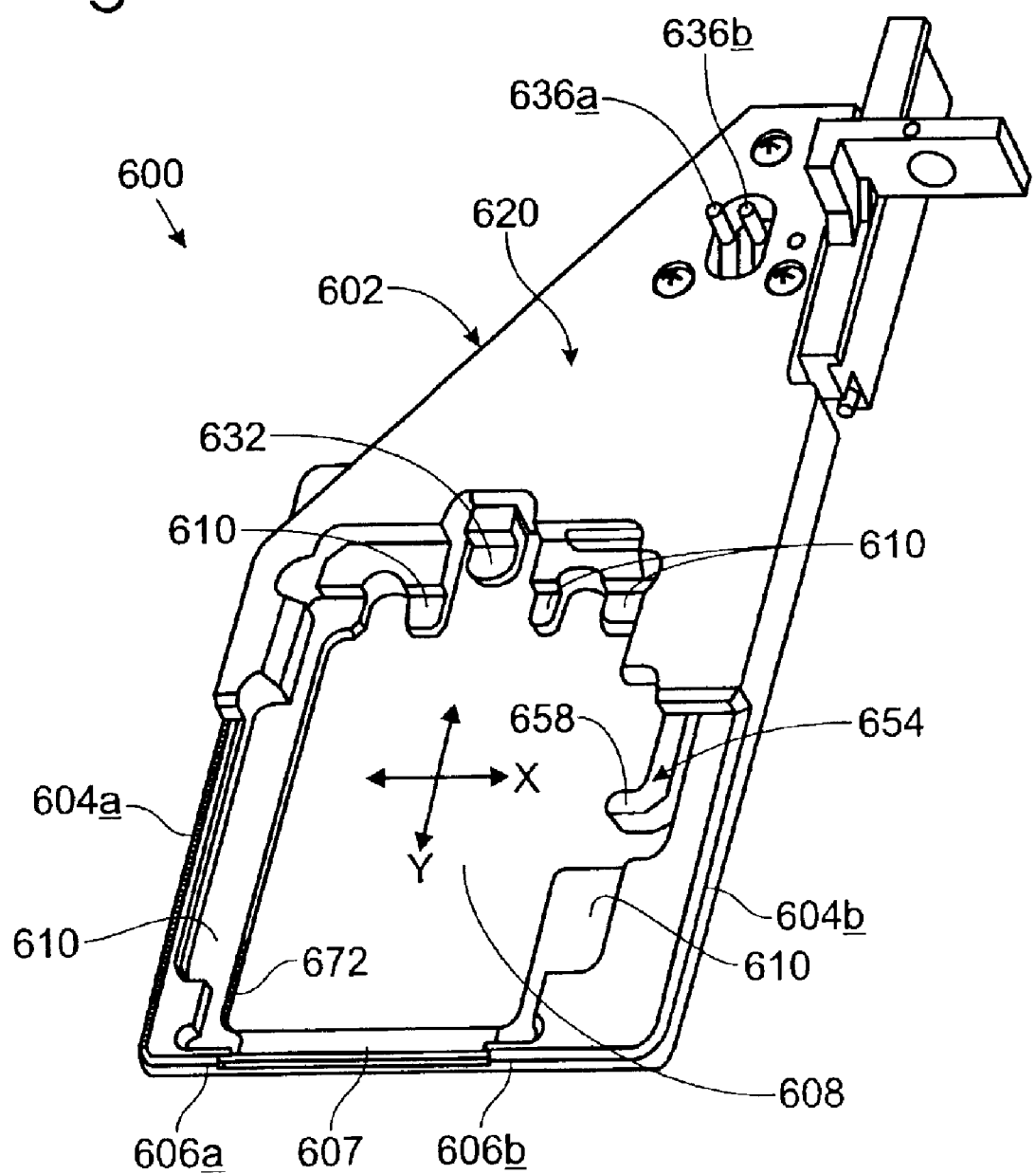
FIG. 40 is a perspective view of the top of a transporter assembly, in accordance with aspects of the invention.
Figure 41:
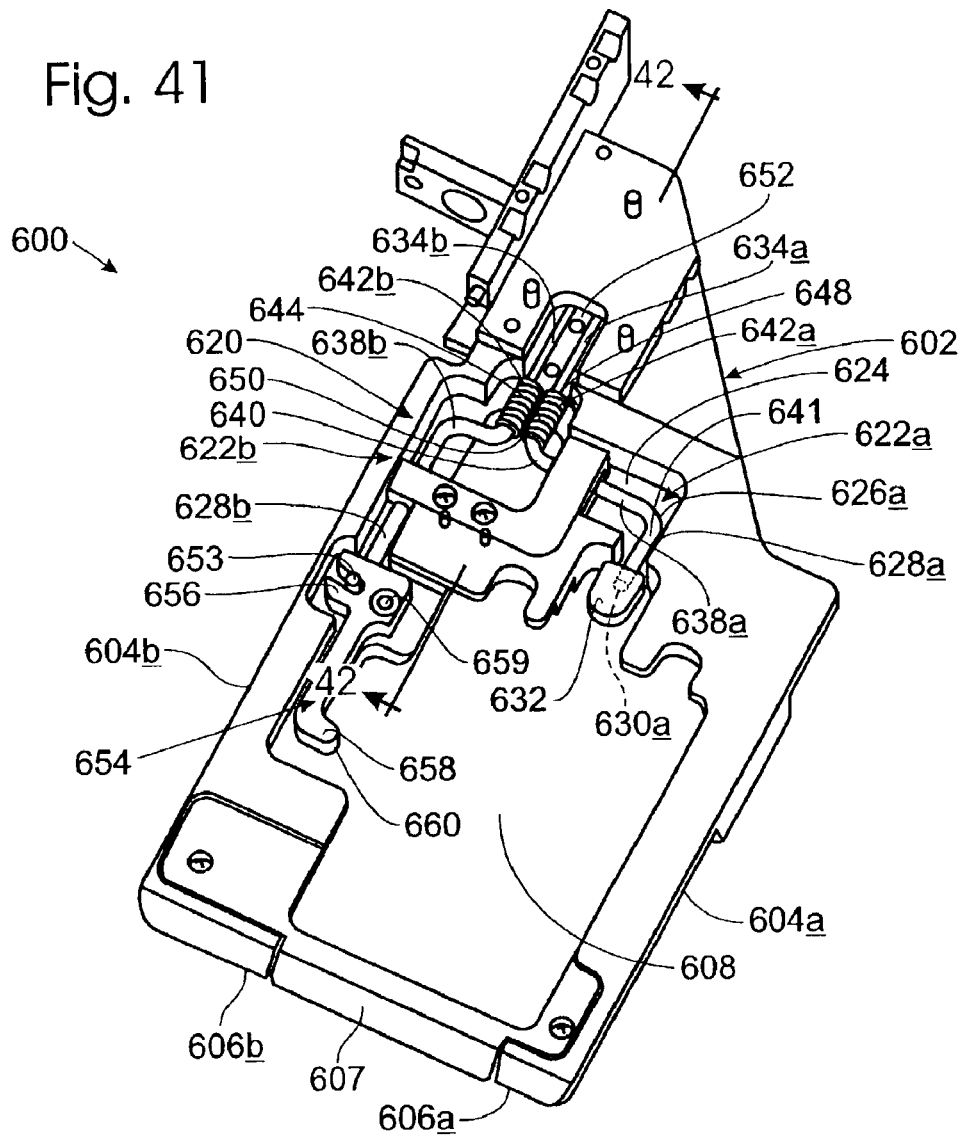
FIG. 41 is a perspective view of the bottom of the transporter assembly shown in FIG. 40.
Figure 42:
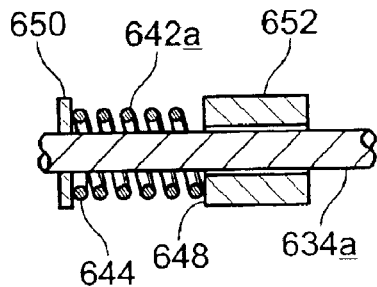
FIG. 42 is a partial cross-sectional view of the transporter assembly shown in FIGS. 40 and 41, taken generally along the line 42—42 in FIG. 41.

FIGS. 40–42 show transporter 600, which includes a transporter body 602 and substantially parallel first and second transporter flanges 604a,b that extend outward from transporter body 602. First and second transporter flanges 604a,b terminate in first and second transporter extensions 606a,b that turn in toward one another without contacting one another. Transporter extensions 606a,b may be joined by a connector portion 607. Transporter body 602, flanges 604a,b, and extensions 606a,b lie substantially in a plane and define a transporter cavity 608 that is larger than the expected peripheral dimension of any sample containers which the transporter is intended to support. The shape of this cavity is chosen to accommodate the shape of the preferred sample containers. In analyzer 90, cavity 608 is generally rectangular to accommodate generally rectangular sample containers, such as microplates. In analyzer 90, long sides of the rectangular sample container are positioned against flanges 604a,b.

Transporter 600 includes a shelf structure and associated frame structure for supporting a microplate or other sample container. For example, transporter shelves 610 along portions of body 602, flanges 604a,b, and extensions 606a,b form a shelf structure that supports the bottom of the sample container. The shelf structure also could include other support mechanisms, such as pins or pegs.

The transporter also includes an automatic sample container positioning mechanism 620 for positioning sample containers precisely and reproducibly within cavity 608. Mechanism 620 includes Y and X axis positioning arms 622a,b that contact the sample container to control its Y and X position, respectively. Here, a Y axis is defined as generally parallel to transporter flanges 604a,b, and an X axis is defined as perpendicular to the Y axis and generally parallel to transporter extensions 606a,b. Other coordinate systems also can be defined, so long as they include two noncolinear directions.

Y-axis positioning arm 622a lies substantially within a channel 624 in body 602. Y-axis positioning arm 622a includes a rod 626a, which is bent at substantially right angles to form three substantially coplanar and equal-lengthed segments. A first end segment 628a of rod 626a terminates near cavity 608 in a bumper 632 for engaging a sample container. A second end segment 634a of rod 626a terminates away from cavity 608 in an actuator tab 636a for controlling movement of arm 622a. Actuator tab 636a is bent away from body 602. First and second end segments 628a, 634a are substantially parallel. A middle segment 638a of rod 626a connects the two end segments at their nontabbed ends 640, 641. An X-axis biasing spring 642a having first and second spring ends 644, 648 is slipped over rod 626a. First spring end 644 is held to second end segment 634a of rod 626a by a clamping-type retaining ring 650. Second spring end 648 rests against a rod bearing 652. The Y-axis biasing spring extends substantially parallel to first and second end segments 628a, 634a. The force from spring 642a is transmitted to rod 626a by the clamping action of retaining ring 650.

X-axis positioning arm 622b also lies substantially within channel 624 in body 602 and is similar to Y-axis positioning arm, except that (1) first end segment 628b is longer and middle segment 638b is shorter in rod 626b of the X-axis positioning arm than in rod 626a of the Y-axis positioning arm, (2) first end segment 628a terminates in a lever tab 653 in the X-axis positioning arm rather than in bumper 632 in the Y-axis positioning arm, and (3) the two rods bend in opposite directions between first end segments 628a,b and second end segments 634a,b.

X-axis positioning arm 622b is connected via lever tab 653 to an X-axis positioning lever 654 that lies along transporter flange 604b. X-axis positioning lever 654 includes first and second lever projections 656, 658 and is pivotally mounted about a lever pivot axis 659 to transporter 600 near the intersection of body 602 and flange 604b. First lever projection 656 is substantially perpendicular to flange 604b and abuts lever tab 630b on X-axis positioning arm 622b for actuating the positioning lever. Second lever projection 658 also is substantially perpendicular to flange 604b and includes an edge 660 for contacting a sample container.

Transporter 600 functions as follows. For loading, the transporter occupies a loading position substantially outside a housing. In this position, actuator tabs 636a,b abut an actuator bar 670, shown in FIG. 43. In addition, biasing springs 642a,b are compressed, and bumper 632 and second projection 658 having edge 660 are pulled out of cavity 608. A person, robot, or mechanical stacker then can place a sample container into cavity 608 so that the bottom of the sample container rests on shelves 610. Cavity 608 is larger than the sample container to facilitate this placement and to accommodate variations in sample container size.

In some configurations, connector portion 607 may be removed, such that transporter 600 has an open end. This open end permits a microplate transfer device to enter cavity 608 and the generally rectangular area of the holder. The microplate transfer device may, after moving into the generally rectangular area, move down relative to transporter 600, thereby gently placing the microplate into the generally rectangular area.

For reading, the transporter must deliver the sample container to an examination site inside the housing. In this process, the transporter moves parallel to second end segments 634a,b, and actuator tabs 636a,b disengage actuator bar 670. Biasing spring 642a pushes Y-axis positioning arm 622a toward cavity 608. Bumper 632 engages the sample container and pushes it away from body 602 until it abuts extensions 606a,b. Biasing spring 642b pushes X-axis positioning arm 622b toward cavity 608. Edge 660 of second projection 658 engages the sample container and pushes it away from flange 604b until it abuts flange 604a.

As long as the sample container is placed in any position on the lower guide shelves, it may be positioned (registered) precisely and reproducibly against a reference corner 672 within cavity 608 under the action of both positioning arms. Biasing springs 642a,b can be chosen to have different strengths, so that the X-Y positioning action is performed less or more forcefully. In analyzer 90, middle segment 638b and first lever projection 656 of positioning lever 654 can be varied in length to cause registration to occur in series, first along the X-axis or first along the Y-axis, and second along the Y-axis or second along the X-axis, respectively. For example, reducing the length of middle segment 638b and reducing the length of projection 656 will cause registration to occur first in the X-axis, and second in the Y-axis.

Positioning lever 654 and bumper 632 are retracted when body 602 of the automatic microplate positioning transporter is moved to the eject position by the X,Y stage. Thus, the microplate is placed on transporter shelf 610 only when the lever and bumper are retracted. Two springs 642a,b are attached to the rods, which run along the length of the transporter body and end perpendicular to the body. When the transporter is moved to the eject position, the two perpendicular ends of the rods encounter a stop 670, which consists of a rectangular structure located above and parallel to the body. The stop prevents the two perpendicular ends of the actuators, and thus the actuators, from moving with the transporter body. This causes the two springs to contract, changing the position of the transporter arms and increasing the amount of room for the microplate. The microplate then can be placed on the guide shelf of the body. When the body of the automatic microplate positioning transporter is moved back away from the stop, the two perpendicular ends of the actuators no longer are blocked, which allows the actuators, springs, and transporter arms to move into their original position. The expansion of the springs pushes the microplate exactly into position, as defined by the reference corner.

Thus, components of transporter 600 act as first and second releasable clamp mechanisms. The first releasable clamp mechanism applies a force against a first (e.g., Y or X) side of the microplate, thereby securing the microplate in the holder. The second releasable clamp mechanism applies a force against a second (e.g., X or Y) side of the microplate, thereby securing the microplate in the holder from two sides. These clamp mechanisms may sandwich a microplate between the positioning arms and opposing portions of the frame structure, such that the positioning arms function as pushers and the opposing portions of the frame structure function as bumpers for the clamp mechanisms.

The invention provides a method of automatically feeding microplates in and out of an analyzer. The method comprises (1) automatically delivering a microplate just outside an opening to the analyzer, (2) moving a gripping device from inside the analyzer, through the opening, to a location immediately below the microplate; and (3) gently placing the microplate onto the gripping device. The method further may comprise clamping the microplate in the holder by applying a first force against a first side of the microplate, applying a second force against a second side of the microplate, and/or serially performing the clamping steps.

Figure 43:
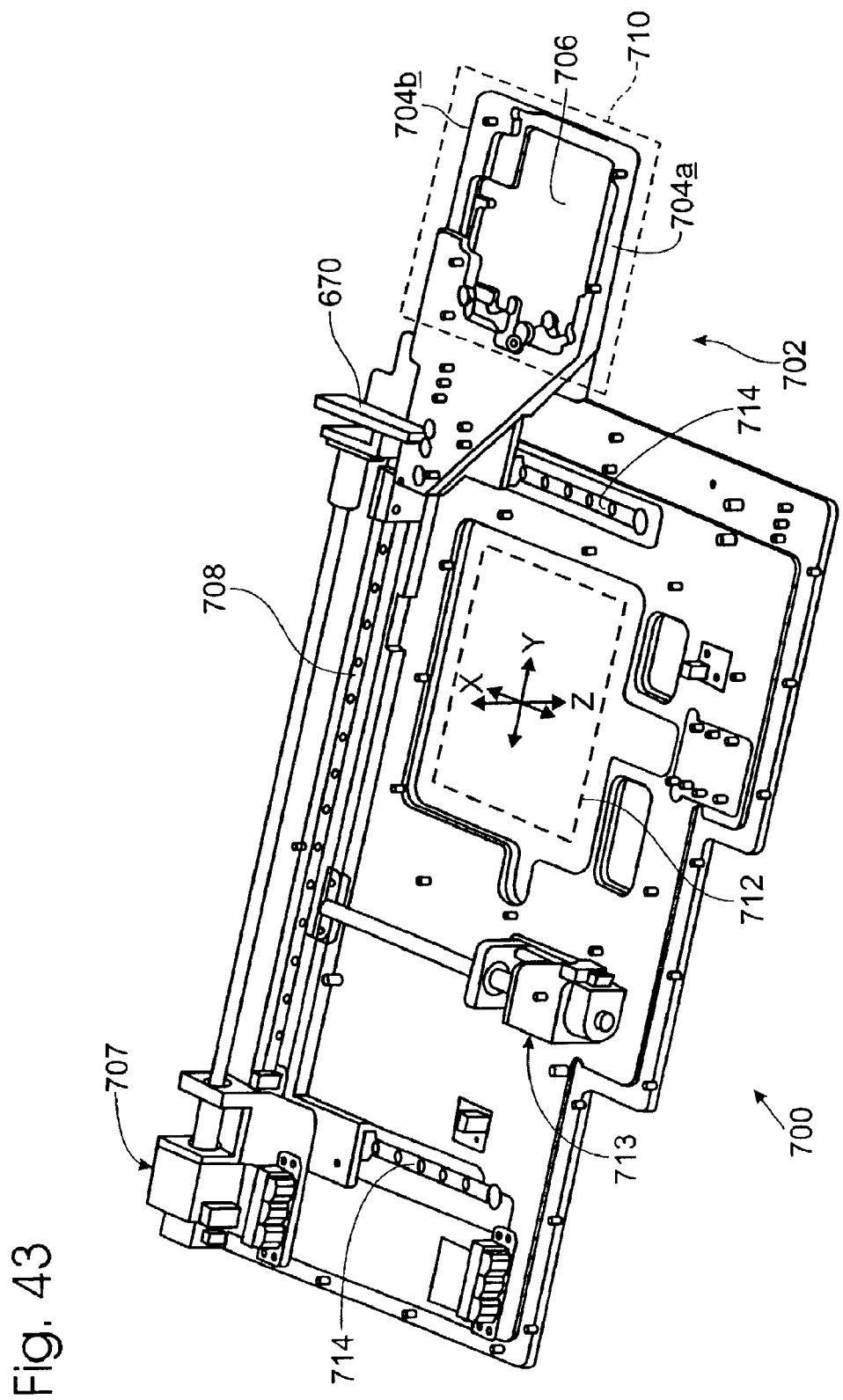
FIG. 43 is a perspective view of a base platform and associated drive mechanisms for moving a transporter along X and Y axes relative to the base platform, in accordance with aspects of the invention.

FIG. 43 shows a base platform 700 with drive mechanisms for moving a transporter 702 between loading and examination positions or sites. As previously described, transporter 702 includes flanges 704a,b defining a cavity 706 for receiving and gripping a microplate (not shown). A Y-axis drive mechanism 707 is provided for moving transporter 702 along a first track 708 relative to the Y-axis, from a loading position 710 toward an examination position 712. An X-axis drive mechanism 713 is provided to move transporter 702 to examination position 712 along a second track 714 relative to the X-axis.

In operation, a microplate is loaded in transporter 702 at loading position 710. This loading position may correspond to the transfer site for a sample feeder, as described below. Transporter 702 is driven toward the examination position (and/or an optional fluid dispense site) by Y-axis drive mechanism 707. A sensor (not shown) detects the presence of the sample container. The analyzer may be configured automatically to read the microplate once the sensor detects its presence, or the analyzer may be configured to signal the system controller through a data port that a microplate has been received and that the analyzer is ready to accept a command to begin reading. The X- and Y-axis drive mechanisms then operate together to align selected microplate wells with an optical axis, substantially parallel to a Z-axis, along which a sensed volume for luminescence detection may be defined by optical components contained in one or both of a top and bottom optics head positioned above and below base platform 700, respectively.

Transporter 700 thus may function both as a sample delivery device in and out of the analyzer, and as a moveable stage for supporting the sample container at the examination site (and/or at the optional fluid dispense site). The cavity in the transporter permits analysis to be carried out from below the holder, when the transporter is functioning as a stage at the examination site.

X- and Y-axis drive mechanisms 707 and 713 may be controlled by a high-performance motion control system that maximizes throughput while minimizing detection errors. A preferred high-performance control system includes precision five-phase stepper motors that employ encoder feedback to move the microplate quickly and accurately to each read position. The control system may optimize the acceleration/deceleration profiles of the microplate to minimize shaking of fluid within the microplate, for example, by minimizing "jerk" (the time rate of change of the acceleration of the microplate). Alternatively, the control system may increase throughput by moving plates more quickly, if higher variation in results due to increased shaking and settling time may be tolerated.

D. Examples

The following numbered paragraphs describe additional and/or alternative aspects of the invention:

1. A support device for a sample container, the device comprising a holder including shelf structure and associated frame structure at least partially defining a support area for supporting a sample container; wherein the holder has a central opening that permits analysis of a sample to be carried out from below the holder; and wherein the holder has an open end that permits a transfer device to enter the support area through a side of the holder, the transfer device being configured to transfer the sample container to the holder.

2. The support device of paragraph 1, wherein the sample container is a microplate.

3. The support device of paragraph 1, wherein the support area is generally rectangular.

4. The support device of paragraph 3, further comprising the transfer device, where the transfer device, after moving into the support area, can move down relative to the holder, thereby placing the sample container into the generally rectangular area of the holder.

5. The support device of paragraph 1 further comprising a removable connector portion configured to close the open end.

6. The support device of paragraph 1 further comprising a first releasable clamp mechanism that applies a force against a first side of the sample container, thereby securing the sample container in the holder.

7. The device of paragraph 6 further comprising a second releasable clamp mechanism that applies a force against a second side of the sample container, thereby securing the sample container in the holder from two sides.

8. The device of paragraph 7, wherein the first and second releasable clamp mechanisms operate in series.

9. The device of paragraph 8, wherein the first and second releasable clamp mechanisms include releasable arm members.

10. The support device of paragraph 1 further comprising a first drive mechanism that moves the holder along an X-axis between a docking station outside an analyzer and an examination site inside the analyzer.

11. The support device of paragraph 10 further comprising a second drive mechanism that moves the holder along a Y-axis perpendicular to the X-axis when the holder is at the examination site, so that the holder can function both as a sample delivery device in and out of the analyzer, and as a moveable stage for supporting the sample container at the examination site.

12. A support device for a sample container, the device comprising (A) a holder; (B) a first drive mechanism that moves the holder along an X-axis between a docking station outside an analyzer and an examination site inside the analyzer; and (C) a second drive mechanism that moves the holder along a Y-axis perpendicular to the X-axis when the holder is at the examination site, so that the holder can function both as a sample delivery device in and out of the analyzer, and as a moveable stage for supporting the sample container at the examination site.

13. The device of paragraph 12, wherein the holder includes shelf structure and associated frame structure at least partially defining a generally rectangular area for supporting a microplate, the generally rectangular area having a central opening so that analysis can be carried out from below the holder when the holder is functioning as a stage at the examination site.

14. The device of paragraph 12, wherein the first and second drive mechanisms are capable of optimizing the acceleration/deceleration profiles of the sample container to minimize shaking of samples contained within the sample container.

15. A method of automatically feeding sample containers in and out of an analyzer, the method comprising (A) automatically delivering a sample container just outside an opening to the analyzer; (B) moving a gripping device from inside the analyzer, through the opening, to a location immediately below the sample container; and (C) placing the sample container onto the gripping device.

16. The method of paragraph 15, wherein the sample container is a microplate.

17. The method of paragraph 15, further comprising clamping the sample container in the holder by applying a first force against a first side of the sample container.

18. The method of paragraph 17, further comprising clamping the sample container in the holder by applying a second force against a second side of the sample container.

19. The method of paragraph 18, further comprising serially performing the clamping steps.

20. The method of paragraph 15, the gripping device having a central aperture and an open end, wherein the step of placing the sample container onto the gripping device includes the steps of entering the central aperture through the open end and moving down relative to the gripping device until the sample container is supported by the gripping device above the central aperture.

VII. Input/Output Mechanisms

This section describes input/output mechanisms for a luminescence analyzer, relating to samples, sample holders, control functions, and data output, among others. These and other aspects of the invention are described below, including (A) overview, (B) sample transporter, (C) sample feeder, (D) moveable control unit, (E) input/output panel, and (F) break-out box. This disclosure is supplemented by the patents, patent applications, and publications identified above under Cross-References, which are incorporated herein by reference in their entirety for all purposes.

A. Overview

Figure 44:
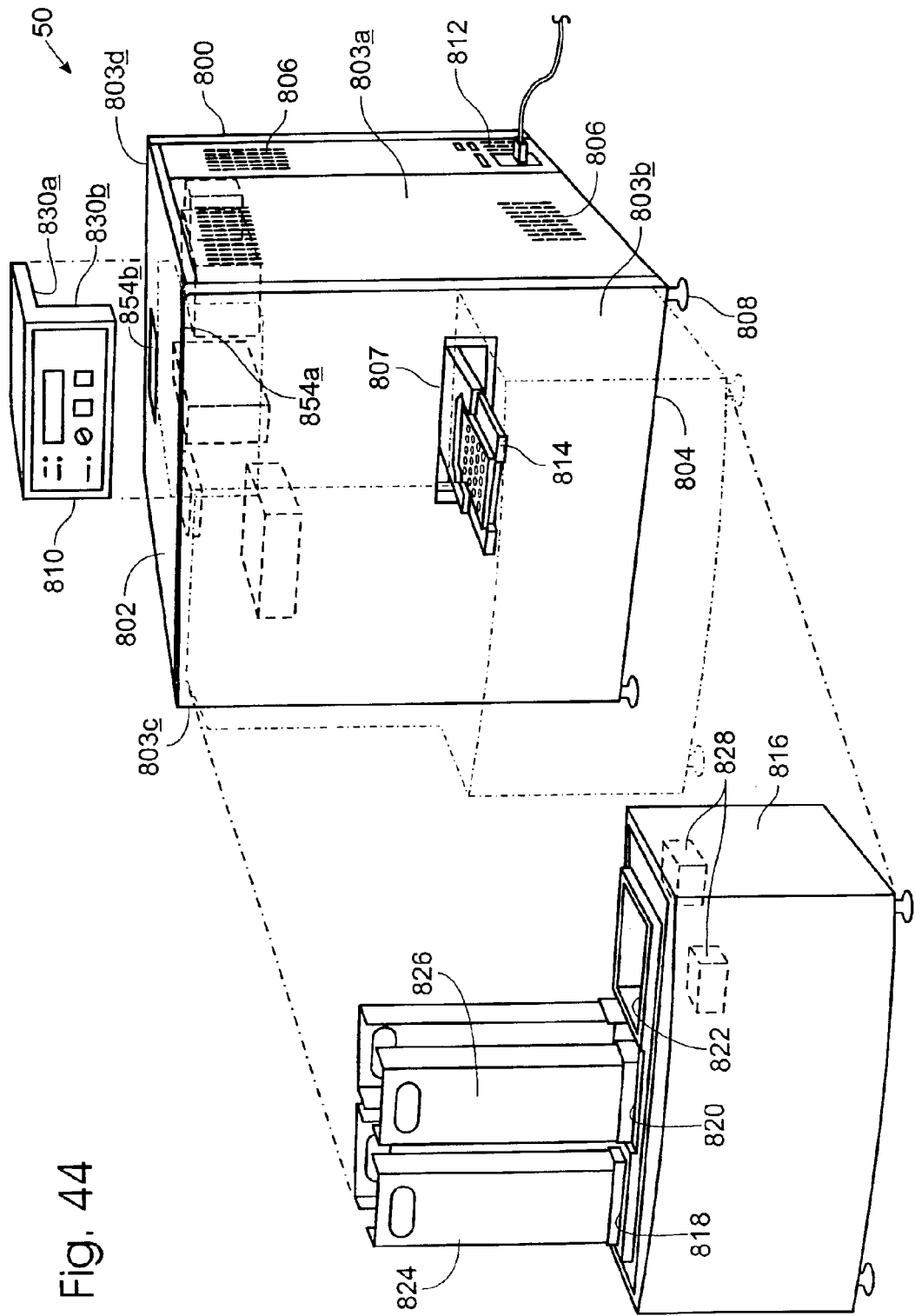
FIG. 44 is a partially exploded perspective view of a housing for an analyzer, in accordance with aspects of the invention.

FIG. 44 shows a high-throughput luminescence analyzer 90 constructed in accordance with the invention. Components of the analyzer are maintained in a housing 800, both for organization and for protection. Housing 800 is substantially rectangular and includes light-tight exterior top 802, side 803a–d, and bottom walls 804 that reduce background in luminescence measurements. The walls may include vents 806 to facilitate airflow through the analyzer and a transporter port 807 for sample input/output. Housing 800 also may include feet 808 to support the analyzer and to permit airflow between the analyzer and any support structure on which the analyzer is placed.

Analyzer 90 is designed for substantially automated input/out. The analyzer is designed so that user interactions occur primarily through a control unit 810, an electronic input/output panel 812, and a break-out box (not shown), each of which supports a variety of input/output functions. The analyzer also is designed so that sample input/output occurs primarily through a transporter/stage 814 and an optional sample feeder 816.

B. Sample Transporter

This section briefly describes transporter 814; a more detailed description appears above, in Section VI. The transporter generally comprises any device for supporting a sample container. In analyzer 90, transporter 814 moves between the interior and exterior of the analyzer, and may be used alone or together with sample feeder 816 for sample input/output.

C. Sample Feeder

This section briefly describes sample feeder 816; a more detailed description appears below, in Section VIII. The sample feeder generally comprises any device for automatically processing multiple samples. In analyzer 90, sample feeder 816 includes a first (input) station 818 for holding sample containers to be read, a third (output) station 820 for holding sample containers that have been read, and a second (direct transporter access) station 822 for inputting or outputting sample containers that bypasses the input and output stations. Input and output stations 818, 820 accommodate preprocessing and postprocessing sample containers bins 824, 826 that hold and organize stacks of sample containers before and after reading, respectively. Sample feeder 816 also may include a barcode reader 828 for automatically identifying labeled sample containers.

D. Moveable Control Unit

This section describes control unit 810. The control unit generally comprises any interface used for direct input/output function. The preferred control unit is moveable, permitting operation of a high-throughput analyzer from a plurality of locations. These and other aspects of the invention are described below, including (1) background, (2) summary, (3) detailed description, and (4) examples. This disclosure is supplemented by the patents, patent applications, and publications identified above under Cross-References, particularly U.S. patent application Ser. No. 09/118,341, filed Jul. 16, 1998, now U.S. Pat. No. 6,025,985. These supplementary materials are incorporated herein by reference in their entirety for all purposes.

D.1 Background

High-throughput analyzers typically are contained in a housing that has a sample input port on one side. For some high-throughput applications, it is most convenient and efficient to use the analyzer in a manual mode, in which an operator stands in front of or near the side of the instrument where the input port is located. In this case, it also is convenient to have a control unit located on the same side as the input port, so that the operator can interact with the control unit while overseeing the sample feeding process.

For other high-throughput applications, it is preferable to employ ancillary robotic mechanisms to feed samples in and out of the instrument automatically, through the input port. Yet, if the control unit is on the same side as the input port, it may be awkward or even impossible for the operator to access the control unit without interfering with or encumbering these ancillary robotic mechanisms.

D.2 Summary

The invention provides systems, including apparatus and methods, for controlling a analyzer, particularly from a plurality of locations.

These systems may include, in one aspect, a device comprising (1) a plurality of control interface docking locations disposed on a housing containing the analyzer, and (2) a control unit that can be mounted at any one of the docking locations, so that a user can control the analyzer by inputting information through the control unit. The control unit can be moved from one docking location to another to provide convenience in different modes of operation.

These systems also may include, in another aspect, a device comprising (1) a first control interface docking location on or near an upper edge of a first side of a housing containing the analyzer, and (2) a control unit that can be operatively mounted at the first control interface docking location. A sample input port is included on the first side of the housing. The control unit can be operatively relocated at a second control interface docking location remote from the first side. The second control interface docking location may be located on or near a second side of the housing, or spaced apart from the housing.

These systems also may include, in yet another aspect, a method of controlling an analyzer capable of being used in a manual mode or a robotic mode comprising (1) providing a control unit that can be mounted at a first or second docking location, wherein the docking locations are disposed on a housing containing the analyzer, (2) mounting the control unit in the first docking location when the analyzer is to be used in the manual mode, and (3) mounting the control unit in the second docking location when the analyzer is to be used in the robotic mode.

The preferred embodiments of these systems may be distinguished, in whole or in part, by particular geometries, functionalities, and docking locations for the control unit, as well as additional control units.

D.3 Detailed Description

Control unit 810 generally comprises any interface used for direct input/output functions. The control unit may be integrated into the analyzer, or it may be a separate unit that can be positioned away from the analyzer or affixed to the analyzer at one or more locations. The control unit also may include more than one unit, each dedicated to different input/output functions or to use at different locations.

The control unit 810 may be used in conjunction with a host computer for a variety of input/output functions. For example, the control unit may be used to input commands, such as signals to start and stop the instrument. Similarly, the control unit may be used to display output information, such as instrument status, instrument diagnostics, measurement results, and other information generated by the analyzer in different assay modes. The control unit is especially useful for automated operations that require manual user intervention.

Figure 45:
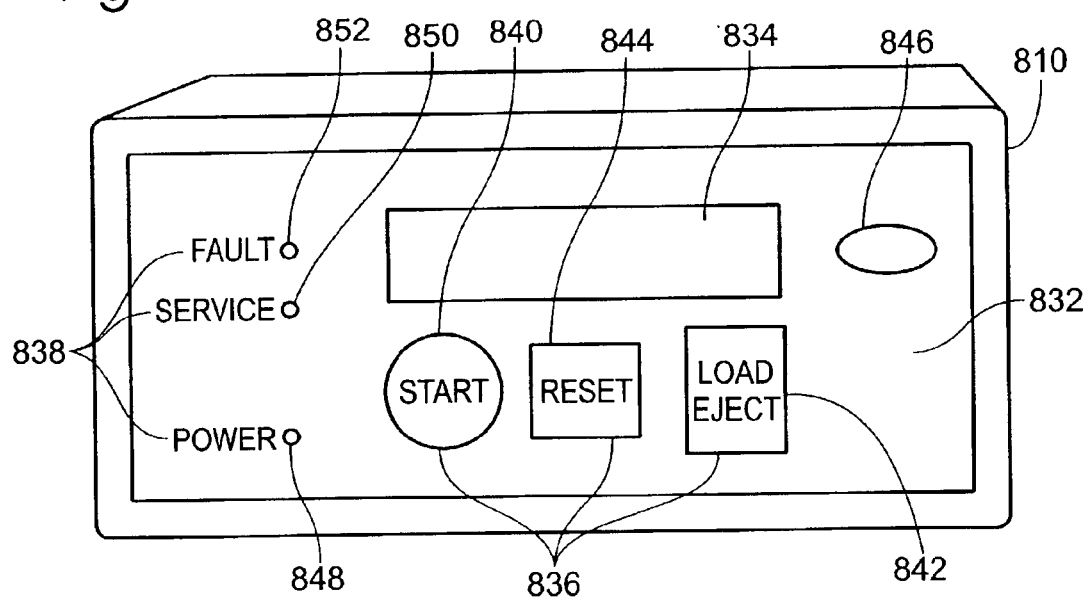
FIG. 45 is a front view of the control unit shown in FIG. 44.

FIG. 45 shows an enlarged isolated view of control unit 810 of analyzer 90. Control unit 810 is a separate unit that statically or swivelably affixes to the analyzer at any one of a plurality of docking locations. Control unit 810 is substantially L-shaped, with substantially perpendicular inner surfaces 830*a,b* that mate with adjacent substantially perpendicular walls of the analyzer including top wall 802 and one of side walls 803*a–d*, although other shapes are possible. In its preferred orientation, control unit 810 is mounted so that front face 832 is substantially parallel with one of side walls 803*a–d* of analyzer 90.

Control unit 810 includes various data input and output components. Front face 832 includes a gas-plasma display 834, keypad 836, and indicator lights 838. Control unit 810 also may include additional and/or alternative components, and their relative organization may deviate from that shown in the drawings and discussed below. Gas-plasma display 834 is located in the upper center of front face 832 and is used to provide messages regarding instrument status. Additional displays and/or alternative display formats, such as light-emitting diodes (LEDs) and liquid crystal displays (LCDs), also may be used.

Keypad 836 is located below and to the right of gas-plasma display 834 and includes four keys. A "start" key 840 initiates the sample-reading process. A "load/eject" key 842 loads or ejects a sample container, such as a microplate, depending upon the current status of the instrument. A "reset" key 844 reinitializes the instrument, sending motors to their home positions and turning off the audible alarm. A "status" key 846 alters the state of a continuous light source or activates reverse stack. Additional keypads and additional and/or alternative keys also may be employed. Alternative methods of data entry, such as a computer mouse or touch screen, also may be employed.

Indicator lights 838 are located to the left of the display and keypad. A "power" light 848 indicates that power is being supplied to the instrument. A "service" light 850 indicates that a service procedure is needed, such as changing a light source. A "fault" light 852 indicates that a critical fault has occurred, which is a fault that requires intervention by an operator. Additional and/or alternative indicator lights also may be provided.

Control unit 810 also may include audio signals. For example, an audible alarm within the interior of control unit 810 may sound in the event of a critical fault. Alternative audio signals, such as prerecorded or synthesized voice messages, also may be used.

Control unit 810 may be moved between at least two control interface docking-panel mounting locations 854*a,b* on the instrument. A first docking location 854*a* is located near an upper edge of sample input side 803*b* of housing 800. This configuration is especially suitable for manual operation, because control unit 810 and transporter port 807 are positioned on the same side of analyzer 90. A second docking location 854*b* is located near an upper edge of back side 803*d* of housing 800. This configuration is especially suitable for robotic operation, because control unit 810 and transporter port 807 are positioned on opposite side of analyzer 90, facilitating robotic access to transporter port 807. Such flexible positioning permits commands to be entered and status information, diagnostic information, measurements, and other information to be read from multiple positions. Flexible positioning is especially convenient when one or more sides of the analyzer are blocked due to analyzer placement or nearby peripherals. Alternatively, it permits two or more control units to be connected at once, increasing convenience and flexibility.

Figure 46:
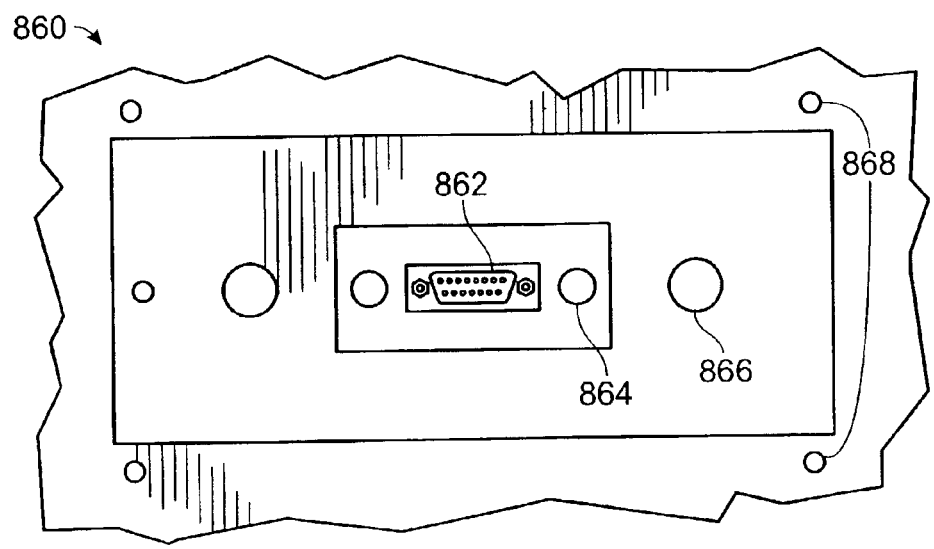
FIG. 46 is a top view of one of the control interface docking locations shown in FIG. 44.

FIG. 46 shows a control interface docking location 860. Control unit 810 includes an electronic connector prong, which can be mated with an electronic connector port 862 at docking location 860. Electronic connector port 862 is connected to a host computer, allowing the computer to communicate with the control unit, so that a user can control the analyzer by inputting information through the control unit. Electronic connector port 862 preferably includes an RS-232 serial port, and preferably is connected to the host computer through an RS-232 cable. Control unit 810 also includes other mating structure, including substantially cylindrical prongs that match with receptors 864 and latches 866, and indentations that match with dimples 868, at docking location 860. Positioning docking location 860 at sites 854*a,b* on top wall 802 of housing 800 reduces the stress on the mating structure when the control unit is mounted; however, docking location 860 also can be positioned at other sites on or off housing 800.

D.4 Examples

The following numbered paragraphs describe additional and/or alternative aspects of the invention:

1. A device for controlling an analyzer, the device comprising (A) a plurality of control interface docking locations disposed on a housing containing the analyzer; and (B) a control unit that can be mounted at any one of the docking locations, so that a user can control the analyzer by inputting information through the control unit; wherein the control unit can be moved from one docking location to another to provide convenience in different modes of operation.

2. The device of paragraph 1, wherein the control unit includes data input and output components.

3. The device of paragraph 1, wherein the control unit is L-shaped and configured to mount on a top edge of the housing.

4. The device of paragraph 1, wherein the control unit has a horizontal panel portion for resting on a top portion of the housing, and a vertical panel portion for resting against a side portion of the housing adjacent the top portion.

5. The device of paragraph 4, wherein an inner side of one of the panels has mating structure that compliments other mating structure provided at each of the docking locations.

6. The device of paragraph 1, wherein the housing has a sample input side, a first docking location being located near an upper edge of the sample input side.

7. The device of paragraph 6, wherein the housing has a back side opposite the sample input side, a second docking location being located near an upper edge of the back side of the housing.

8. The device of paragraph 1, wherein the control unit has a front face containing a display screen for indicating instrument status data.

9. The device of paragraph 8, wherein the front face of the control unit contains at least one data input button for carrying-out one or more of the following command functions: start, reset, load, and eject.

10. The device of paragraph 8, wherein the front face of the control unit contains at least one light indicator for indicating one or more of the following data output functions: power, fault, and service required.

11. A device for controlling an analyzer, comprising (A) a first control interface docking location on or near an upper edge of a first side of a housing containing the analyzer, wherein the first side also includes a sample input port; and (B) a control unit that can be operatively mounted at the first control interface docking location; wherein the control unit can be operatively relocated at a second control interface docking location remote from the first side of the housing.

12. The device of paragraph 11, wherein the second control interface docking location is located on or near a second side of the housing.

13. The device of paragraph 11, wherein the second control interface docking location is spaced apart from the housing.

14. The device of paragraph 11, further comprising a second control unit, wherein a user can control the analyzer by inputting information through either control unit.

15. A method of controlling an analyzer capable of being used in a manual mode or a robotic mode, the method comprising (A) providing a control unit that can be mounted at a first or second docking location, wherein the docking locations are disposed on a housing containing the analyzer; (B) mounting the control unit in the first docking location when the analyzer is to be used in the manual mode; and (C) mounting the control unit in the second docking location when the analyzer is to be used in the robotic mode.

E. Input/output Panel

The section briefly describes input/output panel 812. The input/output panel generally comprises any ports used for basic input/output functions. These include ports for providing and controlling power input to the analyzer, and for inputting and outputting data and commands. Components of the input/output panel may be collected for convenience in one location or positioned at various locations on the analyzer.

Figure 47:
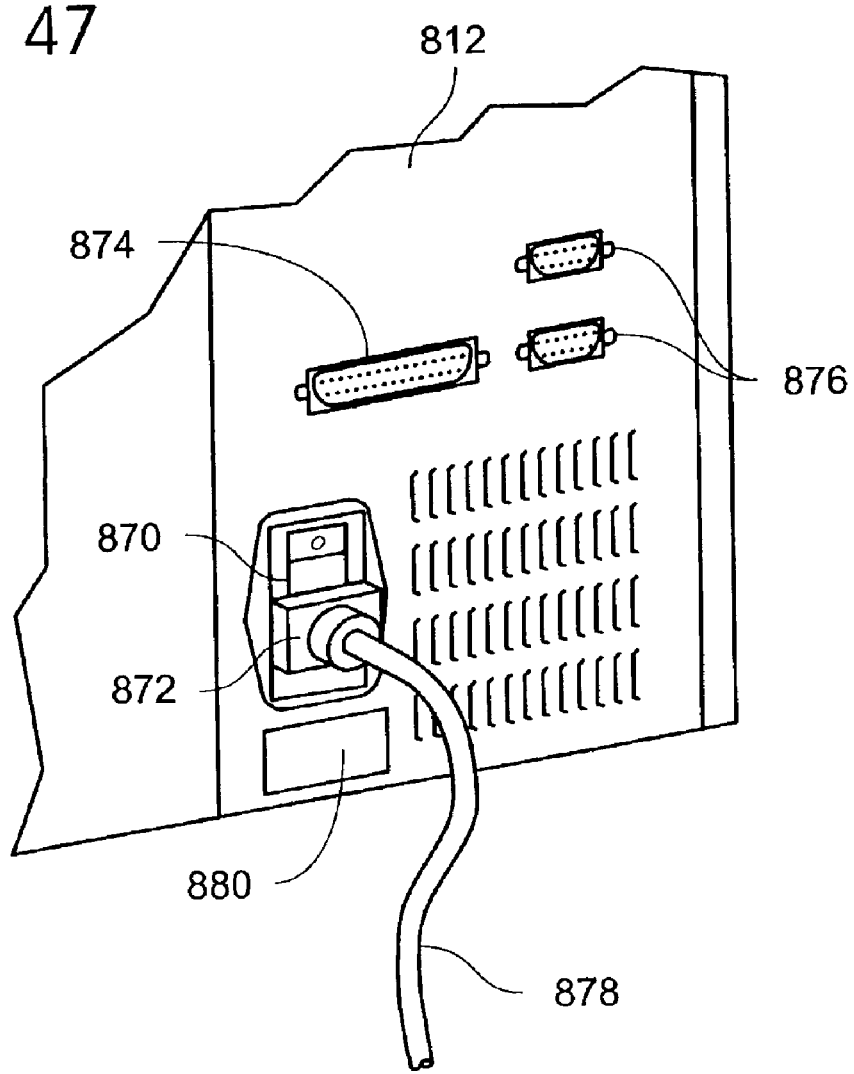
FIG. 47 is a front view of the input/output panel shown in FIG. 44.

FIG. 47 shows an enlarged isolated view of control input/output panel 812. In analyzer 90, input/output panel 812 includes a power switch 870, power entry module 872, auxiliary port 874, and two RS-232 serial ports 876. Power switch 870 is located in the left center of the panel and is used to actuate analyzer 90. Power entry module 872 is located below the power switch and is used to supply power to analyzer 90; power arrives via a standard electrical cord 878 that may be plugged into a wall socket. Auxiliary port 874 and serial ports 876 are located above and to the right of the power entry module and are used for input/output. These ports provide flexibility, because they permit the analyzer to communicate with several different peripherals. Additional power entry modules and additional and/or alternative communication ports for input/output in alternative formats and positions also may be used. A model/regulatory label 880 containing written information regarding the analyzer is provided below power entry module 872 on the input/output panel.

E. Break-Out Box

The section briefly describes the external "break-out" accessory box. The break-out box may be connected to the analyzer or instrument with any suitable connection, such as a cable. The break-out box may include a connection block that allows the analyzer to provide a general purpose and hard-wired electrical interface to external devices, such as lamps, warning alarms, enunciators, associated instruments, and external system controllers. Through the break-out box, the instrument's software can be programmed to send or receive control signals from external systems or to control or provide signals to external devices. These control signals can be conditioned on the occurrence of predetermined internal events, such as when the analyzer finishes reading a plate or when a fault such as a mechanical jam occurs. Through the break-out box, the instrument also can accept signals from external devices or controllers to start reading a plate or perform other programmable functions.

VIII. Sample Feeder

This section describes systems, including apparatus and methods, for automatically feeding sample holders into an analyzer, particularly microplates into a high-throughput analyzer for high-throughput screening supporting. These and other aspects of the invention are described below, including (A) background, (B) summary, (C) detailed description, (D) alternative embodiments, and (E) examples. This disclosure is supplemented by the patents, patent applications, and publications identified above under Cross-References, particularly U.S. Provisional Patent Application Ser. No. 60/085,335, filed May 13, 1998; U.S. Provisional Patent Application Ser. No. 60/167,301, filed Nov. 24, 1999;

U.S. patent application Ser. No. 09/144,578, filed Aug. 31, 1998; and U.S. patent application Ser. No. 09/778,224, filed Feb. 6, 2001. These supplementary materials are incorporated herein by reference in their entirety for all purposes.

A. Background

Sample analyzers preferably are capable of handling a variety of sample containers and assay formats with both analytical flexibility and speed, particularly for high-throughput applications, which may involve repeating the same operations hundreds of thousands of times, greatly magnifying even the smallest shortcomings.

One way to increase analytical flexibility and speed is to use robots and other devices to automate high-throughput screening procedures. For example, robots permit analyzers to run 24 hours a day. Unfortunately, current robotic systems have a number of shortcomings. For example, robots commonly are used to deliver samples to an analyzer for analysis. However, the robot typically must make separate trips to drop off a sample container, such as a microplate, before analysis, to retrieve the sample container after analysis, and then to drop off another sample container for analysis. In this approach, the analyzer is idle during the time that the robot is returning the analyzed microplate and bringing the new microplate. As time and the number of sample containers analyzed increase, the total down time due to robotic transport may become quite significant.

Another way to increase analytical flexibility and speed problem is to permit manual or automated feeding of sample containers. Unfortunately, switching between manual and automated feeding modes with current analyzers has a number of shortcomings. For example, automated microplate feeding systems may not permit manual feeding while the automated feeder is connected to the analyzer. To use such an analyzer in a manual mode, the automatic feeder must be disconnected.

Thus, there is a need for improved sample feeders.

B. Summary

The invention provides systems for automatically feeding sample holders into an analyzer.

These systems may include, in one aspect, a sample feeder that includes (1) a first station that receives and initiates transport of a sample container into an analyzer for analysis, (2) a second station where the sample container is handed off to a transporter that carries the sample container to and from an examination site inside the analyzer, and (3) a third station that collects the sample container after examination. The sample feeder may include a singulation mechanism positioned at the first station and configured to separate a sample container from a stack of sample containers for transport to the analyzer, and/or a stacking mechanism positioned at the third station and configured to add a sample container to a stack of sample containers. The sample feeder further may include a preprocessing bin positioned at the first station for holding a stack of sample containers to be analyzed, and/or a postprocessing bin positioned at the third station for holding a stack of sample containers after they have been analyzed.

These systems also may include, in another aspect, a sample feeder that includes (1) a lifter configured to raise or lower a sample container relative to the bottom of a stack of sample containers, and (2) at least one latch having a pick portion, the latch being mounted so that the pick portion moves in and out of gaps between adjacently stacked sample containers in response to up and down movement of the lifter. The lifter and latch may be designed to remove a single sample container from the bottom of a stack of sample containers, or to add a single sample container to the bottom of a stack of sample containers. The latch may include a pick portion that is urged toward the bottom of the stack by gravity, a spring, or other mechanisms.

These systems also may include, in yet another aspect, a sample feeder that includes (1) a lifter configured to impart a raising or lowering motion to a sample container to transfer the sample container to or from a stack of sample containers, and (2) a drive motor configured to generate a driving motion, wherein the lifter includes a cam operatively connected to the drive motor and configured to convert the driving motion into the raising or lowering motion.

These systems also may include, in yet another aspect, an automated analyzer system that includes (1) an analyzer unit having an internal examination site, and (2) first and second external loading stations, the first external loading station configured to receive a sample container before analysis, the second external loading station configured to receive the sample container after analysis. The automated analyzer system may include a robot programmed to deliver a sample container to the first external loading station, and to retrieve a different sample container from the second loading station in the same trip.

C. Detailed Description

Figure 48:
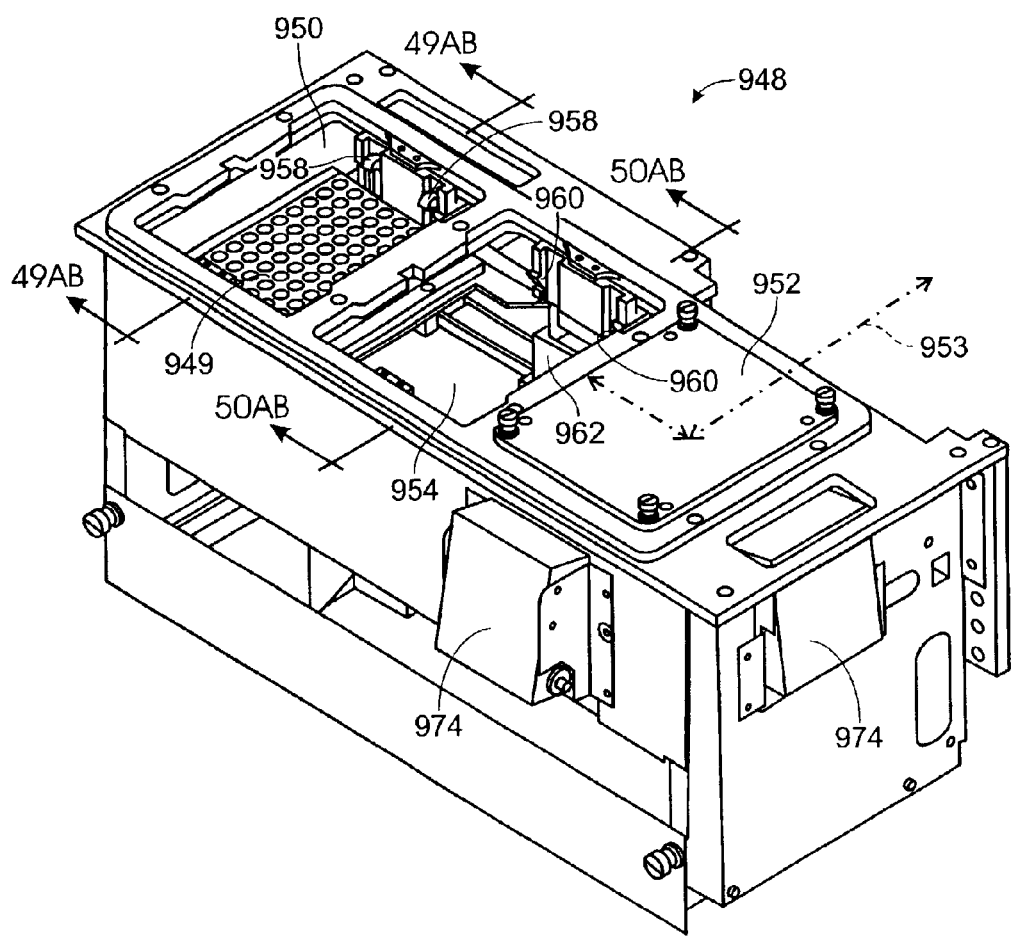
FIG. 48 is a perspective view of a sample feeder, in accordance with aspects of the invention, with bins removed so that internal mechanisms of the sample feeder can be viewed.

FIGS. 48–50 show a sample feeder 948, which generally comprises any mechanism for automatic processing of multiple sample containers. Sample feeder 948 enhances convenience by reducing the amount of human intervention required to run the analyzer. Sample feeder 948 also enhances throughput by reducing the amount of time required to process multiple sample containers.

Generally, sample feeder 948 operates as follows. Before reading, a robot (1) removes a sample container from the bottom of an input stack of sample containers at an input station, (2) transports the sample container to a direct transporter access station, and (3) transfers the sample container to a transporter. After reading, the robot (1) takes the sample container from the transporter, (2) transports the sample container to an output station, and (3) transfers the sample container to the bottom of an output stack of sample containers. Sample feeder 948 requires only two motors to provide these functions with high throughput (~5 seconds for load and unload time).

FIG. 48 shows sample feeder 948 with its preprocessing and postprocessing bins removed, so that internal mechanisms can be viewed. A microplate 949 is loaded from the bottom of a stack of microplates in the input bin into a first (input) station 950. Microplate 949 then is transported on a tray (not shown) to a second (direct transporter access) station 952, where the microplate is handed off to a transporter (not shown). The transporter transports microplate 949 generally along an axis 953 to an examination site inside the analyzer. After analysis, the transporter transports microplate 949 back along axis 953 generally in the opposite direction to second station 952. Microplate 949 then is handed back to the tray, and transported to a third (output) station 954, where the microplate is added to the bottom of a stack of microplates in an output bin.

In analyzer 90, a first linear path defined by axis 953 connects the examination site to the second station, and a second linear path connects the first second and third stations, wherein the first linear path is substantially perpendicular to the second linear path. However, analyzer 90 also may have other configurations. For example, the examination site and the first, second, and third stations may all be positioned along a single substantially linear path.

In input station 950, a combination of two lifters and four latches cooperate to singulate or pick a single microplate from the bottom of a stack. (These lifters are concealed by microplate 949 in FIG. 48.) Latches 958 have pick portions that extend into the cavity of first station 950 and support a stack of microplates. Latches 958 are disposed toward the microplates by configuring the latch to have a center of gravity above and inward relative to a pivot point. As the lifters are raised in the input station, the pick portions of the latches are pushed out of the way, so that the microplate can be supported and lowered by the lifters. After one microplate has passed below the latch, latches 958 move back into a supporting position relative to the remainder of the stack.

In output station 954, a different latch configuration is employed. Latches 960 are urged inward toward the microplates by a spring (not shown). When lifter 962 lifts a microplate against latches 960, the microplate pushes the latches out of the way. After one microplate has passed above the latch, latches 960 move back into a supporting position relative to the remainder of the stack.

Figure 49A:
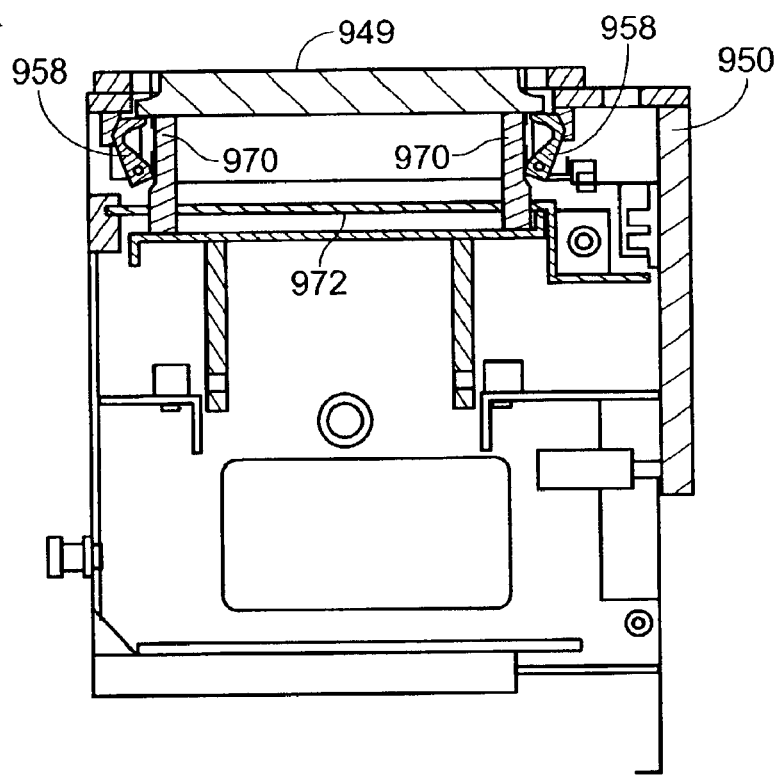
FIGS. 49A and 49B are cross-sectional views through a first (input) station of the sample feeder shown in FIG. 48, taken generally along the line 49AB—49AB in FIG. 48, showing latch and lifter cooperation to remove a microplate from the bottom of a stack.
Figure 49B:
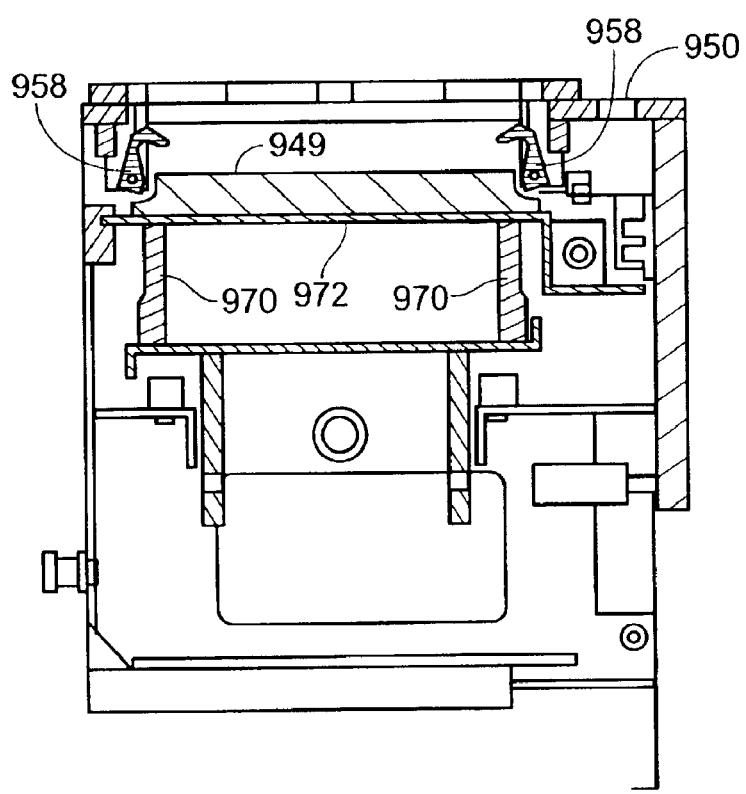

FIGS. 49A and 49B show how input station 950 operates. FIG. 49A shows microplate 949 as it is being picked up at input station 950 prior to analysis. Lifters 970 have moved up through holes in tray 972 to contact the bottom of microplate 949, and in the process have pushed latches 958 out of the way. FIG. 49B shows the same structures as FIG. 49A, except that lifters 970 have dropped, thereby lowering microplate 949 onto tray 972 for transport to the analyzer. Pick portions of latches 958 have moved back into the cavity to support the remainder of the stack.

Figure 50A:
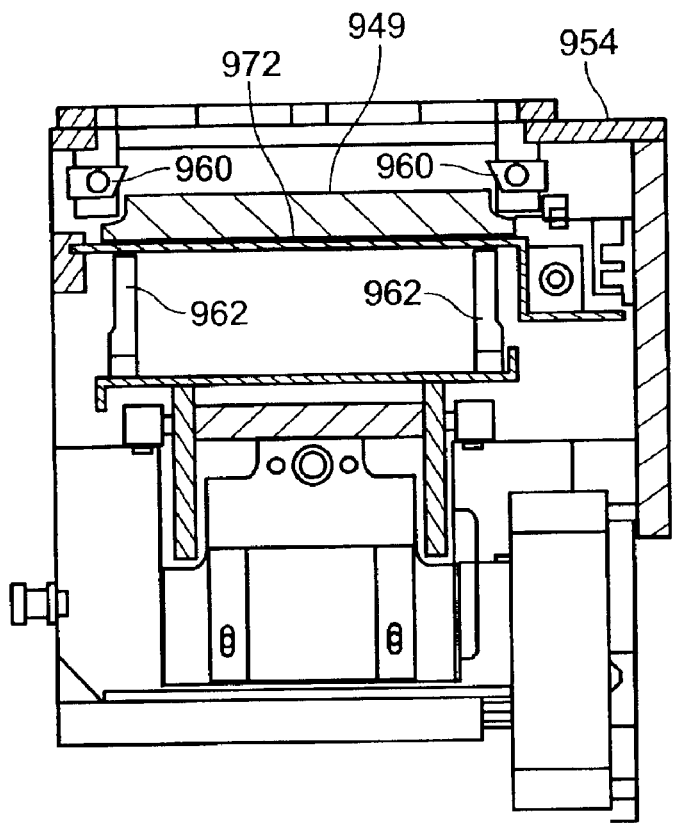
FIGS. 50A and 50B are cross-sectional views through a third (output) station of the sample feeder shown in FIG. 48, taken generally along the line 50AB—50AB in FIG. 48, showing latch and lifter cooperation to add a microplate to the bottom of a stack.
Figure 50B:
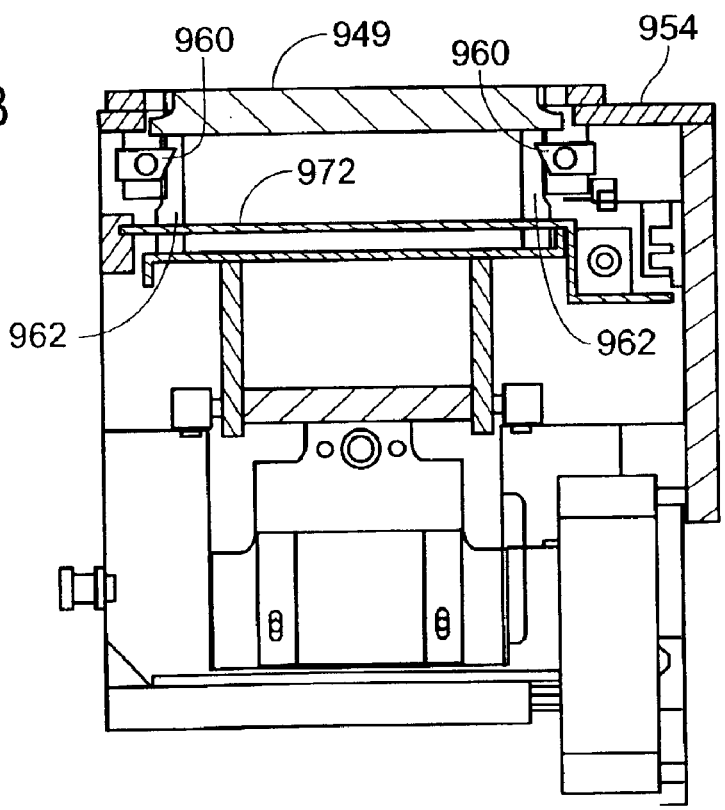

FIGS. 50A and 50B show how output station 954 operates. FIG. 50A shows microplate 949 after it has been delivered to output station 954 following analysis. Lifters 962 then move through holes in tray 972 to raise microplate 949 toward a stack of microplates in the output bin (not shown). FIG. 50B shows the same structures as FIG. 50A, except that lifters 962 have raised microplate 949 past latches 960. Latches 960 are spring biased toward the cavity of third station 954. As lifters 962 raise microplate 949, latches 960 are pushed out of the way by the outer contour of microplate 949. Once microplate 949 is above latches 960, the latches return to their inward position to support the stack of microplates in the output bin. Lifters 962 then retreat downward completely out of the holes in tray 972, so that the tray can translate back to input station 950 to collect another microplate for delivery to the analyzer.

Figure 51:
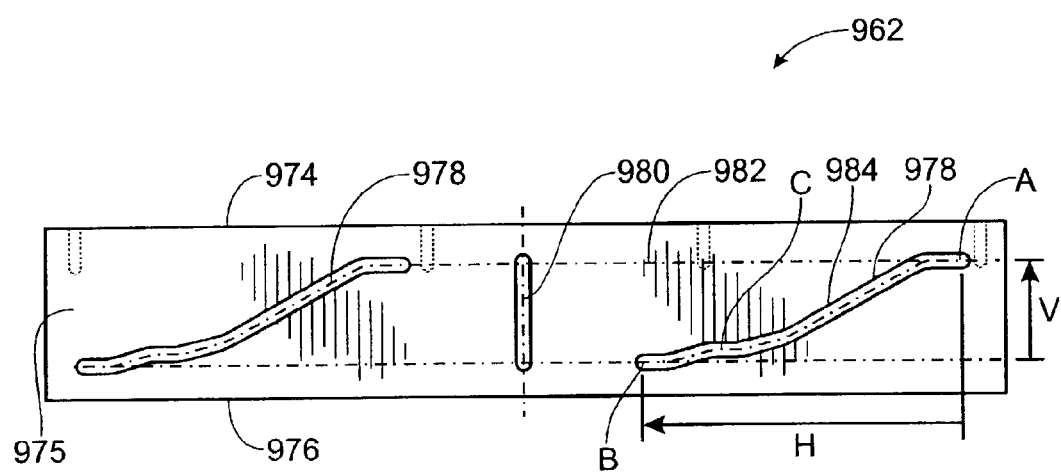
FIG. 51 is a side elevation view of a lifter from the sample feeder shown in FIG. 48.

FIG. 51 shows how lifter 962 operates. Generally, the lifter comprises any mechanism configured to raise or lower a sample container. Lifter 962 is substantially rectangular and includes top 974, side 975, and bottom 976 walls. Each of an opposed pair of side walls 975 includes two sloped drive channels 978, which function as cams, and a vertical guidance channel 980. In sample feeder 948, pins are inserted into drive channels 978 and guide channel 980. In alternative embodiments, pins and channels may be replaced with other components, including ridges, bearings, or rollers. Pins inserted into drive channels 978 are connected to a drive motor, which moves the pins through drive channels 978 between a top position A nearer top wall 974 and a bottom position B nearer bottom wall 976. The pins move horizontally along a line 982, so that the pins push against a side 984 of drive channels 978, urging lifter 962 to move both horizontally and vertically. Pins inserted into guidance channels 980 are connected to relatively fixed portions of sample feeder 948, preventing horizontal motion, but permitting vertical motion, so that lifter 962 only moves vertically. As the pin moves between positions A and B, the pin moves a horizontal distance H and a vertical distance V. It is the vertical displacement that creates the raising and lowering motions. H and V may be optimized for particular sample containers and travel distances; in sample feeder 948, H and V are optimized for microplates and are approximately 10 cm and 3.5 cm, respectively. Lifter 962 is raised when the pin is near position A, and lifter 962 is lowered when the pin is near position B.

In use, the drive motor moves the pins horizontally at a substantially uniform rate; consequently, the slope of drive channel 978 determines the mechanical advantage and the rate of vertical motion. Near positions A, B, and an intermediate position C, the slope of drive channel 978 is substantially zero, so that there is substantially no vertical motion. Stated differently, near positions A, B, and C, a preselected vertical position corresponds to a range of horizontal positions. This configuration makes the vertical position relatively insensitive to motor precision or manufacturing tolerance, because the lifter will be at the same vertical position whenever it simply is near positions A, B, or C. Between positions A and C, and between positions B and C, the slope of drive channel 978 is nonzero, so that there is vertical motion. The slope is largest (approximately 30°) between positions A and C, so that the lifter raises and lowers relatively rapidly when it is farthest from the bottom of the stack of sample containers. The slope is smallest (approximately 15°) between positions B and C, so that the lifter raises and lowers relatively slowly when it is nearest to the bottom of the stack of sample containers.

The drive motor generally comprises any mechanism configured to generate a driving motion. The drive motor used in sample feeder 948 is a stepper motor, which generates a constant torque. Generally, stepper motors and cams provide alternative mechanisms for performing the same function, in this case, generating a varying rate of motion. However, pairing a stepper motor and cam together in the invention provides several advantages. In particular, the cam provides mechanical advantage and positional insensitivity, and permits the stepper motor to be run at a constant, optimal speed. If the stepper motor were used alone, an electronic control system would be necessary to vary raising and lowering speed. Conversely, if the cam were used alone, with a nonstepper motor, an electronic control system with feedback control would be necessary to vary raising and lowering speed.

Together, the lifters and latches form a singulation mechanism configured to separate a microplate (or other sample container) from a stack of microplates in the down-stacking or input operation. This mechanism has inherently low sensitivity to the exact size, shape, construction material, and surface finish of the microplate. As described, the invention may include four inwardly sloping, tapered (or angled) latches that cause the stack of microplates to self-center within the microplates input area to accommodate both relatively small and large microplates sizes. Also as described, the invention may include a feature that causes the microplates to drop gently when the singulation mechanism disengages from the edges of the microplates, thus allowing the microplates to drop onto the lifter mechanism support structure, which lowers the microplates to the tray without spilling fluid from the wells.

The down-stacking latches pivot on pins and are actuated by the lifter mechanism so as to retract when the lifter mechanism rises, thereby releasing the bottom microplate from the stack and allowing it to drop softly onto the lifter. When the latches retract, they pivot on their support pins such that their centers of gravity are offset. Consequently, when the lifter mechanism is lowered, the latches will be activated by gravity to return to their nonretracted or extended state, thereby preventing the next microplates in the stack from dropping as the lifter mechanism is lowered. Because the offset in the center of gravity of the latches is only enough to cause them to return to their extended position, they press only very lightly on the edges of the microplate as it drops. Because the ends of the latches are polished smooth, they exert only a small frictional force on the edges of the microplates so as not to cause the microplate to tilt or otherwise hang up as the lifter mechanism is lowered and the microplate is placed on the tray.

Together, the lifters and latches also form a stacking mechanism configured to add a microplate to a stack of microplates. Generally, the up-stacking mechanism resembles the down-stacking mechanism. The lifter mechanism raises the microplate by a fixed amount, thereby causing it to pass by four spring-loaded latches, which retract as the microplate is raised by the lifter. Once the bottom of the microplate is above the top of the latch, the latches are released, and a spring on each latch causes the latch to extend under the microplate. The lifter mechanism then is lowered, causing the microplate to be captured by the now extended latches. The up-stacked microplate thus is added to the bottom of the output stack.

Sample feeder 948 also may employ alternative singulation mechanisms. For example, singulation mechanisms may (1) take microplates from the bottom of the stack in the input station and add microplates to the bottom of the stack in the output station, as above, (2) take microplates from the bottom of the stack in the input station and add microplates to the top of the stack in the output station, (3) take microplates from the top of the stack in the input station and add microplates to the bottom of the stack in the output station, or (4) take microplates from the top of the stack in the input station and add microplates to the top of the stack in the output station.

Sample feeder 948 permits a robot to deliver a sample container to the input station and to retrieve a different sample container from the output station, both in the same trip. This feature is known as "process compression" and reduces robot hand travel in servicing analyzer 90. For example, if there were only one loading station (e.g., the transporter), the robot would have to remove the analyzed microplate before delivering the unanalyzed microplate. Thus, process compression replaces two separate robot movements with one robot movement. Sample feeder 948 may be configured so that the input and output stations can hold a microplate to facilitate process compression.

Sample feeder 948 is designed to be flexible. The input and output stations can accommodate a variety of commercially available microplates and are large enough to allow microplates to be placed in them by a robot or a human hand. Suitable microplates typically have 96 or 384 wells, but other configurations also can be accommodated. The input and output stations also can accommodate a variety of commercially available preprocessing and postprocessing microplate bins for holding a stack of microplates before and after analysis, respectively. Preprocessing bins may be removed from the input station and replaced with another preprocessing bin containing a new stack of microplates with samples to be analyzed. Similarly, postprocessing bins positioned may be removed from the output station and replaced with another postprocessing bin to receive a new stack of microplates with samples that have been analyzed. Microplate bins may be used with other robotics to dispense, wash, and read without restacking microplates. Suitable microplate bins typically can accommodate 0–60 microplates.

Sample feeder 948 also may include a barcode reader, as shown in FIG. 48, which can be used automatically to identify labeled microplates. The barcode reader 986 preferably is positioned in either of two positions adjacent direct transporter access station 952; these positions permit barcode reader 986 to read barcodes mounted on the long edge or the short edge of microplates. Barcodes are read when sample feeder 948 moves the microplate from input station 950 to direct transporter access station 952. Barcodes cannot be read when microplates are delivered directly to the direct transporter access station 952. Barcode reader 986 can be programmed to decode a variety of symbologies, including SPC (EAN, JAN, UPC), Code 39 (3–43 digits), Codabar (3–43 digits), Standard 2 of 5 (3–43 digits), Interleaved 2 of 5 (4–43 digits), Code 93 (5–44 digits), and MSI-Plessey (4–22 digits), among others. Information obtained from the barcode can be used for various purposes. For example, the barcode can be used to name the report file. The barcode also can be used to convey instructions to the analyzer relating to required changes in assay mode or optics configuration.

D. Alternative Embodiments

Alternative embodiments of systems for feeding samples into an analyzer (or other system) and/or for receiving samples from an analyzer (or other system) are described in the following patent applications, which are incorporated herein by reference in their entirety for all purposes: U.S. Provisional Patent Application Ser. No. 60/167,301, filed Nov. 24, 1999; and U.S. patent application Ser. No. 09/778,224, filed Feb. 6, 2001.

E. Examples

The following numbered paragraphs describe additional and/or alternative aspects of the invention:

1. An apparatus for feeding sample containers in and out of an analyzer, the apparatus comprising (A) a first station that receives and initiates transport of a sample container into the analyzer for analysis; (B) a second station where the sample container is handed off to a transporter that carries the sample container to and from an examination site inside the analyzer; and (C) a third station that collects the sample container after examination.

2. The apparatus of paragraph 1, wherein the sample container is a microplate.

3. The apparatus of paragraph 1, wherein the first station includes a singulation mechanism configured to separate a sample container from a stack of sample containers for transport to the analyzer.

4. The apparatus of paragraph 3, wherein the stack has a top and bottom, the singulation mechanism taking one sample container at a time from the bottom of the stack.

5. The apparatus of paragraph 3, wherein the stack has a top and a bottom, the singulation mechanism taking one sample container at a time from the top of the stack.

6. The apparatus of paragraph 3, further comprising a preprocessing bin positioned at the first station for holding the stack, wherein the preprocessing bin can be removed from the first station and replaced with another preprocessing bin containing a new stack of sample containers with samples to be analyzed.

7. The apparatus of paragraph 1, wherein the second station includes a stacking mechanism configured to add a sample container to a stack of microplates.

8. The apparatus of paragraph 8, wherein the stack has a top and bottom, the stacking mechanism adding one sample container at a time to the bottom of the stack.

9. The apparatus of paragraph 7, wherein the stack has a top and a bottom, the stacking mechanism adding one sample container at a time to the top of the stack.

10. The apparatus of paragraph 7, further comprising a postprocessing bin positioned at the third station for holding the stack, wherein the postprocessing bin can be removed from the third station and replaced with another postprocessing bin to collect a new stack of sample containers with samples after they have been analyzed.

11. The apparatus of paragraph 1, further comprising a tray that carries a microplate between stations.

12. The apparatus of paragraph 11, further comprising a sample container stacking and destacking device operatively associated with the tray, the stacking and destacking device moving with the tray and being capable of taking a sample container one at a time from a first stack of sample containers at the first station, handing off the sample container to the transporter, which carries the sample container to and from an examination site inside the analyzer, and adding the sample container to a second stack of sample containers at the third station after analysis.

13. The apparatus of paragraph 12, wherein the stacking and destacking device includes a lifter and a latch that cooperate to remove a sample container from the first stack, and to add a sample container to the second stack.

14. The apparatus of paragraph 11, wherein the first station has a dedicated first handler that takes a sample container from a first stack of sample containers and deposits the sample container on the tray, the second station has a second handler that hands-off the sample container from the tray to the transporter, which carries the sample container to and from an examination site inside the analyzer, and the third station has a third handler that transfers the sample container from the tray to a second stack of sample containers after analysis.

15. The apparatus of paragraph 14, wherein each handler at the first and third stations includes a lifter and a latch that cooperate to transfer a sample container to or from a stack.

16. The apparatus of paragraph 1, wherein a first linear path connects the examination site to the second station, and a second linear path connects the first, second and third stations, the first linear path being substantially perpendicular to the second linear path.

17. The apparatus of paragraph 1, wherein the examination site and the first, second, and third stations all are positioned along a single substantially linear path.

18. A sample container handling device for handling a sample container, the device comprising (A) a lifter configured to raise or lower a sample container relative to the bottom of a stack of sample containers; and (B) at least one latch having a pick portion, the latch being mounted so that the pick portion moves in and out of gaps between adjacently stacked sample containers in response to up and down movement of the lifter.

19. The device of paragraph 18, wherein the sample container is a microplate.

20. The device of paragraph 18, further comprising a second lifter arranged so that the lifters support opposite sides of a sample container.

21. The device of paragraph 18, further comprising three additional latches, the latches being positioned near four corners of the bottom of a stack of sample containers.

22. The device of paragraph 18, wherein the lifter and latch are designed to remove a single sample container from the bottom of a stack of sample containers, so that the lifter pushes the latch completely out from under the stack as it moves up to support a sample container positioned at the bottom of the stack.

23. The device of paragraph 18, wherein the lifter and latch are designed to add a sample container to the bottom of a stack of sample containers, so that the latch is pushed out of the way by the sample container being pushed up by the lifter until the sample container is high enough for the latch to move inward and underneath the sample container, thereby supporting the stack.

24. The device of paragraph 18, wherein the latch has a pick portion that is urged laterally toward the bottom of the stack.

25. The device of paragraph 24, wherein the pick portion is urged toward the bottom of the stack by configuring the latch so that a center of gravity is positioned upward and toward the stack relative to a pivot point.

26. The device of paragraph 24, wherein the pick portion is urged toward the bottom of the stack by a spring.

27. The device of paragraph 18, wherein the lifter includes a cam configured to vary the rate at which the sample container is raised and lowered.

28. The device of paragraph 18, further comprising a drive motor operatively connected to the lifter and configured to raise and lower the lifter.

29. The device of paragraph 28, wherein the drive motor is a stepper motor.

30. A sample container handling device for handling a sample container, the device comprising (A) a lifter configured to impart a raising or lowering motion to a sample container to transfer the sample container to or from a stack of sample containers; and (B) a drive motor configured to generate a driving motion; wherein the lifter includes a cam operatively connected to the drive motor and configured to convert the driving motion into the raising or lowering motion.

31. The device of paragraph 30, wherein the cam is configured to convert a uniform driving motion into a variable raising and lowering motion.

32. The device of paragraph 30, wherein the drive motor is a stepper motor.

33. An automated analyzer system, the system comprising (A) an analyzer unit having an internal examination site; and (B) first and second external loading stations, the first external loading station configured to receive a sample container before analysis, the second external loading station configured to receive the sample container after analysis.

34. The system of paragraph 33, wherein the sample container is a microplate.

35. The system of paragraph 33, further comprising a robot programmed to deliver a sample container to the first external loading station, and to retrieve a different sample container from the second loading station in the same trip.

36. The system of paragraph 33, wherein the loading stations are adjacent one another.

37. The system of paragraph 33, further comprising a third station, wherein one of the stations receives and initiates transport of a sample container into the analyzer for analysis, another station facilitates hand-off of a sample container to a transporter that carries the sample container to and from an examination site inside the analyzer, and the other station collects the sample container after examination.

IX. Scanning Optics Head

This section describes systems, including apparatus and methods, for optical detection with improved read speed and/or signal-to-noise ratio. These systems may involve, among others, moving a sample substrate while simultaneously detecting light transmitted from one or more sample sites on the substrate by sequentially tracking the sample sites as they move. The systems may include, among others, a stage, a detector, an optical relay structure, and a scanning mechanism. The stage, movable in a first direction, may be used to support the substrate. The detector may be used to detect light emanating from an examination region delimited by a detection initiation position and a detection termination position. The optical relay structure may be used to transmit light from the examination region to the detector, and/or to track the substrate between the detection initiation position and the detection termination position. The scanning mechanism may be used simultaneously to move the optical relay structure and the substrate in the first direction. The systems further may include a housing that encloses some or all of the system components, protecting both the components and the user, and serving as a fixed reference point to describe the motions of moveable portions of the apparatus, such as the scanning mechanism. The systems may be used with microplates, biochips, chromatography plates, microscope slides, and/or other substrates for high-throughput screening, genomics, SNPs analysis, pharmaceutical research and development, life sciences research, and/or other applications.

These and other aspects of the invention are described below in detail, including (A) background, (B) detailed description, and (C) examples. This disclosure is supplemented by the patents, patent applications, and other materials identified above under Cross-References, particularly U.S. Provisional Patent Application Ser. No. 60/142,721, filed Jul. 7, 1999; PCT Patent Application Ser. No. PCT/US00/18547, filed Jul. 7, 2000; and U.S. patent application Ser. No. 09/768,765, filed Jan. 23, 2001, now U.S. Pat. No. 6,310,687. These supplementary materials are incorporated herein by reference in their entirety for all purposes.

A. Background

Optical spectroscopy is the study of the interaction of light with matter. Typically, optical spectroscopy involves monitoring some property of light that is changed by its interaction with matter, and then using that change to characterize the components and properties of a molecular system. Recently, optical spectroscopy has been used in high-throughput screening procedures to identify candidate drug compounds.

Optical spectroscopy is a broad term that describes a number of methods, such as absorption, luminescence (such as photoluminescence and chemiluminescence), scattering/reflectance, circular dichroism, optical rotation, and optical microscopy/imaging, among others. In turn, each of these terms describes a number of more closely related methods; for example photoluminescence includes fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and their phosphorescence analogs, among others.

Unfortunately, optical detection systems for use in optical spectroscopy suffer from a number of shortcomings. In particular, optical detection systems generally involve alignment of a sample and portions of an optical relay structure (such as an optics head) for directing light to and from the sample. Such alignment may be accomplished by physically moving the sample relative to the optical relay structure, or by physically moving the optical relay structure relative to the sample. Typically, such movement is followed by a waiting period before measurement to permit vibrations to subside. Time spent during alignment and subsequent waiting periods is downtime because it is time during which data cannot be collected from the sample. Such downtime is especially significant in high-throughput screening, where tens or hundreds of thousands of samples must be aligned with an optical relay structure to conduct a particular study.

In principle, the number of alignment steps can be reduced by reading simultaneously from a plurality of samples or from a larger area of a single sample. However, simultaneous reading typically will reduce intensities, because excitation light is distributed to a larger area and because the distance between the sample and optical relay structure is increased. Reduced intensities may decrease signal-to-noise ratios, decreasing reliability, especially with less intense nonlaser light sources.

B. Detailed Description

The invention provides apparatus and methods for optical detection with improved read speed and/or signal-to-noise ratio. These apparatus and methods may involve among others moving a sample substrate while simultaneously detecting light transmitted from one or more sample sites on the substrate by sequentially tracking the sample sites as they move. In this way, downtime associated with starting and stopping the sample substrate and with an inability to read during or immediately after moving the substrate may be reduced or eliminated.

C. Examples

The following examples describe without limitation further aspects of the invention.

C.1 Example 1

Figure 52:
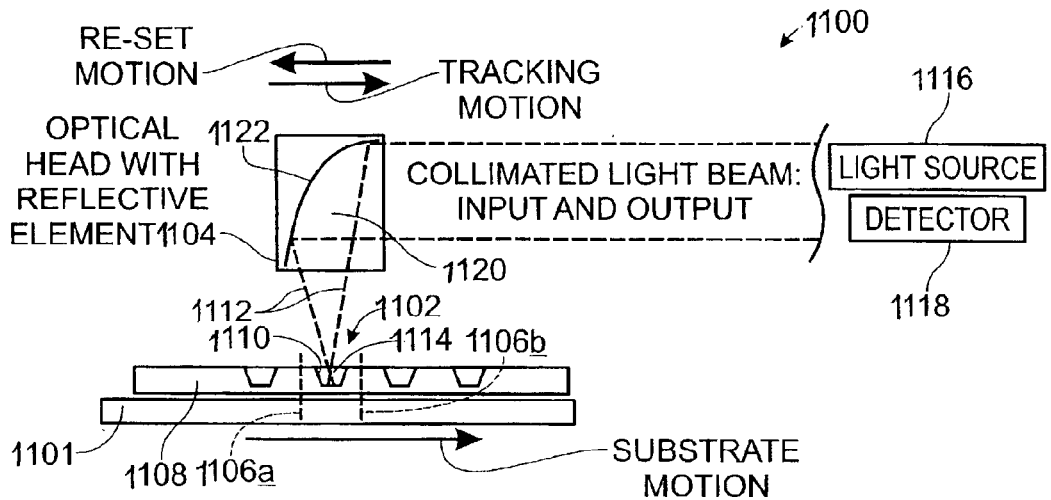
FIG. 52 is a schematic view of a light detection device, in accordance with aspects of the invention, showing the device in use to read from a substrate.

FIG. 52 shows a light detection device 1100 constructed in accordance with aspects of the invention. Device 1100 includes a stage 1101, an examination region 1102, and an optics head 1104. Examination region 1102 is delimited by a detection initiation position 1106a and a detection termination position 1106b. Stage 1101 may be used to support a substrate 1108 having a plurality of sample sites 1110, such as a microplate and associated microplate wells, and optics head 1104 may be used to direct light 1112 to and/or from a sensed volume 1114 positioned in a sample site located in the examination region. Specifically, light may be directed to the sample site from a light source 1116, and/or light may be directed from the substrate to a detector 1118. Typically, the examination region will be larger than the sensed volume, and the separation between adjacent/examined sample sites will be larger than the separation between the initiation position and the termination position. Suitable substrates, light sources, detectors, and optical relay structures for directing light to an optics head and substrate from a light source, and from a substrate and optics head to a detector are described below.

Device 1100 also includes a scanning mechanism 1120 configured to scan the substrate, so that device 1100 may read from a plurality of positions on the substrate. In device 1100, scanning mechanism 1120 includes a reflective surface 1122 and is configured simultaneously to move (at least a portion of) the optics head and substrate, preferably in a single direction. The optics head tracks the substrate between detection initiation position 1106a and detection termination position 1106b, and signal is collected continuously during an integration time over which there typically is no substantial relative motion between the optics head and the sample being analyzed. After the integration time, the position of the sensed volume (or optical beam) may be reset to the detection initiation position so that the sensed volume can track and detect from the next sample site on the substrate. If the reset time is small compared to the integration time, the percentage of time lost will be small. The scanning mechanism improves read time by reducing the time that the detection optics spends over areas of the substrate that do not contain sample to be interrogated. (Any time spent over such areas can be considered downtime.) The scanning mechanism also improves read time because the substrate moves continuously, more rapidly bringing new areas of the substrate into position for reading, and because the need for a waiting period for vibrations to subside is reduced or eliminated if the substrate does not jostle the samples by starting, stopping, or otherwise significantly changing speed. In this regard, the sample sites may move at a substantially constant speed, at least through the examination region.

Device 100 may use any of various strategies to read from multiple sample sites. The device can read from the sample sites sequentially, one-by-one, as described above, or it can read from the sites in groups of two or more. Here, such reading groups may be parallel or perpendicular to the direction of reading, or a combination thereof. The device also can read from a first array in a first direction, move or offset in a second (typically perpendicular) direction, and then read again in the first direction from a second array parallel to the first array. Mechanisms for moving a sample substrate in one, two, or three directions are described in U.S. patent application Ser. No. 09/778,224, filed Feb. 6, 2001, which is incorporated herein by reference in its entirety for all purposes.

Signal from samples on the (moving) substrate may be read by point-to-point reading or by constant velocity scanning. In point-to-point reading, the optics head is fixed relative to the substrate, as described above, while the signal from the detector is integrated for a desired period. In constant velocity scanning, the optical beam is moved relative to the substrate, while the signal from the detector is "binned" into pixels. The size of each pixel is simply the product of the scanning speed (relative to the substrate speed) and the integration time. For example, if the (relative) scanning speed is 10 mm per second and the integration time is 100 milliseconds, the pixel size is 1 mm.

With this technique, a point-to-point reading detection system can read photoluminescent samples essentially as rapidly as a charge-coupled device (CCD)-based reading system with an equivalent light source and numerical aperture. This is because the light source is the limitation, not the detector. A CCD is faster for chemiluminescence, because it collects the light emitted (which is not affected by detector area) from all samples simultaneously. The light output of each well is decreased in large-area photoluminescence, because the illumination per well is reduced, so that the increased speed resulting from collecting light from all wells in parallel is cancelled by the reduced illumination per well. nevertheless, the invention can be effective with fluorescence, phosphorescence, and chemiluminescence measurements, because for a given total read time, more time is spent integrating signal, and less time is spent aligning the optics with new samples. The invention is particularly effective with fluorescence polarization measurements, because good signal-to-noise ratios preferably involve collection of a minimum number of photons (e.g., 10,000) during the integration period, as described in U.S. patent application Ser. No. 09/349,733, which is incorporated herein by reference in its entirety for all purposes.

Figure 53:
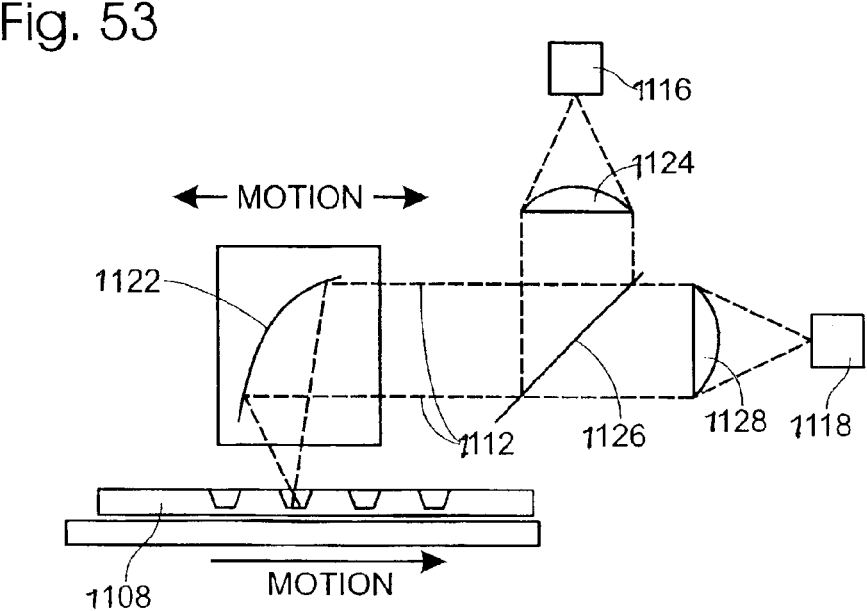
FIG. 53 is an alternative schematic view of the light detection device of FIG. 52.

FIG. 53 is an alternative view of light detection device 1100 showing details of the optical relay structures. Here, light 1112 is directed from light source 1116 (or equivalently from a fiber or other optics operatively connected to light source 1116) through a collimating (e.g., convex-plano) lens 1124 and onto a beamsplitter 1126, which directs a portion of the light toward substrate 1108. Light emitted from the substrate is directed onto the beamsplitter, which transmits a portion of the light through a focusing (e.g., a plano-convex) lens 1128 toward detector 1118 (or equivalently a fiber or other optics operatively connected to detector 1118).

Here, reflective element 1122 (a parabolic section) may be moved to track the plate motion during integration, and then to "fly-back" quickly to the starting position for the next integration. If the input/output light 1112 is collimated, the change in path length will not affect focus, spot size, or light collection, among others. The optics is reflective, which can improve efficiency, optical bandwidth, and cost relative to refractive optics. The moving element can be supported on nonfriction bearings, such as flexures (for example, on a four-bar linkage), because motion is small (~2 mm for a 1536-well plate). Feedback can be provided to reduce positional error of the mirror. In fact, by measuring stage and mirror position and feeding back the error to the mirror drive, the stage and mirror can be locked together so that the mirror tracks the well location substantially exactly, even if the plate motion is not perfectly smooth. This has the significant advantage that substantially precise motion may be accomplished on a much lower mass object (the mirror, instead of the plate and its stage), so that bandwidth is higher and power requirements are lower.

C.2 Example 2

Figure 54:
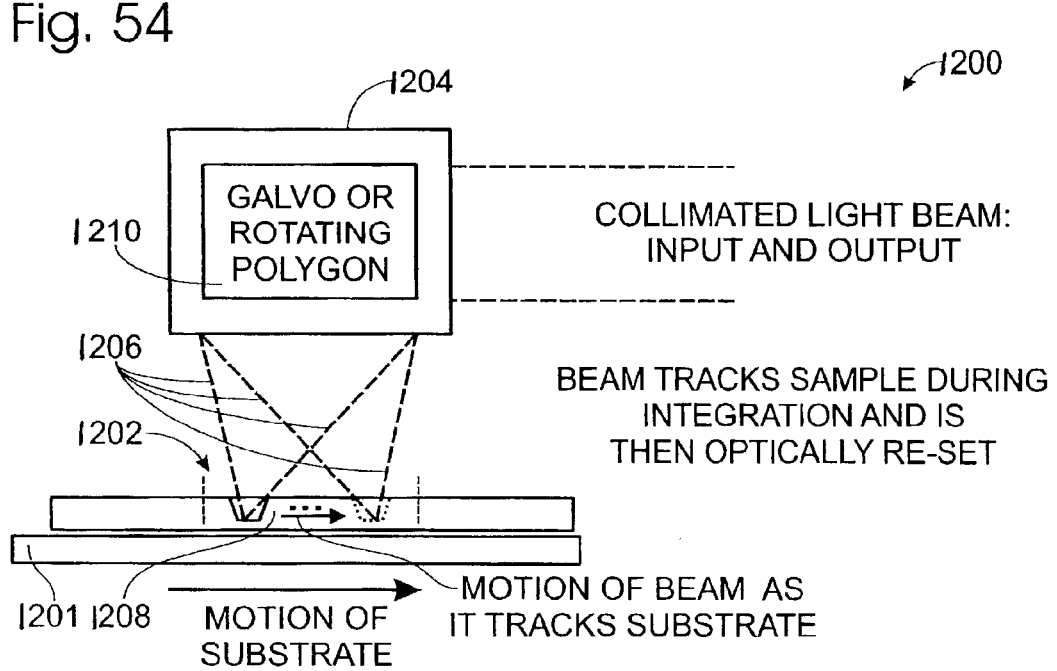
FIG. 54 is a schematic view of an alternative light detection device, in accordance with aspects of the invention, showing the device in use to read from a substrate.

FIG. 54 shows an alternative light detection device 1200 constructed in accordance with aspects of the invention. Device 1200 includes a stage 1201, an examination site 1202 delimited as above, and an optics head 1204 for directing light 1206 to and/or from a substrate 1208 positioned in the examination site. Device 1200 also includes a scanning mechanism 1210 configured to scan the substrate. In device 1200, the scanning mechanism is configured to move the substrate while holding the optics head fixed. More specifically, the scanning mechanism is configured to rotate rather than translate. Scanning mechanism 1212 may include a galvanometer mirror and/or a rotating polygon mirror for matching illumination and/or detection with particular areas of the substrate. Galvanometer mirrors include small planar or convex mirrors attached to the rotating coil of a galvanometer to move a spot of reflected light, among others. Rotating polygon mirrors include a polygonal mirror attached to a driver to move a spot of reflected light, among others.

Device 1200 may be used with any light source, although nonlaser light sources, such as arc lamps or LEDs, present special difficulties. This is because the distance between the source and detector may be relatively long, which may result in lower efficiencies with nonlaser light sources. Some of the difficulty may be overcome by using a high color temperature continuous light source, as described in U.S. patent application Ser. No. 09/349,733, filed Jul. 8, 1999, which is incorporated herein by reference in its entirety for all purposes.

Figure 55:
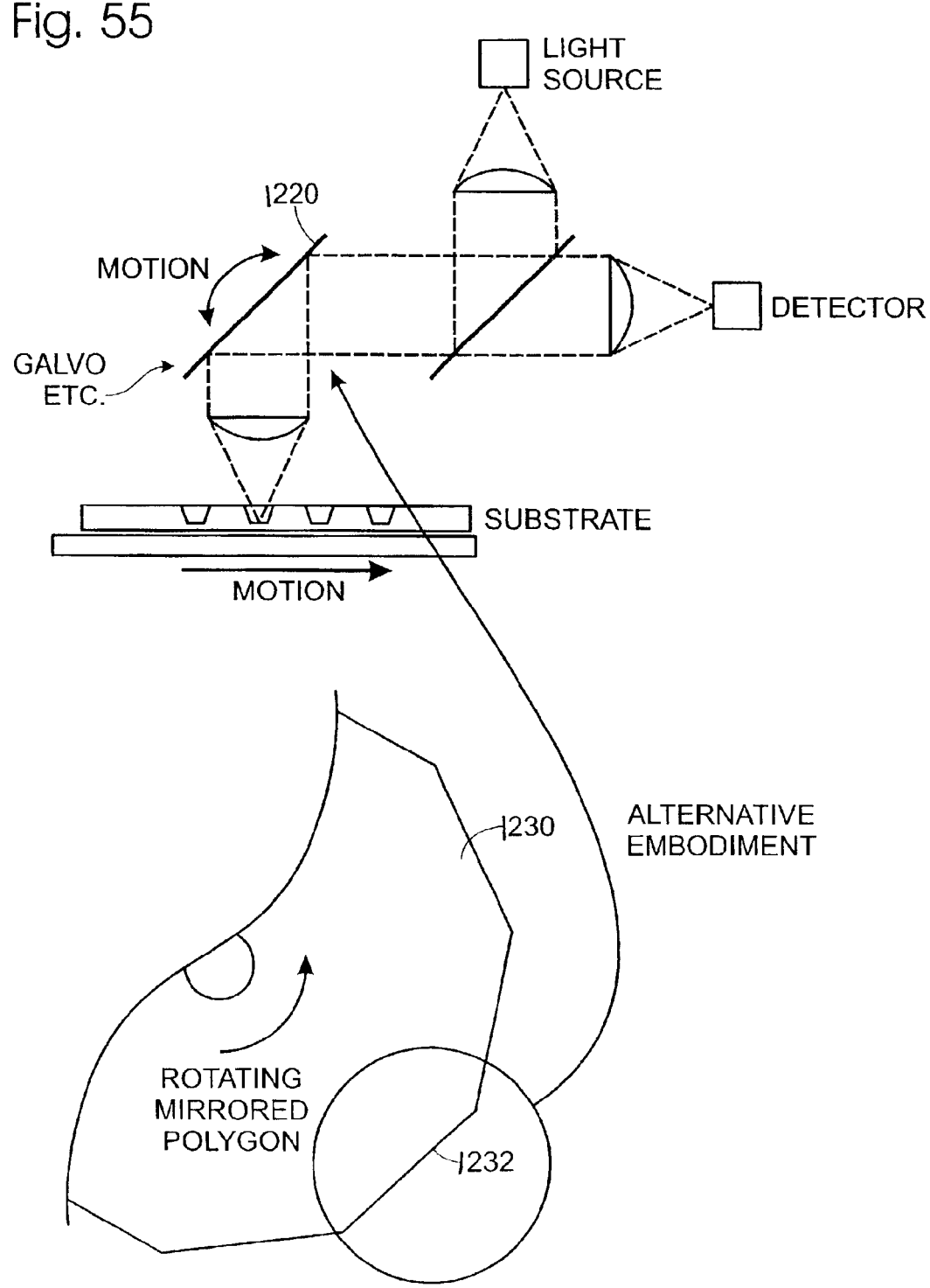
FIG. 55 is an alternative schematic view of the light detection device of FIG. 54.

FIG. 55 shows an alternative view of light detection device 1200, illustrating several techniques, including a galvanometer technique and a rotating polygon technique. The optics are substantially as described above for FIG. 53, except that a lens such as a plano-convex, converging, or other positive strength lens is used between the scanning mechanism and the substrate for field flattening.

The primary drawing in FIG. 55 illustrates a galvanometer technique. Here, driven by a galvanometer-type movement, a mirror 1220 pivots through a small angle and then returns to its start position to repeat the cycle. Suitable drivers include galvanometers, voice-coil drivers, and piezo drivers. The mirror and driver typically are supported by nonfriction bearings, which may include springs, torsion springs, and/or flexures. A lack of stick-slip enables precise, low-power positioning. The system can be resonant, meaning that the compliance of the bearings resonates with the combined mass of the mirror and driver. If the system is resonant, power requirements will drop significantly. Feedback can be provided as above to reduce positional error of the mirror.

The inset in FIG. 55 illustrates a rotating polygon technique. Here, instead of scanning a mirror back-and-forth as above, a polygonal mirror 1230 (or section 1232 thereof) rotates in synchrony with the stage. The motor drive may be much easier: if the mirrors are curved, or if an optic is added, the motion may be at constant angular velocity. To reduce dead time between integrations, the polygon should be large compared to the collimated beam. (Dead time occurs when the beam is on two facets of the mirror at once.)

With both the galvanometer and rotating polygon techniques, the focused spot tends to follow an arc. If the plate is planar, resulting difficulties may be corrected by effectively increasing the radius of curvature of the arc by adding a field-flattening optic, by offsetting the axis of rotation of the galvanometer, and/or by providing a rotating polygon with curved faces. Whether corrected or not, the arc will track the sample site in the same direction over the distance scale of the examination region.

C.3 Example 3

Figure 56A:
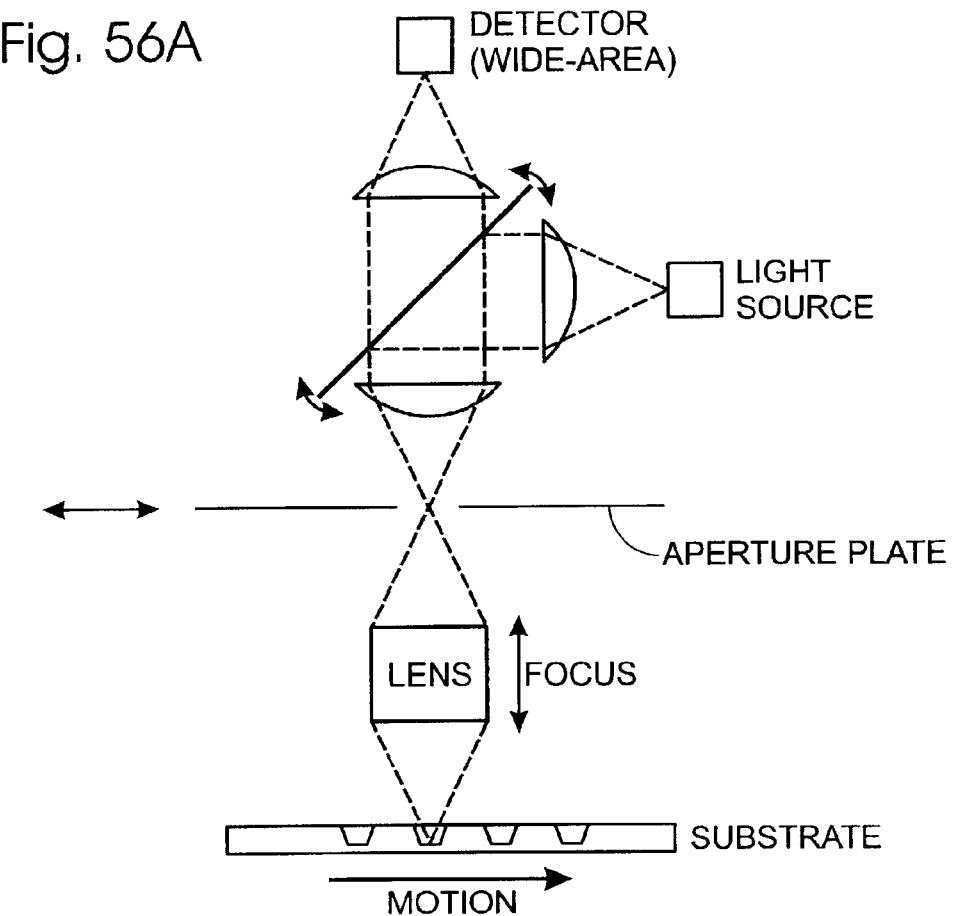
FIGS. 56–58 are schematic views of additional alternative light detection devices, in accordance with aspects of the invention.
Figure 56B:
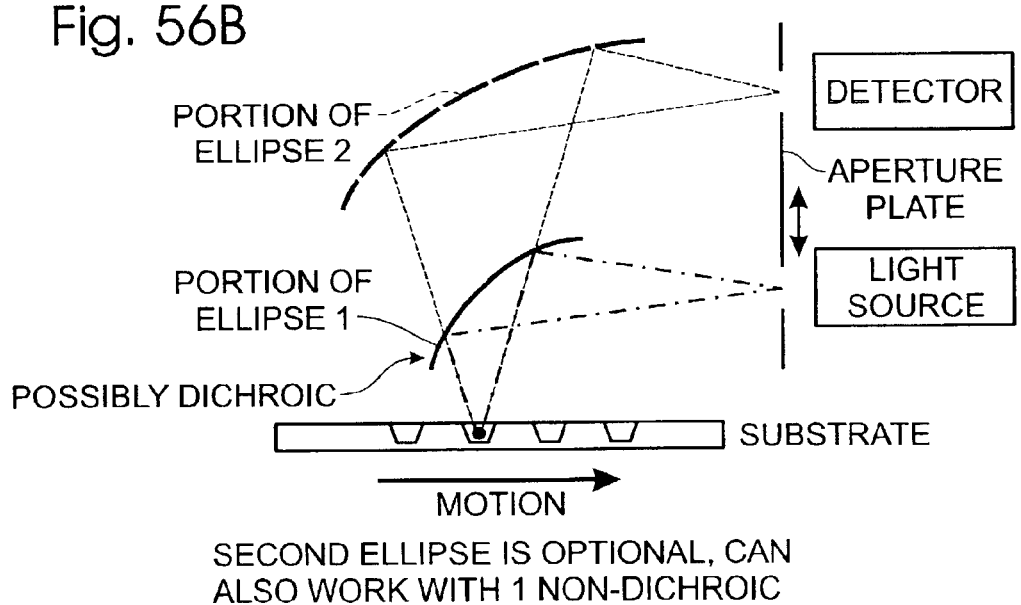
Figure 57A:
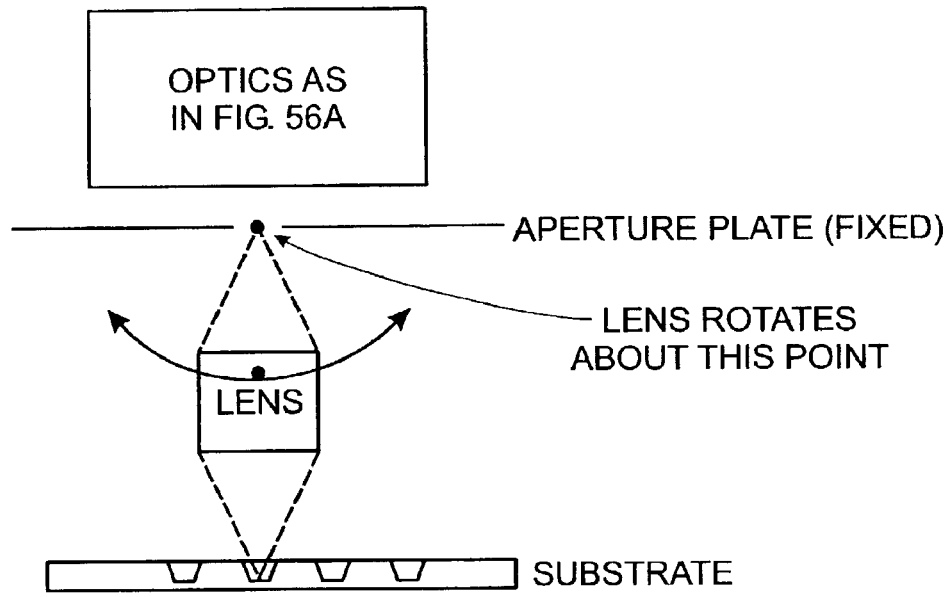
Figure 57B:
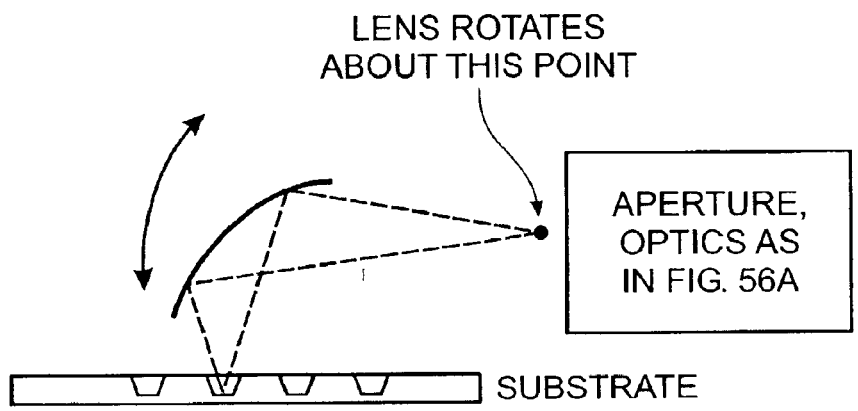

FIGS. 56 and 57 show other alternative light detection devices constructed in accordance with aspects of the invention. These devices involve scanning an aperture over a larger area detector/source. In these (and other) embodiments, the light may not be collimated as it goes through the scanning mechanism.

FIG. 56 shows a first pair of embodiments involving scanning an aperture. If the detector can accommodate the entire motion of the scanned location (e.g., an area of 2.25 mm×4.5 mm for a 1536-well microplate), which is true with a photomultiplier tube (PMT), and if the source can illuminate it, then only an aperture need be scanned. This is accomplished by imaging a small area of the plate adjacent the well being measured onto a second "aperture plate." The aperture plate is moved in synchrony with the sample plate, but in the opposite direction, so that light to and from only one well can make it through the aperture. If the lens demagnifies by a factor 1/m, then the aperture plate should move at a speed m times the sample plate speed. The subsequent optics has much-relaxed imaging requirements because there is little or no possibility of cross-talk. The aperture plate also could have more than one set of associated optics to increase throughput (requiring multiple imaging elements) or to provide "quick-change" capability for different wavelengths, excitations, etc. The dichroic mirror can pivot to reduce the illuminated area requirement.

A sample plate or other substrate can be imaged onto an "aperture plate" refractively or reflectively, among others. A plate can be imaged refractively using a lens. A plate can be imaged reflectively (with advantages as mentioned above) using a mirror, such as a section of an ellipse. The mirror may be dichroic, which can eliminate all lenses and greatly increase bandwidth; this permits the focus to be adjusted without moving the aperture plate or optics (just the imaging unit), so that the light source(s) and detector(s) can be mounted at the optics head, eliminating the cost and light loss associated with fiber optics. Again, mirrors can be scanned or pivoted to reduce illumination requirements.

FIG. 57 shows a second pair of embodiments involving scanning an aperture. The imaging optics (mirror or lens) can be rotated, or a prism inside the imaging optics can be rotated. Alternatively, the techniques described above can be used with an ellipsoidal mirror, with or without demagnification.

C.4 Example 4

Figure 58:
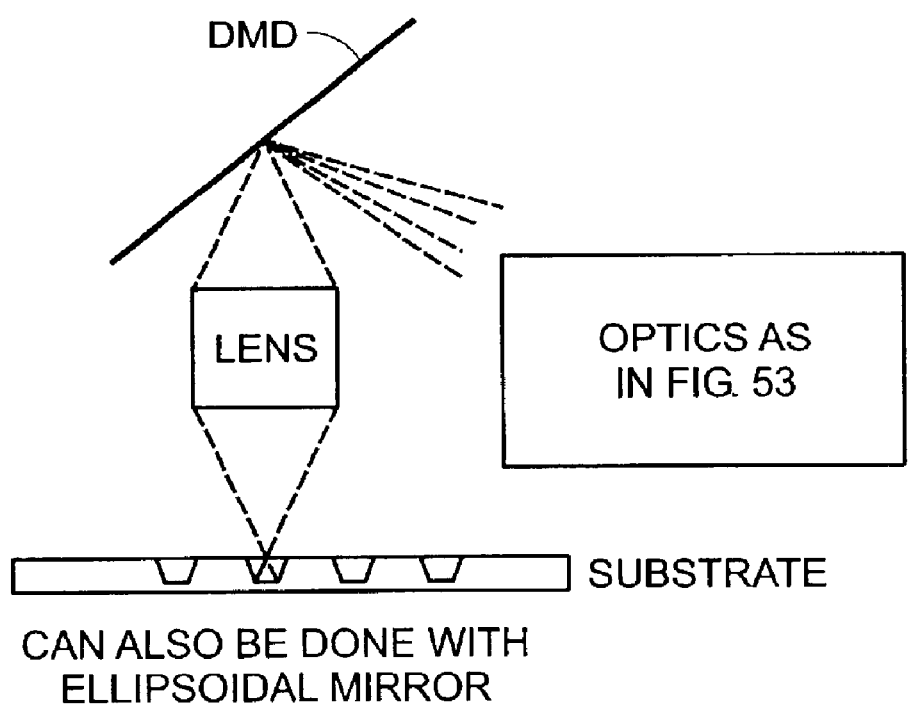

FIG. 58 shows yet another alternative device constructed in accordance with aspects of the invention, using a Digital Mirror Device (DMD). This device has a large array of very small (10–20 micron), very fast mirrors that can be rotated under electronic control. Placed in an image plane, they can be used to control the area that is reflected into the optics. A suitable DMD (used for video projectors) may be obtained commercially from Texas Instruments Inc. (Dallas, Tex.).

C.5 Example 5

The following numbered paragraphs describe additional and/or alternative aspects of the invention:

1. An apparatus for detecting light transmitted from a substrate having a plurality of sample sites, the apparatus comprising (A) a stage for supporting the substrate, the stage being configured to move the substrate in a first direction so that the sample sites pass sequentially through an examination region delimited by a detection initiation position and a detection termination position; (B) a detector configured to detect light; (C) an optical relay structure configured to transmit light from a sensed volume within the examination region to the detector, the sensed volume being smaller than the examination region; and (D) an automated scanning mechanism configured to move the sensed volume in the first direction between the detection initiation position and the detection termination position; wherein the sensed volume tracks a first sample site as it moves between the initiation position and the termination position, so that light transmitted by the first sample can be detected by the detector.

2. The apparatus of paragraph 1, wherein the sensed volume returns to the initiation position after the first sample site passes the termination position to track the next sample site as it moves between the initiation position and the termination position.

3. The apparatus of paragraph 1 further comprising a light source, where the optical relay structure further is configured to transmit light from the light source to the sensed volume.

4. The apparatus of paragraph 1, wherein the sample sites move at a substantially constant speed through the examination region.

5. The apparatus of paragraph 1, wherein the time required for the sensed volume to return to the initiation position is less than the time required for the sensed volume to track a sample site as it moves between the initiation position and the termination position.

6. The apparatus of paragraph 1, wherein the scanning mechanism includes reflective optics.

7. The apparatus of paragraph 6, wherein the reflective optics is selected from the group consisting of a parabolic mirror, a polygonal mirror, and a galvanometer mirror.

8. The apparatus of paragraph 6, wherein at least a portion of the reflective optics undergoes translational motion to track the sample sites.

9. The apparatus of paragraph 6, wherein at least a portion of the reflective optics undergoes rotational motion to track the sample sites.

10. The apparatus of paragraph 1, wherein the scanning mechanism includes refractive optics.

11. The apparatus of paragraph 6, wherein the detector includes a wide area detection device, and the scanning mechanism includes a light blocking member having an aperture positioned between the detection device and the examination region so that sensed volume tracking through the examination region is facilitated by moving the light blocking member relative to the wide area detection device.

12. The apparatus of paragraph 1, wherein the substrate is selected from the group consisting of a microplate, a biochip, and a chromatography plate.

13. The apparatus of paragraph 12, wherein the substrate is a microplate and the sample sites are wells in the microplate.

14. The apparatus of paragraph 1, wherein the separation between the first and second sample sites exceeds the separation between the initiation position and the termination position.

15. The apparatus of paragraph 1 further comprising a housing configured to support and enclose a least a portion of the apparatus, where the initiation position and the termination position are referenced relative to a fixed portion of the housing.

16. The apparatus of paragraph 1, wherein the first sample site moves past the termination position before the second sample site moves into the initiation position.

17. The apparatus of paragraph 1, wherein the light transmitted from the substrate includes light selected from the group consisting of fluorescence, phosphorescence, and chemiluminescence.

18. The apparatus of paragraph 1, the composition being contained in a spatial volume lying between boundary interfaces located at different points along a Z-axis, wherein the Z-axis is substantially perpendicular to the stage 19. The apparatus of paragraph 1, wherein the substrate further includes a third sample site, and wherein the sensed volume returns to the initiation position after the second sample site passes the termination position to track the third sample site as it moves between the initiation position and the termination position.

20. An apparatus for detecting light transmitted from a sample site, the apparatus comprising (A) a stage for supporting a substrate containing the sample site; (B) a detector configured to detect light; (C) an optical relay structure positioned between the stage and the detector and configured to transmit light from a sensed volume to the detector; and (D) a support structure configured to support the stage, the detector, and the optical relay structure; where the stage and the optical relay structure are configured to align the sample site and the sensed volume automatically and to maintain that alignment while moving the sample site relative to a fixed portion of the support structure, so that light transmitted from the sample site can be detected by the detector as the sample site is moved.

21. The apparatus of paragraph 20, wherein the optical relay structure includes an automated scanning mechanism that moves the sensed volume with the sample site relative to the fixed portion of the support structure.

22. The apparatus of paragraph 20, wherein the scanning mechanism includes reflective optics.

23. The apparatus of paragraph 22, wherein the reflective optics is selected from the group consisting of a parabolic mirror, a polygonal mirror, and a galvanometer mirror.

24. The apparatus of paragraph 22, wherein at least a portion of the reflective optics undergoes translational motion to track the sample sites.

25. The apparatus of paragraph 22, wherein at least a portion of the reflective optics undergoes rotational motion to track the sample sites.

26. The apparatus of paragraph 20, wherein the scanning mechanism includes refractive optics.

27. The apparatus of paragraph 22, wherein the detector includes a wide area detection device, and the scanning mechanism includes a light blocking member having an aperture positioned between the detection device and the examination region so that sensed volume tracking through the examination region is facilitated by moving the light blocking member relative to the wide area detection device.

28. The apparatus of paragraph 20, the sample site being a first sample site, where the substrate contains a plurality of sample sites, and where the stage and the optical relay structure are configured to align the sample sites serially with the sensed volume.

29. An apparatus for detecting light transmitted from a sample, the apparatus comprising (A) a support structure having a stage for supporting a substrate containing the sample; and (B) means for detecting light from a sensed volume in the sample while the sensed volume and the sample move substantially together relative to the support structure.

30. A method of detecting light transmitted from a substrate having first and second sample sites, the method comprising (A) moving the substrate in a first direction so that the first and second sample sites pass sequentially through an initiation position and an alignment position; (B) aligning a sensed volume with the first sample site at the initiation position and maintaining the alignment while detecting light transmitted from the sensed volume as the first sample site moves from the initiation position to the termination position; and (C) aligning the sensed volume with the second sample site at the initiation position and maintaining the alignment while detecting light transmitted from the sensed volume as the second sample site moves from the initiation position to the termination position.

31. The method of paragraph 30, wherein each maintaining step includes the step of moving a reflective optics member.

32. The method of paragraph 31, wherein the reflective optics member is selected from the group consisting of a parabolic mirror, a polygonal mirror, and a galvanometer mirror.

33. The method of paragraph 30, wherein each maintaining step includes the step of rotating the reflective optics member.

34. The method of paragraph 30, wherein each maintaining step includes the step of moving a refractive optics member.

X. Arc Lamp Power Supply

This section describes arc lamps, such as xenon arc lamps, having improved high-voltage power supplies. These arc lamps are suitable for use in spectroscopic applications, including but not limited to those described elsewhere in this specification. These and other aspects of the invention are described below in detail, including (A) background, (B) abbreviations, (C) detailed description, and (D) examples. This disclosure is supplemented by the patents, patent applications, and other materials identified above under Cross-References, particularly U.S. Provisional Patent Application Ser. No. 60/197,324, filed Apr. 14, 2000; and U.S. patent application Ser. No. 09/836,575, filed Apr. 16, 2001. These supplementary materials are incorporated herein by reference in their entirety for all purposes.

A. Background

Light sources may be used to produce light for spectroscopic and other applications. These light sources generally include a lamp to produce light and a power supply to provide power for the lamp. A preferred light source for many spectroscopic applications, including photoluminescence assays, is a xenon arc lamp, as described in the following patents and patent applications, which are incorporated herein by reference in their entirety for all purposes: U.S. Pat. No. 6,097,025, issued Aug. 1, 2000; U.S. patent application Ser. No. 09/349,733, filed Jul. 8, 1999; U.S. patent application Ser. No. 09/777,343, filed Feb. 5, 2001; and U.S. Provisional Patent Application Ser. No. 60/197,324, filed Apr. 14, 2000.

Figure 59:
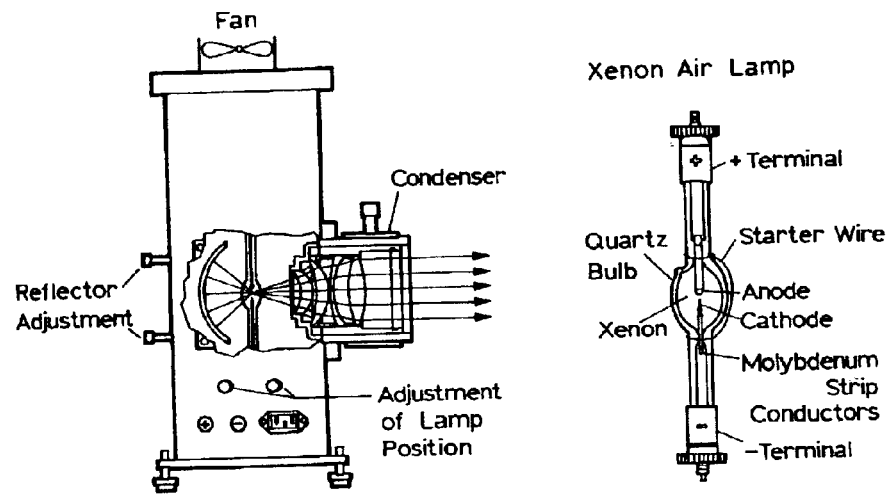
FIG. 59 shows a xenon arc lamp and a typical housing for the lamp.

FIG. 59 shows a xenon arc lamp and a typical housing for the lamp. The lamp includes an anode, a cathode, and a high-pressure xenon atmosphere. Light is produced by the recombination of electrons with ionized xenon atoms created by the flow of electrons across an arc formed between the anode and cathode. The housing is used to support the lamp, to provide protection from excess heat and light, and (in conjunction with a mirror) to collect and collimate light produced by the lamp.

Xenon arc lamps have significant current and voltage requirements, particularly at startup. For example, a CERMAX collimated xenon arc lamp (Model No. LX175F and LX175UV) requires a sequence of three high-voltage pulses for ignition: (1) a 23-kV, 50-ns pulse to start breakdown, (2) a 175-V, 300-ms boost pulse to warm up the arc, and (3) 12 V at 14 A to run the lamp. Additional specifications of this lamp are described in Appendices A and B of U.S. Provisional Patent Application Ser. No. 60/197,324, filed Apr. 14, 2000, which is incorporated herein by reference in its entirety for all purposes. To obtain reliable lamp ignition, existing power supplies for xenon arc lamps require that either the power supply output section or the metal lamp enclosure be ungrounded. This arrangement is necessary to minimize the capacitive load that the power supply must drive. As explained below in more detail, the capacitive load is doubled when the power supply is grounded. When used this way, the ungrounded power supply or lamp enclosure spikes to one-half the lamp ignition voltage, or approximately 11.5 kV, during the lamp ignition process. This causes reliability problems in either the power supply (if the power supply is floating) or the lamp fan (if the enclosure is floating). In addition, it can be mechanically difficult to insulate the lamp enclosure due to the close proximity of other grounded structures.

Figure 60:
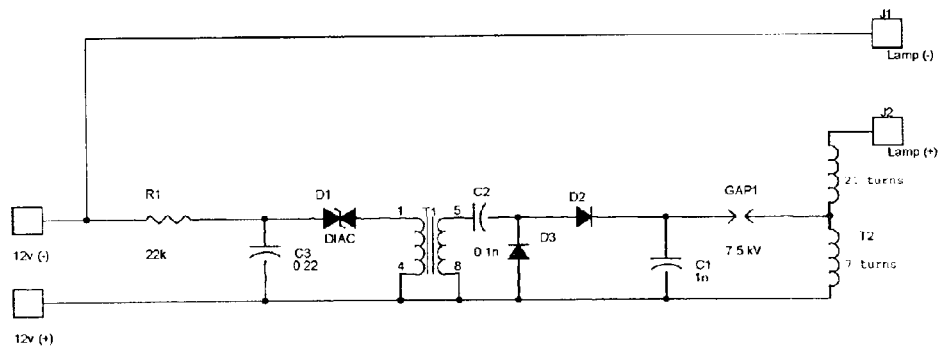
FIG. 60 shows an ignition portion of a prior art xenon arc lamp power supply.
Figure 61:
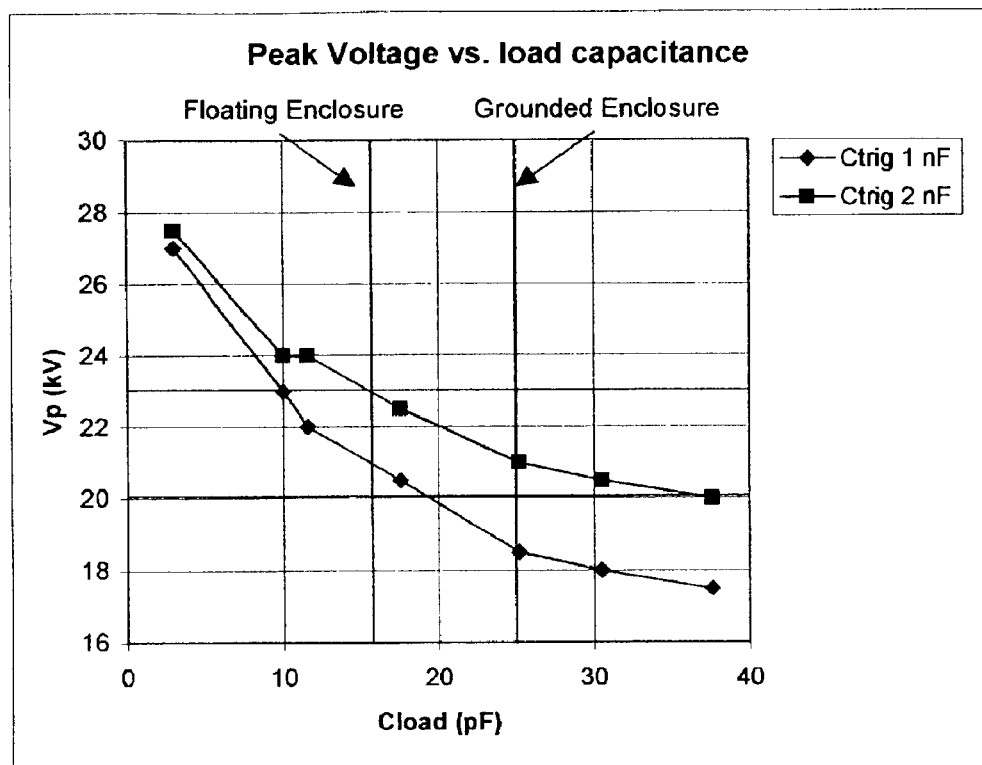
FIG. 61 shows the effect of load capacitance on peak voltage in a power supply, such as the power supply shown in FIG. 59.

FIG. 60 shows a portion of the ignition circuitry from an ASTEX power supply associated with generating the high-voltage ignition pulse. In the circuit of FIG. 60, ignition is initiated by applying a voltage of approximately 175 V across the +12-V and −12-V terminals. This charges capacitor C3 through resistor R1. When the voltage on the capacitor reaches the breakdown voltage of Diac D1, an LC oscillation is created through T1, C3, and D1. The output is stepped up by T1, and fed into the voltage doubler C2, D2, and D3, thereby providing the high voltage to charge the trigger capacitor C1. The ignition pulse is developed when C1 charges up to 7.5 kV, at which time the 7.5-kV spark gap flashes over. The capacitor discharges into a 1:4 autotransformer T2. The output pulse therefore would be 30 kV if there were no load, but the capacitive load of the lamp and housing reduces this voltage, as shown in FIG. 61.

In the design of FIG. 60, the power supply output section floats, i.e., it has no ground reference. As a result, in principle it drives the positive (+) and negative (−) contacts of the lamp symmetrically above and below ground by 11.5 kV during an ignition pulse. In fact, the split is determined by two factors: (1) stray capacitance from each lead to ground, and (2) corona discharge. The circuit tends to minimize corona by floating such that the discharge current is equal from each lead. This means that, potentially, either output can be near ground, and either output can be close to the maximum output voltage. If the split is relatively even, the design of FIG. 60 performs reasonably well.

The design of FIG. 60 has severe disadvantages. First, the circuitry on the output side of the power supply is referenced to the negative (−) end of the lamp, so that the voltage between all of the circuitry and the chassis pulses during ignition to approximately −11.5 kV in 25 ns. At 500 V/ns, a stray capacitance of 1 pF causes a displacement current of 0.5 A. High impedance nodes (FET gates) form a capacitive divider. Several parts of the power supply cannot withstand this voltage reliably, and so the power supply has reliability problems. Second, cooling fan failures occur with the design of FIG. 60. The fan is about 0.5 inches away from the positive (+) end of the lamp, and its leads contact the high-voltage leads to the lamp. Any asymmetry or insulation leakage can lead to discharges into the fan. Because the symmetry is determined by factors such as stray capacitance and corona, it is not guaranteed. Third, the lamp insulation and the insulating wire used on the lamp leads cannot withstand the full 23-kV ignition pulse. In short, while the design nominally works, it is unreliable and susceptible to anything that disturbs the symmetry.

Figure 62:
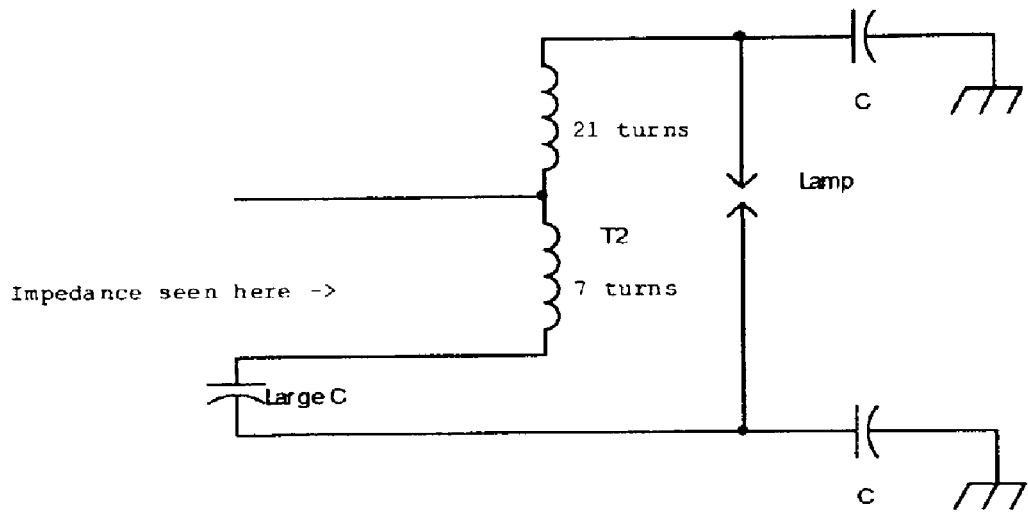
FIG. 62 shows schematically the capacitive loads in the power supply of FIG. 60.

ASTEX recently made modifications to improve the reliability of the supply. In particular, the negative lead of the power supply is now connected to chassis ground through a 3.3-nF capacitor. At the frequencies contained in the ignition pulse, this is essentially a short circuit. This eliminates the reliability problem, but completely unbalances the power supply, causing the entire ignition pulse to appear at the positive (+) lamp lead. It also causes a subtler problem: doubling the load seen by the power supply. To understand this problem, consider the load posed by the cable and housing capacitance and the output circuit of the power supply, as seen by the trigger capacitor. The 12-pF lamp capacitance may be ignored because it is constant in all cases. In the original design, the lamp floats relative to the housing, and the only ground connection is the capacitive coupling to the housing, as shown in FIG. 62. Because no other part of the circuit is connected to ground, the ground connections to the right of the lamp capacitances have only one effect: to connect the capacitors in series. Ignoring the 12-pF lamp capacitance, the load effective capacitance seen on the primary of T2 is therefore:

$$C_{load} = \left(\frac{21+7}{7}\right)^2 \left(\frac{1}{\frac{1}{C}+\frac{1}{C}}\right) = 16\left(\frac{C}{2}\right) = 8C \quad \text{(X-1)}$$

The first term is due to the transformer turns ratio, and the second term is due to the two capacitors in series.

Figure 63:
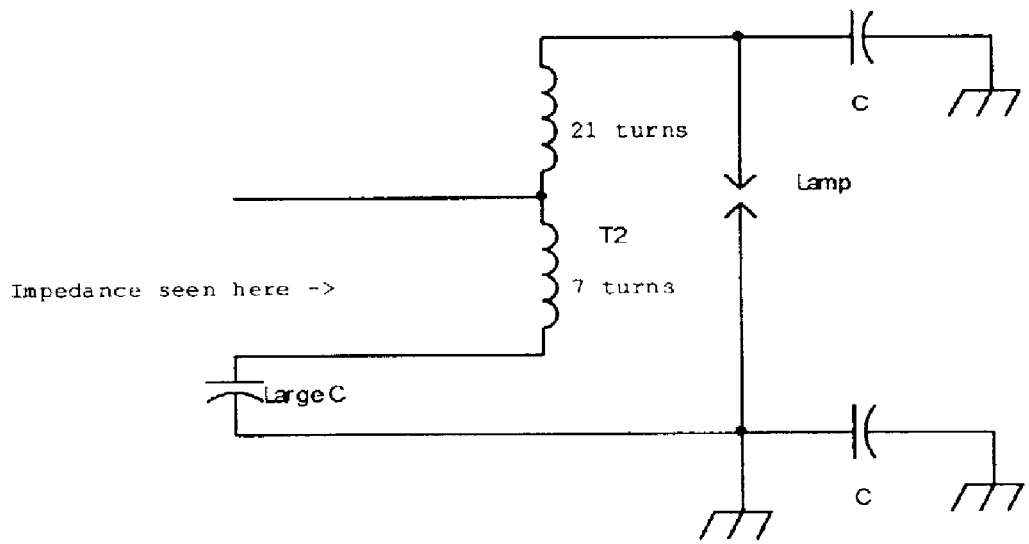
FIG. 63 shows schematically the capacitive loads in the power supply of FIG. 60 with the negative lamp lead grounded.

FIG. 63 shows the effect of coupling the negative lamp lead to ground.

$$C_{load} = \left(\frac{21+7}{7}\right)^2 C = 16C \quad \text{(X-2)}$$

Because there no longer are two capacitors in series, the effective load capacitance due to cable and housing capacitance doubles. Therefore, grounding the negative power supply lead causes at least two problems. First, it doubles the voltage that the wire and lamp insulation must withstand. Second, it doubles the load due to the cable and enclosure capacitance on the power supply.

These shortcomings with xenon arc lamp systems may assume even greater significance in academic and industrial settings that use xenon arc lamps as light sources for spectroscopic applications. In these settings, lamp failure can lead to costly downtime and/or require intervention that exposes potentially unskilled operators to dangers posed by the lamp and power supply. These dangers may be significant. For example, the gas in xenon arc lamps typically is under high pressure (about 10 atmospheres), so that explosion is always a danger. Moreover, as described above, the power supplies for xenon arc lamps may operate at very high currents (about 25 A) and voltages (about 20,000 to 40,000 V), so that electrocution and other health hazards are always a danger. In particular, the power supplies for arc lamps can deliver a lethal shock, and they also can produce transients that damage associated electronic components. Thus, there is a need for a xenon arc lamp system having an improved, more reliable power supply.

B. Abbreviations

The following abbreviations may be used in this section to denote units for current, voltage, time, and capacitance:

| Quantity/Prefix | Abbreviation |
|---|---|
| Amp (measure of current) | A |
| Volt (measure of voltage) | V |
| Second (measure of time) | s |
| Farad (measure of capacitance) | F |
| milli ($10^{-3}$) | m |
| micro ($10^{-3}$) | $\mu$ |
| nano ($10^{-9}$) | n |
| pico ($10^{-12}$) | p |

C. Detailed Description

The invention provides xenon arc lamp systems having improved high-voltage power supplies. The invention may include the arc lamp systems, methods of triggering ignition of the arc lamp systems, and/or use of the arc lamp systems in various applications and apparatus, such as instruments for measuring photoluminescence.

One aspect of the invention includes arc lamp systems, such as a xenon arc lamp having a positive contact and a negative contact, and a power supply having an ignition circuit adapted to generate a voltage pulse to trigger ignition of the arc lamp. The ignition circuit may include a ground, and positive and negative lamp outputs adapted to connect to the positive and negative contacts, respectively, on the lamp. The positive and negative lamp outputs may be ground referenced. Alternatively, or in addition, the positive and negative lamp outputs may be substantially balanced relative to the ground. Alternatively, or in addition, the power supply may include a center-tapped transformer (such as an autotransformer), where the center tap is connected to ground. The lamp may include in each case a grounded or ungrounded lamp enclosure, among others.

Another aspect of the invention includes methods of triggering arc lamp ignition, such as applying a positive pulse to a positive terminal of a lamp and applying a negative pulse to a negative terminal of the lamp, where the pulses are referenced to a frame ground to reduce the capacitive load on the circuitry generating the pulses and to increase the amplitude of the pulses relative to pulses not referenced to ground. The lamp may include a conductive grounded housing or a conductive ungrounded housing, among others.

Yet another aspect of the invention includes an instrument for measuring photoluminescence, such as a xenon arc lamp as described above, a detector, and an optical relay structure configured to direct light from the arc lamp toward an examination site, and to direct photoluminescence light emitted by a sample at the examination site toward the director. The instrument further may include a frame ground, where the power supply ground is electrically coupled to the frame ground.

In each aspect of the invention, the voltage generated on each of the positive and negative contacts may be less than about 15 kV relative to ground, and/or the lamp may be selected from the group consisting of CERMAX and quartz-style lamps, among others.

Figure 64:
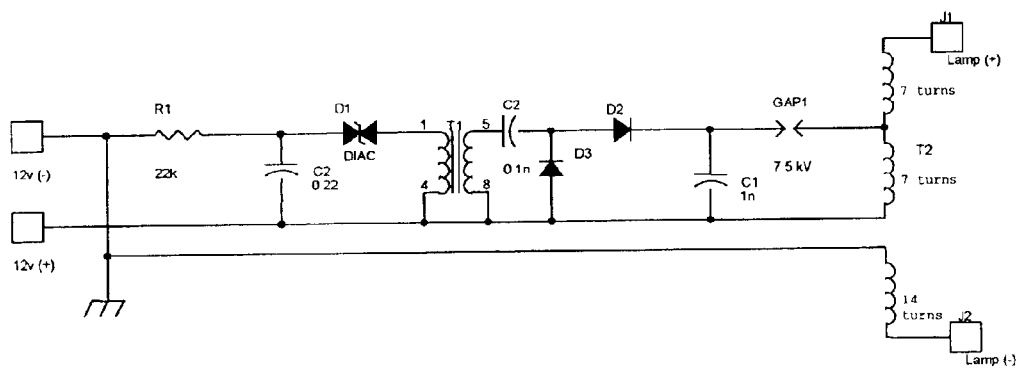
FIG. 64 shows an ignition portion of a xenon arc lamp power supply, in accordance with aspects of the invention.

FIG. 64 shows a power supply circuit constructed in accordance with aspects of the invention. This circuit solves at least two problems. First, it provides a differential ignition pulse to the lamp (±11.5 kV), which also halves the effects of cable and housing capacitance. Second, circuitry of the power supply is referenced to chassis ground, rather than the negative (−) lamp lead. This was done by adding a 14-turn winding to the output transformer (T2 on the trigger PCB) and reducing the 21 turns to 7 turns. The relative voltages are established by the ratios of turns rather than any absolute value, and the invention includes adjusting the specific number of turns to suit the particular application requirements. The circuit ground is attached at the center. This circuit makes the ignition substantially pulse symmetric about ground, as desired.

Figure 65:
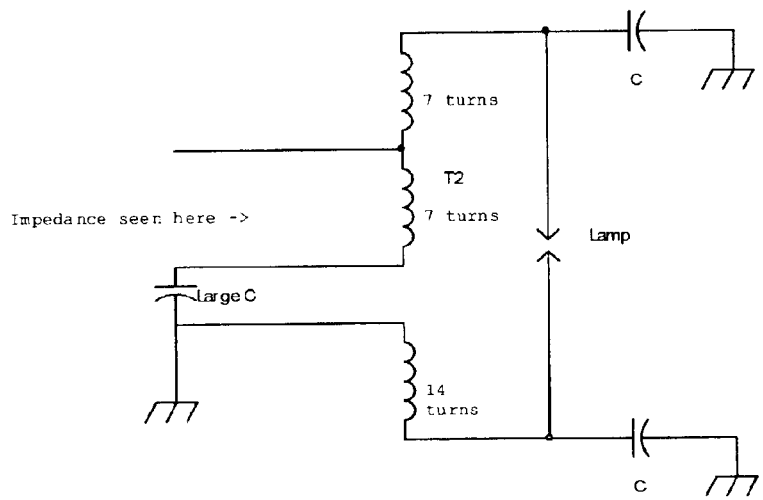
FIG. 65 shows schematically the capacitive loads in the power supply of FIG. 64.

FIG. 65 shows the effective capacitance load created by the circuit of FIG. 64. The effective load capacitance, due to cable and housing capacitance, is:

$$C_{load} = \left(\frac{7+7}{7}\right)^2 C + \left(\frac{14}{7}\right)^2 C = 8C \tag{X-3}$$

The effective capacitance is the same as in the ungrounded circuit of FIG. 60. Thus, this circuit has the advantages of the original circuit (lower effective load capacitance, lower peak output voltage relative to ground (+11.5 kV on one lead, −11.5 kV on the other)), and yet develops the same output voltage between the lamp terminals (23 kV). In addition, it has a significant additional advantage: the power supply circuit is referenced to ground, not −11.5 kV, for improved reliability. Implementation of the above circuit is relatively simple. In particular, T2 is wound slightly differently, essentially adding a tap. The same core, the same wire, and the same number of turns can be used as in the circuit of FIG. 60.

D. Examples

The following examples describe without limitation further aspects of the invention.

D.1 Example 1

To test this circuit, a printed circuit board (PCB) was laid out, built, and tested. It was beneficial to coat the PC board with an insulator such as varnish to reduce arcing and to achieve good high-voltage performance. Additionally, as an alternative mechanism for reducing the effective load capacitance, an insulated housing was built of acrylic rather than the metal used in the prior art.

On the bench, with a lamp housing that had no lamp module (i.e., that had heat sinks, etc., but no bulb, 9GJJ1608), voltage developed:

| Power Supply | Ignition voltage |
|---|---|
| Grounded negative, 1 nF (Prior Art) | 21 kV |
| Split output, 1 nF (FIG. 64) | 25.5 kV (+12.5 kV, −13 kV) |

In an instrument, average number of strikes before a successful ignition:
Lamp statistics: (average number of clicks per ignition for 10 ignitions)

| Lamp | Grounded negative, 1 nF (Prior Art) | Split output, 1 nF (FIG. 64 w/ metal lamp housing) | Acrylic Housing, 1 nF (w/ Prior art circuit) |
|---|---|---|---|
| 0AJJ2541 | 16.8 | 4.2 | 5.5 |
| 9FJJ7101 | 6.3 | 1.0 | 4.6 |
| 0AJJ2532 | 7.9 | 2.4 | 3.0 |
| 0BJJ7049 | 1.5 | 1.4 | 1.0 |

The disclosed trigger circuit with split drive outperforms the prior art design with negative lead grounded, and the plastic housing. In particular, it provides greater reliability and flexibility in installation of the lamp in the instrument in which it is being used. It is equally applicable to CERMAX and quartz-style lamps.

D.2 Example 2

The invention includes apparatus and methods that employ a xenon arc lamp system as described above. For example, the xenon arc lamp system may be used as part of an instrument for spectroscopic analysis, including photoluminescence analysis. Suitable instruments and associated applications are described in any and all of the patents, patent applications, and other publications listed above under Cross-References and incorporated herein by reference in their entirety for all purposes, including, but not limited to, U.S. Pat. No. 6,097,025, issued Aug. 1, 2000; U.S. patent application Ser. No. 09/349,733, filed Jul. 8, 1999; and U.S. patent application Ser. No. 09/777,343, filed Feb. 5, 2001.

D.3 Example 3

The following numbered paragraphs describe additional and/or alternative aspects of the invention:

1. A xenon arc lamp system, comprising (A) a xenon arc lamp including a positive contact and a negative contact; and (B) a power supply including an ignition circuit adapted to generate a voltage pulse to trigger ignition of the arc lamp; wherein the ignition circuit includes a ground, and positive and negative lamp outputs adapted to connect to the positive and negative contacts, respectively, on the lamp; and wherein the positive and negative lamp outputs are ground referenced.

2. The system of paragraph 1, wherein the positive and negative lamp outputs are substantially balanced relative to the ground.

3. The system of paragraph 1, wherein the power supply includes a center tapped transformer, and wherein the center tap is connected to ground.

4. The system of paragraph 3, wherein the transformer is an autotransformer.

5. The system of paragraph 3, wherein the positive and negative lamp outputs are substantially balanced relative to the ground.

6. The system of paragraph 1, wherein the lamp includes a grounded lamp enclosure.

7. The system of paragraph 1, wherein the lamp is selected from the group consisting of CERMAX and quartz-style lamps.

8. The system of paragraph 1, wherein the voltage generated on each of the positive and negative contacts is less than about 15 kV relative to ground.

9. A xenon arc lamp system, comprising (A) a xenon arc lamp including a positive contact and a negative contact; and (B) a power supply including an ignition circuit adapted to generate a voltage pulse to trigger ignition of the arc lamp; wherein the ignition circuit includes a ground, and positive and negative lamp outputs adapted to connect to the positive and negative contacts, respectively, on the lamp; and wherein the ignition circuit is configured to substantially balance positive and negative voltages on the positive and negative lamp outputs.

10. The system of paragraph 9, wherein the power supply includes a center tapped transformer, and wherein the center tap is connected to ground.

11. The system of paragraph 9, wherein the lamp is selected from the group consisting of CERMAX and quartz-style lamps.

12. The system of paragraph 9, wherein the voltage generated on each of the positive and negative contacts is less than about 15 kV relative to ground.

13. A xenon arc lamp system, comprising (A) a xenon arc lamp including a positive contact and a negative contact; and (B) a power supply adapted to generate a voltage pulse to trigger ignition of the arc lamp, wherein the ignition circuit includes a ground, and positive and negative lamp outputs adapted to connect to the positive and negative contacts, respectively, on the lamp; and wherein the power supply includes a center-tapped transformer, the center tap being connected to ground.

14. The system of paragraph 13, wherein the transformer is an autotransformer.

15. The system of paragraph 13, wherein the lamp is selected from the group consisting of CERMAX and quartz-style lamps.

16. The system of paragraph 13, wherein the voltage generated on each of the positive and negative contacts is less than about 15 kV relative to ground.

17. A method of triggering arc lamp ignition comprising applying a positive pulse to a positive terminal of a lamp and applying a negative pulse to a negative terminal of the lamp, wherein the pulses are referenced to a frame ground to reduce the capacitive load on the circuitry generating the pulses and to increase the amplitude of the pulses relative to pulses not referenced to ground.

18. The method of paragraph 17, wherein the lamp includes a conductive housing and the housing is grounded.

19. The method of paragraph 17, wherein the lamp includes a conductive housing and the housing is ungrounded.

20. An instrument for measuring photoluminescence, comprising (A) a xenon arc lamp including a positive contact and a negative contact; (B) a power supply including an ignition circuit, where the ignition circuit includes a ground and positive and negative lamp outputs adapted to connect to the positive and negative contacts, respectively, on the lamp, where the positive and negative lamp outputs are ground referenced; (C) a detector; and (D) an optical relay structure configured to direct light from the arc lamp toward an examination site, and to direct photoluminescence light emitted by a sample at the examination site toward the detector.

21. The instrument of paragraph 20, further comprising a frame ground, wherein the power supply ground is electrically coupled to the frame ground.

XI. Assay Modes

This section describes exemplary systems, including apparatus and methods, for using and/or combining multiple assay modes and methods of optical detection, postprocessing, and/or feedback loops in bioanalytical measurements. These exemplary systems show the versatility and sensitivity of the analyzer. Moreover, additional assays and/or alternative methods for performing the described assays also may be employed in conjunction with the analyzer provided by the invention. These and other aspects of the invention are described below, including (A) background, (B) detailed description, and (C) examples. This disclosure is supplemented by the patents, patent applications, and other materials identified above under Cross-References, including but not limited to U.S. Provisional Patent Application Ser. No. 60/082,253, filed Apr. 17, 1998; U.S. Provisional Patent Application 60/164,633, filed Nov. 10, 1999; U.S. patent application Ser. No. 09/710,061, filed Nov. 10, 2000; Richard P. Haugland, HANDBOOK OF FLUORESCENT PROBES AND RESEARCH CHECIMALS ($6^{th}$ ed. 1996), and Joseph R. Lakowicz, PRINCIPLES OF FLUORESCENCE SPECTROSCOPY ($2^{nd}$ ed. 1999). These supplementary materials are incorporated herein by reference in their entirety for all purposes.

A. Background

The number of bioanalytical measurements performed in life science research is increasing dramatically. This increase is driven in part by advances in genomics and combinatorial chemistry, which have increased both the number of biological targets and the number of compounds for screening them. This increase also is driven in part by advances in assay technologies, especially relating to DNA interactions, protein and peptide interactions, and cell-based assays, which have pushed the number of bioanalytical measurements from hundreds in standard 96-well microplates to millions in even higher-density microplates.

The cost of bioanalytical measurements is roughly proportional to the amount of reagent consumed and to the time spent preparing the reagents, performing the measurements, and analyzing the data. To reduce cost in these measurements, researchers are adopting homogeneous assays and miniaturizing assay volumes. Homogeneous (i.e., "mix and measure") assays generally do not involve filtration steps, which add to the complexity and cost of the measurements. Miniaturizing assay volumes (i.e., miniaturization) generally involves a decrease in assay volume (typically from about 100–200 $\mu$L to about 1–10 $\mu$L) and/or an increase in microplate well density (typically from 96-well formats to 384, 864, 1536, 3456, or denser formats).

Although miniaturization can be an effective cost reduction strategy, smaller sample sizes and larger numbers of measurements generally require larger numbers of secondary measurements to validate the results of the primary measurements. Ideally, the primary measurements should not require secondary analysis; however, false positives must be identified and eliminated. In addition, it is desirable to reduce the frequency of false negatives because these constitute lost information. For example, in the high-throughput screening typically carried out in drug discovery operations, false positives must be identified and eliminated in secondary operations because, by definition, they will not lead to a viable drug. Additionally, false negatives result in an inability to collect information from the affected library compounds.

B. Detailed Description

The invention provides systems, including apparatus and methods, for performing and/or combining multiple modes and methods of optical detection, postprocessing, and/or feedback loops in bioanalytical measurements. These systems may involve multi-mode instruments and a plurality of optical measurement modes. The systems may be used to identify and/or correct for measurement errors, reducing the frequency of false positives and false negatives. The systems also may be used to enable new assays.

Suitable multi-mode instruments and optical measurement modes are described in subsequent sections and in the patents and patent applications incorporated herein by reference, including U.S. Provisional Patent Application Ser. No. 60/164,633, filed Nov. 10, 2000. Suitable instruments include point-reading (e.g., PMT-based) and image-reading (e.g., CCD-based) optical devices. Suitable modes include generally include any mode or method for performing an optical measurement, including absorption, scattering, and luminescence (e.g., photoluminescence and chemiluminescence), among others. These modes include time-resolved and steady-state photoluminescence, including lifetime, intensity, polarization, energy transfer, and total internal reflection. These modes also include trans-absorption, epi-absorption, and trans-flectance. These modes also may include collecting an excitation and/or emission spectrum, for example, by scanning the excitation and/or emission wavelength while holding the other wavelength fixed. Suitable methods include all possible variations in optics and instrument settings to execute these modes and to improve signal detection, including FLARe™ methods of utilizing lamp modulation frequency and phase-and-modulation data to recover signal and suppress background, for example, as described in U.S. patent application Ser. No. 10/012,255, filed Nov. 12, 2001, which is incorporated herein by reference in its entirety for all purposes.

The invention may involve use of two or more different optical measurement modes. Here, modes may be regarded as different if (1) each involves detecting a different property of light (e.g., intensity, polarization, etc.), and/or (2) each involves detecting light created by a different mechanism (e.g., photoluminescence, chemiluminescence, etc.), and/or (3) each involves detecting light modified by a different mechanism (e.g., absorption, scattering, etc.). Multiple measurements performed using a single method are not regarded as multiple modes, for example, measurements made at two different polarizer settings in a polarization assay, or measurements made at two different wavelengths in an energy-transfer or ratio-imaging assay, or measurements made using the same settings to obtain error statistics.

The invention permits the use of multiple detection modes and methods during one or more measurement cycles. For example, a set of methods can be performed on a microplate on a per-well, per-row, per-column, or per-plate basis. Postprocessing can be performed after the results of the first method are collected. One or more additional methods can be subsequently performed based on the results of each successive measurement. Additionally, each measurement or group of measurements can be analyzed in real time, and actions can be initiated based on the analysis of the data. For example, the mean and standard deviation of the fluorescence intensity can be determined for a population of samples or alternatively supplied as input by the user. A postprocessing operation can compare the data obtained from the samples to an acceptable window (or, equivalently, to an unacceptable window), for example, by using a database or look-up table. If the value is too high, a fluorescent contaminant may be present. If the value is too low, a pipetting error may have occurred such that a bubble is present in the well or a reagent is missing. Once it is determined that data values are out of range, a decision can be made automatically to alert a human operator (e.g., to conduct a visual examination) or to perform a preprogrammed task (e.g., such as halting operation of the instrument or system in which it is contained).

Figure 66:
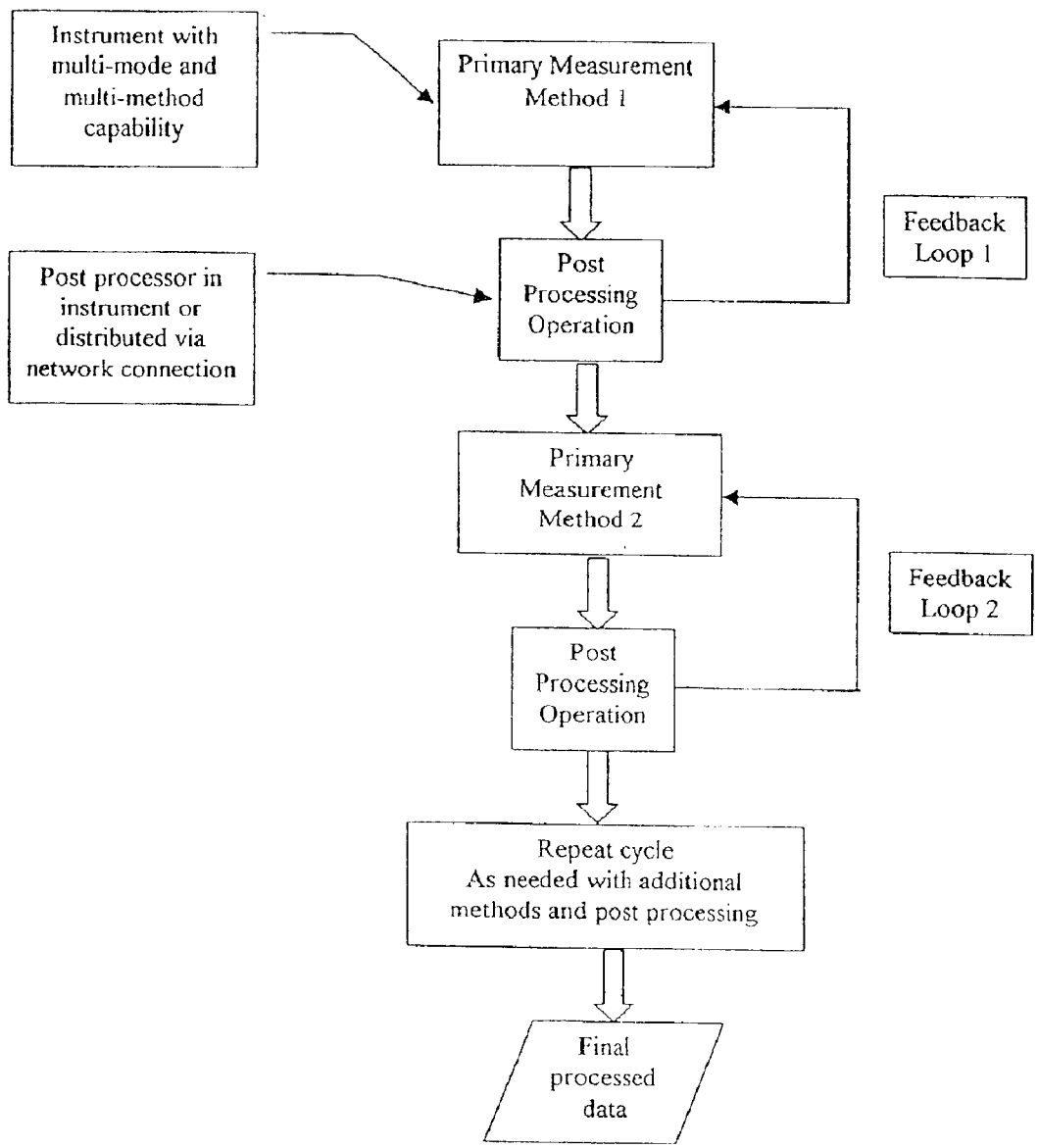
FIG. 66 is a flowchart showing how aspects of the invention may combine modes, methods, postprocessing, and/or feedback loops in optical detection.

FIG. 66 is a flowchart showing more generally how different aspects of the invention may be used and/or combined to combine modes, methods, postprocessing, and feedback loops, and to enable some special functions. For example, information from a first method (Method 1) could be postprocessed, and a decision could be made to halt Method 1 or to re-measure or correct new data points using Method 1 or another method. Information from a second method (Method 2) could be used to detect a problem in Method 1, or vice-versa. For example, Method 2 could be a measurement of the fluorescence intensity of a critical reagent that has been colored with a fluorescent tag, such that a signal that is too high or too low in Method 2 could indicate a pipetting failure that adversely affects Method 1. Another application might be to have two or more targets in each well, such that each target is probed by a different assay and a different method. Another application might be to use a first method to obtain predicate information for a second method, such as using absorption at a first (e.g., infrared) wavelength to determine wavelength to determine path length before doing a measurement to determine an extinction coefficient.

Generally, optical measurements can be combined in various ways to detect (and sometimes also to correct) errors or interferences in assays, including those designed to screen samples (library compounds or natural products) in drug discovery. Some sources of interference are inherent to the sample, including optical absorption (also called "color quenching"), fluorescence, light scattering, static or dynamic quenching of fluorescent label, and enhancement of the label's fluorescence. Other interferences result from the properties of the assay in a particular sample holder; examples include air bubbles, meniscus irregularities, pipetting failure, and imperfections in the holder.

Combining non-luminescence and other methods can be useful. For example, combining an absorption measurement with a luminescence-intensity measurement permits the detection of color quenching and/or the presence of a contaminant. Likewise, combining a light-scattering measurement with a measurement made in another mode permits the detection of interferences due to turbidity in the assay well. In these cases, it is possible to go beyond detection to correction of the interference, by using the secondary measurement to construct a theoretically or empirically based correction factor for the primary measurement.

Combining fluorescence-polarization and fluorescence-intensity measurements also may be useful. Background fluorescence, especially sample fluorescence, interferes with fluorescence polarization measurements: the polarization is an intensity-weighted average of signal and background polarizations, which generally have different values. The overall fluorescence intensity of a sample is proportional to the sum of the intensity detected with parallel polarizers and twice the intensity detected with perpendicular polarizers. Hence, it is possible to synthesize the overall fluorescence intensity from the components of a fluorescence-polarization measurement. If this intensity is higher than control values in wells without sample, the sample must be contributing background fluorescence, and the fluorescence-polarization measurement is suspect.

Interfering background fluorescence is unlikely to have the same spectral and lifetime characteristics as the label, for fluorescence-intensity assays. In the presence of such background, an additional measurement at a different excitation or emission wavelength somewhat different from that of the main measurement would reveal behavior different from that obtained with only the label present. Likewise, the wavelengths could be kept constant, but the lifetime could be probed differently (different integration time-window in the time domain, or different modulation frequency in the frequency domain).

Combining a fluorescence-intensity measurement with a lifetime measurement may allow detection of dynamic quenching, which is attended by a decrease in lifetime.

These examples illustrate, without limitation, the general principle that adding a secondary measurement to an assay method can be used to detect the presence of interferences, independently of whether the method combines the results of the two measurements to yield an assay that has improved rejection of interference. Further aspects of the invention are described without limitation in the following sections: (1) optical measurement modes, and (2) multi-mode instruments.

B.1 Optical Measurement Modes

Optical assays typically involve the study of matter using electromagnetic radiation. These assays can be divided into three broad modes or categories—absorbance, scattering/reflectance, and luminescence—each of which can be further divided into additional modes. Absorbance assays involve relating the amount of incident light that is absorbed by a sample to the type and number of molecules in the sample. Absorbance assays are a powerful method for determining the presence and concentration of an analyte in a sample. Most commonly, absorbance is measured indirectly by studying the portion of incident light that is transmitted by the sample. Scattering assays are similar to absorbance assays, in that the measurement is based on the amount of incident light that emerges or is transmitted from the sample. However, in the case of scattering, the signal increases with the number of interactions, whereas, in the case of absorbance, the signal decreases (inversely) with the number of interactions. Luminescence assays involve electromagnetic emissions from a sample other than the incident light. In each mode, the measurements may be broad spectrum or wavelength-specific, depending on the particular mode.

B.1.a Absorption Assays

Figure 67:
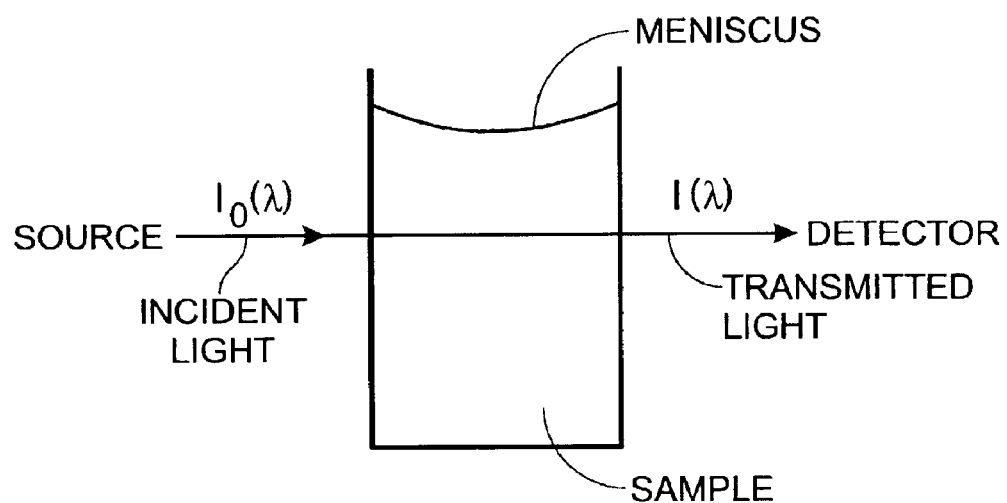
FIG. 67 is a schematic view of a typical absorbance experiment.

Absorption generally comprises the absorption of electromagnetic radiation by one or more components of a composition. FIG. 67 shows a schematic view of a typical absorption experiment, in which incident light is directed from a light source through a composition (and an associated holder), and transmitted light is measured using a detector. Absorption also can be measured using other optical arrangements, such as "epi-absorption," as described in U.S. patent application Ser. No. 09/765,869, filed Jan. 19, 2001, which is incorporated herein by reference in its entirety for all purposes. The amount of light absorbed in passing through a composition can be used to determine the identity, concentration, and electronic energy levels of components of the composition, among other properties.

The amount of light absorbed by a sample in an absorption experiment generally is described by the Beer-Lambert law:

$$\text{Absorbance} = -\log\left(\frac{I(\lambda)}{I_0(\lambda)}\right) = \varepsilon(\lambda)cl \tag{XI-1}$$

The Beer-Lambert law states that when light of wavelength $\lambda_e$ passes through an absorbing sample, its intensity, I, decreases exponentially. Here, $I_0(\lambda)$ is the intensity of the incident light at wavelength $\lambda$, $I(\lambda)$ is the intensity of the transmitted light, $\varepsilon(\lambda)$ is the decadic molar extinction coefficient, c is the concentration of absorbing molecules, and l is the path length. The quantity $-\log(I/I_0)$ is termed the absorbance and is the logarithm of the reciprocal of the fraction of transmitted light. Equation XI-1 shows that absorbance can be increased by increasing the path length and/or the concentration of absorbing molecules. Generally, absorbance measurements are most accurate when the absorbance is in the range 0.1–2.0, corresponding to absorption of about 20–99% of the incident light.

Absorbance measurements may be performed using opposite side (top/bottom or bottom/top) or same-side (top/top or bottom/bottom) illumination and detection, and may involve continuous and/or flash light sources.

B.1.b Scattering Assays

Scattering generally comprises the dispersal of electromagnetic radiation into a range of directions due to physical interactions of the radiation with a composition. Scattering assays can be used to detect the motion, size, concentration, and aggregation state of molecules or other scatterers in a sample, among other properties. For example, by observing the spectral spread of scattered light, the average velocity of scatterers can be determined. By observing the intensity of scattered light, the concentration of scatterers can be measured. By observing the angular distribution of scattered light, various physical characteristics of scatterers can be deduced. Here, the term "scattering sources" describes any molecule, particle, or other object capable of scattering radiation, individually and/or in aggregate.

B.1.c Luminescence Assays

Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence assays are assays that use luminescence emissions from luminescent analytes to study the properties and environment of the analyte, as well as binding reactions and enzymatic activities involving the analyte, among others. In this sense, the analyte may act as a reporter to provide information about another material or target substance that may be the focus of the assay. Luminescence assays may use various aspects of the luminescence, including its intensity, polarization, and lifetime, among others. Luminescence assays also may use time-independent (steady-state) and/or time-dependent (time-resolved) properties of the luminescence. Steady-state assays generally are less complicated than time-resolved assays, but generally yield less information.

Luminescence assays may be conducted using a variety of measurement modes, including chemiluminescence, fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), and fluorescence recovery after photobleaching (FRAP), as well as their phosphorescence and higher-transition analogs, among others.

The remainder of this section describes without limitation four exemplary luminescence measurement modes: (a) intensity modes, (b) polarization modes, (c) energy transfer modes, and (d) steady-state and time-resolved modes.

B.1.c.(i) Intensity Modes

This section describes luminescence intensity assays in accordance with aspects of the invention, including (i) theory, and (ii) implementation.

B.1.c.(i).(a) Theory

Luminescence intensity assays involve monitoring the intensity (or amount) of light emitted from a composition. The intensity of emitted light will depend on the extinction coefficient, quantum yield, and number of the luminophores in the composition, among others. These quantities, in turn, will depend on the environment of the luminophore, among others, including the proximity and efficacy of quenchers and energy transfer partners. Thus, luminescence intensity assays may be used to study binding reactions, among other applications.

B.1.c.(i).(b) Implementation

Luminescence intensity measurements use a continuous light source. Light produced by the light source is routed through a luminophore-specific excitation filter and a low-luminescence fiber optic cable to the optics head. A beamsplitter splits the light, reflecting light into the assay well and transmitting light into a light monitor. The light monitor checks the light source continuously and can be programmed to alert the user if the light source fails. Light emitted from the assay well may pass back through the beamsplitter and then is routed through a fiber optic cable to an emission filter that conditions the light before detection by a photomultiplier tube.

The analyzer may use confocal optics elements to direct excitation light into the assay well and to detect light emitted from the well, all from a sensed volume that may be small compared to the overall volume of the well. Because the sensed volume does not change with the volume of the assay well, performance in different microplates is virtually identical. Z-position within the well may be set manually or automatically. For homogeneous assays, the location with the highest signal-to-noise (S/N) ratio and highest signal-to-background (S/B) ratio typically is in the middle of the well. For cell-based assays, the location with the highest S/N and S/B ratio typically is at the bottom of the well, where luminescence from the cells is maximized and luminescence from the fluid is minimized. Conditions that optimize the S/N and S/B ratios may be determined empirically.

Luminescence intensity measurements may be made from either the top or bottom of the sample well. Bottom reading delivers a higher signal than top reading because the bottom focal area is larger, but bottom reading also delivers a lower S/N ratio because microplates or other sample containers typically autoluminesce.

The user has full control of analyzer settings through software. For luminescence measurements, the user selects the excitation and emission filters, top or bottom reading, and read time. Optional parameters include the magnitude and duration of plate shaking, well-to-well settle time, and Z-height adjustments.

B.1.c.(ii) Polarization Modes

This section describes luminescence polarization assays in accordance with aspects of the invention, including (i) theory, and (ii) implementation.

B.1.c.(ii).(a) Theory

Luminescence polarization assays involve monitoring the absorption and emission (or intensity) of polarized light emitted from a composition. (Polarization describes the direction of light's electric field, which generally is perpendicular to the direction of light's propagation.) Polarization assays typically are used to study molecular rotation and phenomena such as binding that affect rotation. Polarization assays may be homogeneous and ratiometric, making them relatively insensitive to sample-to-sample variations in concentration, volume, and meniscus shape.

Figure 68:
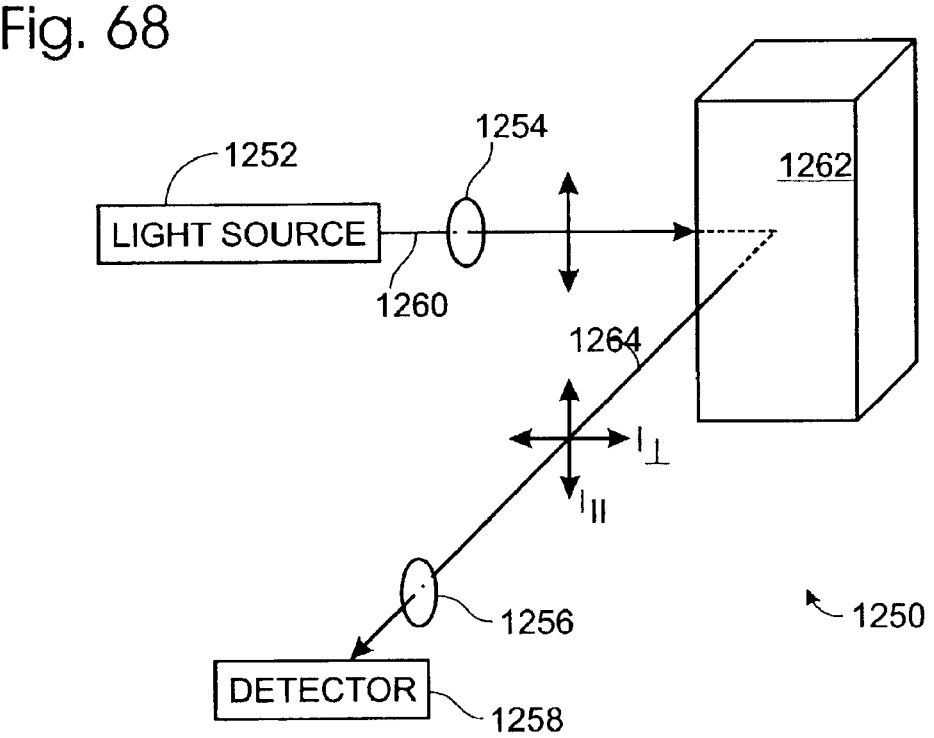
FIG. 68 is a schematic view of an apparatus for detecting polarized light.

FIG. 68 shows a simple apparatus 1250 for performing a polarization assay. Apparatus 1250 includes a light source 1252, an excitation polarizer 1254, an emission polarizer 1256, and a detector 1258. Light 1260 produced by light source 1252 is directed through excitation polarizer 1254, which passes polarized excitation light (indicated by vertical arrow). Polarized excitation light is directed onto a sample 1262, which emits light 1264 in response. Emitted light 1264 may have components oriented parallel ($\parallel$; indicated by vertical arrow) and/or perpendicular ($\perp$; indicated by horizontal arrow) to the polarization of excitation light 1260. The emitted light is directed through emission polarizer 1256, which, depending on its orientation, passes parallel ($I_\parallel$) or perpendicular ($I_\perp$) components of emission light 1264 for detection by detector 1258. Apparatus 1250 also may be used for intensity assays, if the polarizers are held fixed, typically in the same orientation, or removed.

Figure 69:
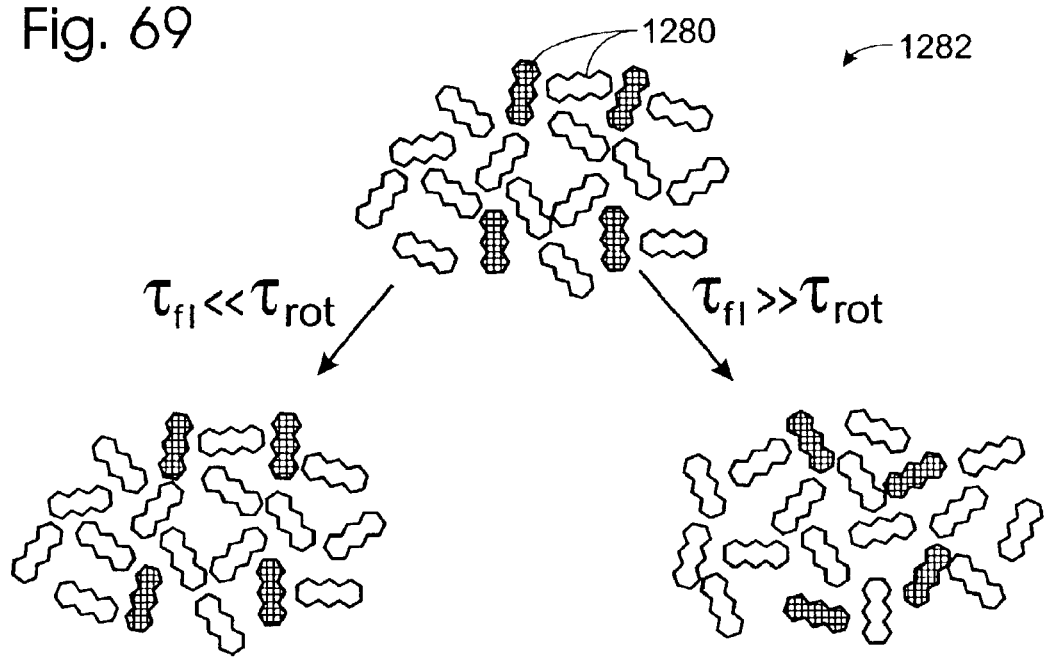
FIG. 69 is a schematic view of luminescently labeled molecules, showing how molecular reorientation affects luminescence polarization.

FIG. 69 is a schematic view showing how luminescence polarization is affected by molecular rotation. In a luminescence polarization assay, specific molecules 1280 within a composition 1282 are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent to which the total emitted light is polarized depends on the extent of molecular reorientation during the time interval between luminescence excitation and emission, which is termed the luminescence lifetime, $\tau$. The extent of molecular reorientation, in turn, depends on the luminescence lifetime and the size, shape, and environment of the reorienting molecule. Thus, luminescence polarization assays may be used to quantify binding/hybridization reactions and enzymatic activity, among other applications. In particular, molecules commonly rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\parallel - I_\perp}{I_\parallel + I_\perp} \tag{XI-2}$$

Here, P is the polarization, $I_{s1}$ is the intensity of luminescence polarized parallel to the polarization of the excitation light, and $I_\perp$ is the intensity of luminescence polarized perpendicular to the polarization of the excitation light. P generally varies from zero to one-half for randomly oriented molecules (and zero to one for aligned molecules). If there is little rotation between excitation and emission, $I_\parallel$ will be relatively large, $I_\perp$ will be relatively small, and P will be close to one-half. (P may be less than one-half even if there is no rotation; for example, P will be less than one-half if the absorption and emission dipoles are not parallel.) In contrast, if there is significant rotation between absorption and emission, $I_{s1}$ will be comparable to $I_\perp$, and P will be close to zero. Polarization often is reported in milli-P (mP) units (1000×P), which for randomly oriented molecules will range between 0 and 500, because P will range between zero and one-half.

Polarization also may be described using other equivalent quantities, such as anisotropy. The relationship between anisotropy and intensity is expressed by the following equation:

$$r = \frac{I_\parallel - I_\perp}{I_\parallel + 2I_\perp} \tag{XI-3}$$

Here, r is the anisotropy. Polarization and anisotropy include the same information, although anisotropy may be more simply expressed for systems containing more than one luminophore. In the description and claims that follow, these terms may be used interchangeably, and a generic reference to one is intended to imply a generic reference to the other.

The relationship between polarization, luminescence lifetime, and rotational correlation time is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \tag{XI-4}$$

Here, $P_0$ is the polarization in the absence of molecular motion (intrinsic polarization), $\tau$ is the luminescence lifetime (inverse decay rate), as described above, and $\tau_{rot}$ is the rotational correlation time (inverse rotational rate), also as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 Dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 Daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 Daltons and 4,000,000 Daltons.

B.1.c.(ii).(b) Implementation

Luminescence polarization measurements may be performed using the same optical configuration as luminescence intensity measurements, with the inclusion of polarizers, as appropriate. (In an exemplary embodiment, polarization measurements are performed using emission and excitation polarization filters and the top optics head.) Light from a continuous light source, preferably a xenon-arc source, is routed through an excitation filter, low-luminescence fiber optic cable, and a polarization filter, which typically is in the S orientation. A beamsplitter then splits the light, reflecting polarized light into the assay well and transmitting light into the light monitor. Light emitted from the assay well may pass back through the beamsplitter and then is routed through a fiber optic cable to an emission and polarization filter (in either the S or P orientation) that conditions the light before detection by a photomultiplier tube.

The analyzer makes two measurements for each assay well, one with excitation and emission polarizers aligned and one with excitation and emission polarizers crossed (as described above). Either polarizer may be static or dynamic, and either polarizer may be set to be S or P.

The continuous light source preferably comprises a high-intensity, high-color temperature light source, such as a xenon arc lamp. Such a lamp minimizes photon noise and hence reduces reading time at a given noise level. When combined with the optimized luminescence detection system, the continuous high-intensity light source increases light throughput and decreases background.

As in luminescence intensity mode, confocal optics elements may direct the excitation light into a small sensed volume in a selected region of the well. The best S/N ratio typically is obtained from the middle of each well, because spurious polarization signals from luminophores bound to the well surfaces is minimized. Conditions that optimize the S/N and S/B ratios may be determined empirically.

The system may be configured to allow the user to select components and/or operational parameters, including the excitation and emission filters, the read time, the magnitude and duration of plate shaking, the well-to-well move time, and/or the Z-height adjustments.

B.1.c.(iii) Energy Transfer Modes

Energy transfer is the transfer of luminescence energy from a donor luminophore to an acceptor without emission by the donor. In energy transfer assays, a donor luminophore is excited from a ground state into an excited state by absorption of a photon. If the donor luminophore is sufficiently close to an acceptor, excited-state energy may be transferred from the donor to the acceptor, causing donor luminescence to decrease and acceptor luminescence to increase (if the acceptor is luminescent). The efficiency of this transfer is very sensitive to the separation R between donor and acceptor, decaying as $1/R^{-6}$. Energy transfer assays use energy transfer to monitor the proximity of donor and acceptor, which in turn may be used to monitor the presence or activity of an analyte, among others.

Energy transfer assays may focus on an increase in energy transfer as donor and acceptor are brought into proximity. These assays may be used to monitor binding, as between two molecules X and Y to form a complex X:Y. Here, colon (:) represents a noncovalent interaction. In these assays, one molecule is labeled with a donor D, and the other molecule is labeled with an acceptor A, such that the interaction between X and Y is not altered appreciably. Independently, D and A may be covalently attached to X and Y, or covalently attached to binding partners of X and Y.

Energy transfer assays also may focus on a decrease in energy transfer as donor and acceptor are separated. These assays may be used to monitor cleavage, as by hydrolytic digestion of doubly labeled substrates (peptides, nucleic acids). In one application, two portions of a polypeptide are labeled with D and A, so that cleavage of the polypeptide by a protease such as an endopeptidase will separate D and A and thereby reduce energy transfer. In another application, two portions of a nucleic acid are labeled with D and A, so that cleave by a nuclease such as a restriction enzyme will separate D and A and thereby reduce energy transfer.

Energy transfer between D and A may be monitored in various ways. For example, energy transfer may be monitored by observing an energy-transfer induced decrease in the emission intensity of D and increase in the emission intensity of A (if A is a luminophore). Energy transfer also may be monitored by observing an energy-transfer induced decrease in the lifetime of D and increase in the apparent lifetime of A.

In a preferred mode, a long-lifetime luminophore is used as a donor, and a short-lifetime luminophore is used as an acceptor. Suitable long-lifetime luminophores include metal-ligand complexes containing ruthenium, osmium, etc., and lanthanide chelates containing europium, terbium, etc. In time-gated assays, the donor is excited using a flash of light having a wavelength near the excitation maximum of D. Next, there is a brief wait, so that electronic transients and/or short-lifetime background luminescence can decay. Finally, donor and/or acceptor luminescence intensity is detected and integrated. In frequency-domain assays, the donor is excited using time-modulated light, and the phase and/or modulation of the donor and/or acceptor emission is monitored relative to the phase and/or modulation of the excitation light. In both assays, donor luminescence is reduced if there is energy transfer, and acceptor luminescence is observed only if there is energy transfer.

B.1.c.(iv) Chemiluminescence Modes

Chemiluminescence is the emission of light due to chemical reactions. Chemiluminescence measurements may be performed using a dedicated read head and photomultiplier tube adjacent the top optics head and separate from those used in photoluminescence measurements. Light emitted from an assay well is collected through a specially-baffled read head and aperture that reduce well-to-well cross-talk. Collected light then is routed through a low-luminescence fiber optic cable to an optimized photomultiplier tube having relatively low dark counts and a blue-green shifted response.

Alternatively, chemiluminescence measurements may use the photoluminescence optical system, especially if it is desirable to sense chemiluminescence from a sensed volume within the sample container. To reduce background in this mode, the light source module in the photoluminescence system may be "parked" between detectors, so that the associated floating head assembly abuts only a solid surface.

For luminescence measurements, the user can select read time. Optional features include plate shaking, well-to-well settle time, and Z-height adjustments.

B.1.c.(v) Steady-State and Time-Resolved Modes

Luminescence assays can be performed in steady-state and time-resolved modes. These modes may be implemented using, for example, apparatus and methods disclosed herein, and/or in the patents, patent applications, and other materials identified above under Cross-References and incorporated herein by reference in their entirety for all purposes. These supplementary materials include without limitation U.S. patent application Ser. No. 10/012,255, filed Nov. 12, 2001; and Joseph R. Lakowicz, PRINCIPLES OF FLUORSCENCE SPECTROSCOPY ($2^{nd}$ ed. 1999).

Steady-state and time-resolved assays may differ in apparatus and/or methodology. Steady-state assays measure luminescence under constant illumination, typically using a continuous light source. Time-resolved assays measure luminescence as a function of time, typically using either a continuous light source, with its intensity appropriately modulated, or a time-varying light source. Time-resolved assays may be conducted in the time domain or in the frequency domain, both of which are functionally equivalent.

In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency f, although other protocols (such as transforming time-domain data into the frequency domain) also may be used. The intensity of the resulting luminescence emission is modulated at the same frequency as the excitation light. However, the emission will lag the excitation by a phase angle (phase) $\phi$, and the intensity of the emission will be demodulated relative to the intensity of the excitation by a demodulation factor (modulation) M.

Figure 70:
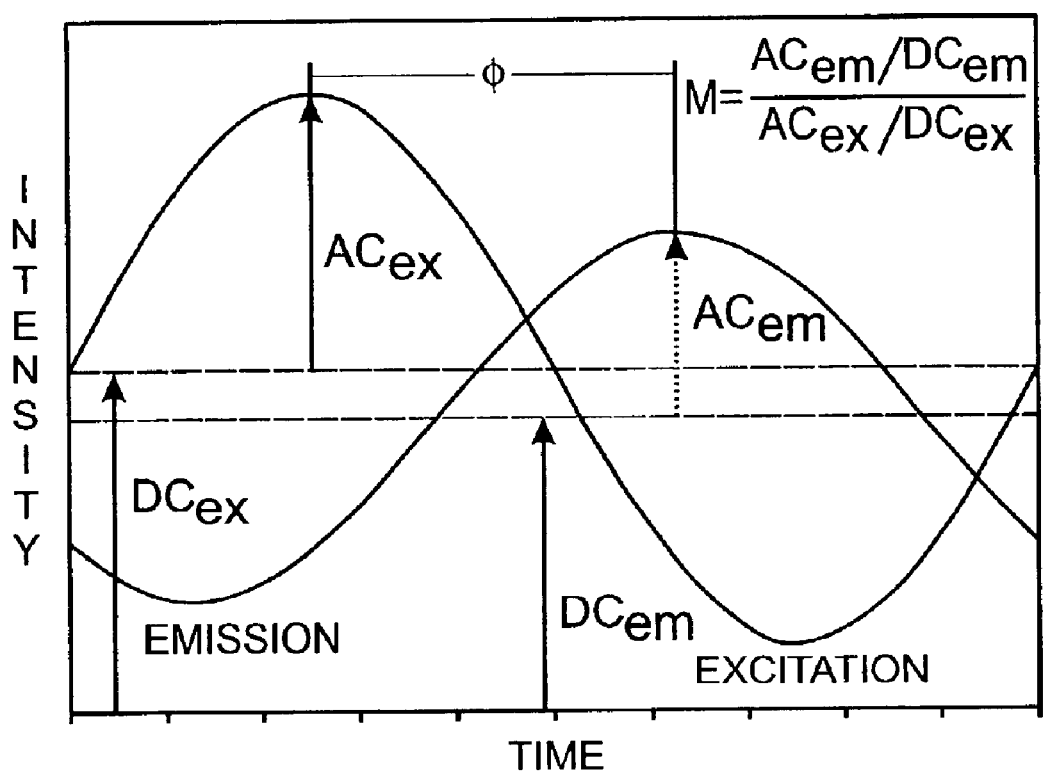
FIG. 70 is a schematic view of a frequency-domain time-resolved measurement, showing the definitions of phase angle (phase) $\phi$ and demodulation factor (modulation) M.

FIG. 70 shows the relationship between emission and excitation in a single-frequency frequency-domain experiment. The phase $\phi$ is the phase difference between the excitation and emission. The modulation M is the ratio of the AC amplitude to the DC offset for the emission, relative to the ratio of the AC amplitude to the DC offset for the excitation. The phase and modulation are related to the luminescence lifetime $\tau$ by the following equations:

$$\omega\tau = \tan(\phi) \quad (\text{XI-5A})$$

$$\omega\tau = \sqrt{\frac{1}{M^2} - 1} \quad (\text{XI-5B})$$

Here, $\omega$ is the angular modulation frequency, which equals $2\pi$ times the modulation frequency. For maximum sensitivity, the angular modulation frequency should be roughly the inverse of the luminescence lifetime. Lifetimes of interest in high-throughput screening vary from less than 1 nanosecond to greater than 1 millisecond. Therefore, instruments for high-throughput screening preferably should be able to handle modulation frequencies from less than about 200 Hz to greater than about 200 MHz.

Time-resolved luminescence measurements use substantially the same optical configuration as luminescence intensity and luminescence polarization measurements, except that time-resolved luminescence methods use the upper optics head and the substitution of a flash lamp, preferably a xenon flash lamp, for a continuous lamp as the light source. The flash lamp creates a brief flash of excitation light, which is followed by time-dependent luminescence. Time-dependent measurements may be delayed to avoid short-lifetime autoluminescence, and hastened to avoid long-lifetime autoluminescence, if desired.

As in luminescence intensity mode, confocal optics elements may direct the excitation light into a small sensed volume in a selected region of the well. The location of the sensed volume can be changed using the Z-height parameter. The optimal S/N and S/B can best be determined empirically.

For time-resolved luminescence, the user selects the excitation and emission filters, delay time, integration time, and cycle time. Optional parameters include the magnitude and duration of plate shaking, well-to-well settle time, and Z-height adjustments.

B.2 Multi-mode Instrument

A multi-mode instrument generally comprises any instrument capable of use in two or more optical measurement modes, such as absorption, luminescence, and/or scattering, and variants thereof. Such use may include analyzing a composition, including qualitative analysis (to determine the nature of the composition and/or its components) and/or quantitative analysis (to determine the amount, relative proportions, and/or activity of the composition and/or its components). Suitable multi-mode instruments are described herein, in other sections.

C. Examples

Selected aspects of the invention also may be described as recited in the following numbered paragraphs:

1. A method of performing optical analysis on a composition, comprising (A) positioning the composition at an examination site in a multi-mode instrument; (B) detecting light transmitted from the composition using the multi-mode instrument in a first optical measurement mode; (C) detecting light transmitted from the composition using the multi-mode instrument in a second optical measurement mode, where the second mode is different than the first mode; and (D) computing a first quantity related to a property of the composition using the light detected in at least one of the optical measurement modes.

2. The method of paragraph 1, where the multi-mode instrument is capable of detecting light in at least two optical measurement modes selected from the group consisting of absorption, luminescence, and scattering.

3. The method of paragraph 1, where the steps of detecting light using the first and second optical modes are performed sequentially.

4. The method of paragraph 3, further comprising automatically switching the multi-mode instrument from the first optical measurement mode to the second optical measurement mode.

5. The method of paragraph 1, where the steps of detecting light using the first and second optical modes are performed simultaneously.

6. The method of paragraph 1, where one or both of the steps of detecting light using the first and second modes are performed simultaneously on a plurality of compositions for optical analysis of the plurality of compositions.

7. The method of paragraph 1, where one or both of the steps of detecting light using the first and second modes are performed successively on a plurality of compositions for optical analysis of the plurality of compositions.

8. The method of paragraph 1, where the step of detecting light using the first mode is performed successively on a plurality of compositions for optical analysis of the plurality of compositions, and then the step of detecting light using the second mode is performed on some or all of the plurality of compositions.

9. The method of paragraph 1, the first quantity being computed using the light detected in the first optical measurement mode, further comprising (A) computing a second quantity using the light detected in the second optical measurement mode; and (B) assessing the presence or effects of a potential source of error on the first quantity using the second quantity.

10. The method of paragraph 9, where the first optical measurement mode is luminescence, and where the second optical measurement mode is selected from the group consisting of absorption and scattering.

11. The method of paragraph 1, where the first optical measurement mode is luminescence.

12. The method of paragraph 11, where the second optical measurement mode is scattering.

13. The method of paragraph 12, further comprising assessing the presence or effects of turbidity on the first quantity using the light detected in the second optical measurement mode.

14. The method of paragraph 11, where the second optical measurement mode is absorption.

15. The method of paragraph 14, further comprising assessing the presence or effects of color quenching and/or a contaminant on the first quantity using the light detected in the second optical measurement mode.

16. The method of paragraph 1, where the first quantity is selected from the group consisting of absorbance, chemiluminescence intensity, photoluminescence intensity, photoluminescence energy transfer, photoluminescence lifetime, and photoluminescence polarization.

17. The method of paragraph 1, where the property of the composition is the presence or activity of a component of the composition.

18. The method of paragraph 1, further comprising detecting light transmitted from the composition using the multi-mode instrument in a third optical measurement mode, where the third mode is different than the first and second modes.

19. The method of paragraph 1, further comprising determining to perform the step of detecting light using the second mode based on an outcome of the step of detecting light using the first mode.

20. The method of paragraph 1, further comprising repeating the step of detecting light using the first mode based on an outcome of the step of detecting light using the second mode.

21. A method of performing optical analysis on a composition, comprising (A) positioning the composition at an examination site in a multi-mode instrument; (B) detecting light transmitted from the composition using the multi-mode instrument in a first optical measurement mode; (C) computing a first quantity related to a property of the composition using the light detected in the first optical measurement mode; (D) comparing the quantity to a preselectable criterion; and (E) if the quantity matches the preselectable criterion, detecting light transmitted from the composition using the multi-mode instrument in a second optical measurement mode, where the second mode is different than the first mode.

22. The method of paragraph 21, where the preselectable criterion is a set of acceptable values for the first quantity, so that light transmitted from the composition is detected using the second mode if the first quantity is an acceptable value.

23. The method of paragraph 21, where the preselectable criterion is a set of unacceptable values for the first quantity, so that light transmitted from the composition is detected using the second mode if the first quantity is an unacceptable value.

24. The method of paragraph 21, further comprising (A) computing a second quantity related to a property of the composition using the light detected in the second optical measurement mode; and (B) assessing the presence or effects of a potential source of error on the first quantity using the second quantity.

25. A system for performing optical analysis on a composition, comprising (A) a multi-mode instrument that is capable of detecting light from a composition in first and second optical measurement modes, where the first mode is different than the second mode; and (B) a processor that uses measurements from more than one optical measurement mode to compute a quantity relating to a characteristic of the composition.

26. The system of paragraph 25, where the multi-mode instrument includes a light source, a detector, an examination site, and an optical relay structure positioned to transmit light from the light source to a composition at the examination site, and from the composition to the detector.

27. A method of performing optical analysis on a composition, comprising positioning the composition at an examination site in a multi-mode instrument, detecting light transmitted from the composition using the multi-mode instrument in a first optical measurement mode, computing a first quantity related to a property of the composition using the light detected in the first optical measurement mode, comparing the quantity to a preselectable criterion, and if the quantity matches the preselectable criterion, detecting light transmitted from the composition using the multi-mode instrument in a second optical measurement mode, where the second mode is different than the first mode.

28. The method of paragraph 27, where the multi-mode instrument is capable of detecting light in at least two optical measurement modes selected from the group consisting of absorption, luminescence, and scattering.

29. The method of paragraph 27, further comprising automatically switching the multi-mode instrument from the first optical measurement mode to the second optical measurement mode.

30. The method of paragraph 27, where one or both of the steps of detecting light using the first and second modes are performed simultaneously on a plurality of compositions for optical analysis of the plurality of compositions.

31. The method of paragraph 27, where one or both of the steps of detecting light using the first and second modes are performed successively on a plurality of compositions for optical analysis of the plurality of compositions.

32. The method of paragraph 27, where the step of detecting light using the first mode is performed successively on a plurality of compositions for optical analysis of the plurality of compositions, and then the step of detecting light using the second mode is performed on some or all of the plurality of compositions.

33. The method of paragraph 27, further comprising computing a second quantity using the light detected in the second optical measurement mode, and assessing the presence or effects of a potential source of error on the first quantity using the second quantity.

34. The method of paragraph 33, where the first optical measurement mode is luminescence, and where the second optical measurement mode is selected from the group consisting of absorption and scattering.

35. The method of paragraph 27, where the first optical measurement mode is luminescence.

36. The method of paragraph 35, where the second optical measurement mode is scattering.

37. The method of paragraph 36, further comprising assessing the presence or effects of turbidity on the first quantity using the light detected in the second optical measurement mode.

38. The method of paragraph 35, where the second optical measurement mode is absorption.

39. The method of paragraph 38, further comprising assessing the presence or effects of color quenching and/or a contaminant on the first quantity using the light detected in the second optical measurement mode.

40. The method of paragraph 27, where the first quantity is selected from the group consisting of absorbance, chemiluminescence intensity, photoluminescence intensity, photoluminescence energy transfer, photoluminescence lifetime, and photoluminescence polarization.

41. The method of paragraph 27, where the property of the composition is the presence or activity of a component of the composition.

42. The method of paragraph 27, further comprising detecting light transmitted from the composition using the multi-mode instrument in a third optical measurement mode, where the third mode is different than the first and second modes.

43. The method of paragraph 27, further comprising repeating the step of detecting light using the first mode based on an outcome of the step of detecting light using the second mode.

XII. Analyzer Setup, Calibration, and Reading

The operation of the analyzers provided by the invention may involve a number of steps or procedures. These steps and other aspects of the invention are described below, including (A) setup, (B) calibration, and/or (C) reading, among others. This disclosure is supplemented by the patents, patent applications, and other materials identified above under Cross-References, including but not limited to U.S. Provisional Patent Application Ser. No. 60/082,253, filed Apr. 17, 1998; and U.S. Provisional Patent Application 60/164,633, filed Nov. 10, 1999. These supplementary materials are incorporated herein by reference in their entirety for all purposes.

A. Setup

Setup of the analyzer may involve the selection of an assay mode and the selection of optical components and conditions to improve or optimize performance in that assay mode. The selection of optical components and conditions may involve knowledge of the assay mode, microplate, fluid level, total fluid volume, and/or sensed volume, among other parameters. Optical components may be changeable manually or automatically, depending on the component. For example, the size of the sensed volume may be adjusted manually by replacing the fiber optic cables adjacent the examination area, and manually or automatically by changing the apertures in front of the fiber optic cables. Similarly, the position of the sensed volume may be adjusted manually, or automatically by scanning a positive control well or wells to obtain the maximum signal given the average fluid level in the wells. Manually changeable components may include standard or "quick-change" components.

B. Calibration

Calibration of the analyzer may include using a calibration plate. A calibration plate may be shaped like a microplate and include features that can be manually, optically, mechanically, and/or electronically recognized. For example, a calibration plate may include precisely located apertures, mirrors, light sources (such as light-emitting diodes (LEDs)), and/or fluorescent reference standards to verify that the optics, detection, and positioning systems are operating properly.

C. Reading

Reading by the analyzer may be performed in five phases, as follows.

Phase 1 comprises loading a microplate in the transporter. During this phase, a person, robot, or microplate feeder mechanism places the microplate on the microplate transporter of the X,Y stage. A computer-controlled X,Y microplate registration mechanism ensures that microplates have the correct alignment relative to the optics beam.

Phase 2 comprises sensing the microplate in the transporter. During this phase, a sensor is activated that tells the local or system controller that the microplate has been delivered. The local controller can begin reading the microplate either after sensing the microplate or after receiving a command from the system controller to start reading.

Phase 3 comprises finding the top of the microplate. During this phase, the top of the microplate is found with the top-of-the-plate sensor located in the optics head, followed by computer-controlled adjustment of the Z-position of the optics head.

Phase 4 comprises reading the microplate. During this phase, the microplate is moved automatically from well to well to allow analysis of the contents of each well by use of a high performance motion control system with preselected acceleration/deceleration profiles and settling times to provide maximum possible throughput with minimum acceptable read error.

Phase 5 comprises unloading the microplate from the transporter.

XIII. Measurement Modes

The analyzers provided by the invention may be used in any suitable measurement mode(s), including but not limited to (A) photon-counting, (B) current-integration, and (C) imaging modes, among others. These exemplary measurement modes are described below to show the versatility and sensitivity of the analyzer. However, as mentioned above, the analyzer also may be used in additional measurement modes and/or with different methods for performing the indicated measurement modes, as necessary or desired. These and other aspects of the invention are described below.

This disclosure is supplemented by the patents, patent applications, and other materials identified above under Cross-References, including but not limited to U.S. Provisional Patent Application Ser. No. 60/082,253, filed Apr. 17, 1998; U.S. Provisional Patent Application 60/164,633, filed Nov. 10, 1999; and Joseph R. Lakowicz, PRINCIPLES OF FLUORSCENCE SPECTROSCOPY ($2^{nd}$ ed. 1999). These supplementary materials are incorporated herein by reference in their entirety for all purposes.

A. Photon-Counting Mode

Transmitted light may be detected in photon-counting mode. In this approach, the photons comprising the detected light are counted, and intensity is reported as the number of counted photons per unit time. Photon counting is well suited for assays with low light levels, because each photon is individually reported. Conversely, photon counting is ill suited for assays with high light levels, because the detector may become saturated and unable to distinguish the arrival of one photon from the arrival of more than one photon. Suitable detectors for practicing this method include PMTs.

B. Current-Integration Mode

Transmitted light also may be detected in current-integration mode. To decrease the average read time per well, the electronics can be configured to integrate the detector current resulting from the luminescence signal until a preset threshold is achieved. This is equivalent to collecting light from the well until a predetermined number of photons are collected. The component of the signal-to-noise ratio due to the photon noise of the emission light then will be equal to the square root of the number of photons collected by the detector. This feature is implemented using an integrating current-to-voltage converter at the detector output coupled to an analog comparator in parallel with an analog-to-digital converter. At the beginning of each measurement cycle, the integrator is reset and the time required for the integrated detector current to trip the comparator is measured. The integration time is a representation of the number of photons collected and hence the signal level. If the signal is too small to cause the comparator to be tripped within the maximum time allowed for the integration, the analog-to-digital converter is used to digitize the voltage appearing at the output of the integrator. Because the value of the integration capacitor and the voltage across it both are known, the number of photons collected can be calculated by taking the product of the integration capacitance and the measured voltage and dividing it by the electronic charge ($1.602 \times 10^{-19}$ Coulombs per electron). Suitable detectors for practicing this method include PMTs.

C. Imaging Mode

Transmitted light also may be detected in imaging mode, allowing simultaneous reading from one or a plurality of wells, typically located in a fixed area of a microplate. Large-area fiber optic bundles and an imaging charged-coupled device (CCD) detector make it possible to excite and detect a fixed area of the microplate at once. Using this method, the detection limit and time to read a microplate is constant regardless of the number of wells on the microplate as long as the fiber size in the bundle is small compared to the smallest well to be measured (e.g., >4 fibers per well) and the CCD pixel size is small compared to the fiber size (e.g., >4 pixels per fiber). If the fiber optic bundle is randomly oriented, a calculation procedure can be used during setup to map each CCD pixel to a specific location on the microplate. For example, a single microplate well containing a fluorescent compound can be used to map the CCD pixels through the fiber bundle to the microplate surface by repositioning the well repeatedly to include all CCD pixels. Suitable detectors for practicing this method include CCDs. Additional and/or alternative imaging detectors and detection strategies are described in U.S. Provisional Patent Application Ser. No. 60/376,969, filed Apr. 30, 2002.

XIV. Broad-Range Light Detection System

This section describes systems, including apparatus and methods, for the broad-range detection of light. These systems may include, in one aspect, apparatus and methods for detecting light with high accuracy over a broad range of intensities. These systems also may include, in another aspect, apparatus and methods for automatically scaling the detection range to improve detection based on the intensity of the detected light. These systems also may include, in yet another aspect, include apparatus and methods for detecting light with increased speed, particularly in applications involving analysis of successive samples.

These and other aspects of the invention are described below in detail, including (A) background, (B) detailed description, and (C) examples. This disclosure is supplemented by the patents, patent applications, and other materials identified above under Cross-References, particularly U.S. Provisional Patent Application Ser. No. 60/075,414, filed Feb. 20, 1998; U.S. Provisional Patent Application Ser. No. 60/100,951, filed Sep. 18, 1998; PCT Patent Application Ser. No. PCT/US99/03678, filed Feb. 19, 1999; U.S. patent application Ser. No. 09/643,221, filed Aug. 18, 2000, now U.S. Pat. No. 6,326,605; U.S. patent application Ser. No. 10/004,647, filed Dec. 3, 2001; and U.S. Provisional Patent Application Ser. No. 60/383,197, filed May 22, 2002. These supplementary materials are incorporated herein by reference in their entirety for all purposes.

A. Background of the Invention

Systems that involve the detection of light are used in a variety of contexts. In particular, systems that involve the detection and subsequent analysis of light are used in performing optical spectroscopic assays, including luminescence and absorption assays. These assays are used to characterize the components and properties of molecular systems, and recently have been used in high-throughput screening procedures to identify candidate drug compounds. Optical spectroscopic assays include fluorescence polarization (FP), fluorescence resonance energy transfer (FRET), fluorescence lifetime (FLT), total internal reflection (TIR) fluorescence, fluorescence correlation spectroscopy (FCS), and fluorescence recovery after photobleaching (FRAP), and their phosphorescence analogs, among others. Optical spectroscopic assays also include absorption assays.

Unfortunately, light detection systems suffer from a number of shortcomings. Such systems may be limited in range, so that they accurately detect light only within some relatively narrow range of intensities. Such systems also may require user intervention to alter the detection range, if the range may be altered at all. Such systems also may be limited to either discrete or analog detection, so that either they discretely count individual quanta or photons of light, or they integrate an analog value corresponding to such quanta, but they do not do both. Such systems also may require significant periods of time to make measurements. These shortcomings may be found singly or in combination, and these shortcomings may be particularly significant in the context of high-throughput screening, where it may be necessary to perform tens or hundreds of thousands of measurements per day.

B. Detailed Description

The invention provides apparatus and methods for detecting light, as described below.

Figure 71:
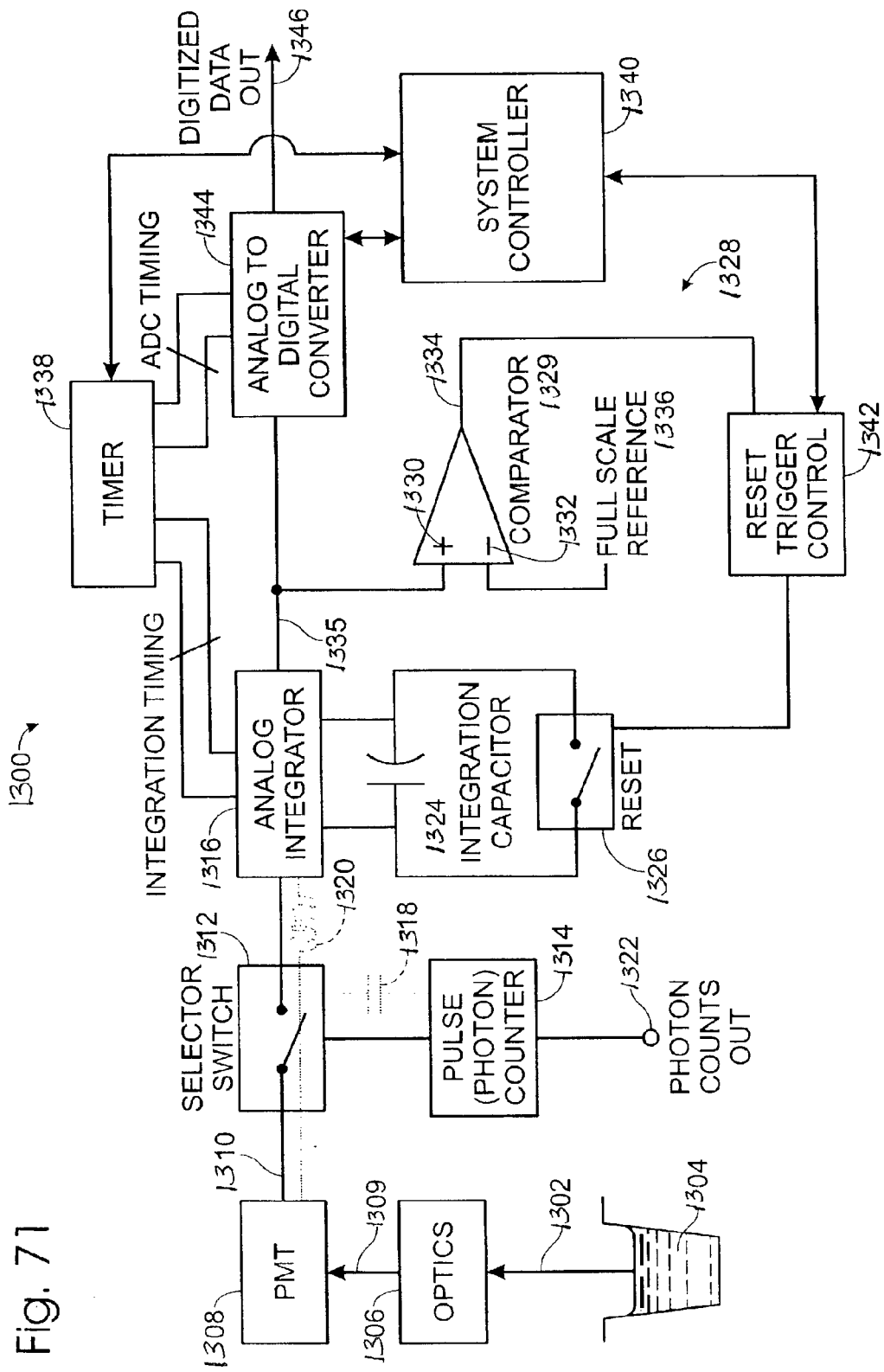
FIG. 71 is a block diagram of a device for detecting light, in accordance with aspects of the invention.

FIG. 71 is a block diagram showing a device 1300 for detecting light in accordance with the invention. In this embodiment, light 1302 leaving a composition 1304 is directed by appropriate optics 1306 to a detector 1308. Optics 1306 and detector 1308 may take various forms, including, for example, forms shown and/or described in other sections herein. Generally, detector 1308 has an input 1309 that receives light and an output 1310 that corresponds to the received light. Output 1310 may take various forms, including current and/or voltage signals. Depending on the intensity of the light being received by the detector, the output may be discrete pulses corresponding to individual photons or an analog voltage or current proportional to the incident light.

In device 1300, output 1310 is directed through a selector switch 1312, which selectively routes the output toward various detection components, including a pulse (photon) counter 1314 and an analog integrator 1316. Selector switch 1312 may be manual, permitting a user to select between detection components. Alternatively, selector switch 1312 may be passive, allowing use of both detection components based on the intensity of light and/or the type of assay, among others. A passive selector switch may be constructed by omitting switch 1312 and connecting a capacitor 1318 from the output of the detector to pulse counter 1314, and an inductor 1320 from the output of the detector to analog integrator 1316. Capacitor 1318 will pass AC components of output 1310 to pulse counter 1314, while inductor 1320 passes the DC component of output 1310 to analog integrator 1316. Typical capacitances for capacitor 1318 range between 1 and 10 nanoFarads, and typical inductances for inductor 1320 range between 0.1 and 1 microHenrys. As another alternative, selector switch may be an electronically controlled switching device such as a solid-state switch or a relay, thereby allowing automatic control of the switch to accommodate expected or measured light levels.

Pulse counter 1314 is used as a discrete accumulator or integrator to monitor or sample the detected light by counting the number of photons in the detected light. Typically, a detector is chosen that generates an output corresponding to each detected photon. For example, photomultiplier tubes (PMTs) generate a current pulse for each photon that strikes the photocathode in the PMT. The discrete output from the detector may be summed over a sampling period or integration time, and the amount of detected light may be reported in units of counts, counts/second, or relative fluorescence units (RFUs), among others, using an associated output port 1322. These results may be corrected for fluctuations in light source intensity if they represent photoluminescence, using a reference detector as described above.

Analog integrator 1316 is used as an analog accumulator to monitor the detected light by generating a signal corresponding to the output of the detector. For example, current pulses from a PMT or other detector may be stored (integrated) using a capacitor 1324 or other storage component in an electronic circuit. As the capacitor is charged, the analog voltage across the capacitor increases in proportion to the total number of photons collected by the PMT during the integration time. Typical capacitances range between 0.22 and 100 nanoFarads. Typical capacitors include low-leakage polystyrene and polyester capacitors to minimize drift error. Results from the analog integrator most naturally are reported in RFUs; however, the invention also provides for reporting results in terms of counts or counts/second. These results also may be corrected using a reference detector, if appropriate.

The size of capacitor 1324 should be selected, manually or automatically, to optimize the precision and range of detection. Generally, the greatest precision is obtained with the smallest capacitor, and the greatest range is obtained with the largest capacitor. Capacitor rating is determined by total counts, not counts/second, because saturation is determined by total counts or its analog counterpart. For a continuous light source, the total number of counts is given by the integral of the counts/second with respect to the integration time. For a flash lamp, the total number of counts is given by the product of the counts per flash and the number of flashes. Generally, the capacitor is zeroed using a reset 1326 before each sampling period, and the capacitor is charged to one-half to three-fourths full during each sampling period, with two-thirds full being a preferred value. To maximize flexibility, the apparatus may include a plurality of capacitors or other storage components, each with different capacities. Alternatively, an amplifier or attenuator can be selectively placed between the detector output and integrator input to scale the output of the detector to a range which can be integrated without exceeding the capacity of the storage component for the expected light intensity. The output can be scaled to account for amplification or attenuation caused by the amplifier or attenuator, respectively.

The output signal from the integrator may be fed to a range monitoring device 1328, which may include a threshold detection device in the form of operational amplifier or comparator 1329. Comparator 1329 includes a positive input 1330, a negative input 1332, and an output 1334. Positive input 1330 is coupled to the output signal from the integrator. Negative input 1332 is connected to a full-scale range reference 1336, which typically is a voltage reference. The reference may be adjustable over a range, for example, by using a potentiometer configured as a voltage divider. The reference also may be fixed at a particular value, for example, by using a Zener diode. The output of the comparator is low as long as the voltage at negative input 1332 exceeds the voltage at positive input 1330. However, when the integrator output signal voltage exceeds reference voltage 1336, the output of the comparator will swing to high. Thus, by monitoring the output of the comparator, it is possible to detect if and when the reference value has been exceeded. The output signal of the integrator may be monitored in other ways as well, including digitally or with other analog circuitry.

The timing of detection may be specified and monitored using one or more timers 1338 and system controllers 1340. Before detecting light from a sample, system controller 1340 may zero timer 1338, and zero analog integrator 1316 using a trigger controller 1342 and reset 1326. After completing the sample period, system controller 1340 may process the integrated signal stored on analog integrator 1316 using an analog-to-digital converter 1344, and output the data and the sampling time using an associated output port 1346. Of course, other mechanisms for preparing the analog integrator for data collection and for outputting data from the analog integrator after data collection also may be employed.

Figure 72:
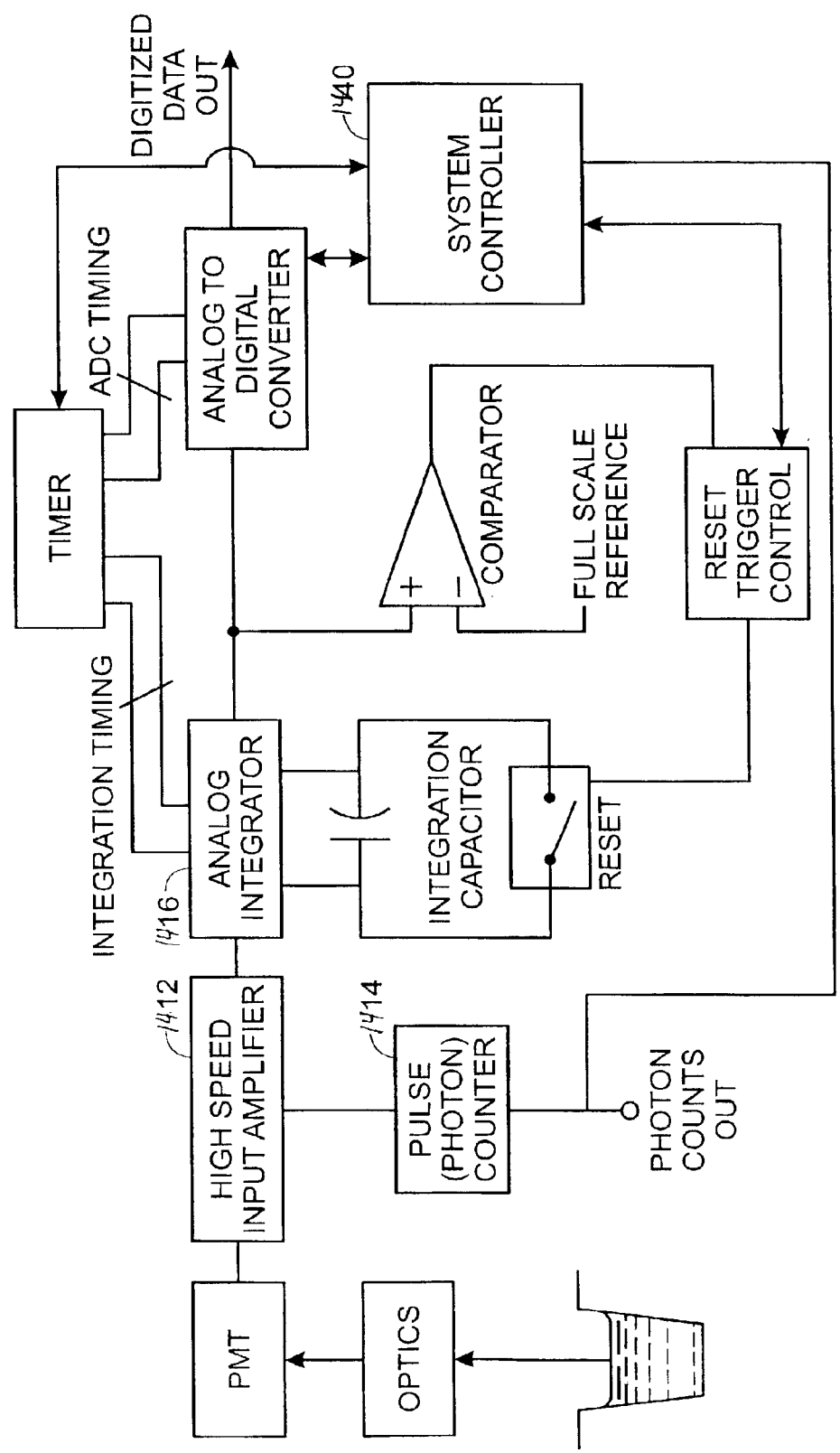
FIG. 72 is a block diagram of an alternative device for detecting light, in accordance with aspects of the invention.

FIG. 72 is a block diagram showing an alternative device 1400 for detecting light in accordance with the invention. Device 1400 is similar to device 1300 in FIG. 71, with a few exceptions. First, selector switch 1312 in device 1300 is replaced by a high-speed input amplifier 1412 in device 1400. High-speed input amplifier 1412 should have accurate signal response from DC to 0.5 or 1 GHz AC to permit simultaneous use of a pulse counter 1414 and an analog integrator 1416. Second, output from the pulse counter in device 1400 is connected to a system controller 1440, unlike in device 1300. Together, these differences extend the range of device 1400 relative to device 1300, because device 1400 may automatically switch or choose between the pulse counter and the analog integrator, as received light levels and/or the system controller dictate.

The sampling or read time in devices 1300 and 1400 may be determined in at least two ways. First, the device may be instructed to integrate the detector output for a predetermined (fixed) time, as determined by the system controller and/or the timer. Second, the device may be instructed to integrate the detector output until a predetermined (fixed) integrated signal is obtained, as determined by the comparator and the value of the full scale reference.

Fixed-time and fixed-signal detection modes may be used to provide overflow protection and to extend dynamic range beyond that available with discrete or analog detection alone. In analog detection, information is lost if the integration capacitor or other storage component reaches its full-range value before the end of the sampling period, even though the PMT or other detector was not saturated. This is because the electronic circuit in analog counting cannot respond to signals above the full-scale count for each capacitor setting. With standard analog detection, each sample brighter than the saturation level will give an identical full-scale result.

The invention permits the intensity of detected light to be determined even if the integrated signal for the entire sample period would substantially exceed the storage capacity of the capacitor. The intensity of light may be expressed as an amount of light per unit time. In the invention, the time required to fully charge the storage component is measured by a timer operatively associated with the comparator. Thus, if the capacitor reaches full charge prior to the end of the sample period, intensity may be determined by relating the storage capacity of the capacitor to the amount of light detected by the detector, and then dividing that amount by the elapsed time in the sample period before reaching full charge. If the capacitor is not fully charged during the sampling period, then the intensity may be computed using the actual charge and the sampling period.

Fixed-time and fixed-signal detection modes also may be used to reduce read time and to provide underflow protection. Generally, optical assays are affected by various sources of error, including photon noise (PN) and pipetting error (PE), among others. The coefficient of variation (CV) associated with the results of an optical assay affected by such sources of error might be represented by the formula:

$$CV(\text{assay}) = [CV(PN)^2 + CV(PE)^2]^{0.5} \quad\quad\quad (\text{XIV-1})$$

where $CV(PN) = (\text{\# detected photons})^{-0.5}$, and CV(PE) typically is in the range of 1–5%. Thus, to obtain a result that is limited by pipetting error, it is necessary only to collect enough photons to reduce CV(PN) to about 0.5–1%. This noise level corresponds to collecting between 10,000 and 20,000 photons. In many assays, good results may be obtained by collecting about this number of photons. For example, in fluorescence polarization assays, the polarization noise in milliPoise (mP) is given by:

$$\text{Polarization noise} = 700/(\text{\# detected photons})^{0.5} \quad \text{(XIV-2)}$$

Polarization assays generally require polarization noise to be less than 10 mP, corresponding to collecting at least about 5,000 photons.

Read time may be reduced by allowing the read time to vary as a function of signal strength, so that samples are analyzed just long enough to obtain a result that is not limited by the amount of light detected. For discrete detection, the pulse counter may be configured to count pulses only until a predetermined number or threshold of pulses is counted. For analog detection, the analog integrator may be configured to integrate the detector output until a preset threshold is achieved, where the threshold corresponds to collection of a predetermined amount of light. Specifically, the integrator may be zeroed, and the time required for the integrated detector current to trip the comparator may be measured. The integration time is a representation of the number of photons collected and hence the signal level.

The integrated detector current necessary to trip the comparator may be changed by changing the electronic gain, the threshold voltage, and/or the integration capacitor, among others. Such a change in comparator trip value will correspond to a change in the number of photons that can be collected (and in the associated signal-to-noise value). To increase the number of photons collected, a larger capacitor and/or a lower gain may be employed. Conversely, to decrease the number of photons collected, a smaller capacitor and/or a shorter time-out period may be employed.

Generally, the desired amount of light (number of photons) will be acquired quickly if the sample is bright and slowly if the sample is dim. If the sample is so dim that the desired number of photons cannot be collected within a preset time limit or timeout period, an underflow occurs. In this case, the measurement is deemed to have "timed out," and the integrator voltage is measured by an analog-to-digital converter, or set to zero or another convenient value representing an underflow condition. Alternatively, if analog integration and photon-counting are performed simultaneously, the counter output determined in photon-counting mode may be used to determine intensity.

Table 2 shows the reduction in read times possible using variable-time reading, assuming that the reading time may be reduced from 100 milliseconds to 1 millisecond per sample. Reductions in read time become significant if numerous samples must be analyzed. For example, in high-throughput screening applications, samples may be housed in microplates that each contain 96, 384, or 1536 samples. Moreover, high-throughput screening applications typically require analyzing many such microplates.

TABLE 2

| Plate Format | 96-well | 384-well | 1536-well |
| --- | --- | --- | --- |
| Move time + fixed read time | 43.2 sec | 115.2 sec | 307.2 sec |
| Move time + variable read time | 33.7 sec | 77.2 sec | 155.1 sec |
| Time saved per plate | 9.5 sec | 38.0 sec | 152.1 sec |
| Time savings (percent) | 23% | 33% | 49.5% |

The read time per microplate may be reduced using the savings in read time per sample, as shown in Table 2. Alternatively, the read time per microplate may be held constant, independent of the read time per sample, if desired. The latter option may be useful if microplate analysis is coupled to other processes that occur at fixed time intervals.

Figure 73:
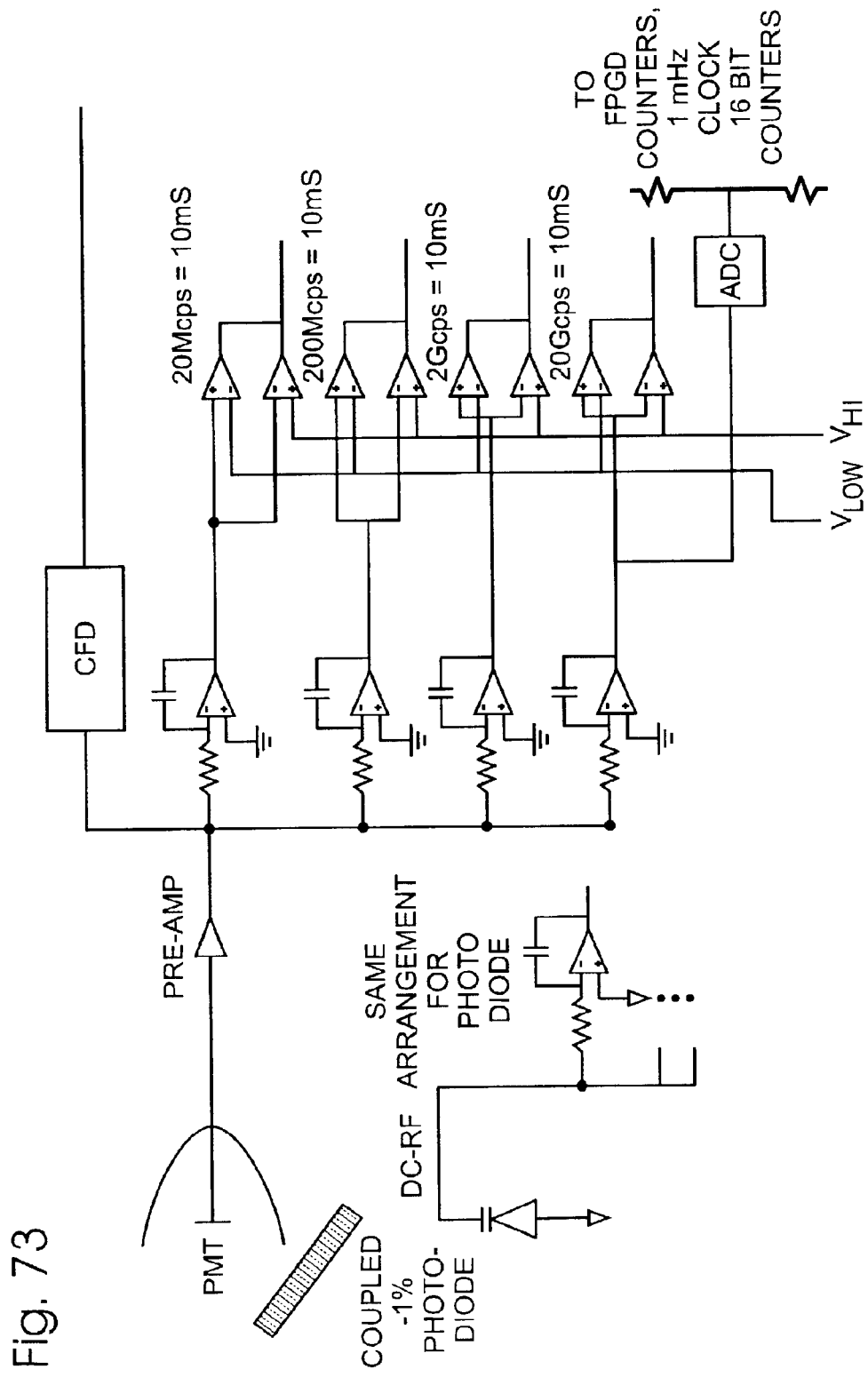
FIG. 73 is a schematic diagram of an integration section similar to those shown in FIGS. 71 and 72, except that it provides additional automatic range scaling.

FIG. 73 is a schematic diagram of an integration section similar to those shown in FIGS. 71 and 72, except that it provides additional automatic range scaling.

The signal output from the PMT is fed to a preamplifier that converts the current output from the PMT to a voltage output. As described above, this preamplifier should have good performance from DC to radio frequency AC.

The output of the preamplifier is fed in parallel to a number of integration devices. One integration device is a photon counter, which is useful for the lowest photon intensities. The other integration devices are four analog integrators, each having substantially identical construction, with the exception of the size of the integration capacitor. In particular, each of the first three analog integrators incorporates a capacitor that is about one order of magnitude smaller than the capacitor of the integrator that follows.

The output of each of the integration devices is fed to a discriminator section, which monitors the output voltage between a preselected high and low voltage, $V_L$ and $V_H$, as illustrated. The output of the individual discriminator sections for each integration device is used to trigger a counter corresponding to that integration device. The counter for each integration device begins counting when the output from the corresponding integration device exceeds $V_L$, and the counter stops counting when the output exceeds $V_H$. Thus, the counters can be used to determine the time required to saturate their associated integration devices. Thus, for a medium-intensity signal, the time required for the lowest range integration device to achieve saturation may be short relative to the overall sampling period. The time required for the next larger range integration device will be approximately an order of magnitude larger. The largest range integration devices may in fact not saturate during a particular sampling period with a medium intensity signal.

When computing a light intensity for a given sample period, it generally is preferable to select the output of an integration device that either recently saturated or was near to saturation. The signals from such devices, or the time required for saturation, as the case may be, will provide the most accurate basis for computing the intensity.

An advantage of this system is that an intensity value always can be computed based solely on the time to saturation for the largest range integration device that saturated. This can be accomplished by dividing the number of photons required for saturation by the time to saturation. If none of the analog integration devices saturated, the integrated signal from the counter can be used. Alternatively, the analog value of the integration device nearest to saturation but not having yet saturated can be measured with an analog-to-digital converter and utilized to compute the intensity.

To further increase the range of intensity that can be measured, an additional type of detector (e.g., photodiode) can be used in parallel with the PMT. The output of the photodiode can be fed to a series of analog integrators like those above. Thus, when the intensity exceeds that which accurately can be measured with a PMT, the photodiode will be in range.

As described above, the sample period may be terminated early if the user is satisfied when a predetermined number of photons are collected. Termination occurs when a corresponding integration signal has been achieved as measured by the integration devices.

Figure 74:
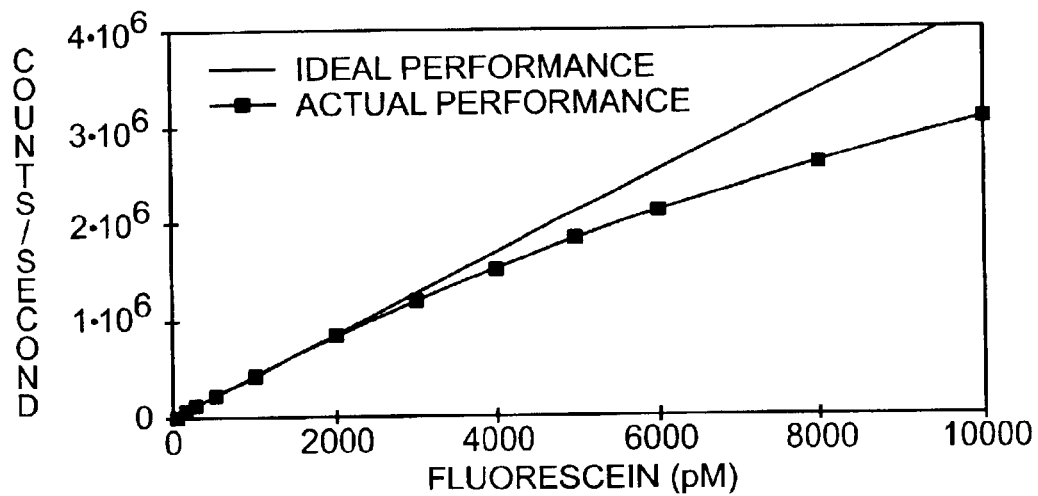
FIGS. 74 and 75 are response curves showing the non-linearity of the digital counting circuit for the apparatus shown in FIGS. 3–6.
Figure 75:
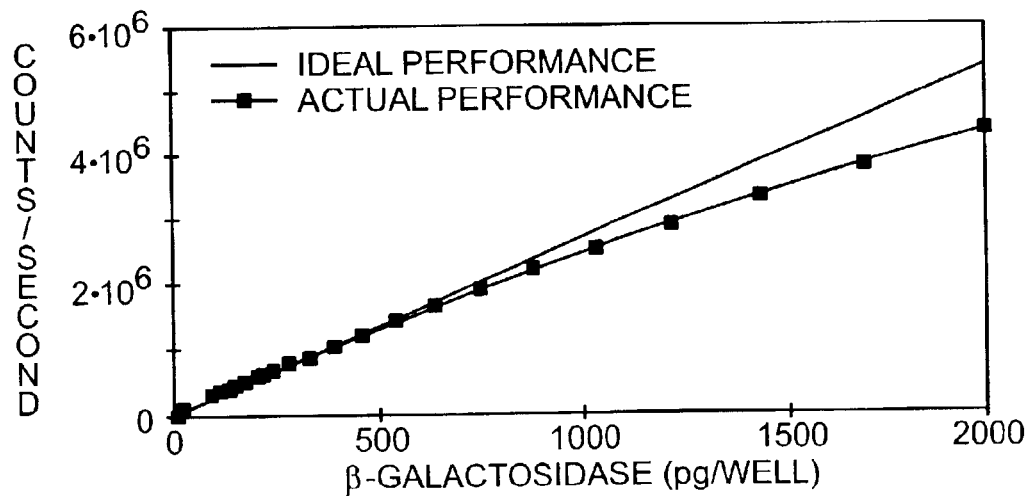

FIGS. 74 and 75 are response curves showing the nonlinearity of the digital counting circuit for an apparatus such as that shown in FIGS. 3–6 (and elsewhere herein). FIG. 74 was generated using the photoluminescence optical system, and shows a nonlinearity of 10% at 1.5 million counts/second, 15% at 2 million counts/second, 23% at 2.5 million counts/second, and 27% at 3 million counts/second. FIG. 75 was generated using the chemiluminescence optical system, and shows a nonlinearity of 5% at 2 million counts/second, 10% at 3 million counts/second, and 20% at 4 million counts/second.

Figure 76:
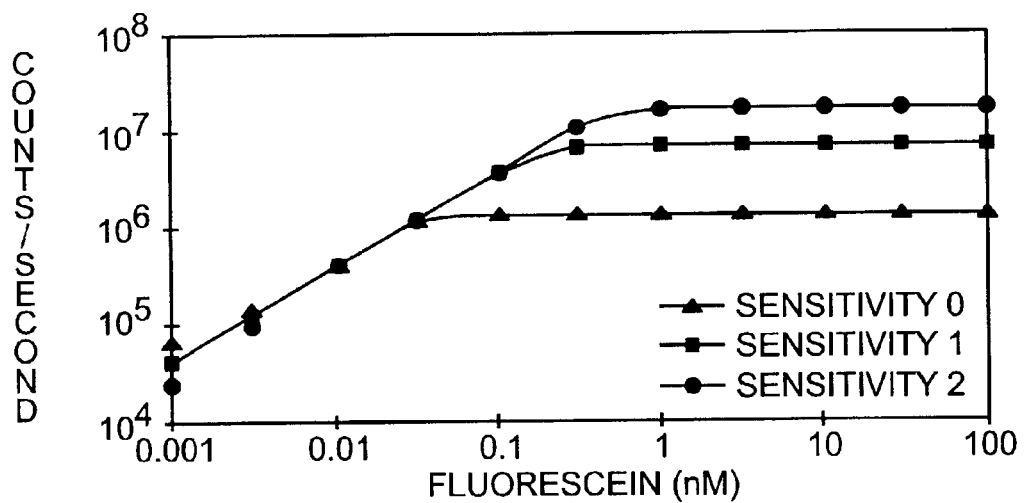
FIG. 76 is a response curve showing the saturation of the integrating capacitor in the analog counting circuit for the apparatus shown in FIGS. 3–6.

FIG. 76 is a response curve showing the saturation of the integrating capacitor in the analog counting circuit for an apparatus such as that shown in FIGS. 3–6 (and elsewhere herein). The curves were generated using a 100 millisecond sampling period. Data are shown for three capacitors, including a relatively large capacitor (sensitivity 0) and a relatively small capacitor (sensitivity 2). The large capacitor saturates at higher light intensities than the small capacitor. The response for the largest capacitor is linear to about 10 million counts/second, which is about tenfold higher than with the digital counting circuit.

Figure 77:
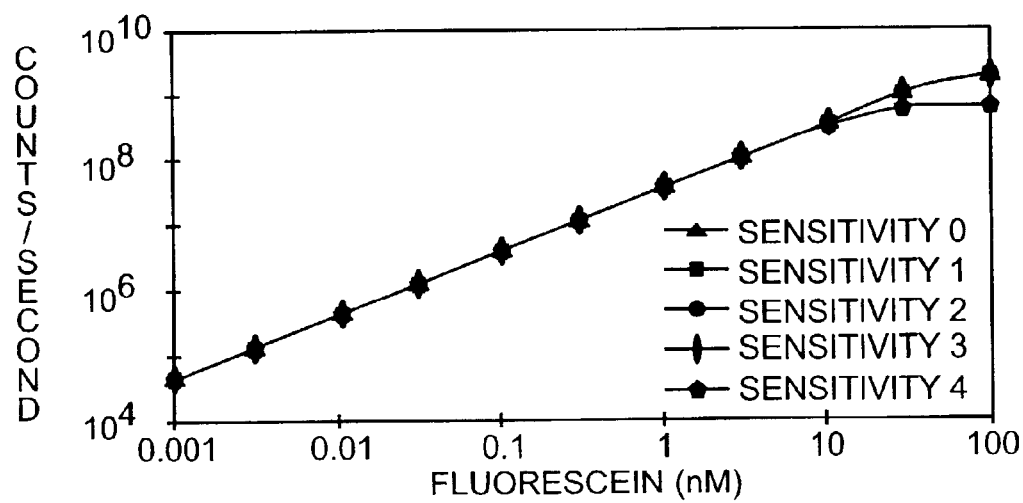
FIG. 77 is a response curve showing the saturation of the analog counting circuit when used with the comparator option for the apparatus shown in FIGS. 3–6.

FIG. 77 is a response curve showing the saturation of the analog counting circuit when used with the comparator option. FIG. 77 was generated using the same apparatus, sample, and 100 millisecond sampling period used in generating FIG. 76. The response is linear to about 1 billion counts/second, at least for the capacitors corresponding to sensitivities 0–3.

Table 3 shows guidelines for selecting appropriate counting options and units based on the assay, light source (if applicable), detector, and light intensity. These guidelines apply only to the embodiment shown in FIGS. 3–6 and 71, because they assume that there are separate chemiluminescence and photoluminescence optical systems, and that there is selectable photon counting or analog integration, with a comparator associated with the analog detection.

TABLE 3

| | Discrete Counter | Analog Integrator | Comparator Option |
|---|---|---|---|
| Chemiluminescence | Optimal performance | Not applicable | Not applicable |
| Fluorescence Intensity (FI) (w/continuous lamp) Units = cps | Low level signals <1.0 M cps | Higher signals or increase in dynamic range compared to digital | Optimal performance (with appropriate capacitor selection, good sensitivity and largest dynamic range) |
| Fluorescence Polarization (FP) (w/continuous lamp) Units = cps | Low level signals <1.0 M cps | Higher signals or increase in dynamic range compared to digital | Optimal performance (with appropriate capacitor selection, good sensitivity and largest dynamic range) |
| Time-Resolved Fluorescence (TRF) (w/flash lamp) Units = counts or cps | Optimal performance Low signal levels <1.0 M cps | Higher signals or increase in dynamic range (useful sensitivity settings 3 or 4) | Not recommended |
| Fluorescence intensity (w/flash lamp) Units = counts | Not recommended (limited utility at the very lowest signal levels) | Optimal performance (with appropriate capacitor selection) | Not recommended |
| Fluorescence Polarization (w/flash lamp) Units = counts | Not recommended (limited utility at the very lowest signal levels) | Optimal performance (with appropriate capacitor selection) | Not recommended |

Discrete (photon) counting sacrifices dynamic range for sensitivity at very low signal levels. Saturation (~1 million counts/second) is determined by the rate at which the detector and counting circuit receive photons. Optimal uses include low-intensity detection in chemiluminescence and time-resolved fluorescence assays.

Analog counting (PMT current integration) trades sensitivity at the lowest signal levels for increased dynamic range. Saturation occurs at much higher count rates (~0.5–1 billion counts/second) than with discrete counting. The maximum integrable signal usually is determined by the size of the integration capacitor. Optimal uses include fluorescence intensity and fluorescence polarization assays conducted using a flash lamp.

Comparator counting (analog+time to full scale) trades sensitivity at the lowest signal levels for the largest dynamic range with a single instrument setting. Saturation is similar to that stated for analog counting. In contrast to purely analog counting, at high signal levels the "comparator" circuit detects when the capacitor is fully charged and automatically measures the time taken for the capacitor to reach full scale. Optimal uses include low-intensity detection and dynamic range readings for fluorescence intensity and fluorescence polarization assays using a continuous lamp.

Additional and/or alternative mechanisms for the broadrange detection of light are described in U.S. Provisional Patent Application Ser. No. 60/383,197, filed May 22, 2002, which is incorporated herein by reference in its entirety for all purposes.

C. Examples

The following numbered paragraphs describe additional and/or alternative aspects of the invention:

1. A device for monitoring the intensity of light, the device comprising (A) a detector configured to detect light; (B) an integrator operatively connected to the detector and configured to generate an integration value based on the integrated output of the detector during a sampling period; (C) a timer configured to measure integration time during the sampling period, at least until the integration value reaches a preselectable value; and (D) an analyzer configured to compute the intensity of the light based on the integration value; wherein if the integration value does not reach the preselectable value within the sampling period, the analyzer computes the intensity of the light using the integration value and the sampling period; and wherein if the integration value reaches the preselectable value within the sampling period, the analyzer computes the intensity of the light using the time measured before the preselectable value was reached.

2. The device of paragraph 1, wherein the detector is selected from a group consisting of photomultiplier tubes, photodiodes, avalanche photodiodes, and charge-coupled devices.

3. The device of paragraph 1, further comprising an amplifier disposed between the detector and the integrator to scale the output of the detector.

4. The device of paragraph 1, wherein the integrator is discrete and generates the integration value by counting pulses from the detector corresponding to quanta of detected light.

5. The device of paragraph 1, wherein the integrator is analog and generates the integration value by charging an integration capacitor, the charge on the capacitor corresponding to the amount of detected light.

6. The device of paragraph 5, wherein the integrator includes a plurality of integration capacitors having substantially different capacities from each other, wherein the amount of detected light required to generate an integration value equal to the preselectable value is selectable by choosing a particular one of the integration capacitors.

7. The device of paragraph 5, wherein the integrator also includes a discrete integrator that integrates the signal by counting pulses from the detector corresponding to quanta of detected light, wherein the device switches between the discrete and analog integrators based on the amount of light detected.

8. The device paragraph 1, wherein the integrator is digital and generates the integration value by digitally measuring and summing the output of the detector at a plurality of discrete times during the sampling period.

9. The device of paragraph 1, further including a plurality of integrators simultaneously operatively connected in parallel to the detector, each integrator being configured to generate an integration value proportional to the integrated output of the detector during the sampling period, wherein the proportionality between the integration value and the amount of detected light is substantially different for the different integrators.

10. The device of paragraph 1, the device being configured to detect light sequentially from a plurality of samples at periodic intervals.

11. The device of paragraph 1, the device being configured to detect light sequentially from a plurality of samples, wherein the time between beginning to detect light from successive samples is variable, the variable time being shorter if the integrated signal exceeds the preselectable value during the sampling period.

12. The device of paragraph 1, further comprising a first light source configured to direct light onto a sample, the detector being configured to detect light leaving the sample.

13. The device of paragraph 12, wherein the first light source is capable of producing polarized light, and wherein the detector is sensitive to the polarization of the light leaving the sample.

14. The device of paragraph 1, wherein the light has a wavelength between 200 nanometers and 2000 nanometers.

15. The device of paragraph 1, wherein the analyzer can report the intensity in units selected from a group consisting of counts per unit time and relative luminescence units per unit time.

16. The device of paragraph 1, further comprising a stage configured to support a sample holder, the sample holder having a plurality of discrete sample locations.

17. A device for monitoring the intensity of light, the device comprising (A) a detector configured to receive light; (B) an accumulator operatively connected to the detector to generate an accumulator signal corresponding to the total light received by the detector during a sampling period, wherein there is a predetermined threshold value associated with the accumulator signal; and (C) an analyzer associated with the accumulator to compute a light intensity, wherein, if the accumulator signal reaches the predetermined threshold value during the sampling period, the analyzer computes the light intensity based, at least in part, on the portion of the sampling period elapsed when the accumulator signal reached the predetermined threshold value.

18. The device of paragraph 17, wherein if the analyzer fails to reach the predetermined threshold value during the sampling period, the analyzer computes the intensity based, at least in part, on the accumulator signal.

19. A device for sampling light, the device comprising (A) a detector having an input to receive light and an output corresponding to the received light; (B) an integrator coupled to the detector to generate an integration signal corresponding to the integrated output of the detector; and (C) a processor adapted to compute the amount of light received by the detector during a sampling period using the integration signal and the default time if the integration signal is less than a predetermined amount at the end of the sampling period, and using the predetermined amount and the time required to reach the predetermined amount if the integration signal reached the predetermined amount during the sampling period.

20. The device of paragraph 19, further comprising a stage configured to support a sample holder with a plurality of discrete sample locations, wherein, for each of a sequence of sample periods and associated sample locations in turn, the detector receives light leaving the associated sample location during the sample period, and wherein, when the device is triggered to move onto a new sample location when the integration signal reaches the predetermined amounted during a sample period.

21. A system for determining the amount of light received by a detector during a sampling period, where the detector produces an output which is a function of light being received, the system comprising (A) a first integration device operatively connected to the output of the detector and adapted to generate a first integration signal during the sampling period, the first integration signal being proportional to the amount of light received by the detector during the sampling period so long as the amount of light received during the sampling period is less than a first predetermined amount; (B) a second integration device operatively connected to the output of the detector and adapted to generate a second integration signal during the sampling period, the second integration signal being proportional to the amount of light received by the detector during the sampling period so long as the amount of light received during the sampling period is less than a second predetermined amount, wherein the second predetermined amount is as least several times greater than the first predetermined amount; and (C) a range selection system connected to the first and second integration devices and configured to automatically select one of the integration signals to use in determining the amount of light received by the detector based upon the amount of light received during the sampling period as represented by the integration signals.

22. The system of paragraph 21, wherein the range selection system selects between the integrations signals based, at least in part, on whether the first integration signal exceeded the first predetermined amount during the sample period.

23. The system of paragraph 21, wherein the first integration device discretely counts pulses from the output of the detector corresponding to photons received by the detector.

24. The system of paragraph 21, wherein the first integration device carries out an analog integration corresponding to the output of the detector to generate the first integration signal.

25. The system of paragraph 21, further including a third integration device operatively connected to the output of the detector and adapted to generate a third integration signal during the sampling period, the third integration signal being proportional to the amount of light received by the detector during the sampling period so long as the amount of light received during the sampling period is less than a third predetermined amount, wherein the third predetermined amount is as least several times greater than the second predetermined amount.

26. The system of paragraph 21, further including a timer associated with the first integration device, the timer being configured to measure the time required for the first integration signal to reach a first threshold value.

27. A device for monitoring the intensity of light, the device comprising (A) a detector having an input to receive light and being adapted to generate an output corresponding to the received light; (B) an integrator operatively connected to the detector and configured to generate an integration signal during a sampling period corresponding to the integrated output of the detector during the sampling period so long as the integration period is less than a preselectable value; wherein if the integration signal reaches the preselectable value within the sampling period, the integrator determines the intensity of the light using the threshold value and the time required to reach the threshold value; and wherein if the integrated signal does not reach the threshold value within the preselectable time, the integrator determines the intensity of the light using the integrated signal and the length of the sampling period.

28. A device for detecting light, the device comprising (A) a detector configured to detect light and to generate an output representative of the detected light; (B) an analog data collection device configured to compute the total amount of light detected based on a signal corresponding to the output of the detector; (C) a discrete data collection device configured to compute the total amount of light detected based on a signal corresponding to the output of the detector; and (D) a system controller configured to select between the analog and discrete devices based on a preselectable criterion.

29. The device of paragraph 28, further comprising at least two light sources, wherein the criterion is the light source.

30. The device of paragraph 28, wherein the criterion is the amount of the light detected.

31. The device of paragraph 28, wherein the criterion is the intensity of the light detected.

32. The device of paragraph 31, wherein the analog device is used to determine whether the amount of light has exceeded the threshold value.

33. The device of paragraph 31, wherein the discrete device is used to determine whether the amount of light has exceeded the threshold value.

34. The device of paragraph 28, wherein the amount of light automatically is determined using the analog processor if the amount of light detected exceeds a threshold value.

35. A device for detecting light from a series of compositions, the device comprising (A) a stage for supporting a composition in an examination site; (B) an automated registration device that automatically brings successive compositions and the examination site into register for successive analysis of the compositions; (C) a detector; (D) an emission optical relay structure that directs light from the composition toward the detector, so that light from the composition may be detected and used to generate a signal corresponding to the detected light; and (E) an analyzer that uses information in the generated signal to quantify the amount of light transmitted from the composition, the analyzer being selectable between an analog mode in which the analyzer quantifies the amount of light in a substantially continuous fashion, and a discrete mode in which the analyzer quantifies the amount of light by counting pulses corresponding to the detected quanta of light.

36. The device of paragraph 35, wherein the stage in configured to support a microplate, and wherein the successive compositions are held in wells formed in the microplate.

37. The device of paragraph 35, wherein the successive samples are located at successive sights on a biochip.

38. The device of paragraph 35, wherein the successive compositions are successive positions along a gel.

39. A method of measuring light, comprising (A) detecting photons incident on a detector during a sampling period; (B) collecting data representative of the cumulative number of photons detected during the sampling period; and (C) terminating the sampling period when the cumulative number of photons detected during the sampling period reaches a predetermined threshold or a predetermined sampling time expires, whichever occurs first.

40. A method of measuring light intensity from a source, comprising (A) detecting photons incident on a detector from the source; (B) generating a first integration signal proportional to the cumulative number of photons incident on the detector during a sampling period so long as the cumulative number of photons is less than a first range value; (C) simultaneously with generating a first integration value, generating a second integration signal proportional to the number of photons incident on the detector during the sampling period so long as the cumulative number of photons is less than a second range value, where the second range value is at least an order of magnitude larger than the first range value; (D) selecting one of the integration signals to use in computing a detected light intensity based on whether the cumulative number of photons incident on the detector during the sampling period exceeded the first range value; and (E) computing a detected light intensity using the selected integration signal.

41. The method of paragraph 40, further comprising simultaneously with generating first and second integration values, generating a third integration signal proportional to the number of photons incident on the detector during the sampling period so long as the cumulative number of photons is less than a third range value, where the third range value is at least an order of magnitude larger than the second range value.

XV. Signal Enhancement

Enhancements of signal-to-noise and signal-to-background ratios may be important in polarization and other luminescence assays, especially those involving dilute samples. For example, binding assays can be used to probe binding between molecules having subnanomolar dissociation coefficients, if acceptable signal-to-noise and signal-to-background ratios can be obtained from compositions having subnanomolar luminophore concentrations. The methods for enhancing signal-to-noise and signal-to-background ratios described below are especially useful with such dilute samples, thereby minimizing reagent cost that otherwise can be considerable.

Sensitivity and dynamic range can be enhanced by selecting optical components having low intrinsic luminescence and high intrinsic throughput; such as the fiber optic cables and beamsplitters described above. In such an approach, some components may be shared by different modes, whereas other components may be unique to a particular mode. For example, photoluminescence intensity and steady-state photoluminescence polarization modes may share a continuous light source; time-resolved luminescence modes may share a time-varying light source, and chemiluminescence modes may not use a light source. Similarly, photoluminescence and chemiluminescence modes may use different detectors, each selected for the application.

Sensitivity also can be enhanced by reducing the contribution of noise to the measurements. In luminescence polarization assays, various factors contribute to noise, such as (1) background noise and (2) intensity noise. Background noise refers to contributions to the signal from luminescent species other than the luminescent species of interest, including luminescent species in the apparatus and sample holder. Intensity noise refers to fluctuations in light intensity, including those arising from photon noise.

Background noise can be reduced by reducing autoluminescence from the apparatus and sample holder. For example, the apparatus may use low luminescence components, such as fused silica fiber optic cables. Similarly, the sample holder or substrate may be constructed of low luminescence materials, such as black polystyrene.

Background noise also can be reduced by reducing detection of luminescence from components of the sample that are bound to the sample holder and immobilized, spuriously increasing polarization. For example, the walls of the sample holder may be constructed and/or treated to reduce binding. Alternatively, in apparatus capable of detecting light transmitted substantially exclusively from a sensed volume (e.g., as shown in FIGS. 3–6), the sensed volume may be positioned near the center of the composition, away from the walls of the sample holder.

Intensity noise can be reduced by correcting for fluctuations in light source intensity, among others. Light source fluctuations arise due to fluctuations in power from the power supply and drift in the position of the arc in arc lamps, among others. Light source fluctuations can lead to luminescence fluctuations, because the amount of luminescence is proportional to the amount of excitation light. Luminescence fluctuations are especially problematic in luminescence polarization assays, because such assays involve comparing the magnitude of successively measured luminescence signals. Light source fluctuations can be reduced by choosing a stable light source and by resealing the luminescence signal using information obtained from a light source monitor, as described above.

Intensity noise also can be reduced by increasing the number of photons (i.e., the amount of light) detected, which reduces photon noise. Photon (or shot) noise arises due to the statistical nature of light and can be described by the same statistical law used to describe radiation decay. In particular, if an average of N photons are detected during a given time interval, the standard deviation in that number due to photon noise will be $\sqrt{N}$. The relative significance of photon noise decreases as the number of detected photons increases, because the ratio of the standard deviation in the signal to the signal goes as $\sqrt{N}/N=1/\sqrt{N}$. Although there may be many sources of intensity noise, the limit set by photon noise can never be overcome; however, the significance of photon noise can be reduced by increasing the number of photons collected by the detector. The number of photons collected can be increased by increasing the intensity of the light source, the efficiency of the detector, and/or the throughput of components of the optical relay structure, such as the beamsplitter, among others.

Photon noise creates noise in luminescence polarization assays. To a very good approximation, the noise in the polarization is proportional to the noise in the luminescence intensities from which the polarization is calculated and corresponds to seven mP standard deviation in polarization for every one percent standard deviation in intensity. This relationship essentially is independent of the degree of polarization. Photon noise puts a premium on simply collecting enough light, especially in rapid high-throughput screening measurements using the optically restrictive microplate format. For additional information, see the calculation in U.S. Provisional Patent Application Ser. No. 60/063,811, filed Oct. 31, 1997, which is incorporated herein by reference in its entirety for all purposes.

Most well-developed polarization assays have maximum polarization changes of between 100 mP and 200 mP, so acceptable standard deviations in the polarization should be no greater than about 5 mP to 10 mP. This requires detection of at least 10,000 photons per intensity measurement to reduce intensity noise to about 1%. The inefficiency of polarization optical systems increases the problem. The number of photons collected is proportional to both the concentration and the detection time, leading to trade-offs between probe concentration and screening throughput. High concentrations of reagents not only are expensive, but also produce insensitive binding assays if they exceed the dissociation constant of the binding reaction.

Figure 78:
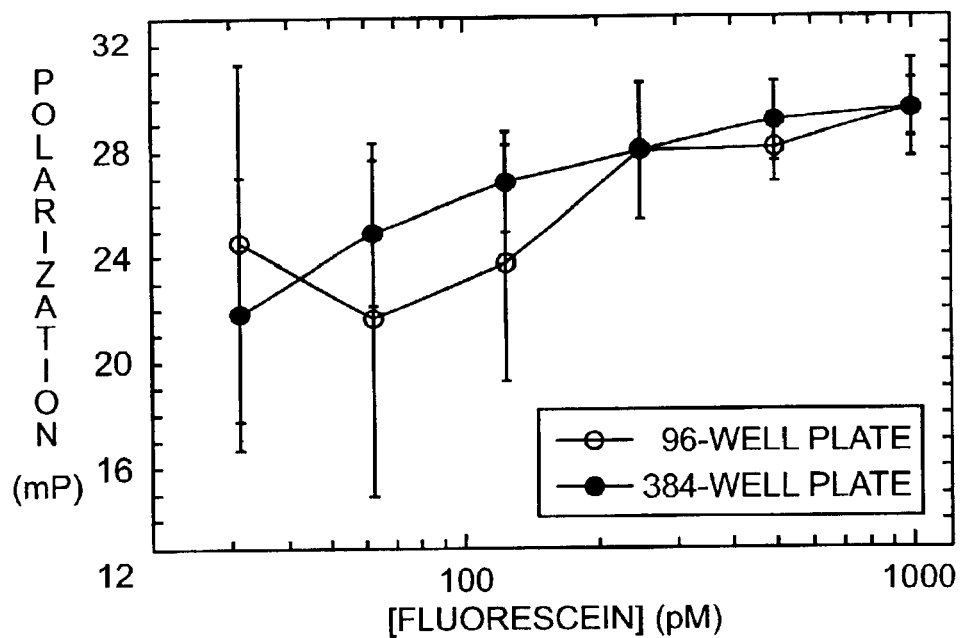
FIG. 78 is a graph of polarization versus fluorescein concentration measured in 96-well and 384-well microplates, showing the sensitivity of the apparatus.
Figure 79:
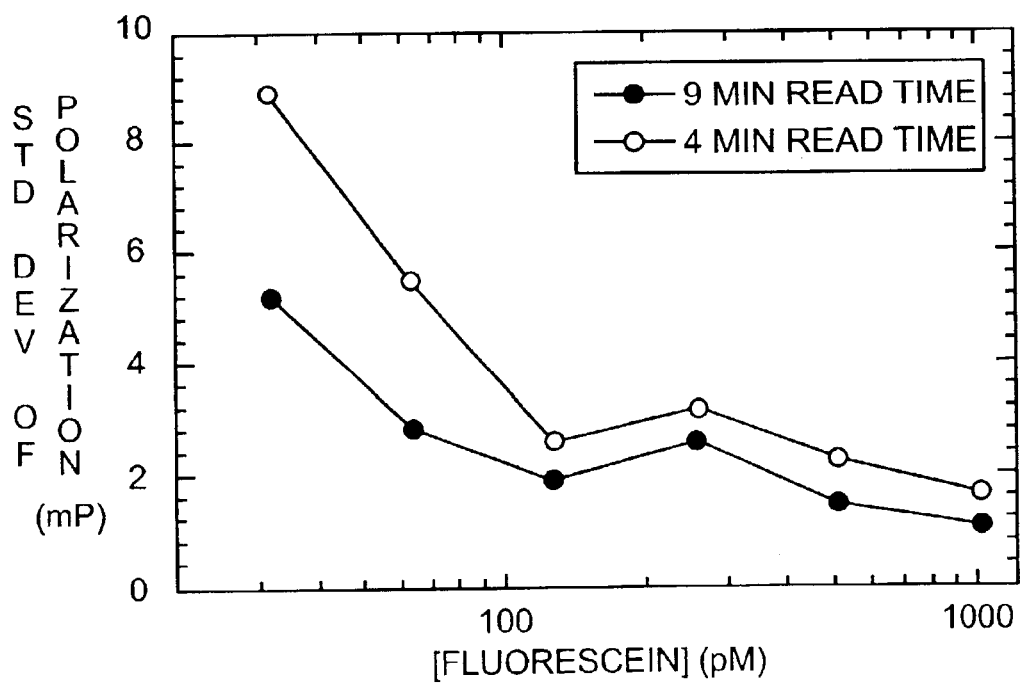
FIG. 79 is a graph of the standard deviation of polarization versus fluorescein concentration measured in 384-well microplates, determined after 4-minute and 9-minute whole microplate read times, showing the sensitivity of the apparatus.

FIGS. 78 and 79 show results that characterize a luminescence polarization apparatus constructed in accordance with the invention. Data were collected at room temperature using the preferred apparatus shown in FIGS. 3–6.

FIG. 78 is a graph showing polarization in a serial dilution of fluorescein in 96- and and 384-well microplates. The graph demonstrates that the polarization of fluorescein can be measured with adequate accuracy and precision down to, or below, 100 pM, because the measured value is substantially independent of concentration down to, or below, this concentration.

FIG. 79 is a graph showing the noise (or standard deviation) in polarization in a serial dilution of fluorescein in 384-well microplates. As described above, noise below 5–10 mP is sufficiently small for most practical polarization assays. Good precision may be obtained at subnanomolar label concentrations in rapidly scanned 384-well microplates, and even better precision may be obtained in more slowly scanned microplates. The size of the error bars shows that the number of photons collected by the detector exceeds 10,000 in 100 milliseconds from a 100-picomolar fluorescein solution at pH 7.5.

XVI. Preferred Light Sources

Photon noise can be reduced by using a sufficiently high-intensity light source, such as a continuous high color temperature xenon arc lamp or a laser, among others, as described above. The following table compares preferred continuous and time-varying light sources:

| Summary | Continuous Light Source | Flash Lamp Light Source | Comparison (Flash/ Continuous) |
|---|---|---|---|
| Life of light source | 300 hrs | 10,000 hrs | 6% |
| Total power of light source | 13,000 mW | 830 mW | 5% |
| Visible power (390–770 nm) | 5100 mW | 230 mW | 3% |
| Infrared power (>770 nm) | 7300 mW | 190 mW | 11% |
| Ultraviolet power (300–390 nm) | 620 mW | 68 mW | 4% |
| Apparatus power (485 nm) | 7.1 mW $1.7 \times 10^{16}$ photons/sec | 0.29 mW $7.1 \times 10^{14}$ photons/sec | 4% |
| Photons/sec from a 1 Nm luminophore solution (estimated) | $1 \times 10^8$ photons/sec | $5 \times 10^6$ photons/sec | 5% |
| Photons/sec from a 10 pM luminophore solution (estimated) | $1 \times 10^6$ photons/sec | $5 \times 10^4$ photons/sec | 5% |

The lifetime of the continuous lamp is only 1/33 the lifetime of the flash lamp. The lifetime of the continuous lamp was taken directly from the manufacturer's specifications. The lifetime of the flash lamp was computed using the manufacturer's specification. Specifically, the flash lamp is run at 100 flashes per second, using 250 mJ of electrical power per flash; at this power level, the lifetime of the flash lamp is rated at $1\times10^9$–$1\times10^{10}$ flashes, corresponding to a lifetime of about 10,000 hours ($5\times10^9$ flashes/[100 flashes/sec$\times$3600 sec/hour]).

The continuous lamp provides about 20 times more light than the flash lamp. The total optical power of the continuous lamp (collected by a F/1.0 optical system) is 13 W over the wavelength range 300–4000 nm. The total optical power of the flash lamp (collected by a F/1.0 optical system) is 830 mW over the wavelength range 100–4000 nm. The total optical power of the flash lamp was derived from the electrical energy, the electrical-to-optical conversion efficiency, the optical collection efficiency, and the repetition rate (250 mJ$\times$50%$\times$6.6%$\times$100 Hz). The optical powers of the different spectra of the flash lamp were derived by multiplying the total optical power of the flash lamp by the fraction of the power in each wavelength range, i.e., ultraviolet (300–390 nm) 8.3%, visible (390–770 nm) 28%, and infrared (770+ nm) 24%.

The optical power in the preferred apparatus was determined after passage through a bandpass filter (center 485 nm, bandwidth 20 nm). The optical power in photons per second was calculated by assuming that all photons had a wavelength of 485 nm (energy=1240 eV$\times$nm/wavelength).

High-throughput screening requires that light be collected quickly and efficiently, so that assays can be accurately and rapidly performed. A 1% error in intensity, corresponding to a 7 mP error in polarization, requires collection of at least 10,000 photons, as described above. For high-throughput screening, these photons should be collected within 100 ms, corresponding to a collection rate of 100,000 photons/sec. Both lamps produce more than 100,000 photons/sec, but the criterion is to collect 100,000 luminescence photons/sec, not to produce 100,000 excitation photons/sec. Specifically, the criterion is to count at least 10,000 photons in 100 msec ($1\times10^5$ photon/sec) for low concentrations of luminophore (less than 1 nM). The preferred apparatus achieves this photon limit at roughly 10–100 pM for polarization assays.

The detection efficiency is given by the product of an emission efficiency, a collection efficiency, a transmission efficiency, and a detector quantum efficiency, as calculated below.

The emission efficiency is determined by a product of the fractional absorption and quantum yield. The fractional absorption is determined by the Beer-Lambert law, $-\log[I/I_0]=\epsilon cl$, where I is transmitted intensity, to is incident intensity, $\epsilon$ is extinction coefficient, c is concentration, and l is path length. The molar extinction coefficient of typical luminophores is about 50,000 per molar per centimeter, and the path length in typical microplates is about 5 mm. Thus, the fraction of photons absorbed is about $6\times10^{-5}$ in a 1 nM solution and about $6\times10^{-7}$ in a 10 pM solution. The quantum yield (ratio of photons emitted to photons absorbed) of typical luminophores is 0.9, so that about $5\times10^{-5}$ of the incoming photons are converted to luminescence emission photons (at 1 nM). This is effectively the emission efficiency.

The collection efficiency is determined by numerical aperture. Luminescence is emitted over all angles, whereas luminescence is collected over limited angles. Specifically, luminescence is collected over a cone angle $\theta$ given by the formula $\theta=2\arcsin[(NA)/n)]$, where NA is numerical aperture and n is index of refraction. The optical collection efficiency is about 3% for an NA of 0.39 and about 1% for an NA of 0.22.

The transmission efficiency is determined by the optics through which the light passes between the sample and detector. The transmission efficiency in the preferred apparatus probably is about 2%.

The detector quantum efficiency is determined by the detector. For example, the detector quantum efficiency of a photomultiplier tube (PMT) typically is about 20–25%, and the detector quantum efficiency of a photodiode or other solid-state device typically is about 80%.

The preferred detector may vary with experimental conditions. At low light levels, a PMT may be preferred, because a PMT typically will have a lower background (i.e., dark count) and so contribute less noise to the system under these conditions. At higher light levels, a photodiode may be preferred, because a photodiode typically has a higher detector quantum efficiency and because any shortcoming in background relative to a PMT should be offset by a higher quantum efficiency.

Thus, the overall detection efficiency assumes values as follows:

| Concentration | Detection Efficiency (Estimated) |
|---|---|
| 1 nM | $5 \times 10^{-5} \times 0.03 \times 0.02 \times 0.25 = 8 \times 10^{-9}$ |
| 10 pM | $5 \times 10^{-7} \times 0.03 \times 0.02 \times 0.25 = 8 \times 10^{-11}$ |

To determine if the continuous and/or flash lamps satisfy the collection criterion of 100,000 photons per second, the detection efficiency was multiplied by the excitation flux to yield an estimated measurable flux at 1 nM and 10 pM (measured in photons/sec). The estimated measurable flux shows that the continuous lamp fails the criterion of 100,000 photons per second somewhere below 10 pM for a typical luminophore, whereas the flash lamp fails the criterion somewhere near 200 pM (roughly 20 times higher). Thus, the continuous lamp satisfies the collection criteria, whereas the flash lamp does not. Specifically, the flash lamp has enough optical power to make statistically significant measurements at 1 nM, but not at 10 pM, where it leads to the collection of fewer than $1 \times 10^5$ photons/sec.

In summary, the continuous lamp has a power of greater than 1 watt over the visible wavelength range of 390 to 770 nm, and is sufficient to reduce photon noise to less than 1 percent of a light signal emitted from a 100 picomolar fluorescein solution at pH 7.5.

XVII. Epi-Absorbance Systems

This section describes systems, including apparatus and methods, for detecting and/or measuring light transmitted from a sample. The apparatus may include a stage, a light source, and a detector. The stage, in turn, may be configured to hold a microplate having a plurality of sample wells. The apparatus may be configured to take measurements of one or more of absorbance, scattering, reflectance and luminescence, sequentially and/or simultaneously. These and other aspects of the invention are described below in detail, including (A) detailed description, and (B) examples. This disclosure is supplemented by the patents, patent applications, and other materials identified above under Cross-References, particularly U.S. Provisional Patent Application Ser. No. 60/094,275, filed Jul. 27, 1998; U.S. Provisional Patent Application Ser. No. 60/117,278, filed Jan. 26, 1999; U.S. Provisional Application Ser. No. 60/136,566, filed May 28, 1999; PCT Patent Patent Application Ser. No. PCT/US99/16621, filed Jul. 23, 1999; and U.S. patent application Ser. No. 09/765,869, filed Jan. 19, 2001. These supplementary materials are incorporated herein by reference in their entirety for all purposes.

A. Detailed Description

This section describes assays in accordance with aspects of the invention, including (i) absorbance assays, and (ii) scattering assays.

A.1 Absorbance Assays

Figure 80:
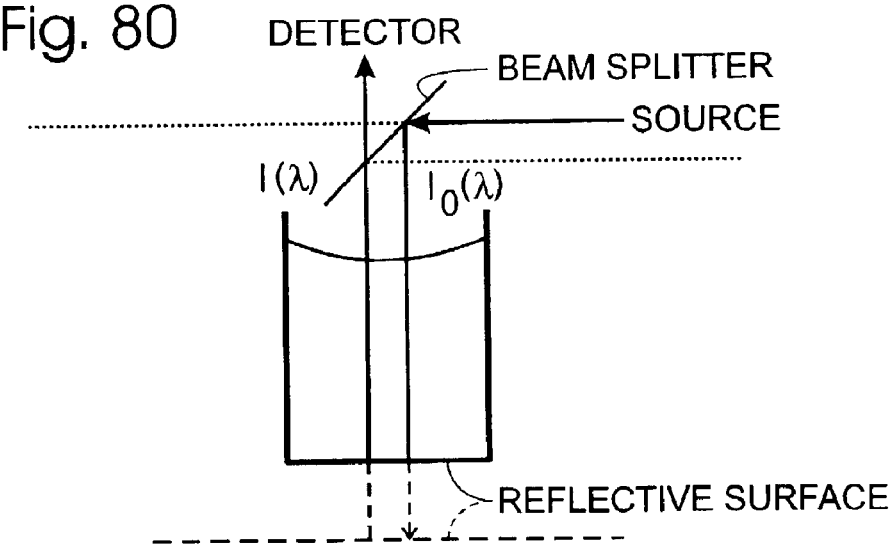
FIG. 80 is a schematic view of an absorbance experiment in accordance with aspects of the invention.

FIG. 80 shows a schematic view of an absorbance assay performed in accordance with aspects of the invention. Incident light from a light source is reflected onto the sample by a beam splitter. The light passes a first time through the sample, bounces off a reflective surface at the far side of the sample, and passes back a second time through the sample. Transmitted light emerges from the sample and passes through the beam splitter to a detector. The optical paths between the light source and sample, and the sample and light detector, may lie along different optical axes, or they may lie along the same optical axis, as when a fiber optic bundle having parallel excitation and emission fibers is employed.

In a preferred embodiment, the absorbance assay is performed using a high-throughput analyzer, such as described above and disclosed in the patent applications cross-referenced above. In this embodiment, a 50/50 beam splitter is employed, one of the two spectral filters normally used for luminescence is removed, and the other of the two spectral filters is selected to match an absorbance band of interest of the sample. In addition, the focal plane of the confocal optics is adjusted so that the instrument focuses on the far side of the sample container. It should be noted that than attenuator may be necessary between the sample and the detector to reduce the light level to a range useable by the detector. Because luminescence levels are typically very low compared to incident light levels and reflected light levels, the majority of the light reaching the detector will consist of reflected light that has passed twice through the sample in the described arrangement. Where reflected light levels are lower, it is also possible to filter out luminescence light or other light sources so that primarily reflected light reaches the detector. A reference sample well containing a blank, i.e. without the analyte of interest, may be used to correct for absorbance by the solution, optics, or other non-sample components of the assay. In a preliminary experiment in a 96-well microplate, absorbance over a range of 1.2 ODs was measured with about 0.1 OD resolution and acceptable linearity.

The reflective surface may include the sample wall or an additional surface. For example, the reflective surface may include a partially reflective sample wall, such as the bottom of a clear microplate, the interior surface of a white microplate, or a totally reflective sample wall, such as sample wall with a silvered surface. Alternatively, the reflective surface may include an additional surface, such as a mirror placed inside or outside the sample container, as shown by the dashed lines in FIG. 80. Reflection from the reflective surface may occur by a variety of mechanisms, including total internal reflection.

Figure 81:
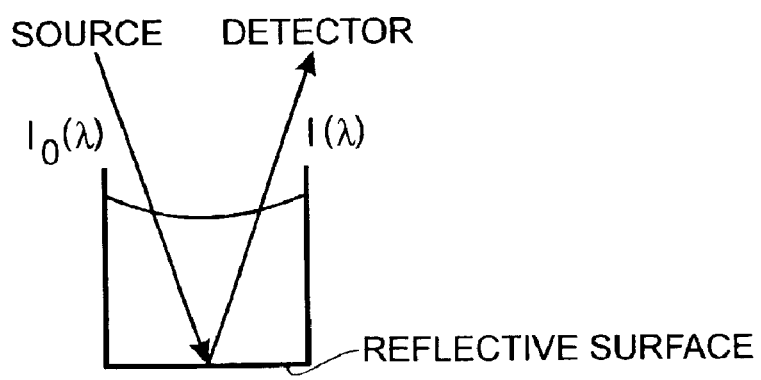
FIG. 81 is a schematic view of an alternative absorbance experiment in accordance with aspects of the invention.

FIG. 81 shows a schematic view of an alternative absorbance assay performed in accordance with aspects of the invention. Light enters and exits through an open side of the sample container, and may be reflected by the sample wall or by a mirror inside or outside the sample wall. This alternative absorbance assay does not involve a beam splitter, and may not involve passage of light through any wall of the sample container. This alternative absorbance assay does provide an extended path length, which arises because light travels through the sample at an angle, further increasing absorbance. Path length similarly may be extended in other embodiments, including embodiments incorporating beam splitters.

Figure 82:
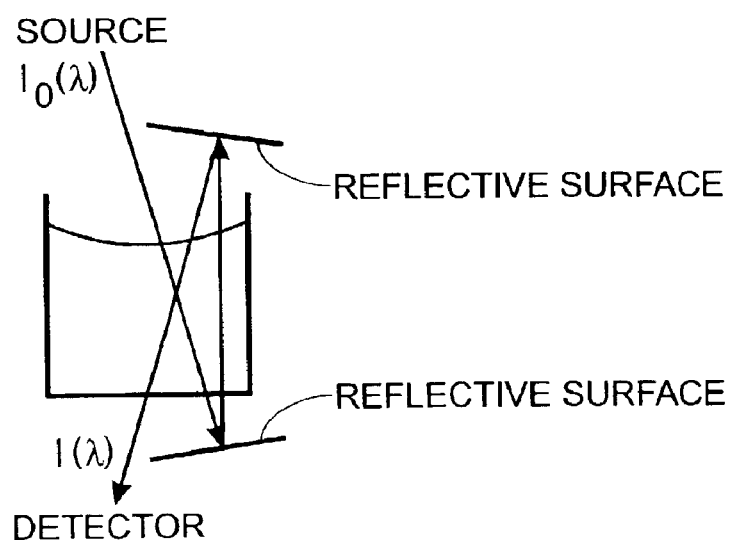
FIG. 82 is a schematic view of another alternative absorbance experiment in accordance aspects of with the invention.

FIG. 82 shows that light may be directed through the sample more than twice.

The absorbance assay minimizes the influence of the sample meniscus on assay results. In particular, refractive effects due to the meniscus are minimized because they are reversed on the return trip after the light reflects off the far side of the sample container. Additional corrections for effects such as meniscus variations may be made by referencing a measurement at the wavelength at which absorbance is to be determined by an absorbance-mode measurement in the same sample container at one or more other wavelengths where there is no absorption, essentially a ratiometric strategy.

As mentioned above, absorbance assays also may be used to improve fluorescence and other luminescence assays. For example, absorbance measurements can be paired with luminescence measurements to detect "color quenching" of fluorescence assays. "Color quenching" is a term used to describe the absorbance of excitation or luminescence emission light in samples that happen to have significant extinction coefficients at those wavelengths. The result is a decrease in the measured luminescence intensity, which may significantly interfere with assay interpretation. The result of an absorbance measurement can be used to correct the measured luminescence back to the value that would have been obtained in the absence of absorbance.

A separate, simultaneous or subsequent absorbance measurement made at the excitation and/or emission wavelength can identify the existence of color quenching and may provide a means of correcting the luminescence signal for this interference. If a dichroic beamsplitter is used for the luminescence measurements, the beamsplitter will significantly attenuate the signal used in the absorbance measurement. It is preferable not to have to switch to a wavelength-insensitive (e.g., 50/50) beamsplitter when making the absorbance measurement after the luminescence measurement. The intensity of the reflected light used in the absorbance measurement generally will be much higher than the intensity of luminescence and may be attenuated before reaching the detector; the attenuation caused by the dichroic beam splitter likely can serve this function.

Figure 83:
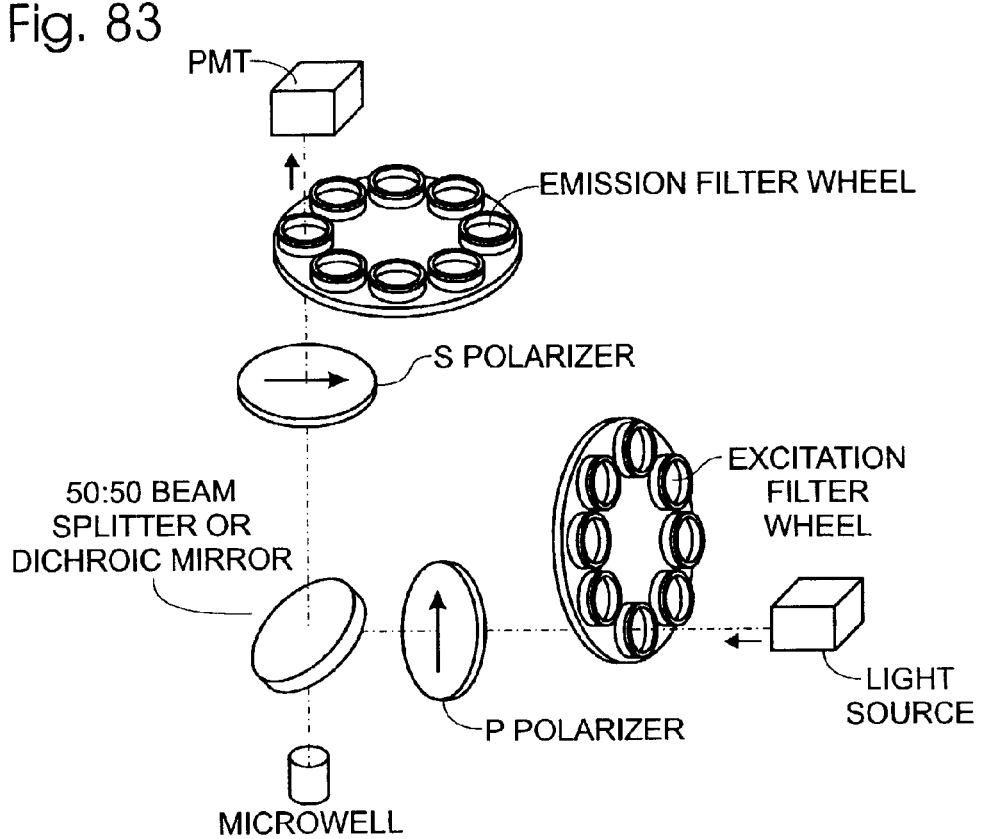
FIG. 83 is a schematic view of an apparatus for conducting an absorbance experiment, in which the apparatus is constructed in accordance with aspects of the invention.

FIG. 83 shows an apparatus for conducting an absorbance measurement constructed in accordance with aspects of the invention. The apparatus employs the reflective absorbance configured as described above. The apparatus can give a simultaneous indication of reflectance, scattering, and absorbance of a sample in a microplate well or other sample container in a top down (i.e., non-transmissive) configuration. This method can be used with white, black, or clear bottom microplates. The sensitivity of the method can be enhanced with the insertion of crossed polarizers. Reflective absorbance sensitivity is further optimized by selection of the appropriate focal height within the sample well.

The response linearity of this method can be improved by determining the amount of "excess intensity" (which includes background light and reflected light) and subtracting it from the raw intensities prior to calculating the absorbance. Mathematically, the raw intensity $I_{Raw}$ was assumed to include light that passed through the sample $I_{Sample}$ and instrument background $I_{Bkg}$:

$$I_{Raw} = I_{Sample} + I_{Bkg} \quad \text{(XVII-1)}$$

The raw intensities then were curve-fit to a pseudo-Beer's law model, where $I_{Bkg}$ and K were selected using a nonlinear least-squares fitting method:

$$A = -\log_{10}\left[\frac{I_{Raw} - I_{Bkg}}{I_{RawBuffer} - I_{Bkg}}\right] = K \times C_{Sample} \quad \text{(XVII-2)}$$

This simple linearization scheme can be used to produce reasonably linear responses over >2 optical density (OD) units in certain cases.

Reflective absorbance is particularly suitable for use with white microplates or any plate with a strong scatterer settled on the bottom, due to the strong scattering effect at the inner surface of the microplate wells. This scattering (and depolarizing) effect can be caused by the addition of a high dielectric constant material like titanium dioxide to the plastic from which the microplate is molded. Alternatively, scattering and depolarization can be caused by the presence of an optically active layer of small beads on the bottom of the well that have scattering properties (e.g., scintillation proximity assay (SPA) beads). The excitation light that is back-scattered from the well inner surface emerges from the microplate well highly depolarized. The use of crossed polarizers in the configuration shown in FIG. 83 causes back-reflected polarized light to be strongly attenuated by the second polarizer, enhancing the signal-to-background ratio. Highly polarized input light travels through the sample and is scattered and de-polarized when it hits the bottom surface of the microplate well. Back-scattered depolarized light that passed through the sample (and is absorbed or reflected by it) is preferentially passed through the crossed polarizers, whereas back-reflected polarized light from optical surfaces or the meniscus in the microplate well is highly attenuated because it retains a high polarization. In some applications, it may be possible to eliminate undesired contributions to a signal using two polarizers in alternative orientations, including generally parallel.

If the measurement conditions are optimized, reflective absorbance can be used in high throughput screening to detect and potentially correct for potential interferences from absorbing, scattering, compounds, targets, reagents, contaminants, etc. For example, reflective absorbance could be used to correct for color quenching in scintillation proximity assays or absorbing or luminescing compounds in intensity-based luminescence or chemiluminescence based assays.

Figure 84:
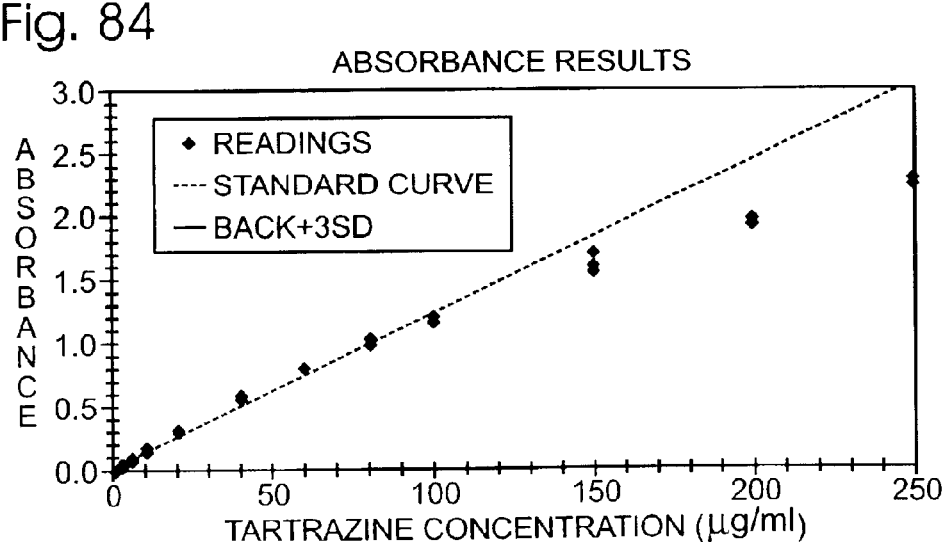
FIG. 84 is a graph of reflective absorbance results obtained in accordance with aspects of the invention.
Figure 85:
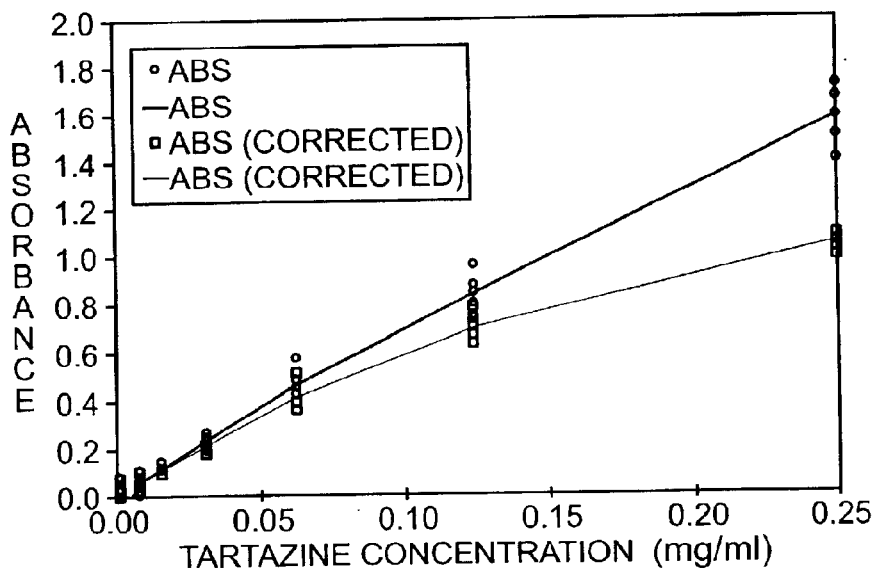
FIG. 85 is a graph of reflective absorbance results obtained in accordance with aspects of the invention, showing that the resolution of the assay may be improved using information obtained from a blank.

FIGS. 84 and 85 show experimental results obtained in accordance with aspects of the invention. The apparatus employed an ANALYST high-throughput detection platform, which included a confocal optical arrangement and a 50/50 beam splitter. The adjustable z height was set so that the instrument focused on the bottom of the well. Transmission (or absorbance) was measured by bouncing light off the bottom of a clear bottom microplate to get two passes through the liquid. The change in signal between a reference well and the sample well provides a measure of transmission or absorbance (T=$10^{-A}$). Obtaining a twofold increase in path length is especially important for high-density microplates, because smaller volumes imply shorter path lengths and hence lower sensitivity. The invention, which includes two passes through the sample, helps to increase the sensitivity in high-density low-volume wells. FIG. 85 shows results before and after correction using Equation XVII-2.

For these experiments, one of the two spectral filters normally used for luminescence was removed, and the other filter was selected to match an absorbance band of interest of the sample. The refractive effects of the meniscus are minimized since they are reversed on the return trip after the light reflects off the bottom of the microplate well. In a preliminary experiment in a 96-well microplate, a 1.2 OD range was measured with about 0.1 OD resolution and acceptable linearity.

Figure 86:
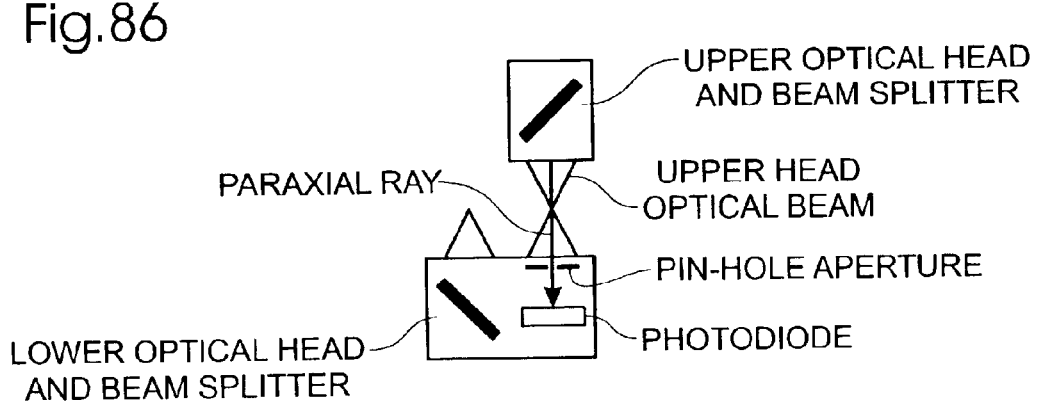
FIG. 86 is a schematic view of a system for measuring absorbance in accordance with aspects of the invention.

FIG. 86 shows another system for measuring absorbance in a trans configuration according to the invention. In the disclosed embodiment described above, the detector takes the form of an upward-facing photodiode positioned directly below the optical axis of the upper head. A pin-hole aperture is disposed between the sample and the photodiode to limit the entry of light.

This system allows measurement of absorbance while luminescence or reflectance are measured by the optics in the upper head by the photomultiplier tube. The absorbance (or excitation) wavelength is selected using the excitation filter wheel. The reflectance or emission wavelength is selected using the emission filter wheel. A 50:50 beam splitter works well for absorbance/reflectance measurements, while a dichroic mirror may be more suitable from absorbance/luminescence measurements.

Measurement of absorbance in conjunction with other assays is useful in high-throughput screening. Abnormal absorbance measurements may indicate a quality-control problem, such as contamination or an air bubble. The absorbance data also could be used to detect or analyze false negatives or positives. It should be understood that the detector signal providing absorbance information may be processed to generate an actual absorbance value or may only be used to compute some quantity related to absorbance, such as a relative intensity of the signal.

An additional use for the design shown in FIG. 86 is to use the multi-mode measurement capabilities to determine location of reference fiducials on microplates, as described in the following U.S. patent applications, which are incorporated herein by reference in their entirety for all purposes: Ser. No. 09/156,318, filed Sep. 28, 1998, now U.S. Pat. No. 6,258,326; and Ser. No. 09/478,819, filed Jan. 5, 2000. For example, transmission or reflection measurements can be used to detect a hole or other such optically identifiable feature on the surface of a microplate. The location of the fiducial can be determined by scanning the microplate under the detector while continuously measuring the transmission and searching for a maximum or minimum. The XYZ stage coordinates are recorded at each fiducial. This provides the location of fiducials in stage coordinates. Since the positions of the fiducials are known relative to other features on the plate, any feature on the plate can be accurately found by determining an appropriate offset from the known fiducial location.

A.2 Scattering Assays

Figure 87:
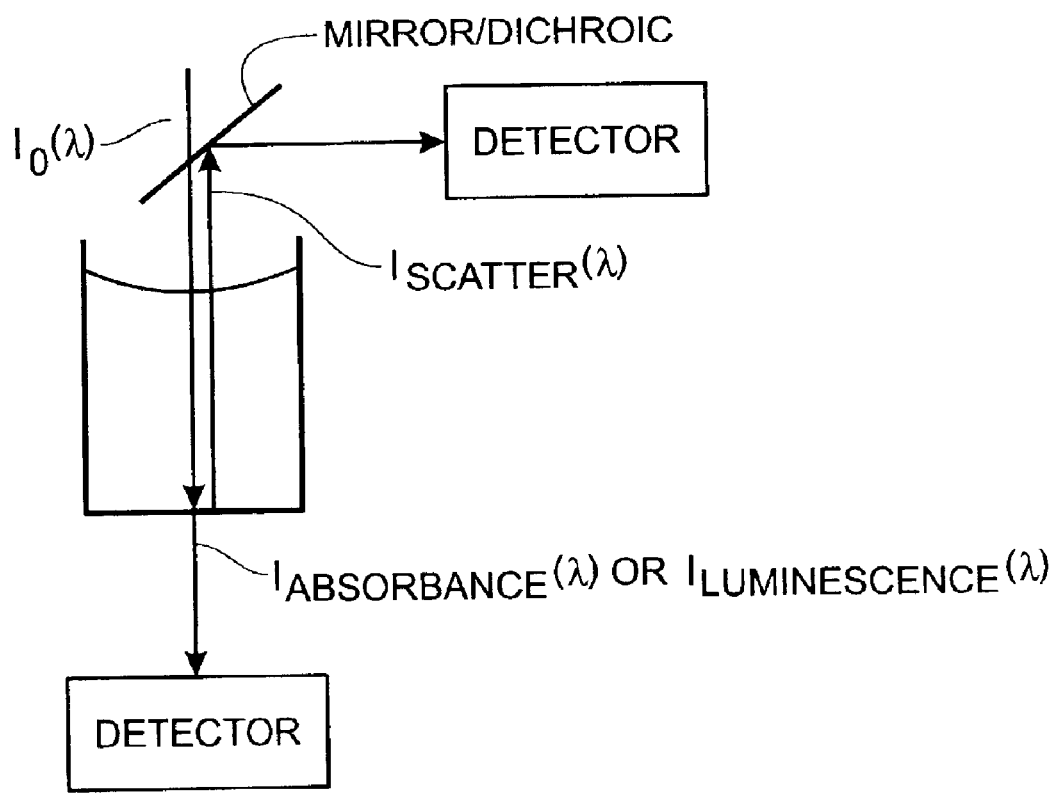
FIG. 87 is a schematic view of a system for measuring scattering in accordance with aspects of the invention.
Figures 92, 93, 94, 95:
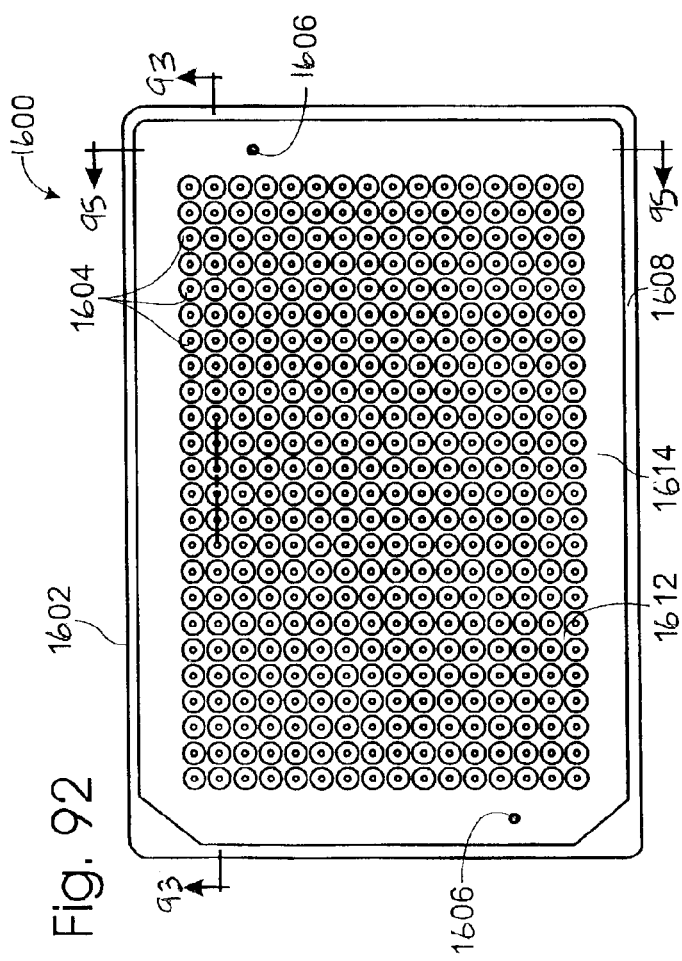
FIG. 92 is a top view of a 384-well microplate, in accordance with aspects of the invention.
FIG. 93 is a cross-sectional view of the microplate in FIG. 91, taken generally along line 93—93 in FIG. 92.
FIG. 94 is an enlarged portion of the cross-sectional view in FIG. 93, showing details of a sample well.
FIG. 95 is an enlarged cross-sectional view of the microplate in FIG. 92, taken generally along line 95—95 in FIG. 92, showing details of a reference fiducial.

FIG. 87 schematically shows a scattering assay according to the invention in which scattered light is measured. Incident light $I_0$ is shone onto a sample. The sample includes a constituent that scatters the incident light. A component of the scattered light is received by a detector. The previously described technique of utilizing two polarizers also may be effective to reduce the effect of reflections on the scattering measurement. The best results for this type of scattering assay are obtained with a black or clear microplate that does not reflect or scatter significant amounts of the incident light.

A scattering assay according to the invention can be used alone or in conjunction with another spectroscopic assay. For example, the scattering assay can be conducted simultaneously with a luminescence assay to account for color quenching of the luminescence. In such a combined assay, the scattering is preferably monitored from the direction of the incident light as depicted in FIG. 87. Luminescence can be measured in either an epi- or trans- configuration as desired. This simultaneous measurement is facilitated by the wavelength (Stokes') shift of the luminescence relative to the incident (excitation) light, allowing separation of scattered and luminescence light.

It also is possible to conduct a combined scattering and absorbance assay. In a scattering/absorbance assay, the absorbance preferably is measured in the trans-direction, while the scattering preferably is measured in the epi-direction. It also is possible to conduct simultaneous scattering, luminescence and absorbance measurements by combining the scattering/absorbance, and scattering/luminescence assays. Moreover, it is also possible to conduct combined assays sequentially. In the case of sequential assays, it is possible to utilize the same detector for two or more types of measurements, such as scattering and luminescence.

Use of combined assays permits monitoring for various properties of the sample. Absorbance or scattering measurements outside a given range may indicate some problem with the sample, as described above. For example, an increase in scattering levels during a luminescence experiment can signal that a precipitate has formed in the sample, as might occur in a dilution series. Formation of a precipitate may decrease the luminescence signal. Without the scattering measurement, such a decrease might be falsely interpreted as a real decrease in the luminescence of the sample.

B. Examples

The following numbered paragraphs describe additional and/or alternative aspects of the invention:

1. A method of measuring absorbance of a sample, comprising (A) directing incident light from a light source to a measurement region; (B) sequentially positioning each of a series of samples in the measurement region so that the incident light passes through each of the samples in a first direction, and for each of the samples (i) reflecting the incident light back through the sample in a second direction generally opposed to the first direction; (ii) receiving the reflected light; and (iii) computing a quantity related to the absorbance of the sample based on the amount of reflected light received.

2. The method of paragraph 1 further comprising the step of placing the samples in a corresponding series of sample wells in a sample plate.

3. The method of paragraph 2, wherein the sample wells in the sample plate have a surface that scatters light.

4. The method of paragraph 1 further comprising, for each of the samples, measuring luminescence of the sample while the sample is positioned in the measurement region.

5. The method of paragraph 1 further comprising separating light transmitted from the sample into a luminescence component and a reflected component.

6. A spectroscopic assay wherein a plurality of samples are automatically and sequentially placed into a measurement region and comprising for each sample (A) directing light from a light source onto the sample from a first side; (B) detecting a first fraction of the incident light that passes through the sample to a second side without absorbance or scattering; and (C) simultaneously detecting a second fraction of light transmitted from the sample on the first side generally opposite the direction of the incident light.

7. The assay of paragraph 6, wherein the second fraction of light is luminescence light.

8. The assay of paragraph 6, wherein the second fraction of light is scattered light.

9. The assay of paragraph 6, wherein one of the samples is a blank for calibration.

10. The assay of paragraph 9, wherein the blank sample is opaque.

11. The assay of paragraph 10 further comprising the step of detecting the first fraction with the blank and using the detected value to compensate for background absorbance signal in subsequent samples.

12. The assay of paragraph 6 further comprising passing the incident light through a first polarizer.

13. The assay of paragraph 12 further comprising (A) passing the second fraction of light through a second polarizer; and (B) orienting the second polarizer to reduce an undesired contribution to the signal.

14. The assay of paragraph 13, wherein the second polarizer is oriented generally transverse to the first polarizer.

15. The assay of paragraph 13, wherein the second polarizer is oriented generally parallel to the first polarizer.

16. A method of measuring luminescence, comprising (A) providing a sample plate including a plurality of sample wells containing a corresponding plurality of samples; (B) positioning a first sample well for measurement; (C) illuminating the first sample well with incident light of a first wavelength, where light is transmitted from the sample as a result of illumination with incident light, the transmitted light including light at the first wavelength and light at a luminescence wavelength shifted from the first wavelength; (D) filtering at least part of the transmitted light from the sample to extract light at the luminescence wavelength; (E) detecting the extracted luminescence light; and (F) measuring transmitted light at the first wavelength.

17. The method of paragraph 16, wherein the steps of measuring and detecting are conducted simultaneously.

18. The method of paragraph 16, wherein the step of measuring is configured to detect scattered incident light.

19. The method of paragraph 16 further comprising the step of computing a quantity related to absorbance of the sample based on the measured transmitted light at the first wavelength.

20. The method of paragraph 19 further comprising utilizing the computed quantity related to absorbance to correct the detected luminescence to a level that would be detected without absorbance.

21. The method of paragraph 16, wherein the step of illuminating includes the substep of polarizing the incident light.

22. The method of paragraph 21, wherein the step of measuring includes the substep of passing the transmitted light through a polarizer prior to measuring.

23. The method of paragraph 16, wherein the sample wells in the sample plate have a surface that scatters incident light.

24. The method of paragraph 16 further comprising the step of placing a blank in one of the sample wells for use in calibrating the measurement obtained in step of measuring.

25. An apparatus for measuring absorbance, comprising (A) a light source; (B) a sensor positioned to measure a quantity proportional to the amount of light output by the light source; (C) a system for directing light from the light source to a measurement region; (D) a stage configured to hold a plate containing a plurality of sample wells adapted to hold samples, the stage further being configured to place a selected one of the samples in the sample wells into the measurement region; (E) a reflector disposed to reflect light that has passed through a sample back through the sample as second time; (F) a detector configured to receive reflected light emitted from a sample well in the measurement region; and (G) a processor adapted to compute an output based on the amount of reflected light received by the detector and based on the amount of light output by the light source.

26. A system for measuring absorbance, comprising (A) a light source; (B) a stage configured to hold a plate containing a plurality of sample wells adapted to hold samples, the stage further being configured to place a selected one of the samples in the sample wells into a measurement region; (C) a detector; and (D) an optical system adapted to direct light in a path from the light source through the sample at least twice and then to the detector, wherein the majority of the light reaching the detector has passed at least twice through the sample.

27. The system of paragraph 26, wherein the optical system includes a reflective surface disposed on a bottom of the sample wells.

28. A system for measuring absorbance, comprising (A) a light source; (B) a sample holder adapted to hold a sample in a measurement position, the sample holder having an open top and a reflective interior surface; (C) an optical system configured to deliver light from the light source to the open top into the sample; and (D) a detector positioned to receive primarily light reflected off the reflective interior surface.

29. The system of paragraph 28, wherein the sample holder is opaque to light from the light source.

30. The system of paragraph 28, wherein the sample holder is transparent to light from the light source with a scattering interior surface.

31. The system of paragraph 28 further including a filter disposed between the sample and the detector to block luminescence light preferentially to light from the light source.

32. The system of paragraph 28, wherein the optical system includes a polarizer disposed between the light source and the sample and a polarizer disposed between the sample and the detector.

33. An instrument for detecting light, comprising (A) a stage for holding a sample plate with a plurality of sample wells; (B) an upper optical head having an optical axis perpendicular to the stage configured for epi-style light detection from a sample contained in a selected one of the sample wells in the sample plate on the stage; and (C) a lower optical head including a light detector configured for trans-style light detection through a bottom of the selected sample well.

34. The instrument of paragraph 33, wherein the light detector in the lower optical head is positioned directly along the optical axis below the stage.

35. The instrument of paragraph 33, wherein the light detector is a photodiode.

XVIII. Sample Holders

This section describes a variety of sample holders, and features thereof, for use independent of and/or together with the systems described elsewhere in this specification. A "sample holder," as used here, generally comprises any substrate or material capable of (i.e., having a shape and/or rigidity suitable for) supporting one or more samples so that the sample holder and associated sample(s) can be transported by an automatic transport module and subjected to a function such as optical analysis or fluid dispensing. Sample holders may be used alone, in stacks, or in combination with seals or covers. Sample holders may support samples at low, intermediate, or high density, and be designed for single or multiple use.

Exemplary sample holders include microplates, PCR plates, biochips, slides, supported gels, and/or chromatography plates, among others. A microplate is a multiwell sample holder, typically but not exclusively used for luminescence applications. Preferred microplates are described below. A PCR plate is a multiwell sample holder used for performing PCR. Preferred PCR plates would include a footprint, well spacing, and well shape similar to those of the preferred microplates, while possessing a stiffness adequate for automated handling and a thermal stability adequate for PCR. A biochip is a small, flat surface (such as a glass or silicon wafer) onto which biomolecules (such as nucleic acids and proteins) are immobilized in distinct spots or arrays. Biochips include DNA chips, DNA microarrays, gene arrays, and gene chips, among others. Preferred biochips are described in Bob Sinclair, EVERYTHING'S GREAT WHEN IT SITS ON A CHIP: A BRIGHT FUTURE FOR DNA ARRAYS, 13 THE SCIENTIST, May 24, 1999, at 18. A chromatography plate is a flat surface used for performing chromatography, such as thin-layer chromatography.

Microplates are a preferred sample holder, and the system and its components may be designed for use with microplates having some or all of the features described here. (The term "microplate," as used in this specification, is intended to be synonymous with the term "sample holder," unless it is clear from the context or proposed or described use that the term truly is limited to "microplate.") Suitable microplates may include microplates having any number of wells, including 96, 384, and 1536, among others. Suitable microplates also may include microplates having wells with elevated bottoms, frusto-conical shapes, and/or low volumes, or wells configured to reduce the formation and/or trapping of bubbles, as described in the following U.S. patent applications, which are incorporated herein by reference in their entirety for all purposes: Ser. No. 08/840,553, filed Apr. 14, 1997; and Ser. No. 09/478,819, filed Jan. 5, 2000. Suitable microplates also may include microplates having reference fiducials in or around a perimeter portion of the microplate (or elsewhere), as described in U.S. patent application Ser. No. 09/156,318, filed Sep. 18, 1998, now U.S. Pat. No. 6,258,326, which is incorporated herein by reference in its entirety for all purposes. Such reference fiducials may be molded into the plate and/or applied to the plate by silkscreen, color transfer, hot stamping, and/or application of reflective paint, among others. Suitable microplates also may include microplates having a barcode for reading by a barcode reader, as described in U.S. patent application Ser. No. 09/160,533, filed Sep. 24, 1998, now U.S. Pat. No. 6,097,025, which is incorporated herein by reference in its entirety for all purposes. Suitable microplates also may be useable in combination with seals for sealing individual wells in a microplate, and/or spacer members for separating individual microplates in a stack, as described in the following U.S. patent applications, which are incorporated herein by reference in their entirety for all purposes: U.S. Provisional Patent Application Ser. No. 60/130,149, filed Apr. 20, 1999; U.S. Provisional Patent Application Ser. No. 60/132,263, filed May 3, 1999; U.S. patent application Ser. No. 09/556,030, filed Apr. 20, 2000; and U.S. patent application Ser. No. 09/778,224, filed Feb. 6, 2001. Suitable microplates (or other sample holders) also may be adapted for particular uses, for example, as described in the following U.S. patent applications, which are incorporated herein by reference in their entirety for all purposes: Ser. No. 09/759,711, filed Jan. 12, 2001 (for total internal reflection); and Ser. No. 09/767,434, filed Jan. 22, 2001 (for binding and/or hybridization assays).

FIGS. 88–100 show a set of preferred microplates that have similar heights and footprints but that differ in well shape, well size, and/or well density. These microplates include (A) 96-well microplates, (B) 384-well microplates, (C) 1536-well microplates, (D) miscellaneous microplates; and (E) exemplary microplates.

1. 96-Well Microplates

Figures 88, 89, 90, 91:
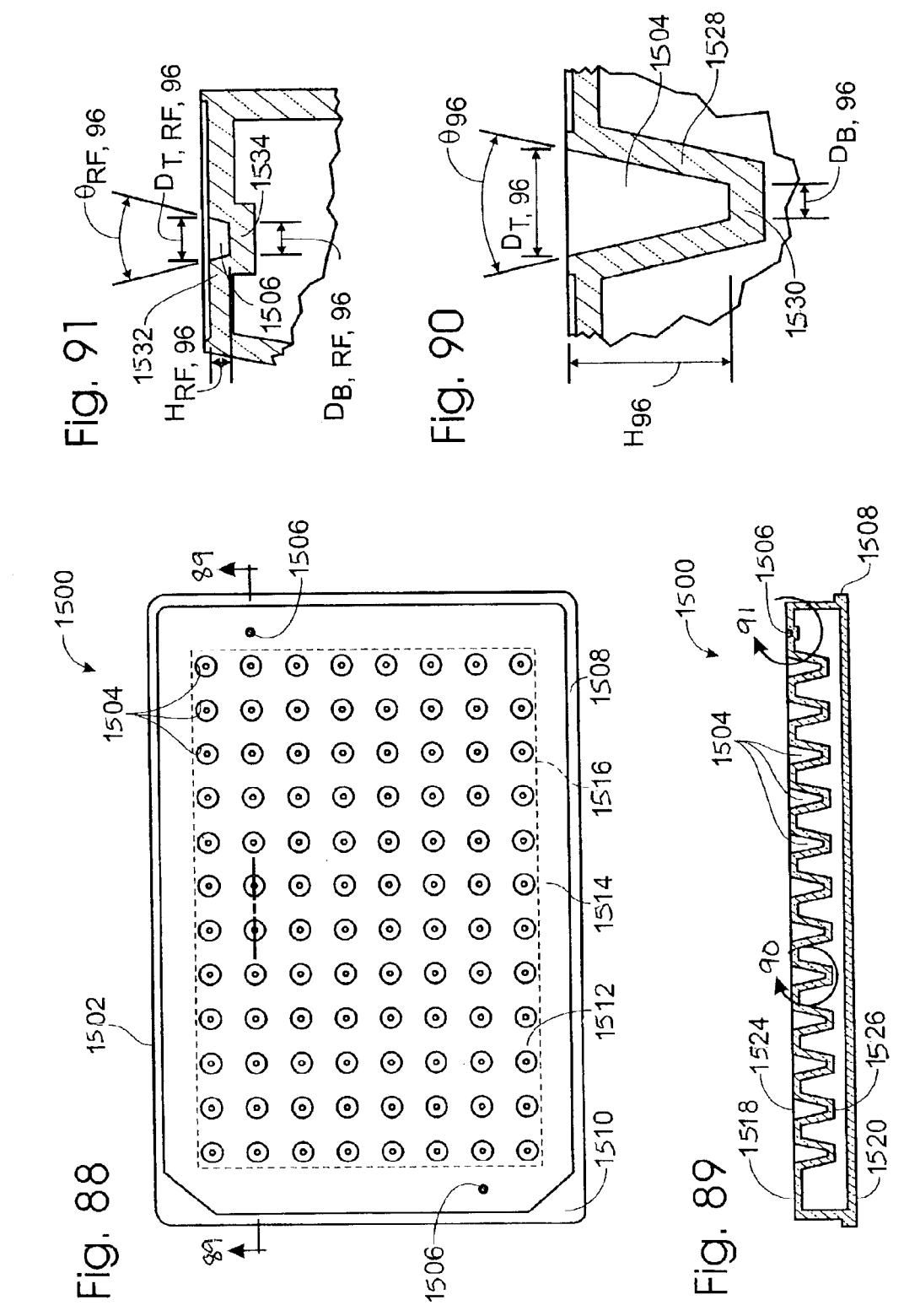

FIG. 88 is a top view of a 96-well microplate 1500 constructed in accordance with aspects of the invention. Microplate 1500 includes a frame 1502 and a plurality of sample wells 1504 disposed in the frame. In some embodiments, microplate 1500 may include one or more reference fiducials 1506 disposed in the frame.

Frame 1502 is the main structural component of microplate 1500. The frame may have various shapes and various dimensions. In microplate 1500, frame 1502 is substantially rectangular, with a major dimension X of about 127.8 mm and a minor dimension Y of about 85.5 mm. Tolerances in plate dimensions typically are about ±0.5–1.0 mm for polystyrene plates, but may increase to about ±2 mm for polypropylene plates, especially if the polypropylene plates are produced using molds designed for polystyrene plates. Frame 1502 may be adapted for ease of use and manufacture. For example, frame 1502 may include a base 1508 to facilitate handling and/or stacking, and frame 1502 may include notches 1510 to facilitate receiving a protective lid. Frame 1502 may be constructed of a material, such as a thermoplastic, that is sturdy enough for repeated, rugged use and yet minimally photoluminescent to reduce background upon illumination.

Frame 1502 includes a sample well region 1512 and an edge region 1514 forming a perimeter 1516 around the sample well region. Sample wells may be disposed in the sample well region in various configurations. In microplate 1500, sample wells 1504 are disposed in sample well region 1512 in a substantially rectangular 8×12 array, with a pitch (i.e., center-to-center interwell spacing) along both X and Y of about 9 mm. This pitch corresponds to a density of wells of about one well per 81 mm$^2$.

Reference fiducials 1506 may be used for identification, alignment, and/or calibration of the microplate. Reference fiducials may be disposed in the sample well region and/or the edge region in various configurations. In microplate 1500, reference fiducials 1506 are disposed in edge region 1514, substantially aligned with a row of sample wells along the X dimension, although reference fiducials also may be offset from the rows of sample wells. Reference fiducials preferentially are positioned in corners of the microplate, near where optical analysis begins, so that they may quickly be identified and analyzed. Reference fiducials may be positioned in rotationally symmetric positions, so that microplates may be loaded into an optical device and analyzed backwards without difficulty. Alternatively, reference fiducials may be positioned in rotationally asymmetric positions, so that the system can ascertain which way the microplate is oriented; information on orientation is useful because samples typically are not positioned symmetrically within the microplate. Further aspects of reference fiducials are described in the following U.S. patent applications, which are incorporated herein by reference in their entirety for all purposes: Ser. No. 09/156,318, filed Sep. 18, 1998, now U.S. Pat. No. 6,258,326; and Ser. No. 09/478,819, filed Jan. 5, 2000.

FIG. 89 is a cross-sectional view of microplate 1500, showing sample wells 1504, reference fiducial 1506, and base 1508. In microplate 1500, frame 1502 has a top 1518, a substantially parallel bottom 1520, and substantially perpendicular sides 1522. Top 1518 may have various shapes, although it typically is flat. (Top 1518 may be surrounded by a raised edge to facilitate stacking.) Frame 1502 has a height H of about 12 mm, corresponding generally to the separation between top 1518 and bottom 1520. Tolerances in plate height typically are about 0.5 mm or less. Sample wells 1504 are disposed with open, optically transparent ends 1524 directed toward top 1518, and closed, optically opaque ends 1526 directed toward bottom 1520. In some embodiments, optically opaque ends 1526 may be replaced by optically transparent ends to permit bottom illumination and/or detection. Reference fiducial 1506 is disposed on top 1518, although reference fiducials also may be disposed on bottom 1520 and/or sides 1522.

The preferred plate height is determined by a variety of considerations. Generally, taller plates with elevated bottoms and/or filled wells put the samples closer to the detector for analysis, increasing numerical aperture and hence signal. Conversely, shorter plates allow more plates to be stacked into processing bins for longer periods of unattended operation. The specified height of about 12 mm generally is large enough to facilitate handling by sample handlers and/or a stage, and yet small enough to permit optical analysis of the entire well. Moreover, the specified height generally is sufficient to ensure that the microplates are sufficiently flat for analysis.

FIG. 90 is a first enlarged portion of the cross-sectional view in FIG. 89, showing details of sample wells 1504. Sample wells may have various shapes and various dimensions, as described in detail in subsequent sections. In microplate 1500, sample wells 1504 are substantially frusto-conical, with substantially straight side walls 1528 and a substantially flat bottom wall 1530. In microplate 1500, optically opaque ends 1526 are positioned about 6.7 mm below top 1518, and about 5.3 mm above bottom 1520. Sample well 1504 is characterized by a top diameter $D_{T,96}$, a bottom diameter $D_{B,96}$, a height $H_{96}$, and a cone angle $\theta_{96}$. Here, $\theta_{96}$ is the included angle between side walls 1528. In microplate 1500, $D_{T,96}$ is about 4.5 mm, $D_{B,96}$ is about 1.5 mm, $H_{96}$ is about 6.7 mm, and $\theta_{96}$ is about 25.4°. Sample well 1504 has a total volume of about 50 µL, and a smallest practical working volume of about 1–40 µL.

FIG. 91 is a second enlarged portion of the cross-sectional view in FIG. 89, showing details of reference fiducial 1506. Reference fiducials may have various shapes and various dimensions, as described in detail in subsequent sections. In microplate 1500, reference fiducial 1506 is substantially frusto-conical, with substantially straight side walls 1532 and a substantially flat bottom wall 1534. Reference fiducial 1506 is characterized by a top diameter $D_{T,RF,96}$, a bottom diameter $D_{B,RF,96}$, a height $H_{RF,96}$, and a cone angle $\theta_{RF,96}$. Here, $D_{B,RF,96}$ and $\theta_{RF,96}$ are substantially equal to $D_{B,96}$ and $\theta_{96}$, the corresponding values for sample well 1504. $H_{96}$ is about 1 mm, and $D_{T,RF,96}$ is specified by the other parameters. In some applications, the reference fiducial may contain a luminescent material or solution so that it is easier to locate. In other applications, the reference fiducial may be used as a blank for determining background, or as an additional sample well for holding an additional sample. In these applications, the reference fiducial may be located and/or analyzed using the same optical system used to analyze samples in conventional sample wells.

2. 384-Well Microplates

FIGS. 92–95 are views of a 384-well microplate 1600 constructed in accordance with aspects of the invention. Microplate 1600 is similar in many respects to microplate 1500 and includes a frame 1602 and a plurality of sample wells 1604 disposed in a sample well region 1612 of the frame. In some embodiments, microplate 1600 may include one or more reference fiducials 1606 disposed in an edge region 1614 or other region of the frame.

The external dimensions of microplate 1600 are similar to the external dimensions of microplate 1500. However, the density of sample wells in microplate 1600 is four times higher than the density of sample wells in microplate 1500. Consequently, the pitch (i.e., the center-to-center interwell spacing) in microplate 1600 is about 4.5 mm, or about one-half the pitch in microplate 1500. This pitch corresponds to a density of wells of about four wells per 81 mm². In microplate 1600, reference fiducial 1606 is positioned about midway between two rows of sample wells along the X direction; in contrast, in microplate 1500, reference fiducial 1506 is positioned about in line with a row of sample wells along the X direction. This is because the reference fiducials are positioned in approximately the same position in each microplate, but the center line of one row of sample wells in microplate 1500 because the center line between two rows of sample wells in microplate 1600 as the density of wells is quadrupled.

Sample wells 1604 in microplate 1600 are similar to sample wells 1504 in microplate 1500. Sample wells 1604 may be characterized by a top diameter $D_{T,384}$, a bottom diameter $D_{B,384}$, a height $H_{384}$, and a cone angle $\theta_{384}$. The preferred values of $D_{B,384}$ and $\theta_{384}$ for microplate 1600 are substantially similar to the preferred values of $D_{B,96}$ and $\theta_{96}$ for microplate 1500. However, the preferred value for $D_{T,384}$, which is about 4.7 mm, is smaller than the preferred value for $D_{T,384}$, which is about 6.7 mm. In microplate 1600, the upper diameter must be smaller than the upper diameter of the sample wells in microplate 1500, because the sample wells are close packed, leaving no more interwell spacing than necessary for moldability. In turn, the preferred value for $H_{384}$ is about 4.7 mm, so that the wells are elevated by about 7.3 mm. Sample well 1604 has a total volume of about 25 µL, and a smallest practical working volume of about 1–12 µL.

Reference fiducial 1606 in microplate 1600 may be essentially identical to reference fiducial 1506 in microplate 1500.

3. 1536-Well Microplates

FIGS. 96–100 are views of a 1536-well microplate 1650 constructed in accordance with aspects of the invention. Microplate 1650 is similar in many respects to microplates 1500 and 1600, and includes a frame 1652 and a plurality of sample wells 1654 disposed in the frame. The pitch in microplate 1650 is about 2.25 mm, or about one-half the pitch in microplate 1600 and about one-fourth the pitch in microplate 1500. This pitch corresponds to a density of wells of about sixteen wells per 81 mm².

Sample wells 1654 may be exclusively frusto-conical, like sample wells 1504 in microplate 1500 and sample wells 1604 in microplate 1600. However, due to spatial constraints, the volume of such wells would have to be small, about 1–2 µL. Smaller wells are easier to mold and keep within tolerances, but they provide less flexibility and place more stringent demands on fluid dispensing and analytical equipment. Alternatively, sample wells 1654 may have a frusto-conical lower portion 1606 coupled to a cylindrical upper portion 1608. The volume of such wells may be larger, for example, about 7–8 µL. Larger wells are more difficult to mold, but they permit use of a wider range of sample volumes and therefor a wider range of assay formats. Larger sample volumes may be useful if the microplate is used in conjunction with standard fluid dispensing equipment, because the standard equipment may have difficulty dispensing small volumes. Larger sample volumes also may be useful if reagents are to be added to the well from stock solutions, such as 100× DMSO or DMF stock solutions, because they make it less necessary to dispense very tiny amounts of stock solution to obtain adequate dilution. Larger sample volumes also may be useful for cell-based assays, because cells may live longer in a larger volume of medium.

Reference fiducials in microplate 1650 may be essentially identical to reference fiducials 1506 in microplate 1500 and reference fiducials 1606 in microplate 1600. However, reference fiducials in microplate 1650 may be more important than reference fiducials in plates 1500 and 1600 because the well dimensions in microplate 1650 may approach the molding tolerances, making it more likely that wells will be significantly displaced from their nominal positions.

4. Miscellaneous Microplates

The system and its components also may be designed for use with some or all of the following microplates:

(a) A microplate having a frame portion and a top portion, where an array of wells is formed in the top portion. The wells are organized in a density of at least about 4 wells per 81 mm². Each well has a bottom wall that is elevated at least about 7 millimeters above a plane defined by a bottom edge of the frame.

(b) A microplate having an array of conical wells organized in a density of at least about 4 wells per 81 mm².

(c) A microplate having an array of conical wells, where each well has a maximum volume capacity of less than about 55 microliters. A preferred small-volume well design has a volume capacity of 1–20 microliters.

(d) A microplate having an array of wells in the top portion, where each well has a maximum volume capacity of less than about 55 microliters and a well bottom that is elevated at least about 7 millimeters above a plane defined by a bottom edge of the frame.

(e) A microplate having an array of wells in a top portion, organized in a density of at least about 4 wells per 81 mm², where each well has a conical portion characterized by a cone angle of at least about 8°.

(f) A microplate having an array of conical wells characterized by a cone angle θ, where θ=2arcsin (NA/n) and NA is equal to or greater than about 0.07.

(g) A microplate having an array of wells organized in a density of at least about 16 wells per 81 mm², where each well has a frusto-conical bottom portion and a substantially cylindrical upper portion.

(h) A microplate comprising a frame and a plurality of frusto-conical sample wells disposed in the frame, where the sample wells are characterized by a cone angle of at least about 8°. The microplate further may include a reference fiducial that provides information to facilitate sample analysis.

(i) A microplate having 864 sample wells, 3456 sample wells, or 9600 sample wells.

(j) A microplate formed of black, white, or clear material, or a combination thereof.

(k) A microplate suitable for performing PCR.

E. Exemplary Microplates

Selected aspects of the invention also may be described as recited in the following numbered paragraphs:

1. A system for detecting light transmitted from a sensed volume, the system comprising (A) an optical device capable of detecting light substantially exclusively from a sensed volume; and (B) a sample holder configured to support a sample so that the shape of the sample substantially conforms to a conical portion of the sensed volume.

2. The system of paragraph 1, wherein the sample holder has a frusto-conical shape.

3. The system of paragraph 1, further comprising at least a second sample holder, wherein the sample holders are disposed in a microplate.

4. The system of paragraph 1, wherein the sensed volume has a waist.

5. The system of paragraph 1, wherein the sensed volume has an hourglass shape, and wherein the sample holder has a conical shape configured to conform to substantially one-half of the hourglass shape.

6. The system of paragraph 1, wherein the sensed volume has an hourglass shape, and wherein the sample holder has a frusto-conical shape configured to conform to substantially one-half of the hourglass shape.

7. The system of paragraph 6, wherein the conical portion of the frusto-conical shape is characterized by a cone angle of at least about 8°.

8. The system of paragraph 6, wherein the conical portion of the frusto-conical sample holder is characterized by a cone angle of about 25°.

9. The system of paragraph 1, wherein the sensed volume has an hourglass shape, and wherein the sample holder has a cylindrical shape configured to correspond to substantially all of the hourglass shape.

10. The system of paragraph 1, wherein the optical device includes (A) an examination site; (B) a light source positioned to deliver light to the examination site; (C) a detector positioned to receive light transmitted from the examination site; and (D) an optical relay structure capable of transmitting light substantially exclusively from a sensed volume of a sample positioned at the examination site to the detector.

11. The system of paragraph 1, wherein the optical device includes (A) an examination site; (B) a light source positioned to deliver light to the examination site; (C) a detector positioned to receive light transmitted from the examination site; and (D) an optical relay structure capable of delivering light from the light source substantially exclusively to a sensed volume of a sample positioned at the examination site.

12. The system of paragraph 11, wherein the optical relay structure also is capable of transmitting light to the detector substantially exclusively from a sensed volume of a sample positioned at the examination site.

13. The system of paragraph 1, wherein the optical device includes a low-luminescence fused-silica fiber optic cable.

14. The system of paragraph 1, the optical device characterized by a numerical aperture, wherein the sensed volume is determined in part by the numerical aperture.

15. The system of paragraph 1, the optical device including a confocal optics element, wherein the sensed volume is determined in part by the confocal optics element.

16. The system of paragraph 1, wherein the sample holder includes a reference fiducial configured to provide information that facilitates the luminescence assay.

17. The system of paragraph 1, wherein the sample holder also is configured to reduce the formation and trapping of bubbles as the sample well is filled with a fluid sample.

18. A system for detecting light transmitted from a sample, the system comprising (A) an optical device configured to detect light originating substantially exclusively within a maximum cone; and (B) a sample holder for supporting the sample that includes a conical portion having a shape that substantially conforms to the shape of at least a portion of the maximum cone.

19. The system of paragraph 18, wherein the conical portion has a shape that substantially conforms to the shape of at least a portion of the maximum cone when the cone angle of the conical portion is within 10° of the cone angle of the maximum cone.

20. The system of paragraph 18, the maximum cone having a cone angle θ, wherein θ is given by the formula θ=2arcsin(NA/n), where "NA" is the numerical aperture of the optical device, and "n" is the index of refraction of the medium adjacent the optical device.

21. The system of paragraph 20, wherein the numerical aperture lies in a range from about 0.07 to about 0.5.

22. The system of paragraph 21, wherein the index of refraction lies in a range from about 1.0 to about 1.25.

23. The system of paragraph 18, the maximum cone having a cone angle θ, the optical device having an objective lens and a focal plane, wherein θ is the angle subtended at the focal plane by the objective lens.

24. The system of paragraph 18, the maximum cone having a cone angle θ, the optical device having an optical axis, wherein θ is twice the angle made by a marginal ray relative to the optical axis.

25. The system of paragraph 18, the conical portion having a cone axis, wherein the sample holder also includes a planar portion having an orientation substantially perpendicular to the cone axis.

26. The system of paragraph 25, the planar portion characterized by a planar portion diameter, the optical device having a confocal aperture characterized by an aperture diameter, wherein the planar portion diameter is approximately equal to the aperture diameter.

27. The system of paragraph 18, wherein the maximum cone is characterized by a cone angle equal to or greater than about 8°.

28. A method of improving signal detection in luminescence assays, the method comprising (A) selecting an optical device capable of detecting light substantially exclusively from a sensed volume having a conical portion; (B) selecting a sample holder having a shape configured to conform to the shape of the conical portion of the sensed volume; and (C) performing a luminescence assay using the optical device and the sample holder.

29. The method of paragraph 28, further comprising aligning the sensed volume with the sample holder.

30. The method of paragraph 28, wherein the sample holder is a sample well in a microplate.

31. The method of paragraph 28, wherein the sample holder includes a reference fiducial configured to provide information that facilitates the luminescence assay.

32. A microplate for holding a plurality of samples, the microplate comprising (A) a frame; and (B) a plurality of frusto-conical sample wells disposed in the frame, each well having a cone angle of at least about 8°, and a maximum volume capacity of less than about 55 microliters.

33. The microplate of paragraph 32, wherein the cone angle of the frusto-conical sample wells is about 25°.

34. The microplate of paragraph 33, each sample well having a top and a bottom, wherein the diameter of the bottom of each sample well is about 1.5 millimeters.

35. The microplate of paragraph 33, further comprising at least one reference fiducial that is not a sample well disposed in the frame, each reference fiducial configured to provide information that facilitates analysis of the samples.

36. The microplate of paragraph 32, wherein each sample well is configured to reduce the formation and trapping of bubbles as the sample well is filled with a fluid sample.

37. A microplate comprising (A) a frame portion, (B) a top portion contained within the frame portion, and (C) an array of conically-shaped wells in the top portion, each well having a maximum volume capacity of less than about 55 microliters.

38. The microplate of paragraph 37, further comprising at least one reference fiducial that is not a sample well disposed in the frame.

39. The microplate of paragraph 37, wherein each well has a frusto-conical shape.

40. The microplate of paragraph 37, wherein each well has a cone angle of at least about 8°.

41. The microplate of paragraph 37, wherein each well has a bottom wall that is elevated by at least about 7 millimeters relative to a plane defined by a bottom edge of the frame.

42. The microplate of paragraph 37, wherein each well has a reagent bound to an interior wall, the reagent being selected from the group including polypeptides, polynucleotides, and luminescent compounds.

43. The microplate of paragraph 37, wherein the wells are organized in a density of at least about 1 well per 81 $mm^2$.

44. The microplate of paragraph 37, wherein the wells are organized in a density of at least about 4 wells per 81 $mm^2$.

45. A microplate comprising (A) a top portion defining an array of wells for containing samples to be optically analyzed, each well having a maximum volume capacity of less than about 55 microliters; and (B) a frame having a bottom edge and a height of approximately 12 to 16 millimeters.

46. The microplate of paragraph 45, wherein each well has a bottom wall that is at least about 7 millimeters above a plane defined by the bottom edge of the frame.

47. The microplate of paragraph 45, wherein the wells are organized in a density of at least about 4 wells per 81 $mm^2$.

48. The microplate of paragraph 45, wherein each well has a conical shape.

49. The microplate of paragraph 48, wherein each well has a frusto-conical shape.

50. The microplate of paragraph 45, wherein each well has a depth of between about 1.5 to 7.1 millimeters.

51. The microplate of paragraph 45, wherein the frame has a height of approximately 12 millimeters.

52. A microplate comprising (A) a top portion defining an array of wells for containing samples to be optically analyzed, each well having a bottom wall and a maximum volume capacity of less than about 55 microliters; and (B) an elevation structure that positions the bottom walls of the wells at least about 7 millimeters above a flat surface at an optical examination site when samples in the wells are being analyzed.

53. The microplate of paragraph 52, wherein the wells are organized in a density of at least about 4 wells per 81 $mm^2$.

54. The microplate of paragraph 52, wherein the elevation structure includes a frame having a height of approximately 12 millimeters.

55. A plate for holding a plurality of samples so that light emitted by the samples can be detected by an optical detector positioned above the plate, the plate comprising (A) a frame having a bottom edge that defines a plane; and (B) a plurality of wells, for holding the samples, disposed in the frame, each well having a well bottom that is elevated substantially above the plane, so that small-volume samples are moved closer to the detector.

56. The plate of paragraph 55, wherein each well bottom is elevated at least about 7 millimeters above the plane.

57. The plate of paragraph 55, wherein each well has a maximum volume capacity of less than about 55 milliliters.

58. The plate of paragraph 55, the frame having a base that facilitates stacking the plate on top of another plate, wherein each well bottom is elevated substantially above the base.

59. The plate of paragraph 55, wherein the plate is a microplate.

60. The plate of paragraph 55, wherein the plate is compatible with standard microplate handling equipment.

61. The plate of paragraph 55, wherein the samples are fluids, and wherein the well bottoms are impervious to fluids.

62. A plate for holding a plurality of samples so that light emitted by the samples can be detected by an optical detector, the plate comprising (A) a frame having a bottom edge that defines a plane; and (B) a plurality of small-volume wells for holding the samples, disposed in the frame, each well having a maximum volume capacity of less than about 55 microliters, and a well bottom that is elevated substantially above the plane, so that the distance from the small-volume well to the optical detector approximates the distance from an upper portion of a large-volume well to the optical detector, wherein the large-volume well has a maximum volume capacity of at least about 200 microliters, and is formed in a standard microplate.

63. The plate of paragraph 62, each sample forming a meniscus in a portion of the sample closest to the optical detector, wherein the distance from the meniscus of a small-volume sample in the small-volume well to the optical detector is substantially the same as the distance from the meniscus of a large-volume sample in a standard-microplate well to the optical detector.

64. The plate of paragraph 62, wherein the dimension of the small-volume well along a direction perpendicular to the plane is less than about 7 millimeters, and wherein the dimension of the standard-microplate well along a corresponding direction is about 12 millimeters.

65. The plate of paragraph 64, wherein the dimension of the small-volume well along a direction perpendicular to the plane is between 3 and 5 millimeters.

66. The plate of paragraph 62, the plate extending a first height above the plane, wherein the first height is sufficient to accommodate a large volume well.

67. The plate of paragraph 66, wherein the first height is about 12 millimeters.

68. A method of using an optical detector to detect light emitted by a small-volume sample of between about 5 to 55 microliters, the method comprising (A) providing an optical detector configured to detect light emitted by a large-volume sample of at least about 100 microliters in a standard microplate; (B) providing at least one small-volume sample, the small-volume sample being held in an alternate plate that includes a frame and a plurality of wells disposed in the frame, the wells being elevated by the frame configured to position small-volume samples closer to the optical detector than would the standard microplate; and (C) detecting the light emitted by the sample using the optical detector.

69. The method of paragraph 68, the frame having a bottom edge that defines a plane, each well having a well bottom that is elevated substantially above the plane.

70. The method of paragraph 68, each well having a volume of less than about 55 microliters.

71. A microplate comprising (A) a frame portion, (B) a top portion contained within the frame portion, (C) an array of wells in the top portion, each well having a maximum volume capacity of less than about 55 microliters, and a well bottom that is elevated at least about 7 millimeters above a plane defined by a bottom edge of the frame.

72. The microplate of paragraph 71, further comprising at least one reference fiducial that is not a sample well disposed in the frame.

73. The microplate of paragraph 71, wherein each well has a conical shape.

74. The microplate of paragraph 73, wherein each well has a frusto-conical shape.

75. The microplate of paragraph 73, wherein each well has a cone angle of at least about 8°.

76. The microplate of paragraph 71, wherein each well has a substantially flat bottom.

77. The microplate of paragraph 71, wherein each well has a circular cross-section.

78. The microplate of paragraph 71, wherein the frame portion has a ledge to facilitate stacking.

79. The microplate of paragraph 71, wherein each well has a maximum volume capacity of 25 microliters or less.

80. The microplate of paragraph 71, wherein each well has a reagent bound to an interior wall, the reagent being selected from the group including polypeptides, polynucleotides, and luminescent compounds.

81. A microplate comprising (A) a frame portion, (B) a top portion contained within the frame portion, and (C) an array of conical wells in the top portion, wherein the top portion has a density of wells of at least about 4 wells per 81 mm$^2$.

82. The microplate of paragraph 81, further comprising at least one reference fiducial that is not a sample well disposed in the frame.

83. The microplate of paragraph 81, wherein each well has a frusto-conical shape.

84. The microplate of paragraph 81, wherein each well has a cone angle of at least about 8°.

85. The microplate of paragraph 81, wherein each well has a substantially flat bottom.

86. The microplate of paragraph 81, wherein each well has a bottom wall that is elevated by at least about 7 millimeters relative to a plane defined by a bottom edge of the frame.

87. The microplate of paragraph 81, wherein the frame portion has a ledge to facilitate stacking of microplates.

88. The microplate of paragraph 81, wherein each well has a reagent bound to an interior wall, wherein the reagent is selected from the group including polypeptides, polynucleotides, and luminescent compounds.

89. The microplate of paragraph 81, wherein each well has a maximum volume capacity of less than about 55 microliters.

90. A microplate comprising (A) a frame portion, (B) a top portion contained within the frame portion, and (C) an array of wells in the top portion organized in a density of at least about 4 wells per 81 mm$^2$, wherein each well has a conical portion characterized by a cone angle of at least about 8°.

91. The microplate of paragraph 90, further comprising at least one reference fiducial that is not a sample well disposed in the frame.

92. The microplate of paragraph 90, wherein the wells are organized in a density of at least about 16 wells per 81 mm$^2$.

93. The microplate of paragraph 90, wherein each well has a frusto-conical shape.

94. The microplate of paragraph 90, wherein each well has a cone angle of approximately 25°.

95. The microplate of paragraph 90, wherein each well has a bottom wall that is elevated by at least about 7 millimeters above a plane defined by a bottom edge of the frame.

96. The microplate of paragraph 90, wherein each well has a reagent bound to an interior wall, the reagent being selected from the group including polypeptides, polynucleotides, and luminescent compounds.

97. The microplate of paragraph 90, wherein each well also has a substantially cylindrical portion above the conical portion.

98. The microplate of paragraph 97, wherein the wells are organized in a density of at least about 16 wells per 81 mm$^2$.

99. A microplate comprising (A) a frame portion, (B) a top portion contained within the frame portion, and (C) an array of wells in the top portion, wherein the top portion has a density of wells of at least about 4 wells per 81 mm$^2$, and each well has a bottom wall that is elevated at least about 7 millimeters above a plane defined by a bottom edge of the frame.

100. The microplate of paragraph 99, further comprising at least one reference fiducial that is not a sample well disposed in the frame.

101. The microplate of paragraph 99, wherein each well has a conical shape.

102. The microplate of paragraph 99, wherein each well has a frusto-conical shape.

103. The microplate of paragraph 99, wherein each well has a cone angle of at least about 8°.

104. The microplate of paragraph 99, wherein each well has a substantially flat bottom.

105. The microplate of paragraph 99, wherein each well has a circular cross-section 106. The microplate of paragraph 99, wherein the frame portion has a ledge to facilitate stacking.

107. The microplate of paragraph 99, wherein each well has a reagent bound to an interior wall, the reagent being selected from the group including polypeptides, polynucleotides, and luminescent compounds.

108. The microplate of paragraph 99, wherein each well has a maximum volume capacity of less than about 55 microliters.

109. A plate for holding a plurality of samples, the plate comprising (A) a frame having a base that facilitates stacking the plate on top of another plate; and (B) a plurality of wells, for holding the samples, disposed in the frame, each well having a well bottom that is elevated substantially above the base.

110. The plate of paragraph 109, the frame also having an upper portion, wherein the cross-sectional area of the base is greater than the cross-sectional area of the upper portion, so that the base of a first plate can fit over the upper portion of a second plate when the first plate is stacked on top of the second plate.

111. The plate of paragraph 110, wherein the base includes a stop element that limits how far the bottom of the first plate fits over the upper portion of the second plate when the first plate is stacked on top of the second plate.

112. The plate of paragraph 109, the frame also having an upper portion, wherein the base includes a stop element that determines the relative positions of the well bottoms of a first plate and the upper portion of a second plate when the first plate is stacked on top of the second plate.

113. The plate of paragraph 112, the frame also having a bottom edge, the bottom edge defining a plane, wherein the stop element includes a ledge oriented substantially parallel to the plane, and wherein the ledge contacts the upper portion of the second plate to determine the relative positions of the well bottoms of the first plate and the upper portion of the second plate when the first plate is stacked on top of the second plate.

114. The plate of paragraph 112, wherein the well bottoms of the first plate are elevated substantially above the upper portion of the second plate when the first plate is stacked on top of the second plate.

115. The plate of paragraph 109, wherein the plate is a microplate.

116. The plate of paragraph 109, wherein the plate is compatible with standard microplate handling equipment.

117. The plate of paragraph 109, wherein the samples are fluids, and wherein the well bottoms are impervious to fluids.

118. A microplate for holding a plurality of samples, the microplate comprising (A) a frame; and (B) a plurality of sample wells disposed in the frame, each sample well configured to reduce the formation and trapping of bubbles as the sample well is filled with a fluid sample.

119. The microplate of paragraph 118, wherein the sample well is configured to reduce the formation and trapping of bubbles through the choice of sample well coating.

120. The microplate of paragraph 118, wherein the sample well is configured to reduce the formation and trapping of bubbles through the geometry of the sample well.

121. The microplate of paragraph 118, wherein each sample well also is configured to support a sample so that the shape of the sample substantially conforms to the shape of at least a conical portion of a sensed volume.

XIX. Luminescence Polarization System

This section describes systems, including apparatus and methods, for performing luminescence polarization assays, particularly using a light source with a high photon flux light source such as a continuous high color temperature light source. These and other aspects of the invention are described below, including (A) background, (B) summary, (C) representative assays, and (D) examples. This disclosure is supplemented by the patents, patent applications, and publications identified above under Cross-References, particularly U.S. Provisional Patent Application Ser. No. 60/063,811, filed Oct. 31, 1997; and U.S. patent application Ser. No. 09/349,733, filed Jul. 8, 1999. These supplementary materials are incorporated herein by reference in their entirety for all purposes.

A. Background

Luminescence polarization assays have been conducted using various light sources. In academic research laboratories, light sources for luminescence polarization assays have included lasers and arc lamps (e.g., xenon arc lamps). Unfortunately, these light sources suffer from a number of shortcomings. The gas in xenon arc lamps is under high pressure (about 10 atmospheres), so that explosion is always a danger. The power supplies for lasers and xenon arc lamps operate at very high currents (about 25 amps) and voltages (about 20,000 to 40,000 volts), so that electrocution and other health hazards are always a danger. In particular, the power supplies for arc lamps produce ozone and may deliver a lethal shock when the lamps are started. The power supplies also may produce transients that can damage other electronic components of the system. The light emitted by lasers and xenon arc lamps is very intense, so that eye damage is always a danger. In particular, the extreme brightness may damage the retina, and ultraviolet light emitted by xenon arc lamps and some lasers may damage the cornea. The spectral output of lasers and some (e.g., mercury) arc lamps is very limited, so that desired excitation wavelengths may not be available. The lifetime of arc lamps may be very short, typically around 300 hours, so that the lamp must be changed frequently, further exposing the operator to dangers posed by the lamp and power supply.

These shortcomings assume even greater significance outside the research laboratory. For example, in high-throughput screening applications, the light source may be used nearly continuously, so that the dangers posed by lasers and arc lamps are ever present. The light source also may be used by relatively unskilled operators, who may be unfamiliar with or unreceptive to safety issues.

In high-throughput screening laboratories, light sources for luminescence polarization assays have included incandescent (e.g., tungsten) lamps and flash lamps. Incandescent lamps are relatively common and inexpensive, and include lamps from overhead projectors. Incandescent lamps put out broad-spectrum light, so that they may be used with a variety of luminescent compounds. Flash lamps are more exotic, but provide some advantages over incandescent lamps. In particular, flash lamps may be used for both time-resolved and steady-state measurements. This flexibility allows the same light source to be used in instruments that perform multiple assays, such as steady-state and time-resolved luminescence polarization assays. Moreover, flash lamps may have long lifetimes, as long as 10,000 hours.

B. Summary

The invention provides systems, including highly sensitive apparatus and methods, for measuring polarized light emitted from compositions. The apparatus may include a light source, detector, and stage, where the stage is configured to support a container such as a microplate at an examination site. An excitation optical relay structure may direct light from the light source through an excitation polarizer toward a composition in the container at the examination site. An emission optical relay structure may transmit light emitted from the composition through an emission polarizer toward a detector. The components of the apparatus may be selected and configured so that photon noise is reduced or minimized relative to the magnitude of light emitted from small concentrations of luminophore at the examination site. In a preferred embodiment, the light source is a continuous high color temperature lamp, such as a xenon arc lamp. The light source also may be a laser or a light-emitting diode. The functional elements of the apparatus may be contained in one or more rigid housings that are configured to minimize potential hazards associated with high temperature lamps.

C. Representative Assays

The systems provided by the invention may be used for any suitable polarization measurement and/or assay, including but not limited to (1) binding assays, (2) protease assays, (3) kinase assays, (4) phosphatase assays, (5) cyclase assays, (6) phosphodiesterase assays, (7) nucleotide hybridization assays, and (8) nucleotide polymorphism assays, among others. These and other assays are described in detail in the following U.S. patent applications, which are incorporated herein by reference in their entirety for all purposes: Ser. No. 09/349,733, filed Jul. 8, 1999; Ser. No. 09/768,742, filed Jan. 23, 2001; Ser. No. 09/767,316, filed Jan. 22, 2001; Ser. No. 09/770,720, filed Jan. 25, 2001; Ser. No. 09/770,724, filed Jan. 25, 2001; Ser. No. PCT/US/16012, filed Jun. 9, 2000; Ser. No. 09/813,107, filed Mar. 19, 2001; Ser. No. 09/596,444, filed Jun. 19, 2000; and Ser. No. 09/844,655, filed Apr. 27, 2001.

D. Examples

Selected aspects of the invention also may be described as recited in the following numbered paragraphs:

1. An apparatus for measuring the polarization of light emitted from a composition, the apparatus comprising (A) a stage configured to hold a microplate having an array of sample wells; (B) a continuous high color temperature light source; (C) an excitation optical relay structure having an excitation polarizer, wherein the excitation optical relay structure directs light from the light source through the excitation polarizer toward a composition contained in at least one of the sample wells; (D) a detector; and (E) an emission optical relay structure having an emission polarizer, wherein the emission optical relay structure directs light emitted from the composition through the emission polarizer toward the detector.

2. The apparatus of paragraph 1, wherein the continuous high color temperature light source has a color temperature of at least about 3500 Kelvin.

3. The apparatus of paragraph 1, wherein the continuous high color temperature light source is a xenon arc lamp.

4. The apparatus of paragraph 1 further comprising a housing that surrounds at least a portion of the light source.

5. The apparatus of paragraph 1 further comprising a processor that determines polarization or anisotropy based on light intensity sensed by the detector.

6. The apparatus of paragraph 1, wherein the emission optical relay structure directs phosphorescent or fluorescent light emitted from the composition.

7. The apparatus of paragraph 1 further comprising a microplate having a plurality of wells organized in a density of at least about 4 wells per 81 mm$^2$.

8. The apparatus of paragraph 7, wherein each of at least some of the wells have a conical shape.

9. The apparatus of paragraph 7, wherein each of at least some of the wells have a cone angle of at least about 8°.

10. The apparatus of paragraph 7, wherein each of at least some of the wells have a maximum volume capacity of 55 microliters or less.

11. The apparatus of paragraph 7, wherein each of at least some of the wells have a maximum volume capacity of 25 microliters or less.

12. The apparatus of paragraph 7, wherein the wells are organized in a density of at least about 16 wells per 81 mm$^2$.

13. The apparatus of paragraph 1 further comprising a Z-height adjustment mechanism that automatically controls the height of a sensed volume in the composition so that signal-to-noise is maximized.

14. The apparatus of paragraph 1 further comprising a chopper device positioned to intermittently interrupt transmission of light from the source.

15. The apparatus of paragraph 1, wherein the apparatus is configured to perform luminescence polarization assays and at least one of the following additional assays: luminescence intensity, chemiluminescence, photoluminescence lifetime, absorbance, luminescence resonance energy transfer, and luminescence imaging.

16. The apparatus of paragraph 15, wherein the excitation polarizer and the emission polarizer are crossed to reduce background from immobilized species in the additional assays.

17. The apparatus of paragraph 1, wherein adjacent the composition light directed toward the detector by the emission optical relay structure travels anti-parallel to light directed toward the composition by the excitation optical relay structure.

18. The apparatus of paragraph 1, wherein the apparatus is capable of detecting light transmitted substantially exclusively from a sensed volume of the composition.

19. The apparatus of paragraph 18, the composition being contained in a spatial volume lying between boundary interfaces, wherein the sensed volume is spaced substantially away from at least one of the boundary interfaces.

20. The apparatus of paragraph 1 further comprising a second light source, wherein the high color temperature light source is configured for steady-state polarization assays, and wherein the second light source is configured for time-resolved polarization assays.

21. The apparatus of paragraph 1, wherein the excitation and emission optical relay structures each include a fiber optic cable.

22. The apparatus of paragraph 1, wherein the excitation and emission optical relay structures share a dichroic beamsplitter.

23. The apparatus of paragraph 22, wherein the dichroic beamsplitter has a cutoff wavelength preselected to increase transmission of fluorescence signal and to decrease transmission of background noise.

24. The apparatus of paragraph 1 further comprising a modulator mechanism configured to vary the intensity of light incident on the composition without varying the intensity of light produced by the light source.

25. The apparatus of paragraph 1, wherein the excitation and emission optical relay structures share a multichroic beamsplitter.

26. An apparatus for measuring the polarization of light emitted from a composition, the apparatus comprising (A) a stage for supporting the composition at an examination site; (B) an automated registration device that automatically brings successive compositions and the examination site into register for successive analysis of the compositions; (C) a continuous high color temperature light source; (D) an excitation optical relay structure having an excitation polarizer, wherein the excitation optical relay structure directs light from the light source through the excitation polarizer toward the composition; (E) a detector; and (F) an emission optical relay structure having an emission polarizer, wherein the emission optical relay structure directs light emitted from the composition through the emission polarizer toward the detector.

27. The apparatus of paragraph 26 further comprising a processor that determines polarization or anisotropy based on light intensity sensed by the detector.

28. The apparatus of paragraph 26, wherein the emission optical relay structure directs phosphorescent or fluorescent light emitted from the composition.

29. The apparatus of paragraph 26 further comprising a Z-height adjustment mechanism that automatically controls the height of a sensed volume in the composition so that signal-to-noise is maximized.

30. An apparatus for measuring the polarization of light emitted from a composition, the apparatus comprising (A) a stage for supporting the composition at an examination site; (B) a continuous light source; (C) a time-varying light source; (D) an excitation optical relay structure having an excitation polarizer, wherein the excitation optical relay structure directs light through the excitation polarizer toward the composition; (E) a switching mechanism configured to interchangeably connect either the continuous light source or the time-varying light source to the optical relay structure; (F) a detector; and (G) an emission optical relay structure having an emission polarizer, wherein the emission optical relay structure directs light emitted from the composition through an emission polarizer toward the detector.

31. The apparatus of paragraph 30 further comprising a processor that determines polarization or anisotropy based on light intensity sensed by the detector.

32. The apparatus of paragraph 30, wherein the emission optical relay structure directs phosphorescent or fluorescent light emitted from the composition.

33. The apparatus of paragraph 30 further comprising a Z-height adjustment mechanism that automatically controls the height of a sensed volume in the composition so that signal-to-noise is maximized.

34. The apparatus of paragraph 30, wherein the continuous light source is used for steady-state polarization measurements, and the time-varying light source is used for time-resolved fluorescence polarization measurements.

35. The apparatus of paragraph 30, wherein the continuous light source is a continuous high color temperature light source.

36. The apparatus of paragraph 30, wherein the continuous light source is selected from the group consisting of a high color temperature light source, a laser, and a light emitting diode.

37. An apparatus for measuring the polarization of light emitted from a composition, the apparatus comprising (A) a stage configured to support a microplate having an array of sample wells; (B) a light source; (C) an excitation optical relay structure having an excitation polarizer, wherein the excitation optical relay structure directs light through the excitation polarizer toward a composition contained in at least one of the sample wells; (D) a detector; and (E) an emission optical relay structure having an emission polarizer, wherein the emission optical relay structure directs light emitted from the composition through an emission polarizer toward the detector; wherein the light source, detector, and excitation and emission optical relay structures are chosen so that the number of photons collected by the detector exceeds 10,000 in 100 milliseconds from a 100 picomolar fluorescein solution at pH 7.5.

38. The apparatus of paragraph 37 further comprising a processor that determines polarization or anisotropy based on light intensity sensed by the detector.

39. The apparatus of paragraph 37, wherein the emission optical relay structure directs phosphorescent or fluorescent light emitted from the composition.

40. The apparatus of paragraph 37 further comprising a Z-height adjustment mechanism that automatically controls the height of a sensed volume in the composition so that signal-to-noise is maximized.

41. The apparatus of paragraph 37, wherein the light source is selected from the group consisting of a high color temperature light source, a laser, and a light emitting diode.

42. The apparatus of paragraph 41, wherein the light source is a continuous high color temperature light source.

43. The apparatus of paragraph 37, wherein adjacent the composition light directed toward the detector by the emission optical relay structure travels anti-parallel to light directed toward the composition by the excitation optical relay structure.

44. The apparatus of paragraph 43, wherein the excitation and emission optical relay structures share a dichroic beamsplitter.

45. The apparatus of paragraph 43, wherein the dichroic beamsplitter has a cutoff wavelength preselected to increase transmission of fluorescence signal and to decrease transmission of background noise.

46. The apparatus of paragraph 43, wherein the excitation and emission optical relay structures share a multichroic beamsplitter.

47. The apparatus of paragraph 37, wherein the fluorescein solution has a volume less than 500 microliters.

48. The apparatus of paragraph 37, wherein the florescent solution has a volume less than 10 millimeters.

49. The apparatus of paragraph 37, the light having a cross-sectional area in the composition, wherein the area has a minimum diameter that is no larger than 2 millimeters.

50. An apparatus for measuring the polarization of light emitted from a composition, the apparatus comprising (A) a stage for supporting the composition at an examination site; (B) a light source; (C) an excitation optical relay structure for directing light from the light source through an excitation polarizer and onto the composition; (D) a detector for detecting light emitted from the composition; (E) an emission optical relay structure for directing light emitted from the composition through an emission polarizer toward the detector; and (F) means for producing, directing, and detecting light so that the number of photons collected by the detector exceeds 10,000 in 100 milliseconds from a 100 picomolar fluorescein solution at pH 7.5.

51. An apparatus for measuring the polarization of light emitted from a composition, the apparatus comprising (A) a stage configured to support a microplate having an array of sample wells; (B) a light source; (C) an excitation optical relay structure having an excitation polarizer, wherein the excitation optical relay structure directs light through the excitation polarizer toward a composition contained in at least one of the sample wells; (D) a detector; and (E) an emission optical relay structure having an emission polarizer, wherein the emission optical relay structure directs light emitted from the composition through an emission polarizer toward the detector; wherein the light source emits sufficient light in a range of 390 to 770 nm so that photon noise is less than 1 percent of a light signal emitted from a 100 picomolar fluorescein solution at pH 7.5 in one of the sample wells.

52. The apparatus of paragraph 51 further comprising a processor that determines polarization or anisotropy based on light intensity sensed by the detector.

53. The apparatus of paragraph 51, wherein the emission optical relay structure directs phosphorescent or fluorescent light emitted from the composition.

54. The apparatus of paragraph 51 further comprising a Z-height adjustment mechanism that automatically controls the height of a sensed volume in the composition so that signal-to-noise is maximized.

55. The apparatus of paragraph 51, wherein the light source has a power of at least 1 watt over the range of 390 to 770 nm.

56. The apparatus of paragraph 51, wherein the light source is a laser.

57. The apparatus of paragraph 51, wherein the light source delivers multichromatic light over a continuous range of 390 to 770 nm.

58. The apparatus of paragraph 51, wherein the light source is a continuous xenon arc lamp.

59. The apparatus of paragraph 51, wherein the light source has a power of at least 5 watts over the range of 390 to 770 nm.

60. An apparatus for measuring a polarization of light emitted from a composition, the apparatus comprising (A) a stage configured to support a microplate having an array of sample wells; (B) a light source having a power of at least 1 watt over a wavelength range of 390 to 770 nm; (C) an excitation optical relay structure having an excitation polarizer, wherein the excitation optical relay structure directs light through the excitation polarizer toward a composition contained in at least one of the sample wells; (D) a detector; and (E) an emission optical relay structure having an emission polarizer, wherein the emission optical relay structure directs light emitted from the composition through an emission polarizer toward the detector.

61. The apparatus of paragraph 60 further comprising a processor that determines polarization or anisotropy based on light intensity sensed by the detector.

62. The apparatus of paragraph 60, wherein the emission optical relay structure directs phosphorescent or fluorescent light emitted from the composition.

63. The apparatus of paragraph 60 further comprising a Z-height adjustment mechanism that automatically controls the height of a sensed volume in the composition so that signal-to-noise is maximized.

64. The apparatus of paragraph 60, wherein the light source is a laser.

65. The apparatus of paragraph 60, wherein the light source delivers multichromatic light over a continuous range of 390 to 770 nm.

66. The apparatus of paragraph 60, wherein the light source is a continuous xenon arc lamp.

67. The apparatus of paragraph 60, wherein the excitation optical relay structure transmits sufficient light from the light source so that the number of photons collected by the detector exceeds 10,000 in 100 milliseconds from a 100 picomolar solution of pH 7.5.

68. The apparatus of paragraph 67, wherein the fluorescein solution has a volume less than 500 microliters.

69. The apparatus of paragraph 67, wherein the fluorescein solution has a volume less than 10 microliters.

70. A method of measuring polarization of light emitted from a composition, comprising (A) constantly polarizing and transmitting high temperature color light to an examination site as successive samples are automatically, serially aligned in an optical path intersecting the examination site, and (B) detecting polarized light emitted from each sample.

71. The method of paragraph 70 further comprising determining polarization or anisotropy based on detected light intensity.

72. The method of paragraph 70, wherein the detecting step includes the step of sensing fluorescent or phosphorescent light emitted from the composition.

73. The method of paragraph 70, wherein the detecting step includes the step of sensing luminescence emitted from a compound bound to a nucleic acid target.

74. The method of paragraph 70 further comprising depositing the samples in microplate wells.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. An apparatus for detecting light emitted from a composition, comprising:
    a stage for supporting a composition in an examination site, the composition being contained in a spatial volume lying between boundary interfaces located a different points along a Z-axis, wherein the Z-axis is substantially perpendicular to the stage;
    an automated registration device that automatically brings successive compositions, held in adjacent wells of a microplate, and the examination site into register for successive analysis of the composition;
    an arc lamp light source positioned to deliver light to the composition in the examination site;
    a detector positioned to receive light transmitted from the composition in the examination site;
    an optical relay structure located between the light source and the detector, the optical relay structure being capable of transmitting light substantially from a sensed volume of the composition, wherein the sensed volume is spaced away from at least one of the boundary interfaces of the composition; and
    an automated Z-axis optical adjustment device that automatically adjusts the position of the sensed volume along the Z-axis between and spaced away from the boundary interfaces.

2. The apparatus of claim 1, the optical relay structure including confocal optics elements substantially contained within an optics head positioned above or below the stage, wherein the Z-axis optical adjustment device includes a drive mechanism that moves the optics head relative to the Z-axis.

3. The apparatus of claim 1, wherein the sensed volume is spaced substantially away from all the boundary interfaces.

4. The apparatus of claim 1, the sensed volume having a waist region in a sample plane, and a Z-pick-up, wherein the diameter of the waist region is approximately half the dimension of the Z-pick-up.

5. The apparatus of claim 1, wherein the optical relay structure includes an aperture substantially centered about the Z-axis and contained in an image plane conjugate to a sample plane intersecting the sensed volume.

6. The apparatus of claim 1, further comprising an automated registration device controller for preprogramming the relative movement into registration of successive compositions and the examination site.

7. The apparatus of claim 1, the light source being one of a plurality of light sources positioned at a source station, further comprising a switching mechanism for interchangeably connecting different light sources, selected from among the plurality of light sources, to the optical relay structure for different applications.

8. The apparatus of claim 1, wherein the detector is a photomultiplier tube, or a photodiode, or a charge-coupled device.

9. The apparatus of claim 1, wherein the sensed volume is diffraction limited.

10. The apparatus of claim 1, wherein the light source produces high-intensity, high-color temperature light.

11. The apparatus of claim 1, wherein the optical relay structure includes a first aperture and a first lens positioned along a light path between the light source and the examination site or between the detector and the examination site.

12. The apparatus of claim 11, wherein the optical relay structure includes a second aperture and a second lens, the first aperture and the first lens being positioned along a light path between the light source and the examination site, the second aperture and the second lens being positioned along a light path between the detector and the examination site, so that light is transmitted substantially to and from the same sensed volume in a composition at the examination site.

13. The apparatus of claim 11, the optical relay structure including at least one fiber optic element, wherein the first aperture is defined by the dimension of an end of the fiber optic element.

14. The apparatus of claim 11, the optical relay structure including a second aperture, the first and second apertures having different dimensions, further comprising an aperture switching mechanism for interchangeably positioning a selected aperture in the light path leading to or from a sensed volume in a composition at the examination site, so that the size of the sensed volume can be altered by switching between the first and second apertures.

15. The apparatus of claim 11, wherein the diameter of the first aperture is adjustable.

16. The apparatus of claim 11, wherein the first aperture and the first lens are contained in a first optics head positioned near the stage.

17. The apparatus of claim 16, the first optics head being positioned above the stage, wherein the optical relay structure includes a second optics head positioned below the stage, each optics head having a light entrance port optically connected to the light source, and a light exit port optically connected to the detector, and a switch control mechanism capable of interchangeably configuring any one of the following light transmission routes to and from a sensed volume in a composition located at the examination site: (a) top-illumination and top-detection, (b) top-illumination and bottom-detection, (c) bottom-illumination and top-detection, and (d) bottom-illumination and bottom-detection.

18. An apparatus for measuring the polarization of light emitted from a composition, comprising:

a stage for supporting the composition at an examination site;

an automated registration device that automatically brings successive compositions and the examination site into register for successive analysis of the compositions;

a continuous high color temperature light source;

an excitation optical relay structure having an excitation polarizer, wherein the excitation optical relay structure directs light from the light source through the excitation polarizer toward the composition;

a detector; and an emission optical relay structure having an emission polarizer, wherein the emission optical relay structure directs light emitted from the composition through the emission polarizer toward the detector.

19. The apparatus of claim 18, wherein the continuous high color temperature light source has a color temperature of at least about 3500 Kelvin.

20. The apparatus of claim 18, wherein the continuous high color temperature light source is a xenon arc lamp.

21. The apparatus of claim 18, wherein the apparatus is capable of detecting light transmitted substantially from a sensed volume of the composition.

22. The apparatus of claim 21, the composition being contained in a spatial volume lying between boundary interfaces, wherein the sensed volume is spaced substantially away from at least one of the boundary interfaces.

23. The apparatus of claim 18, further comprising a second light source, wherein the high color temperature light source is configured for steady-state polarization assays, and wherein the second light source is configured for time-resolved polarization assays.

24. The apparatus of claim 18, further comprising a modulator mechanism configured to vary the intensity of light incident on the composition without varying the intensity of light produced by the light source.

25. The apparatus of claim 1, the light source having a positive contact and a negative contact, further comprising a power supply having an ignition circuit adapted to generate a voltage pulse to trigger ignition of the arc lamp, wherein the ignition circuit includes a ground, and positive and negative lamp outputs adapted to connect to the positive and negative contacts, respectively, on the lamp, and wherein the positive and negative lamp outputs are ground referenced.

26. The apparatus of claim 1, wherein the arc lamp light source includes a xenon arc lamp light source.

27. The apparatus of claim 18, wherein the continuous high color temperature light source includes a light-emitting diode.

\* \* \* \* \*